United States Patent
Hirano et al.

(10) Patent No.: US 12,129,249 B2
(45) Date of Patent: Oct. 29, 2024

(54) METHOD FOR PRODUCING OPTICALLY ACTIVE COMPOUND

(71) Applicant: DAY ONE BIOPHARMACEUTICALS, INC., South San Francisco, CA (US)

(72) Inventors: Sayuri Hirano, Osaka (JP); Yoshiyuki Takeda, Osaka (JP); Koji Nakamoto, Osaka (JP); Motoki Ikeuchi, Osaka (JP); Masato Kitayama, Osaka (JP); Masatoshi Yamada, Osaka (JP); Jun-ichi Kawakami, Osaka (JP)

(73) Assignee: DAY ONE BIOPHARMACEUTICALS, INC., Brisbane, CA (US)

( * ) Notice: Subject to any disclaimer, the term of this patent is extended or adjusted under 35 U.S.C. 154(b) by 806 days.

(21) Appl. No.: 17/180,127

(22) Filed: Feb. 19, 2021

(65) Prior Publication Data
US 2021/0347769 A1   Nov. 11, 2021

Related U.S. Application Data

(63) Continuation of application No. 16/617,914, filed as application No. PCT/IB2018/053822 on May 29, 2018, now Pat. No. 10,988,469.

(30) Foreign Application Priority Data

May 30, 2017 (JP) .................. 2017-106280

(51) Int. Cl.
C07D 417/12 (2006.01)
C07D 417/14 (2006.01)

(52) U.S. Cl.
CPC ......... *C07D 417/14* (2013.01); *C07D 417/12* (2013.01)

(58) Field of Classification Search
CPC .................................................. C07D 417/12
See application file for complete search history.

(56) References Cited

U.S. PATENT DOCUMENTS 7,709,500 B2   5/2010   Alcaraz et al.
7,968,536 B2   6/2011   Cossrow et al.
(Continued)

FOREIGN PATENT DOCUMENTS

CN   101784545 A   7/2010
CN   104144929 A   11/2014
(Continued)

OTHER PUBLICATIONS

Pan et al. Asymmetric Transfer Hydrogenation of Imines using Alcohol: Efficiency and Selectivity are Influenced by the Hydrogen Donor . Angew Chem Int Ed 55:9615-9619 (2016).
(Continued)

*Primary Examiner* — Brenda L Coleman
(74) *Attorney, Agent, or Firm* — Wilson Sonsini Goodrich & Rosati

(57) ABSTRACT

The aim of the present invention is to provide a method capable of producing an optically active pyrimidinamide derivative on an industrial scale.
Compound (I) or a salt thereof is subjected to an asymmetric reduction reaction, the obtained compound (II) or a salt thereof is subjected to a deprotection reaction, and the obtained compound (III) or a salt thereof is reacted with compound (VI) or a salt thereof to obtain compound (V) or a salt thereof.

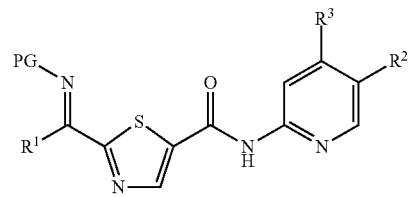

(I)

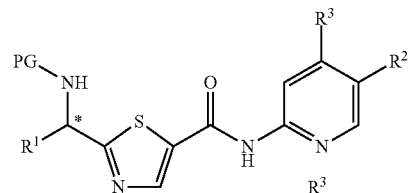

(II)

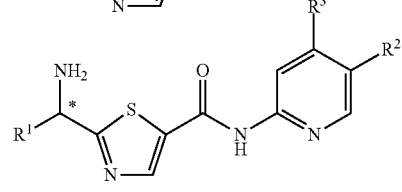

(III)

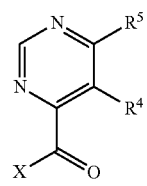

(IV)

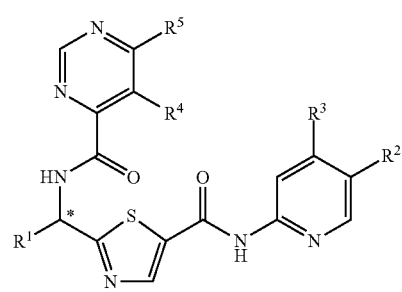

(V)

wherein each symbol is as defined in the specification.

15 Claims, No Drawings

(56) References Cited

U.S. PATENT DOCUMENTS

| | | |
|---|---|---|
| 9,238,667 B2 | 1/2016 | Yamano et al. |
| 9,556,177 B2 | 1/2017 | Chen et al. |
| 10,988,469 B2 | 4/2021 | Hirano et al. |
| 2002/0187988 A1 | 12/2002 | Sturr et al. |
| 2009/0005359 A1 | 1/2009 | Cossrow et al. |
| 2009/0036419 A1 | 2/2009 | Chen et al. |
| 2020/0317659 A1 | 10/2020 | Hirano et al. |

FOREIGN PATENT DOCUMENTS

| | | |
|---|---|---|
| CN | 105008325 A | 10/2015 |
| CN | 105524111 A | 4/2016 |
| JP | 2010532380 A | 10/2010 |
| KR | 20100033384 A | 3/2010 |
| WO | WO-2005095395 A2 | 10/2005 |
| WO | WO-2009006389 A2 | 1/2009 |
| WO | WO-2013146987 A1 | 10/2013 |
| WO | WO-2015178846 A1 | 11/2015 |
| WO | WO-2018220533 A2 | 12/2018 |
| WO | WO-2018220533 A3 | 2/2019 |

OTHER PUBLICATIONS

Xu et al. Nickel-Catalyzed Asymmetric Transfer Hydrogenation of Hydrazones and Other Ketimines. Angew Chem Int Ed 54:5112-5116 (2015).

Doucet et al. trans-[RuCl2(phosphane)2(1,2-diamine)] and Chiral trans-[RuCl2(diphosphane)(1,2-diamine)]: Shelf-Stable Precatalysts for the Rapid, Productive, and Stereoselective Hydrogenation of Ketones. Angew. Chem. Int. Ed. vol. 37, Issue 12, pp. 1703-1707 (1998). First published Dec. 17, 1998.

Enders et al. Asymmetric organocatalytic reduction of ketimines with catecholborane employing a N-triflyl phosphoramide Brønsted acid as catalyst. Tetrahedron Letters, vol. 54, Issue 6, pp. 470-473 (Feb. 6, 2013).

Ferraris et al. Diastereo- and Enantioselective Alkylation of α-Imino Esters with Enol Silanes Catalyzed by (R)-Tol-BINAP-CuClO4•(MeCN)2.J. Org. Chem. 1998, 63, 18, 6090-6091. DOI: https://doi.org/10.1021/jo981079h.

Fujii et al. Mechanism of Palladium Complex-Catalyzed Enantioselective Mannich-Type Reaction: Characterization of a Novel Binuclear Palladium Enolate Complex. J. Am. Chem. Soc. 1999, 121, 23, 5450-5458. DOI: https://doi.org/10.1021/ja9902827.

Genet et al. General synthesis of novel chiral ruthenium catalysts and their use in asymmetric hydrogenation. Tetrahedron: Asymmetry, vol. 2, Issue 1, 1991, pp. 43-46. DOI: https://doi.org/10.1016/S0957-4166(00)82155-2.

Greene et al. Protective Groups in Organic Synthesis, Third Edition, John Wiley & Sons, Inc., pp. 579-583 (1999).

Hearn et al. Hydrogenolytic Cleavage Reactions of Phenylhydrazides. Synthetic Communications, vol. 10, 1980—Issue 3, pp. 253-259. Published online Dec. 5, 2006. DOI: https://doi.org/10.1080/00397918008064230.

Huang et al., "Direct Asymmetric Reductive Amination for the Synthesis of Chiral β-Arylamines", Angewandte Chem. Int. Ed. (2016),55, 5309-5312.

International Search Report, mailed Nov. 30, 2018, of corresponding PCT/IB2018/053822.

Jiang Xiao-bin et al., "Application of monodentate secondary phosphine oxides, a new class of chiral ligands, in Ir(i)-catalyzed asymmetric imine hydrogenation", Organic Letters, (2003), 5, 1503-1506.

Kagan et al. Asymmetric catalytic reduction with transition metal complexes. I. A catalytic system of rhodium(I) with (−)-2,3-0-isopropylidene-2,3-dihydroxy-1,4-bis(diphenylphosphino)butane, a new chiral diphosphine. J. Am. Chem. Soc. 1972, 94, 18, 6429-6433. DOI: https://doi.org/10.1021/ja00773a028.

Kitamura et al. Practical synthesis of BINAP-ruthenium(II) dicarboxylate complexes. J. Org. Chem. 1992, 57, 14, 4053-4054. DOI: https://doi.org/10.1021/jo00040a068.

Laurent et al. A New Method of N-Benzhydryl Deprotection in 2-Azetidinone Series. Synthesis 2003(4): 0570-0576. DOI: 10.1055/s-2003-37653.

Mashima et al. Cationic BINAP-Ru(II) Halide Complexes: Highly Efficient Catalysts for Stereoselective Asymmetric Hydrogenation of .alpha.- and .beta.-Functionalized Ketones. J. Org. Chem. 1994, 59, 11, 3064-3076. DOI: https://doi.org/10.1021/jo00090a026.

Mashima et al. Chemoselective asymmetric hydrogenation of α,β-unsaturated carbonyl compounds to allylic alcohols catalysed by [Ir(binap)(cod)]BF4-aminophosphine,Journal of Organometallic Chemistry, vol. 428, Issues 1-2, Apr. 28, 1992, pp. 213-222. DOI: https://doi.org/10.1016/0022-328X(92)83231-6.

Neumann et al. The stereoselective synthesis of functionalized vicinal diamine systems by the double allylation reactions of "protected" 1,2-bis-imine precursors. Tetrahedron Letters, vol. 32, Issue 42, Oct. 14, 1991, pp. 5865-5868. DOI: https://doi.org/10.1016/S0040-4039(00)79412-3.

Ozawa et al. Palladium-catalyzed asymmetric arylation of 2,3-dihydrofuran with phenyl triflate. A novel asymmetric catalysis involving a kinetic resolution process. Organometallics 1993, 12, 10, 4188-4196. DOI: https://doi.org/10.1021/om00034a064.

PCT/IB2018/053822 Written Opinion dated Nov. 30, 2018.

Ryglowski et al. Preparation of 1-aminoalkylphosphonic acids and 2-aminoalkylphosphonic acids by reductive amination of oxoalkylphosphonates. Tetrahedron, vol. 52, Issue 32, Aug. 5, 1996, pp. 10685-10692. DOI: https://doi.org/10.1016/0040-4020(96)00590-X.

Sampson et al. Oxidative Deprotection of Diphenylmethylamines. Org. Lett. 1999, 1, 9, 1395-1397. Published online Sep. 25, 1999. DOI: https://doi.org/10.1021/ol990956i.

Tani et al. (R)-(−)-N,N-Diethyl-(E)-Citronellalenamine and (R)-(+)-Citronellal Via Isomerization of N,Ndiethylgeranylamineor N,N-Diethylnerylamine. Organic Syntheses, Coll. vol. 8, p. 183 (1993); vol. 67, p. 33 (1989). DOI:10.15227/orgsyn.067.0033. 8 pages.

Jiang Xiao-bin et al., Supporting information for: "Monodentate Secondary Phosphine Oxides, a New Class of Chiral Ligands. Their Application in Ir(I)-Catalyzed Asymmetric Imine Hydrogenation", Organic Letters, (2003), 5, S1-S4. Retrieved Dec. 30, 2020 from URL: https://pubs.acs.org/doi/10.1021/ol034282u.

Nugent et al. Chiral Amine Synthesis—Recent Developments and Trends for Enamide Reduction, Reductive Amination, and Imine Reduction. Advanced Synthesis & Catalysis, vol. 352, Issue 5, pp. 753-819 (Mar. 12, 2010). DOI: https://doi.org/10.1002/adsc.200900719.

U.S. Appl. No. 16/617,914 Notice of Allowance dated Dec. 16, 2020.

U.S. Appl. No. 16/617,914 Office Action dated Aug. 5, 2020.

METHOD FOR PRODUCING OPTICALLY ACTIVE COMPOUND

TECHNICAL FIELD

The present invention relates to a production method of an optically active amine compound which is useful for producing an optically active pyrimidinamide derivative, and a production method of an optically active pyrimidinamide derivative using the optically active amine compound.

BACKGROUND OF THE INVENTION

The pyrimidinamide derivative represented by the below-mentioned formula (V) is known as a Raf protein kinase inhibitor and a therapeutic drug for cancer and the like.

The following method is known as a production method of the optically active form.

Patent Document 1 discloses that an optically active form of an amine compound represented by the below-mentioned formula (III) is produced by subjecting the corresponding ketone compound successively to oximation, reduction, and optical resolution with di-p-toluoyl-(D)-tartaric acid, and the objective optically active form of a pyrimidinamide derivative represented by the below-mentioned formula (V) is produced from the optically active amine compound.

As a production method of an optically active amine compound, non-Patent Document 1 discloses a reductive asymmetric amination reaction of an aryl acetone with benzhydrylamine using an iridium complex as a catalyst, and non-Patent Document 2 discloses an asymmetric reduction reaction of a compound having a diphenylmethylimino group.

DOCUMENT LIST

Patent Document

[Patent Document 1] WO 2009/006389

Non-Patent Document

[Non-Patent Document 1] Huang et al., Angew. Chem. int. Ed. (2016), 55, 5309-5317
[Non-Patent Document 2] Jiang Xiao-bin et al., Org. Lett. (2003), 5, 1503

SUMMARY OF THE INVENTION

Problems to be Solved by the Invention

The aim of the present invention is to provide a method capable of producing an optically active pyrimidinamide derivative on an industrial scale.

In order to produce an optically active form of an amine compound represented by the below-mentioned formula (III), which is necessary for the production of an optically active form of a pyrimidinamide derivative represented by the below-mentioned (V), by asymmetric reduction of the corresponding imino compound, it is important that an appropriate protecting group is introduced into the imino compound, and that the asymmetric reduction reaction is developed.

The diphenylmethyl group as a protecting group is previously little-known. In the method of Non-Patent Document 1, the optically active compound having a diphenylmethylamino group is obtained as a product of the reductive asymmetric amination reaction, which is extremely different in structure from an optically active form of an amine compound represented by the below-mentioned formula (II). In the method of Non-Patent Document 2, the asymmetric reduction reaction of the compound having a diphenylmethylimino group results in extremely low yield and low enantioselectivity.

Means of Solving the Problems

The present inventors have conducted intensive studies to solve the above-mentioned problems, and have found that, by subjecting an imino compound having an appropriate protecting group (which is represented by the below-mentioned formula (I), or a salt thereof) to an asymmetric reduction reaction, followed by deprotection, an optically active form of an amine compound represented by the below-mentioned formula (III) or a salt thereof (which is a key intermediate) can be produced with good optical purity in good yield, and therefore, an optically active form of a pyrimidinamide derivative represented by the below-mentioned formula (V) (which is an objective compound) can be produced on an industrial scale, and completed the present invention based on these findings.

Accordingly, the present invention provides the following.

[1] A method of producing an optically active form of a compound represented by the following formula (II):

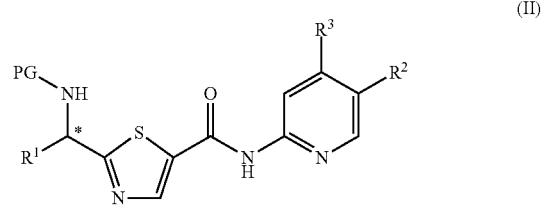

wherein
$R^1$ is a $C_{1-6}$ alkyl group;
$R^2$ is a hydrogen atom or a halogen atom;
$R^3$ is a hydrogen atom or an optionally halogenated $C_{1-6}$ alkyl group;
PG is a protecting group; and
the carbon atom marked with * is an asymmetric carbon atom (hereinafter, the optically active form of the compound represented by the formula (II) is to be referred to as compound (II)),
or a salt thereof, which comprises subjecting a compound represented by the following formula (I):

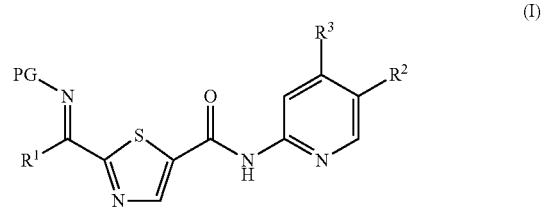

wherein each symbol is as defined above (hereinafter to be referred to as compound (I)), or a salt thereof, to an asymmetric reduction reaction.

[2] A method of producing an optically active form of a compound represented by the following formula (V):

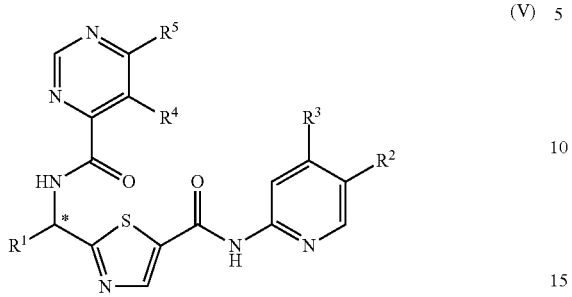

(V)

wherein
R¹ is a $C_{1-6}$ alkyl group;
R² is a hydrogen atom or a halogen atom;
R³ is a hydrogen atom or an optionally halogenated $C_{1-6}$ alkyl group;
R⁴ and R⁵ are each independently a hydrogen atom, a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group, or an optionally substituted silyl group; and
the carbon atom marked with * is an asymmetric carbon atom (hereinafter, the optically active form of the compound represented by the formula (V) is to be referred to as compound (V)),
or a salt thereof, which comprises a step of subjecting a compound represented by the following formula (I);

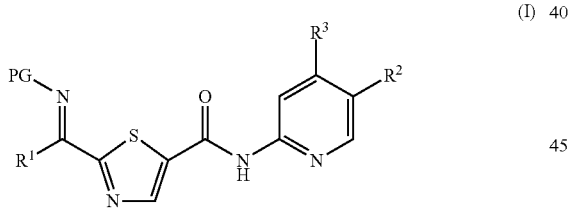

(I)

wherein
PG is a protecting group, and
and the other symbols are as defined above,
or a salt thereof, to an asymmetric reduction reaction to obtain an optically active form of a compound represented by the following formula (II);

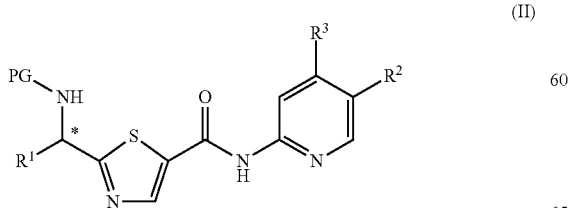

(II)

wherein each symbol is as defined above, or a salt thereof.

[3] The method of the above-mentioned [2], which further comprises
a step of subjecting an optically active form of a compound represented by the following formula (II);

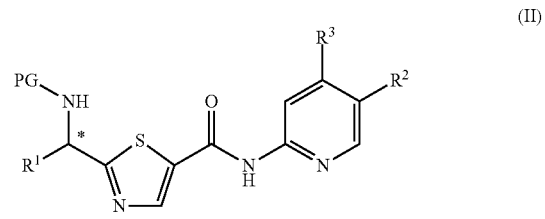

(II)

wherein
R¹ is a $C_{1-6}$ alkyl group;
R² is a hydrogen atom or a halogen atom;
R³ is a hydrogen atom or an optionally halogenated $C_{1-6}$ alkyl group;
PG is a protecting group; and
the carbon atom marked with * is an asymmetric carbon atom, or a salt thereof, to a deprotection reaction, and
a step of reacting the obtained optically active form of a compound represented by the following formula (III);

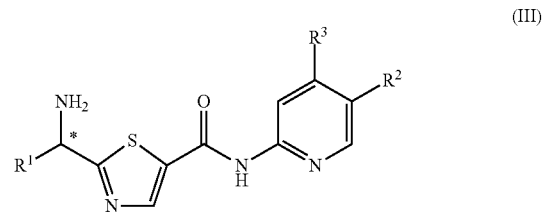

(III)

wherein each symbol is as defined above (hereinafter, the optically active form of the compound represented by the formula (III) is to be referred to as compound (III)), or a salt thereof, with a compound represented by the following formula (IV);

(IV)

wherein
X is a leaving group; and
R⁴ and R⁵ are each independently a hydrogen atom, a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group, or an optionally substituted silyl group (hereinafter to be referred to as compound (IV)),
or a salt thereof.

[4] The method of the above-mentioned [3], wherein the optically active form of the compound represented by the formula (III) or a salt thereof is a salt of the optically active form of the compound represented by the formula (III) with mandelic acid.

[5] The method of the above-mentioned [3] or [4], wherein X is a hydroxy group.

[6] The method of any one of the above-mentioned [1] to [5], wherein the asymmetric reduction reaction is an asymmetric hydrogenation reaction in the presence of a transition metal complex.

[7] The method of the above-mentioned [6], wherein the transition metal complex is an iridium complex.

[8] The method of any one of the above-mentioned [1] to [7], wherein PG is represented by the following formula (VI):

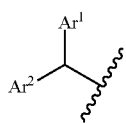

(VI)

wherein
Ar$^1$ is a hydrogen atom or an optionally substituted C$_{6-14}$ aryl group; and
Ar$^2$ is an optionally substituted C$_{6-14}$ aryl group.

[9] The method of the above-mentioned [8], wherein Ar$^1$ and Ar$^2$ are each independently an optionally substituted phenyl group.

[10] A compound represented by the following formula (VII):

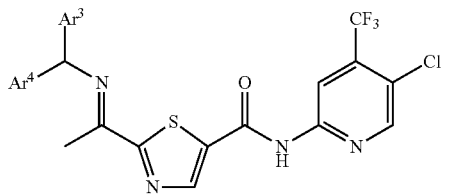

(VII)

wherein Ar$^3$ and Ar$^4$ are each independently an optionally substituted C$_{6-14}$ aryl group (hereinafter to be referred to as compound (VII)), or a salt thereof.

[11] An optically active form of a compound represented by the following formula (VIII):

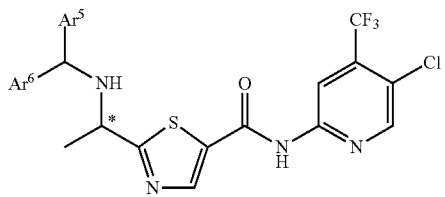

(VIII)

wherein
Ar$^5$ and Ar$^6$ are each independently an optionally substituted C$_{6-14}$ aryl group, and the carbon atom marked with * is an asymmetric carbon atom (hereinafter, the optically active form of the compound represented by the formula (VIII) is to be referred to as compound (VIII)), or a salt thereof.

[12] A method of producing an optically active form of a compound represented by the formula (III) or a salt thereof, which comprises subjecting a compound represented by the following formula (A-c)

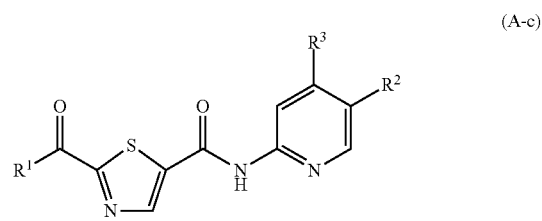

(A-c)

wherein
R$^1$ is a C$_{1-6}$ alkyl group;
R$^2$ is a hydrogen atom or a halogen atom; and
R$^3$ is a hydrogen atom or an optionally halogenated C$_{1-6}$ alkyl group
(hereinafter, to be referred to as compound (A-c)) or a salt thereof, to an asymmetric reductive amination reaction.

[13] The method of the above-mentioned [12], wherein the asymmetric reductive amination reaction is carried out by reacting a compound represented by the formula (A-c) or a salt thereof with an amine source and a reducing agent in the presence of an organic metal complex.

Effect of the Invention

According to the present invention, compound (III) or a salt thereof, which is a key intermediate, can be produced with good optical purity in good yield, by subjecting compound (I) or a salt thereof to an asymmetric reduction reaction, followed by deprotection. Particularly, after the deprotection, by crystallization of the diastereomer salt with optically active di-p-toluoyl-tartaric acid or optically active mandelic acid, the salt of compound (III) can be produced with better optical purity. Therefore, the objective compound (V) or a salt thereof can be produced on an industrial scale.

Detailed Description of the Invention

The present invention is explained below in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "C$_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated C$_{1-6}$ alkyl group" include a C$_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{1-6}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5-to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3, 4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5-to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5-to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5-to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5-to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A". Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

The definitions of each symbol in the formula (I), formula (II), formula (III), formula (IV), formula (V), formula (VII) and formula (VIII), and the compounds are explained below in detail.

$R^1$ is a $C_{1-6}$ alkyl group, preferably methyl.

$R^2$ is a hydrogen atom or a halogen atom, preferably a chlorine atom.

$R^3$ is a hydrogen atom or an optionally halogenated $C_{1-6}$ alkyl group, preferably a fluorinated $C_{1-6}$ alkyl group, particularly preferably trifluoromethyl.

PG is a protecting group. Examples of the "protecting group" include a group represented by the formula (VI-1):

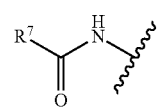

(VI-1)

wherein $R^7$ is an optionally substituted $C_{6-14}$ aryl group or an optionally substituted $C_{1-6}$ alkoxy group, and a group represented by the formula (VI):

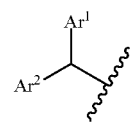

(VI)

wherein $Ar^1$ is a hydrogen atom or an optionally substituted $C_{6-14}$ aryl group; and $Ar^2$ is an optionally substituted $C_{6-14}$ aryl group.

Examples of the "substituent" of the "optionally substituted $C_{6-14}$ aryl group" represented by $R^7$ include the above-mentioned "substituents". The number of the substituents in the "optionally substituted $C_{6-14}$ aryl group" represented by $R^7$ is, for example, 1 to 5, preferably 1 to 3, at substitutable position(s). When the number of the substituents is two or more, the respective substituents may be the same or different.

Examples of the "substituent" of the "optionally substituted $C_{1-6}$ alkoxy group" represented by $R^7$ include the above-mentioned "substituents". The number of the substituents in the "optionally substituted $C_{1-6}$ alkoxy group" represented by $R^7$ is, for example, 1 to 5, preferably 1 to 3, at substitutable position(s). When the number of the substituents is two or more, the respective substituents may be the same or different.

$R^7$ is preferably a $C_{6-14}$ aryl group having no substituent or a $C_{1-6}$ alkoxy group having no substituent, more preferably phenyl or tert-butoxy, particularly preferably phenyl.

The substituent of the "optionally substituted $C_{6-14}$ aryl group" represented by $Ar^1$ or $Ar^2$ and a number thereof are similar to those exemplified in the above-mentioned "optionally substituted $C_{6-14}$ aryl group" represented by $R^7$. Preferred is a $C_{1-6}$ alkoxy group, and particularly preferred is methoxy.

PG is preferably a group represented by the formula (VI). In this case, $Ar^1$ and $Ar^2$ are preferably each independently an optionally substituted $C_{6-14}$ aryl group, more preferably each independently optionally substituted phenyl, further more preferably each independently phenyl optionally substituted by $C_{1-6}$ alkoxy group(s), particularly preferably both phenyl.

As preferable embodiment, a compound represented by the formula (I) is a compound represented by the formula (VII):

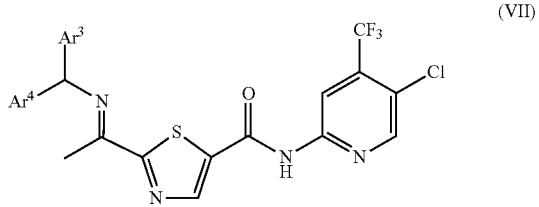

(VII)

wherein
$Ar^3$ and $Ar^4$ are each independently an optionally substituted $C_6$-aryl group, and
an optically active form of a compound represented by the formula (II) is an optically active form of a compound represented by the formula (VIII):

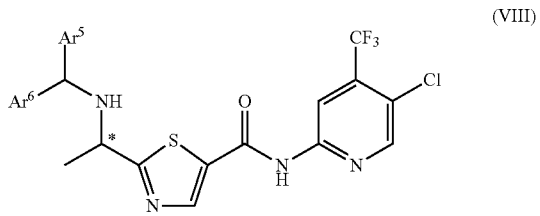

(VIII)

wherein
$Ar^5$ and $Ar^6$ are each independently an optionally substituted $C_{6-14}$ aryl group, and
the carbon atom marked with * is an asymmetric carbon atom.

The substituent of the "optionally substituted $C_{6-14}$ aryl group" represented by $Ar^3$, $Ar^4$, $Ar^5$ or $Ar^6$ and a number thereof are similar to those exemplified in the above-mentioned "optionally substituted $C_{6-14}$ aryl group" represented by $R^7$. Preferred is a $C_{1-6}$ alkoxy group, and particularly preferred is methoxy.

$Ar^3$ and $Ar^4$ are preferably each independently optionally substituted phenyl, more preferably each independently phenyl optionally substituted by $C_{1-6}$ alkoxy group(s), particularly preferably both phenyl.

$Ar^5$ and $Ar^6$ are preferably each independently optionally substituted phenyl, more preferably each independently phenyl optionally substituted by $C_{1-6}$ alkoxy group(s), particularly preferably both phenyl.

As the most preferable embodiment, a compound represented by the formula (I) is (E)-2-(1-(benzhydrylimino)ethyl)-N-(5-chloro-4-(trifluoromethyl)pyridin-2-yl)-1,3-thiazole-5-carboxamide; and an optically active form of a compound represented by the formula (II) is 2-((1R)-1-(benzhydrylamino)ethyl)-N-(5-chloro-4-(trifluoromethyl)pyridin-2-yl)-1,3-thiazole-5-carboxamide.

$R^4$ and $R^5$ are each independently a hydrogen atom, a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group, or an optionally substituted silyl group.

Examples of the "optionally substituted hydrocarbon group" represented by $R^4$ or $R^5$ include those exemplified as the above-mentioned "optionally substituted hydrocarbon group".

Examples of the "optionally substituted heterocyclic group" represented by $R^4$ or $R^5$ include those exemplified as the above-mentioned "optionally substituted heterocyclic group".

Examples of the "acyl group" represented by $R^4$ or $R^5$ include those exemplified as the above-mentioned "acyl group".

Examples of the "optionally substituted amino group" represented by $R^4$ or $R^5$ include those exemplified as the above-mentioned "optionally substituted amino group".

Examples of the "optionally substituted carbamoyl group" represented by $R^4$ or $R^5$ include those exemplified as the above-mentioned "optionally substituted carbamoyl group".

Examples of the "optionally substituted thiocarbamoyl group" represented by $R^4$ or $R^5$ include those exemplified as the above-mentioned "optionally substituted thiocarbamoyl group".

Examples of the "optionally substituted sulfamoyl group" represented by $R^4$ or $R^5$ include those exemplified as the above-mentioned "optionally substituted sulfamoyl group".

Examples of the "optionally substituted hydroxy group" represented by $R^4$ or $R^5$ include those exemplified as the above-mentioned "optionally substituted hydroxy group".

Examples of the "optionally substituted sulfanyl (SH) group" represented by $R^4$ or $R^5$ include those exemplified as the above-mentioned "optionally substituted sulfanyl (SH) group".

Examples of the "optionally substituted silyl group" represented by $R^4$ or $R^5$ include those exemplified as the above-mentioned "optionally substituted silyl group".

$R^4$ is preferably a hydrogen atom, a halogen atom, a cyano group, an optionally substituted hydrocarbon group, an acyl group, or an optionally substituted hydroxy group, more preferably a hydrogen atom or a halogen atom, particularly preferably a chlorine atom.

$R^5$ is preferably a hydrogen atom, an optionally substituted hydrocarbon group, an optionally substituted heterocyclic group, an acyl group, an optionally substituted amino group, an optionally substituted carbamoyl group, an optionally substituted hydroxy group, or an optionally substituted sulfanyl (SH) group, more preferably a hydrogen atom, or an optionally substituted amino group, particularly preferably an amino group.

Examples of the leaving group represented by X include a halogen atom, an optionally substituted hydroxy group, an azido group, and an optionally substituted imidazolyl group.

Examples of the "optionally substituted hydroxy group" represented by X include those exemplified as the above-mentioned "optionally substituted hydroxy group".

Examples of the substituent of the "optionally substituted imidazolyl group" represented by X include a $C_{1-6}$ alkyl group. Preferred is methyl.

X is preferably a hydroxy group.

As the most preferable embodiment,
a compound represented by the formula (IV) is 6-amino-5-chloropyrimidine-4-carboxylic acid; and an optically active form of a compound represented by the formula (V) is 6-amino-5-chloro-N-((1R)-1-(5-((5-chloro-4-(trifluoromethyl)pyridin-2-yl)carbamoyl)-1,3-thiazol-2-yl)ethyl)pyrimidine-4-carboxamide.

The compound represented by the formula (I), (II), (IV), (V), (VII) or (VIII) may be a salt.

Examples of the salt of the compound represented by the formula (I), (II), (IV), (V), (VII) or (VIII) include metal salts, ammonium salts, salts with an organic base, salts with an inorganic acid, salts with an organic acid, salts with a basic or acidic amino acid, and the like.

Preferable examples of the metal salt include alkali metal salts such as sodium salt, potassium salt and the like; alkaline-earth metal salts such as calcium salt, magnesium salt, barium salt and the like; aluminium salt, and the like.

Preferable examples of the salt with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salt with an inorganic acid include salts with hydrofluoric acid, hydrochloric acid, hydrobromic acid, hydriodic acid, nitric acid, sulfuric acid, sulfurous acid, phosphoric acid, phosphorous acid, carbonic acid, bicarbonic acid and the like.

Preferable examples of the salt with an organic acid include salts with a carboxylic acid (i.e., an organic compound having one or more carboxy groups; specific examples thereof include formic acid, acetic acid, benzoic acid, trifluoroacetic acid, phthalic acid, fumaric acid, oxalic acid, tartaric acid, a tartaric acid derivative, mandelic acid, maleic acid, citric acid, succinic acid, malic acid, and the above-mentioned basic or acidic amino acid wherein the amino group is protected, and the like); and a sulfonic acid (i.e., an organic compound having one or more sulfo groups; specific examples thereof include methanesulfonic acid, trifluoromethanesulfonic acid, benzenesulfonic acid, p-toluenesulfonic acid, camphorsulfonic acid and the like).

Examples of the salt with a tartaric acid derivative include salts with di-p-toluoyl-tartaric acid, dibenzoyltartaric acid, di-p-anisoyltartaric acid and the like.

Preferable examples of the salt with a basic amino acid include salts with arginine, lysine, ornithine and the like. Preferable examples of the salt with an acidic amino acid include salts with aspartic acid, glutamic acid and the like.

Examples of the protecting group for the basic or acidic amino acid wherein the amino group is protected include ter-butoxycarbonyl, acetyl and the like.

The optically active form of the compound represented by the formula (III) is preferably in the form of a salt.

Examples of the salt of the optically active form of the compound represented by the formula (III) include salts with an inorganic acid, salts with an organic acid, salts with a basic or acidic amino acid, and the like.

Preferable examples of the salt of the optically active form of the compound represented by the formula (III) with an inorganic acid include those exemplified as the salt of the compound represented by the formula (I), (II), (IV), (V), (VII) or (VIII) with an inorganic acid.

Preferable examples of the salt of the optically active form of the compound represented by the formula (III) with an organic acid include those exemplified as the salt of the compound represented by the formula (I), (II), (IV), (V), (VII) or (VIII) with an organic acid.

Preferable examples of the salt of the optically active form of the compound represented by the formula (III) with a basic or acidic amino acid include those exemplified as the salt of the compound represented by the formula (I), (II), (IV), (V), (VII) or (VIII) with a basic or acidic amino acid.

The optically active form of the compound represented by the formula (III) is preferably in the form of a salt, more preferably in the form of a salt with an optically active organic acid or a salt with an optically active basic or acidic amino acid, further more preferably in the form of a salt with optically active di-p-toluoyl-tartaric acid (preferably di-p-toluoyl-(D)-tartaric acid when the optically active form of the compound represented by the formula (III) is (R)-form) or a salt with optically active mandelic acid (preferably (S)-mandelic acid when the optically active form of the compound represented by the formula (III) is (R)-form), particularly preferably in the form of a salt with optically active mandelic acid (preferably (S)-mandelic acid when the optically active form of the compound represented by the formula (III) is (R)-form).

As the most preferable embodiment, the optically active form of the compound represented by the formula (III) is 2-((1R)-1-aminoethyl)-N-(5-chloro-4-(trifluoromethyl)pyridin-2-yl)-1,3-thiazole-5-carboxamide; and the optically active form of the compound represented by the formula (V) is 6-amino-5-chloro-N-((1R)-1-(5-((5-chloro-4-(trifluoromethyl)pyridin-2-yl)carbamoyl)-1,3-thiazol-2-yl)ethyl)pyrimidine-4-carboxamide.

In the most preferable embodiment, the salt of the optically active form of the compound represented by the formula (III) is a salt with (S)-mandelic acid.

The compound represented by the formula (I), (II), (III), (IV), (V), (VII) or (VIII), or a salt thereof may be each a solvate (e.g., a hydrate, an ethanolate, etc.) or a non-solvate (e.g., a non-hydrate, etc.), which is encompassed in the compound represented by the formula (I), (II), (III), (IV), (V), (VII) or (VIII), or a salt thereof.

The compound labeled with an isotope and the like, or a salt thereof is also encompassed in the compound represented by the formula (I), (II), (III), (IV), (V), (VII) or (VIII), or a salt thereof.

A deuterium conversion form wherein $^1$H is converted to $^2$H(D) is also encompassed in the compound represented by the formula (I), (II), (III), (IV), (V), (VII) or (VIII), or a salt thereof.

The production method (Production Method (A)) of compound (III) or a salt thereof, and the production method (Production Method (B)) of compound (V) or a salt thereof using compound (III) or a salt thereof obtained in the Production Method (A) are explained below in detail.

[Production Method (A)]

Compound (III) or a salt thereof can be produced according to Production Method (A) shown in the following scheme.

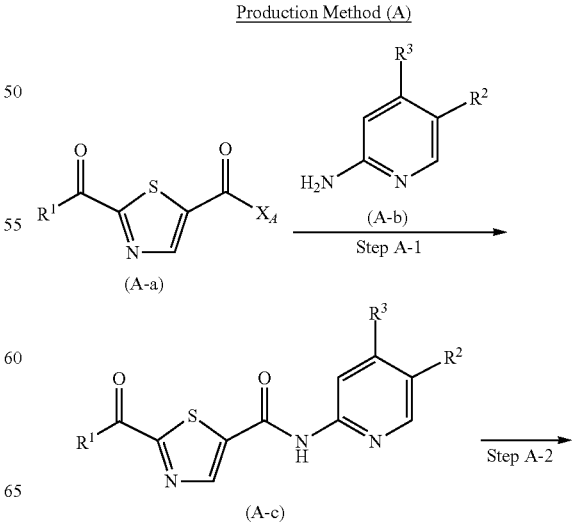

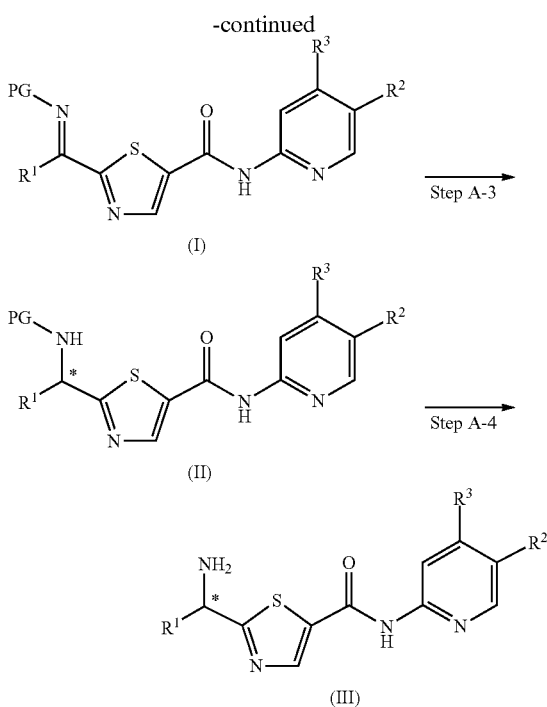

wherein $X_A$ is a leaving group, and the other symbols are as defined above.

Examples of the leaving group represented by $X_A$ include those exemplified as the above-mentioned the leaving group represented by X.

$X_A$ is preferably a hydroxy group or a chlorine atom.

The reagent and condition used in each step of Production Method (A) are explained in detail.

[Step A-1]

Step A-1 is a step of producing a compound represented by the formula (A-c) (hereinafter to be referred to as compound (A-c)) or a salt thereof by a method forming an amide bond from a compound represented by the formula (A-a) (hereinafter to be referred to as compound (A-a)) or a salt thereof and a compound represented by the formula (A-b) (hereinafter to be referred to as compound (A-b)) or a salt thereof.

Compound (A-a) or a salt thereof may be a commercially available product.

Examples of the salt of compound (A-a) include metal salts, ammonium salts, salts with an organic base, salts with a basic amino acid, and the like.

Preferable examples of the metal salt of compound (A-a) include those exemplified as the metal salt of compound (I), (II), (IV), (V), (VII) or (VIII).

Preferable examples of the salt of compound (A-a) with an organic base include those exemplified as the salt of compound (I), (II), (IV), (V), (VII) or (VIII) with an organic base.

Preferable examples of the salt of compound (A-a) with a basic amino acid include those exemplified as the salt of compound (I), (II), (IV), (V), (VII) or (VIII) with a basic amino acid.

Compound (A-b) can be produced, for example, according to the method described in WO 2009-006389.

Examples of the salt of compound (A-b) include salts with an inorganic acid, salts with an organic acid, salts with an acidic amino acid, and the like.

Preferable examples of the salt of compound (A-b) with an inorganic acid include those exemplified as the salt of compound (I), (II), (IV), (V), (VII) or (VIII) with an inorganic acid.

Preferable examples of the salt of compound (A-b) with an organic acid include those exemplified as the salt of compound (I), (II), (IV), (V), (VII) or (VIII) with an organic acid.

Preferable examples of the salt of compound (A-b) with an acidic amino acid include those exemplified as the salt of compound (I), (II), (IV), (V), (VII) or (VIII) with an acidic amino acid.

The salt of compound (A-b) is particularly preferably a hydrochloride.

The above-mentioned method "forming an amide bond" can be carried out according to a method known per se, such as the method described in Tetrahedoron, vol., 61, page 10827, 2005.

The method "forming an amide bond" is preferably a method of producing compound (A-c) or a salt thereof by condending compound (A-a) wherein $X_A$ is a halogen atom (an acid halide) and compound (A-b) or a salt thereof. Among them, a method using compound (A-a) wherein $X_A$ is a chlorine atom (an acid chloride) is particularly preferable.

For preparation of the acid chloride, the hydroxy group of $X_A$ is converted to a chlorine atom by a method using a chlorinating agent such as thionyl chloride, oxalyl chloride, phosphorus oxychloride, phosphorus trichloride, phosphorus pentachloride and the like.

As the "chlorinating agent", thionyl chloride, oxalyl chloride and phosphorus oxychloride are preferable, and oxalyl chloride is particularly preferable.

When oxalyl chloride is used as a "chlorinating agent", the reaction is preferably carried out in the presence of N,N-dimethylformamide. The amount of the N,N-dimethylformamide to be used is a catalytic amount, preferably 0.0001 to 0.1 mol, more preferably 0.001 to 0.01 mol, per 1 mol of the oxalyl chloride.

While the amount of the oxalyl chloride to be used varies depending on the kind of the solvent and the other reaction condition, it is generally 0.1 to 10 mol, preferably 0.8 to 1.2 mol, per 1 mol of the substrate compound (A-a) or a salt thereof.

While the reaction for the preparation of the acid chloride using oxalyl chloride as a "chlorinating agent" may be carried out without a solvent, it is generally carried out in a solvent. The solvent is not particularly limited as long as it does not inhibit the reaction and can dissolve the raw material compound and additive, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; halogenated hydrocarbons such as chloroform, dichloromethane, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; nitromethane and the like. These solvents may be used in a mixture in an appropriate ratio. As the solvent used in the reaction for the preparation of the acid chloride using oxalyl chloride as a "chlorinating agent", ethers are preferable, and 1,2-dimethoxyethane is particularly preferable.

The amount of the solvent to be used is appropriately determined depending on the solubility of the substrate compound (A-a) or a salt thereof, and the like. For example, when an ether (preferably 1,2-dimethoxyethane) is used as a solvent, the reaction can be carried out nearly without a solvent or in a solvent in an amount of 100 parts by weight or less per 1 part by weight of the substrate compound (A-a) or a salt thereof, preferably in a solvent in an amount of 1 to 10 parts by weight per 1 part by weight of the substrate compound (A-a) or a salt thereof.

The temperature in the reaction for the preparation of the acid chloride using oxalyl chloride as a "chlorinating agent" is generally −10 to 80° C., preferably 0 to 40° C. The reaction time is generally 0.1 to 12 hr, preferably 0.5 to 4 hr.

The obtained acid chloride of compound (A-a) may be purified according to a means known per se (evaporation of low-boiling components such as solvent by concentration, distillation, etc.). Preferably, the reaction solution is used directly in the condensation reaction with compound (A-b) or a salt thereof.

While the amount of compound (A-b) or a salt thereof to be subjected to the condensation reaction with the acid chloride of compound (A-a) varies depending on the kind of the solvent and the other reaction condition, it is generally 0.1 to 10 mol, preferably 0.8 to 1.2 mol, per 1 mol of compound (A-a) or a salt thereof.

When the salt of compound (A-b) is used, it is preferably converted to the free form in advance by reacting with a base, prior to the condensation reaction with the acid chloride of compound (A-a). Examples of the base include inorganic bases and organic bases.

Examples of the inorganic base include alkali metal hydroxides such as lithium hydroxide, potassium hydroxide, sodium hydroxide, cesium hydroxide and the like; alkali metal alkoxides having 1 to 6 carbon atoms such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide and the like; alkali metal thioalkoxides having 1 to 6 carbon atoms such as sodium thiomethoxide and the like; carbonates such as sodium carbonate, potassium carbonate, cesium carbonate and the like; hydrogencarbonates such as sodium hydrogencarbonate, potassium hydrogencarbonate and the like; acetates such as sodium acetate, potassium acetate and the like; phosphates such as tripotassium phosphate, sodium phosphate and the like; and monohydrogen phosphates such as potassium monohydrogen phosphate, sodium monohydrogen phosphate and the like.

Examples of the organic base include aliphatic amines such as trimethylamine, triethylamine, N-methylmorpholine, N,N-diisopropylethylamine, diethylamine, diisopropylamine, cyclohexylamine, ethylenediamine, 1,8-diazabicyclo[5.4.0]undecene and the like; aromatic amines such as pyridine, picoline, N,N-dimethylaniline and the like; and basic amino acids such as arginine, lysine, ornithine and the like. These bases may be used in a mixture in an appropriate ratio.

As the base for the conversion of the salt of compound (A-b) to the free form, pyridine is particularly preferable.

While the amount of the base to be used varies depending on the kind of the solvent and the other reaction condition, it is generally 0.1 to 100 mol, preferably 0.5 to 20 mol, more preferably 0.8 to 5 mol, per 1 mol of the substrate salt of compound (A-b). When the base is a liquid, it can also be used as a solvent.

While the reaction for the conversion of the salt of compound (A-b) to the free form may be carried out without a solvent, it is generally carried out in a solvent. The solvent is not particularly limited as long as it does not inhibit the reaction and can dissolve the raw material compound and additive, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, 2-propanol, n-butanol, 2-butanol, t-butyl alcohol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; esters such as ethyl acetate, isopropyl acetate, n-propyl acetate, n-butyl acetate, isobutyl acetate, methyl acetate, ethyl formate and the like; nitromethane; water and the like. These solvents may be used in a mixture in an appropriate ratio. As the solvent used in the reaction for the conversion of the salt of compound (A-b) to the free form, nitriles are preferable, and acetonitrile is particularly preferable.

The amount of the solvent to be used is appropriately determined depending on the solubility of the substrate salt of compound (A-b), and the like. For example, when a nitrile (preferably acetonitrile) is used as a solvent, the reaction can be carried out nearly without a solvent or in a solvent in an amount of 100 parts by weight or less per 1 part by weight of the substrate salt of compound (A-b), preferably in a solvent in an amount of 1 to 10 parts by weight per 1 part by weight of the substrate salt of compound (A-b).

The temperature in the reaction for the conversion to the free form is generally −20 to 40° C., preferably −10 to 20° C. The reaction time is generally 0.01 to 2 hr, preferably 0.1 to hr.

Compound (A-b) obtained in the reaction for the conversion to the free form may be isolated and purified according to a means known per se (concentration, concentration under reduced pressure, solvent extraction, crystallization, recrystallization, phase transfer, chromatography and the like). Alternatively, the reaction solution may be used directly in the condensation reaction with the acid chloride of compound (A-a).

The "condensation reaction" is generally carried out in a solvent. The solvent is not particularly limited as long as it does not inhibit the reaction and can dissolve the raw material compound and additive, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1- diethoxypropane, 1,1-dimethoxymethane, 2,2-dimethoxypropane, anisole and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; halogenated hydrocarbons such as chloroform, dichloromethane, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; nitromethane and the like. These solvents may be used in a mixture in an appropriate ratio. As the solvent used in the above-mentioned "condensation reaction", ethers are preferable, and 1,2-dimethoxyethane is particularly preferable.

The amount of the solvent to be used is appropriately determined depending on the solubility of the substrate acid chloride of compound (A-a) and compound (A-b) or a salt thereof and the like. For example, when an ether (preferably 2-dimethoxyethane) is used as a solvent, the reaction can be carried out nearly without a solvent or in a solvent in an amount of 100 parts by weight or less per 1 part by weight of the substrate acid chloride of compound (A-a), preferably in a solvent in an amount of 1 to 10 parts by weight per 1 part by weight of the substrate acid chloride of compound (A-a).

The temperature in the condensation reaction is generally to 120° C., preferably 10 to 70° C. The reaction time is generally 0.1 to 12 hr, preferably 0.5 to 6 hr.

Compound (A-c) or a salt thereof obtained in the condensation reaction may be isolated and purified according to a means known per se (concentration, concentration under reduced pressure, solvent extraction, crystallization, recrystallization, phase transfer, chromatography and the like). Compound (A-c) or a salt thereof is preferably isolated and purified by crystallization, particularly preferably by crystallization with addition of water.

[Step A-2]

Step A-2 is a step of producing compound (I) or a salt thereof, which is a substrate for asymmetric reduction, by subjecting compound (A-c) or a salt thereof to imination.

When PG is a group represented by the formula (VI-1), compound (A-c) or a salt thereof is reacted with a compound represented by the formula (VI-1'):

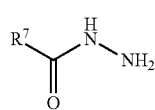

(VI-1')

wherein each symbol is as defined above (hereinafter to be referred to as compound (VI-1')) or a salt thereof.

When PG is a group represented by the formula (VI), compound (A-c) or a salt thereof is reacted with a compound represented by the formula (VI'):

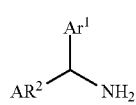

(VI-1')

wherein each symbol is as defined above (hereinafter to be referred to as compound (VI')) or a salt thereof.

Examples of the salt of compound (VI-1') or compound (VI') include salts with an inorganic acid, salts with an organic acid, salts with an acidic amino acid, and the like.

Preferable examples of the salt of compound (VI-1') or compound (VI') with an inorganic acid include those exemplified as the salt of compound (I), (II), (IV), (V), (VII) or (VIII) with an inorganic acid.

Preferable examples of the salt of compound (VI-1') or compound (VI') with an organic acid include those exemplified as the salt of compound (I), (II), (IV), (V), (VII) or (VIII) with an organic acid.

Preferable examples of the salt of compound (VI-1') or compound (VI') with an acidic amino acid include those exemplified as the salt of compound (I), (II), (IV), (V), (VII) or (VIII) with an acidic amino acid.

While the amount of compound (VI-1') or a salt thereof, or compound (VI') or a salt thereof to be used varies depending on the kind of the solvent and the other reaction condition, it is generally 0.1 to 100 mol, preferably 0.5 to 20 mol, more preferably 0.8 to 5 mol, per 1 mol of compound (A-c) or a salt thereof. When compound (VI-1') or compound (VI') is a liquid, it can also be used as a solvent.

When the salt of compound (VI-1') or compound (VI') is used, it is prepreably converted to the free form in advance by reacting with a base or acid.

In the reaction of Step A-2, an additive such as a base, an acid, a salt and the like may be added, if necessary. The additive may be used in a mixture of two or more kinds thereof. The additive may be added to a reaction container before or during the reaction.

Examples of the base which may be added to the reaction system of Step A-2 include inorganic bases and organic bases.

Examples of the inorganic base include alkali metal hydroxides such as lithium hydroxide, potassium hydroxide, sodium hydroxide, cesium hydroxide and the like; alkali metal alkoxides having 1 to 6 carbon atoms such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide and the like; alkali metal thioalkoxides having 1 to 6 carbon atoms such as sodium thiomethoxide and the like; carbonates such as sodium carbonate, potassium carbonate, cesium carbonate and the like; hydrogencarbonates such as sodium hydrogencarbonate, potassium hydrogencarbonate and the like; acetates such as sodium acetate, potassium acetate and the like; phosphates such as tripotassium phosphate, sodium phosphate and the like; and monohydrogen phosphates such as potassium monohydrogen phosphate, sodium monohydrogen phosphate and the like.

Examples of the organic base include aliphatic amine as such as trimethylamine, triethylamine, N-methylmorpholine, N,N-diisopropylethylamine, diethylamine, diisopropylamine, cyclohexylamine, ethylenediamine and the like; aromatic amines such as pyridine, picoline, N,N-dimethylaniline and the like; and basic amino acids such as arginine, lysine, ornithine and the like.

While the amount of the base to be used varies depending on the kind of the solvent and the other reaction condition, it is generally about 0.01 mol or more, per 1 mol of the substrate compound (A-c) or a salt thereof. The base can also be used as a solvent.

Examples of the acid which may be added to the reaction system of Step A-2 include mineral acids (specifically hydrofluoric acid, hydrochloric acid, hydrobromic acid, hydriodic acid, nitric acid, sulfuric acid, sulfurous acid, phosphoric acid, phosphorous acid, carbonic acid, bicarbonic acid and the like); carboxylic acids (i.e., compounds having one or more carboxy groups; specifically formic acid, acetic acid, trifluoroacetic acid, benzoic acid, phthalic acid, fumaric acid, oxalic acid, tartaric acid, maleic acid, citric acid, succinic acid, malic acid and the like); acidic amino acids (specifically aspartic acid, glutamic acid and the like); sulfonic acids (i.e., compounds having one or more sulfo groups; specifically methanesulfonic acid, trifluoromethanesulfonic acid, benzenesulfonic acid, p-toluenesulfonic acid, camphorsulfonic acid and the like); and Lewis acids (specifically aluminium chloride, tin chloride, zinc chloride, zinc bromide, titanium tetrachloride, boron trifluoride-ethyl ether complex and the like). Where necessary, the acid may be used in a mixture of two or more kinds thereof.

While the amount of the acid to be used varies depending on the kind of the solvent and the other reaction condition, it is generally about 0.01 mol or more, per 1 mol of the substrate compound (A-c) or a salt thereof. The acid can also be used as a solvent.

Examples of the salt which may be added to the reaction system of Step A-2 include salts which contain the above-mentioned "acid" as an acid component, in addition to salts exemplified as the above-mentioned "inorganic base".

While the amount of the salt to be used varies depending on the kind of the solvent and the other reaction condition, it is generally about 0.01 to 100 mol, per 1 mol of the substrate compound (A-c) or a salt thereof.

As the additive used in the reaction of Step A-2, acids are preferable, acetic acid, p-toluenesulfonic acid (it may be used as a monohydrate) and zinc chloride are more preferable, and acetic acid is particularly preferable.

While the reaction of Step A-2 may be carried out without a solvent, it is generally carried out in a solvent. The solvent is not particularly limited as long as it does not inhibit the reaction and can dissolve the raw material compound and additive, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, 2-propanol, n-butanol, 2-butanol, t-butyl alcohol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; esters such as ethyl acetate, isopropyl acetate, n-propyl acetate, n-butyl acetate, isobutyl acetate, methyl acetate, ethyl formate and the like; nitromethane; water and the like. These solvents may be used in a mixture in an appropriate ratio.

As the solvent used in the reaction of Step A-2, ethers, alcohols and aromatic hydrocarbons are preferable, tetrahydrofuran, methanol, ethanol and toluene are more preferable, and ethanol is particularly preferable.

The amount of the solvent to be used is appropriately determined depending on the solubility of compound (A-c) or a salt thereof, compound (VI-1') or a salt thereof, or compound (VI') or a salt thereof, and the like. For example, when an ether (preferably tetrahydrofuran), an alcohol (preferably methanol, ethanol) or an aromatic hydrocarbon (preferably toluene) is used as a solvent, the reaction can be carried out nearly without a solvent or in a solvent in an amount of 100 parts by weight or less per 1 part by weight of the substrate compound (A-c) or a salt thereof, preferably in a solvent in an amount of 1 to 10 parts by weight per 1 part by weight of the substrate compound (A-c) or a salt thereof.

The temperature in the reaction of Step A-2 is generally to 180° C., preferably 20 to 120° C. The reaction time is generally 0.1 to 24 hr, preferably 0.5 to 12 hr.

Since water is generated with the process of the reaction of Step A-2, dehydration may be carried out by adding molecular sieve to the reaction solution or using Dean-Stark trap, and the like during the reaction.

The compound (I) or a salt thereof in the reaction of Step A-2 may be isolated and purified according to a means known per se (concentration, concentration under reduced pressure, solvent extraction, crystallization, recrystallization, phase transfer, chromatography and the like).

[Step A-3]

Step A-3 is a step of producing compound (II) or a salt thereof by subjecting compound (I) or a salt thereof to an asymmetric reduction reaction.

The "asymmetric reduction reaction" is preferably carried out by subjecting compound (I) or a salt thereof to a hydrogenation reaction in the presence of an organic metal complex.

Examples of the "organic metal complex" include typical metal complexes such as boron complexes, aluminium complexes, gallium complexes and the like, in addition to a "transition metal complex (an organic transition metal complex)".

The "organic metal complex" is preferably a "transition metal complex (an organic transition metal complex)".

Examples of the "transition metal complex" include compounds prepared by coordinating a "ligand" (preferably an optically active "ligand") to a "transition metal" which have the ability to catalyze an asymmetric hydrogenation reaction. Examples of the "ligand" include monophosphine ligands, diphosphine ligands, amine ligands, diamine ligands, phosphine amine ligands and the like, and include specific examples described herein and optical isomers thereof. The valence of the "transition metal" is, for example, 0 to 6, preferably 0 to 4, particularly preferably 0 to 3.

Preferable examples of the "transition metal complex" include rhodium complexes, ruthenium complexes, iridium complexes, palladium complexes, nickel complexes, copper complexes, osmium complexes, platinum complexes, iron complexes, gold complexes, silver complexes, zinc complexes, titanium complexes, cobalt complexes, zirconium complexes, samarium complexes and the like; more preferred are rhodium complexes, ruthenium complexes, iridium complexes, palladium complexes, nickel complexes and copper complexes; further more preferred are rhodium complexes, ruthenium complexes, palladium complexes and iridium complexes; still more preferred are rhodium complexes and iridium complexes; and particularly preferred are iridium complexes.

Among the "transition metal complexes", specific examples of the rhodium complexes, ruthenium complexes, iridium complexes, palladium complexes, nickel complexes and copper complexes are shown below, wherein, in the transition metal complexes, L is a diphosphine ligand, a PN ligand, or two phosphine ligands (the two monophosphine ligand, each monophosphine ligand is the same or different), Ar is benzene optionally having substituent(s) (the substituent is preferably a $C_{1-6}$ alkyl group), Cp* is pentamethylcyclopentadienyl, Cp is cyclopentadienyl, cod is 1,5-cyclooctadiene, Tf is trifluoromethanesulfonyl, nbd is norbornadiene, Ph is phenyl, Ac is acetyl, Et is ethyl, dmf is N,N-dimethylformamide, 2-methylallyl is $\eta^3$-2-methylallyl, en is ethylenediamine, dpen is 1,2-diphenylethylenediamine, daipen is 1,1-di(4-anisyl)-2-isopropyl-1,2-ethylenediamine, and n is an integer of 1 or more. 1,2-Diphenylethylenediamine and 1,1-di(4-anisyl)-2-isopropyl-1,2-ethylenediamine may be (R)-form, (S)-form and a mixture of (R)-form and (S)-form (the ratio is not limited), preferably an optically active form.

rhodium complexes: [RhCl(L)]$_2$, [RhBr(L)]$_2$, [RhI(L)]$_2$, [RhCp*(L)]$_2$, [Rh(cod)(L)]OTf, [Rh(cod)(L)]BF$_4$, [Rh(cod)(L)]ClO$_4$, [Rh(cod)(L)]PF$_6$, [Rh(cod)(L)]SbF$_6$, [Rh(cod)(L)]BPh$_4$, [Rh(cod)(L)]B{3,5-(CF$_3$)$_2$C$_6$H$_3$}$_4$, [Rh(nbd)(L)]OTf, [Rh(nbd)(L)]BF$_4$, [Rh(nbd)(L)]ClO$_4$, [Rh(nbd)(L)]PPF$_6$, [Rh(nbd)(L)]SbF$_6$, [Rh(nbd)(L)]BPh$_4$, [Rh(nbd)(L)]B{3,5-(CF$_3$)$_2$C$_6$H$_3$}$_4$, [Rh(L)(CH$_3$OH)$_2$]OTf, [Rh(L)(CH$_3$OH)$_2$]BF$_4$, [Rh(L)(CH$_3$OH)$_2$]ClO$_4$, [Rh(L)(CH$_3$OH)$_2$]PF$_6$, [Rh(L)(CH$_3$OH)$_2$]BPh$_4$;

ruthenium complexes: [RuCl$_2$(L)]n, [RuBr$_2$(L)]n, [RuI$_2$(L)]n, [Ru(OAc)$_2$(L)], [Ru(OCOCF$_3$)$_2$(L)], (NH$_2$Me$_2$)[{RuCl(L)}$_2$(μ-Cl)$_3$], (NH$_2$Et$_2$)[{RuCl(L)}$_2$(μ-Cl)$_3$], (NH$_2$Me$_2$)[{RuBr(L)}$_2$(μ-Br)$_3$], (NH$_2$Et$_2$)[{RuBr(L)}$_2$(μ-Br)$_3$], (NH$_2$Me$_2$)[{RuI(L)}$_2$(μ-I)$_3$], (NH$_2$Et$_2$)[{RuI(L)}$_2$(μ-I)$_3$], [Ru$_2$Cl$_4$(L)$_2$(NEt$_3$)], [RuCl$_2$(L)(dmf)$_n$], [Ru(2-methylallyl)$_2$(L)], [RuCl(Ar)(L)]Cl, [RuCl(Ar)(L)]Br, [RuCl(Ar)(L)]I, [RuCl(Ar)(L)]OTf, [RuCl(Ar)(L)]ClO$_4$, [RuCl(Ar)(L)]PF$_6$, [RuCl(Ar)(L)]BF$_4$, [RuCl(Ar)(L)]BPh$_4$, [RuBr(Ar)(L)]Cl, [RuBr(Ar)(L)]Br, [RuBr(Ar)(L)]I, [RuI(Ar)(L)]Cl, [RuI(Ar)(L)]Br, [RuI(Ar)(L)]I, [Ru(L)](OTf)$_2$, [Ru(L)](BF$_4$)$_2$, [Ru(L)](ClO$_4$)$_2$, [Ru(L)](PF$_6$)$_2$, [Ru(L)](BPh$_4$)$_2$, [RuH(L)$_2$]Cl, [RuH(L)$_2$]OTf, [RuH(L)$_2$]BBF$_4$, [RuH(L)$_2$]ClO$_4$, [RuH(L)$_2$]PPF$_6$, [RuH(L)$_2$]BPh$_4$, [RuH(CH$_3$CN)(L)]Cl, [RuH(CH$_3$CN)(L)]OTf, [RuH(CH$_3$CN)(L)]BF$_4$, [RuH(CH$_3$CN)(L)]ClO$_4$, [RuH(CH$_3$CN)(L)]PF$_6$, [RuH(CH$_3$CN)(L)]BPh$_4$, [RuCl(L)]OTf, [RuCl(L)]BF$_4$, [RuCl(L)]ClO$_4$, [RuCl(L)]PF$_6$, [RuCl(L)]BPh$_4$, [RuBr(L)]OTf, [RuBr(L)]BF$_4$, [RuBr(L)]ClO$_4$, [RuBr(L)]PF$_6$, [RuBr(L)]BPh$_4$, [RuI(L)]OTf, [RuI(L)]BBF$_4$, [RuI(L)]ClO$_4$, [RuI(L)]PF$_6$, [RuI(L)]BPh$_4$, [RuCl$_2$(L)(en)], [RuCl$_2$(L)(dpen)], [RuCl$_2$(L)(daipen)], [RuH(η$^1$-BH$_4$)(L)(en)], [RuH(η$^1$-BH$_4$)(L)(daipen)], [RuH(η$^1$-BH$_4$)(L)(dpen)](Examples of the diamine ligands corresponding to en, dpen and daipen, which are the diamine ligands in the [RuCl$_2$(L)(en)], [RuCl$_2$(L)(dpen)] and [RuCl$_2$(L)(daipen)], include 1,2-cyclohexanediamine, 1,2-cycloheptanediamine, 2,3-dimethylbutanediamine, 1-methyl-2,2-diphenyl-1,2-ethylenediamine, 1-isobutyl-2,2-diphenyl-1,2-ethylenediamine, 1-isopropyl-2,2-diphenyl-1,2-ethylenediamine, 1,1-di(4-anisyl)-2-methyl-1,2-ethylenediamine, 1,1-di(4-anisyl)-2-isobutyl-1,2-ethylenediamine, 1,1-di(4-anisyl)-2-benzyl-1,2-ethylenediamine, 1-methyl-2,2-dinaphthyl-1,2-ethylenediamine, 1-isobutyl-2,2-dinaphthyl-1,2-ethylenediamine, 1-isopropyl-2,2-dinaphthyl-1,2-ethylenediamine, propanediamine, butanediamine, phenylenediamine and the like, in addition to en, dpen and daipen);

iridium complexes: [IrCl(L)]$_2$, [IrBr(L)]$_2$, [IrI(L)]$_2$, [IrCp*(L)]$_2$, [Ir(cod)(L)]OTf, [Ir(cod)(L)]BF$_4$, [Ir(cod)(L)]ClO$_4$, [Ir(cod)(L)]PF$_6$, [Ir(cod)(L)]SbF$_6$, [Ir(cod)(L)]BPh$_4$, [Ir(nbd)(L)]B{3,5-(CF$_3$)$_2$C$_6$H$_3$}$_4$, [Ir(nbd)(L)]OTf, [Ir(nbd)(L)]BF$_4$, [Ir(nbd)(L)]ClO$_4$, [Ir(nbd)(L)]PFE, [Ir(nbd)(L)]SbF$_6$, [Ir(nbd)(L)]BPh$_4$, [Ir(nbd)(L)]B{3,5-(CF$_3$)$_2$C$_6$H$_3$}$_4$, [Ir(r-allyl)(L)((C,O)-substituted-benzoate)];

palladium complexes: [PdCl$_2$(L)], [PdBr$_2$(L)], [PdI$_2$(L)] [Pd(r-allyl)(L)]Cl, [Pd(r-allyl)(L)]OTf, [Pd(r-allyl)(L)]BF$_4$, [Pd(r-allyl)(L)]ClO$_4$, [Pd(n-allyl)(L)]PF$_6$, [Pd(n-allyl)(L)]BPh$_4$, [Pd(L)](OTf)$_2$, [Pd(L)](BF$_4$)$_2$, [Pd(L)](ClO$_4$)$_2$, [Pd(L)](PF$_6$)$_2$, [Pd(L)](BPh$_4$)$_2$, [Pd(L)$_2$], [Pd(L)$_2$](OAc)$_2$, [Pd(L)(H$_2$O)$_2$](OTf)$_2$, [Pd(L)(H$_2$O)$_2$](BF$_4$)$_2$, [Pd(L)(H$_2$O)$_2$](ClO$_4$)$_2$, [Pd(L)(H$_2$O)$_2$](PF$_6$)$_2$, [Pd(L)(H$_2$O)$_2$](BPh$_4$)$_2$, [{Pd(L)}$_2$(μ-OH)$_2$](OTf)$_2$, [{Pd(L)}$_2$(μ-OH)$_2$](BF$_4$)$_2$, [{Pd(L)}$_2$(μ-OH)$_2$](ClO$_4$)$_2$, [{Pd(L)}$_2$(μ-OH)$_2$](PF$_6$)$_2$, [{Pd(L)}$_2$(μ-OH)$_2$](BPh$_4$)$_2$;

nickel complexes: [NiCl$_2$(L)], [NiBr$_2$(L)], [NiI$_2$(L)], [Ni(π-allyl)(L)]Cl, [Ni(cod)(L)], [Ni(nbd)(L)];

copper complexes: [CuCl(L)], [CuBr(L)], [CuI(L)], [CuH(L)], [Cu(η$^1$-BH$_4$)(L)], [Cu(Cp)(L)], [Cu(Cp*)(L)], [Cu(L)(CH$_3$CN)$_2$]OTf, [Cu(L)(CH$_3$CN)$_2$]BF$_4$, [Cu(L)(CH$_3$CN)$_2$]ClO$_4$, [Cu(L)(CH$_3$CN)$_2$]PF$_6$, [Cu(L)(CH$_3$CN)$_2$]BPh$_4$ Examples of the above-mentioned diphosphine ligand represented by L include 2,2'-bis(diphenylphosphino)-1,1'-binaphthyl (hereinafter to be referred to as BINAP);

BINAP derivatives having substituent(s) such as a $C_{1-6}$ alkyl group, a $C_{6-14}$ aryl group and the like on the naphthyl ring(s) of BINAP, for example, 2,2'-bis(diphenylphosphino)-6,6'-dimethyl-1,1'-binaphthyl;

BINAP derivatives wherein the naphthyl ring(s) of BINAP is/are partially hydrogenated, for example, 2,2'-bis(diphenylphosphino)-5,6,7,8,5',6',7',8'-octahydro-1,1'-binaphthyl (H8BINAP);

BINAP derivatives having 1 to 5 substituents such as a $C_{1-6}$ alkyl group, a halogen atom, a mono- or di-$C_{1-6}$ alkylamino group, a $C_{1-6}$ alkoxy group, a pyrrolidinyl group and the like on the benzene ring(s) bonded to the phosphorus atom of BINAP, for example, 2,2'-bis[bis(4-chlorophenyl)phosphino)-1,1'-binaphthyl, 2,2'-bis(di-p-tolylphosphino)-1,1'-binaphthyl (tol-BINAP), 2,2'-bis[bis(3,5-dimethylphenyl)phosphino]-1,1'-binaphthyl (xyl-BINAP), 2,2'-bis[bis(3,5-diethylphenyl)phosphino]-1,1'-binaphthyl, 2,2'-bis[bis(3,5-diisopropylphenyl)phosphino]-1,1'-binaphthyl, 2,2'-bis[bis(3,5-di-tert-butylphenyl)phosphino]-1,1'-binaphthyl, 2,2'-bis[bis(4-dimethylaminophenyl)phosphino]-1,1'-binaphthyl, 2,2'-bis[bis(4-dimethylamino-3,5-dimethylphenyl)phosphino]-1,1'-binaphthyl, 2,2'-bis[bis(4-dimethylamino-3,5-diethylphenyl)phosphino]-1,1'-binaphthyl, 2,2'-bis[bis(4-dimethylamino-3,5-diisopropylphenyl)phosphino]-1,1'-binaphthyl, 2,2'-bis[bis(4-diethylaminophenyl)phosphino]-1,1'-binaphthyl, 2,2'-bis[bis[4-(pyrrolidin-1-yl)phenyl]phosphino]-1,1'-binaphthyl, 2,2'-bis(di-p-methoxyphenylphosphino)-1,1'-binaphthyl, 2,2'-bis[bis(3,5-dimethyl-4-methoxyphenyl)phosphino]-1,1'- binaphthyl, 2,2'-bis[bis(3,5-di-tert-butyl-4-methoxyphenyl)phosphino]-1,1'-binaphthyl (DTBM-BINAP); 2,2'-bis(dicyclohexylphosphino)-6,6'-dimethyl-1,1'-biphenyl(BICHEP), 2,2'-bis(diphenylphosphino)-6,6'-dimethoxybiphenyl (MeO-BIPHEP), 2,3-bis(diphenylphosphino)butane (CHIRAPHOS), 1-cyclohexyl-1,2-bis(diphenylphosphino)ethane (CYCPHOS), 1,2-bis[(2-methoxyphenyl)phenylphosphino]ethane (DIPAMP), 1,2-bis(diphenylphosphino)propane (PROPHOS), 2,4-bis(diphenylphosphino)pentane (SKEWPHOS), SKEWPHOS derivative having 1 to 5 substituents such as a $C_{1-6}$ alkyl group and the like on the benzene ring(s) bonded to the phosphorus atom of SKEWPHOS, 1-[1',2-bis(diphenylphosphino)ferrocenyl]ethylenediamine (BPPFA), 1-substituted-3,4-bis(diphenylphosphino)pyrrolidine (DEGPHOS), 2,3-O-isopropylidene-2,3-dihydroxy-1,4-bis(diphenylphosphino)butane (DIOP), substituted-1,2-bisphosphoranobenzene (DuPHOS), substituted-1,2-bisphosphoranoethane (BPE), 5,6-bis(diphenylphosphino)-2-norbornene (NORPHOS), N,N'-bis(diphenylphosphino)-N,N'-bis(1-phenylethyl) ethylenediamine (PNNP), 2,2'-diphenylphosphino-1,1'-bicyclopentyl (BICP), 4,12-bis(diphenylphosphino)-[2,2]-paracyclophane (PhanePHOS), N-substituted-N-diphenylphosphino-1-[2-(diphenylphosphino) ferrocenyl]ethylamine (BoPhoz), 1-[2-(disubstituted-phosphino)ferrocenyl]ethyl-disubstituted-phosphine (Josiphos), 1-[2-(2'-disubstituted-phosphinophenyl)ferrocenyl]ethyl-disubstituted-phosphine (Walphos), 2,2'-bis(α-N,N-dimethylaminophenylmethyl)-1,1'-bis(disubstituted-phosphino)ferrocene (Mandyphos), disubstituted-phosphino-2-[α-(N,N-dimethylamino)-o-disubstituted-phosphinophenyl-methyl]ferrocene (Taniaphos), 1,1-bis(disubstituted-phosphotano)ferrocene (FerroTANE), 7,7'-bis(diphenylphosphino)-3,3',4,4'-tetrahydro-4,4'-dimethyl-8,8'-bi(2H-1,4-benzoxazine) (Solphos), substituted-1,1'-bisphosphoranoferrocene (Ferrocelane) and the like.

The above-mentioned diphosphine ligand is preferably an optically active form.

Examples of the above-mentioned two phosphine ligands represented by L (the two monophosphine ligand, each monophosphine ligand is the same or different) include a compound represented by the formula (IX):

(IX)

wherein

A is an optically active skeleton; and
$R^{8a}$ and $R^{8b}$ are each independently an optionally substituted $C_{1-6}$ alkyl group, or an optionally substituted $C_{6-14}$ aryl group; a compound represented by the formula (X):

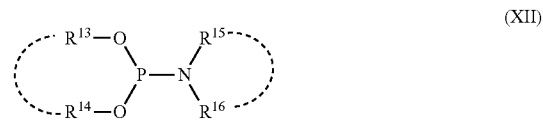

(X)

wherein $A^1$ and $A^2$ are each independently an optically active carbon skeleton;
$R^9$ is a hydrogen atom, an optionally substituted $C_{1-6}$ alkyl group, an optionally substituted $C_{6-14}$ aryl group, an optionally substituted amino group, an optionally substituted hydroxy group, ferrocenyl or ferrocenylmethyl; and
$A^1$ and $A^2$ in combination optionally form a 4- to 8-membered ring together with the adjacent atom;
a compound represented by the formula (XI):

(XI)

wherein $R^{10}$ and $R^{11}$ are each independently an optionally substituted $C_{1-6}$ alkyl group, or an optionally substituted $C_{6-14}$ aryl group;
$R^{12}$ is a hydrogen atom, an optionally substituted $C_{1-6}$ alkyl group, an optionally substituted $C_{6-14}$ aryl group, an optionally substituted hydroxy group, or optionally substituted ferrocenyl; and
$R^{10}$ and $R^{11}$ in combination optionally form a 4- to 8-membered ring together with the adjacent atoms; and
a compound represented by the formula (XII):

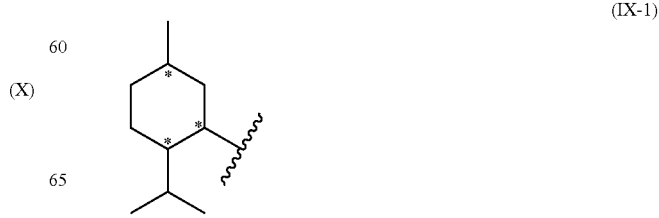

(XII)

wherein $R^{13}$ and $R^{14}$ are each independently a hydrogen atom, an optionally substituted $C_{1-6}$ alkyl group, or an optionally substituted $C_{6-14}$ aryl group;
$R^{15}$ and $R^{16}$ are each independently an optionally substituted $C_{1-6}$ alkyl group, or an optionally substituted $C_{6-14}$ aryl group;
$R^{13}$ and $R^{14}$ in combination optionally form a 4- to 8-membered ring together with the adjacent atoms; and
$R^{15}$ and $R^{16}$ in combination optionally form a 4- to 8-membered ring together with the adjacent atom.

Examples of the above-mentioned optically active skeleton represented by A include skeletons represented by the following formulas.

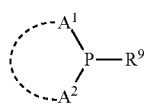

(IX-1)

-continued (IX-2)

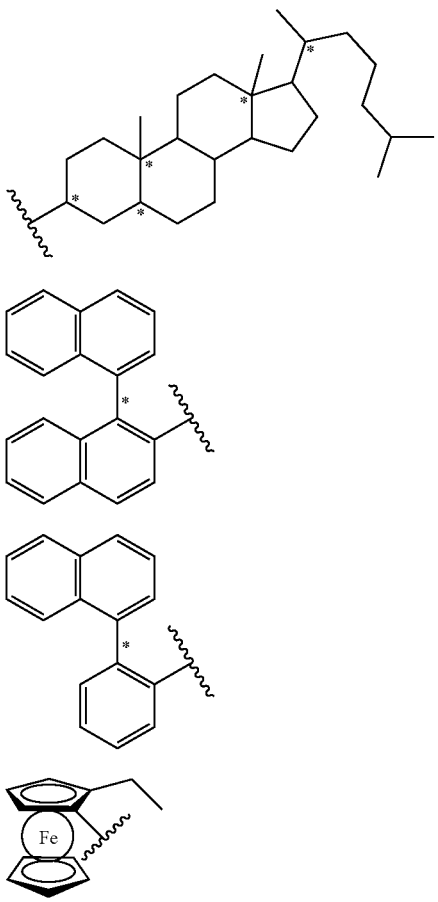

(IX-3)

(IX-4)

(IX-5)

wherein
the carbon atom marked with * is an asymmetric carbon atom; and the bond axis marked with * is an asymmetric axis.

Examples of the "substituent" of the "optionally substituted $C_{1-6}$ alkyl group" represented by $R^{8a}$ or $R^{8b}$ include the above-mentioned "substituents". The number of the substituents in the "optionally substituted $C_{1-6}$ alkyl group" represented by $R^{8a}$ or $R^{8b}$ is, for example, 1 to 5, preferably 1 to 3, at substitutable position(s). When the number of the substituents is two or more, the respective substituents may be the same or different.

The substituents in the "optionally substituted $C_{6-14}$ aryl group" represented by $R^{8a}$ or $R^{8b}$ and a number thereof are similar to those exemplified in the above-mentioned "optionally substituted $C_{6-14}$ aryl group" represented by $R^7$.

Examples of the optically active skeleton represented by $A^1$ or $A^2$ include skeletons represented by the following formulas.

(IX-1)

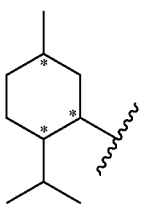

-continued (X-1)

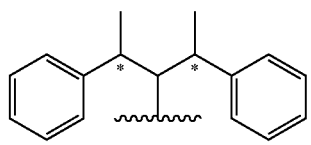

wherein each symbol is as defined above.

When $A^1$ and $A^2$ in combination form a 4- to 8-membered ring together with the adjacent atom, examples of the compound (X) include
a compound represented by the formula (X-a):

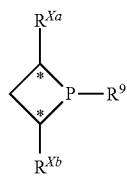

(X-a)

wherein
$R^{Xa}$ and $R^{Xb}$ are each independently a $C_{1-6}$ alkyl group, a $C_{3-10}$ cycloalkyl group, an optionally substituted $C_{6-14}$ aryl group, a $C_{7-16}$ aralkyl group, an optionally substituted ferrocenyl, or ferrocenylmethyl, and
the other symbols are as defined above;
a compound represented by the formula (X-b):

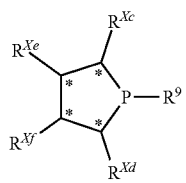

(X-b)

wherein
$R^{Xc}$ and $R^{Xd}$ are each independently a hydrogen atom, a $C_{1-6}$ alkyl group, a $C_{3-10}$ cycloalkyl group, an optionally substituted $C_{6-14}$ aryl group, or a $C_{7-16}$ aralkyl group;
$R^{Xe}$ and $R^{Xf}$ are each independently a hydrogen atom, or an optionally substituted hydroxy group, and the other symbols are as defined above;
a compound represented by the formula (X-c):

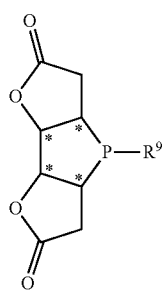

(X-c)

wherein each symbol is as defiend above;
a compound represented by the formula (X-d):

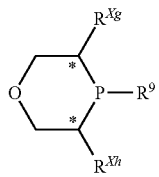

(X-d)

wherein
$R^{Xg}$ and $R^{Xh}$ are each independently a hydrogen atom, a $C_{1-6}$ alkyl group, a $C_{3-10}$ cycloalkyl group, an optionally substituted $C_{6-14}$ aryl group, or a $C_{7-16}$ aralkyl group, and the other symbols are as defined above; and
a compound represented by the formula (X-e):

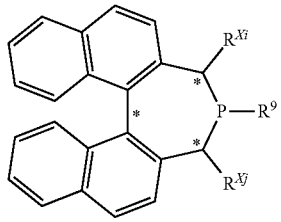

(X-e)

wherein
$R^{Xi}$ and $R^{Xj}$ are each independently a hydrogen atom, a $C_{1-6}$ alkyl group, a $C_{3-10}$ cycloalkyl group, an optionally substituted $C_6$-$1_4$ aryl group, or a $C_{7-16}$ aralkyl group, and
the other symbols are as defined above.

Preferable examples of the substituent of the "optionally substituted $C_{6-14}$ aryl group" represented by $R^{Xa}$, $R^{Xb}$, $R^{Xc}$, $R^{Xd}$, $R^{Xg}$, $R^{Xh}$, $R^{Xi}$ or $R^{Xj}$ include a halogen atom, a $C_{1-6}$ alkyl group and a $C_{1-6}$ alkoxy group.

Preferable examples of the substituent of the "optionally substituted ferrocenyl" represented by $R^{Xa}$ or $R^{Xb}$ include a $C_{1-6}$ alkyl group.

Preferable examples of the substituent of the "optionally substituted hydroxy group" represented by $R^{Xe}$ or $R^{Xf}$ include a $C_{1-6}$ alkyl group and a $C_{7-16}$ aralkyl group.

$R^9$ is preferably a hydrogen atom, an optionally substituted $C_{1-6}$ alkyl group, an optionally substituted $C_{6-14}$ aryl group, an optionally substituted amino group, or an optionally substituted hydroxy group.

Preferable examples of the substituent of the "optionally substituted $C_{1-6}$ alkyl group" include a $C_{6-14}$ aryl group.

Preferable examples of the substituent of the "optionally substituted $C_{6-14}$ aryl group" include a halogen atom, a $C_{1-6}$ alkyl group and a $C_{1-6}$ alkoxy group.

Preferable examples of the substituent of the "optionally substituted amino group" include
  (1) a $C_{1-6}$ alkyl group optionally substituted by $C_{6-14}$ aryl group(s) optionally having 1 to 3 of $C_{1-6}$ alkoxy groups or $C_{1-6}$ alkyl groups and
  (2) a $C_{6-14}$ aryl group optionally having 1 to 3 of $C_{1-6}$ alkoxy groups or $C_{1-6}$ alkyl groups.

Preferable examples of the substituent of the "optionally substituted hydroxy group" include
  (1) a $C_{1-6}$ alkyl group optionally substituted by $C_{6-14}$ aryl group(s) optionally having 1 to 3 of $C_{1-6}$ alkoxy groups or $C_{1-6}$ alkyl groups, and
  (2) a $C_{6-14}$ aryl group optionally having 1 to 3 of $C_{1-6}$ alkoxy groups or $C_{1-6}$ alkyl groups.

Examples of the cyclic structural moiety in compound (XI) when $R^{10}$ and $R^{11}$ in combination form a 4- to 8-membered ring together with the adjacent atoms, and the cyclic structural moiety in compound (XII) when $R^{13}$ and $R^{14}$ in combination form a 4- to 8-membered ring together with the adjacent atoms, include a cyclic structural moiety represented by the formula (XI-1), (XI-2) or (XI-3)

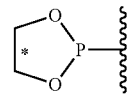

(XI-1)

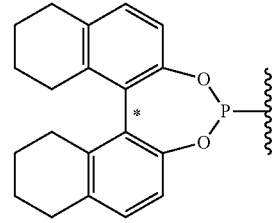

(XI-2)

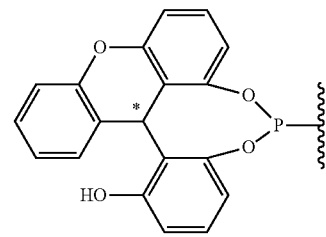

(XI-3)

wherein each symbol is as defined above;
a cyclic structural moiety represented by the formula (XI-a):

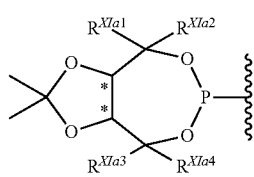

(XI-a)

wherein
$R^{XIa1}$, $R^{XIa2}$, $R^{XIa3}$ and $R^{XIa4}$ are each independently an optionally substituted $C_{6-14}$ aryl group, and
the other symbols are as defined above;
a cyclic structural moiety represented by the formula (XI-b):

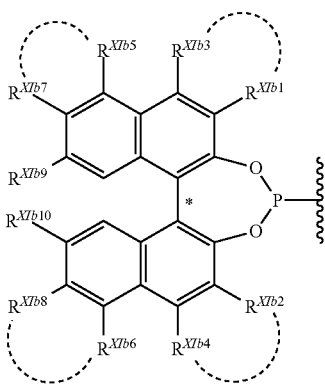

(XI-b)

wherein
$R^{XIb1}$, $R^{XIb2}$, $R^{XIb3}$, $R^{XIb4}$, $R^{XIb5}$, $R^{XIb6}$, $R^{XIb7}$, $R^{XIb8}$, $R^{XIb9}$ and $R^{XIb10}$ are each independently a hydrogen atom, a halogen atom, a $C_{1-6}$ alkyl group, an optionally substituted $C_{6-14}$ aryl group, or a $C_{1-6}$ alkoxy group;
$R^{XIb1}$ and $R^{XIb3}$ in combination optionally form a 4- to 8-membered ring together with the adjacent atoms;
$R^{XIb2}$ and $R^{XIb4}$ in combination optionally form a 4- to 8-membered ring together with the adjacent atoms;
$R^{XIb5}$ and $R^{XIb7}$ in combination optionally form a 4- to 8-membered ring together with the adjacent atoms;
$R^{XIb6}$ and $R^{XIb8}$ in combination optionally form a 4- to 8-membered ring together with the adjacent atoms; and
the other symbols are as defined above;
a cyclic structural moiety represented by the formula (XI-c):

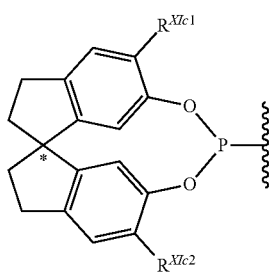

(XI-c)

wherein
$R^{XIc1}$ and $R^{XIc2}$ are each independently a hydrogen atom, a halogen atom, a $C_{1-6}$ alkyl group, an optionally substituted $C_{6-14}$ aryl group, or a $C_{1-6}$ alkoxy group; and
the other symbols are as defined above;
a cyclic structural moiety represented by the formula (XI-d):

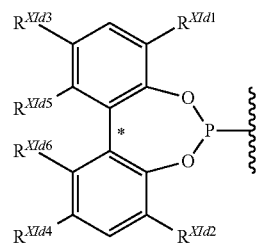

(XI-d)

wherein $R^{XId1}$, $R^{XId2}$, $R^{XId3}$, $R^{XId4}$, $R^{XId5}$ and $R^{XId6}$ are each independently a hydrogen atom, a halogen atom, a $C_{1-6}$ alkyl group, an optionally substituted $C_{6-14}$ aryl group, or a $C_{1-6}$ alkoxy group; and
the other symbols are as defined above;
a cyclic structural moiety represented by the formula (XI-e):

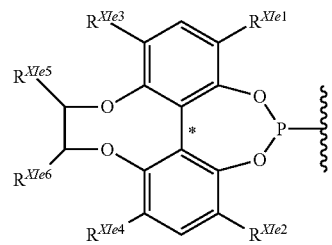

(XI-e)

wherein
$R^{XIe1}$, $R^{XIe2}$, $R^{XIe3}$ and $R^{XIe4}$ are each independently a hydrogen atom, a halogen atom, a $C_{1-6}$ alkyl group, an optionally substituted $C_{6-14}$ aryl group, or a $C_{1-6}$ alkoxy group;
$R^{XIe5}$ and $R^{XIe6}$ are each independently a hydrogen atom, a $C_{1-6}$ alkyl group, or an optionally substituted $C_{6-14}$ aryl group; and
the other symbols are as defined above; and
a cyclic structural moiety represented by the formula (XI-f):

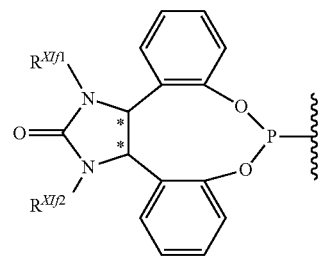

(XI-f)

wherein
$R^{XIf1}$, and $R^{XIf2}$ are each independently a hydrogen atom, a halogen atom, or a $C_{1-6}$ alkyl group; and
the other symbols are as defined above.

Preferable examples of the substituent of the "optionally substituted $C_{6-14}$ aryl group" represented by $R^{XIa1}$, $R^{XIa2}$, $R^{XIa3}$, $R^{XIa4}$, $R^{XIb1}$, $R^{XIb2}$, $R^{XIb3}$, $R^{XIb4}$, $R^{XIb5}$, $R^{XIb6}$, $R^{XIb7}$, $R^{XIb8}$, $R^{XIb9}$, $R^{XIb10}$, $R^{XIc1}$, $R^{XIc2}$, $R^{XId1}$, $R^{XId2}$, $R^{XId3}$, $R^{XId4}$, $R^{XId5}$, $R^{XId6}$, $R^{XIe1}$, $R^{XIe2}$, $R^{XIe3}$, $R^{XIe4}$, $R^{XIe5}$ or $R^{XIe6}$ include a halogen atom, a $C_{1-6}$ alkyl group and a $C_{1-6}$ alkoxy group.

Preferably, $R^{10}$ and $R^{11}$ in combination form a 4- to 8-membered ring together with the adjacent atoms, and the cyclic structural moiety is preferably the structure represented by the formula (XI-1).

Preferably, $R^{13}$ and $R^{14}$ in combination form a 4- to 8-membered ring together with the adjacent atoms, and the cyclic structural moiety is preferably the structure represented by the formula (XI-1).

$R^{12}$ is preferably an optionally substituted $C_{1-6}$ alkyl group, an optionally substituted $C_{6-14}$ aryl group, or an optionally substituted hydroxy group.

Preferable examples of the substituent of the "optionally substituted $C_{1-6}$ alkyl group" include a $C_{6-14}$ aryl group.

Preferable examples of the substituent of the "optionally substituted $C_{6-14}$ aryl group" include a halogen atom, a $C_{1-6}$ alkyl group and a $C_{1-6}$ alkoxy group.

Preferable examples of the substituent of the "optionally substituted hydroxy group" include (1) a $C_{1-6}$ alkyl group optionally substituted by
   (a) a $C_{6-14}$ aryl group optionally having 1 to 3 of $C_{1-6}$ alkoxy groups or $C_{1-6}$ alkyl groups, or
   (b) an amino group optionally having 1 to 2 $C_{1-6}$ alkyl groups,
(2) a $C_{3-10}$ cycloalkyl group optionally having 1 to 3 of $C_{1-6}$ alkoxy groups or $C_{1-6}$ alkyl groups, and,
(3) a $C_{6-14}$ aryl group optionally having 1 to 3 of $C_{1-6}$ alkoxy groups or $C_{1-6}$ alkyl groups.

$R^{15}$ and $R^{16}$ are preferably each independently an optionally substituted $C_{1-6}$ alkyl group.

The number of the substituents in the "optionally substituted $C_{1-6}$ alkyl group" is, for example, 1 to 5, preferably 1 to 3, at substitutable position(s). When the number of the substituents is two or more, the respective substituents may be the same or different.

Preferable examples of the substituent of the "optionally substituted $C_{1-6}$ alkyl group" include a $C_{6-14}$ aryl group optionally having 1 to 3 of $C_{1-6}$ alkoxy groups or $C_{1-6}$ alkyl groups.

Examples of the cyclic structural moiety in compound (XII) when $R^{15}$ and $R^{16}$ in combination form a 4- to 8-membered ring together with the adjacent atom include a cyclic structural moiety represented by the formula (XI-g):

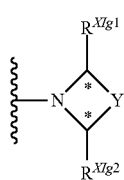

(XI-g)

wherein $R^{XIg1}$ and $R^{XIg2}$ are each independently a hydrogen atom, an optionally substituted $C_{1-6}$ alkyl group, an optionally substituted $C_{3-10}$ cycloalkyl group, or an optionally substituted $C_{6-14}$ aryl group;

Y is —$(CH_2)_2$—, —$(CH_2)_3$— or —$CH_2$—O—$CH_2$—; and the other symbols are as defined above; and a cyclic structural moiety represented by the formula (XI-h):

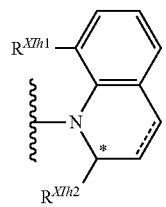

(XI-h)

wherein $R^{XIh1}$ is a hydrogen atom, a halogen atom, a $C_{1-6}$ alkyl group, an optionally substituted $C_{6-14}$ aryl group, or a $C_{1-6}$ alkoxy group;

$R^{XIh2}$ is a hydrogen atom, a $C_{1-6}$ alkyl group, or an optionally substituted $C_{6-14}$ aryl group; and the other symbols are as defined above.

Examples of the "substituent" of the "optionally substituted $C_{1-6}$ alkyl group" represented by $R^{XIg1}$ or $R^{XIg2}$ include the above-mentioned "substituents". The number of the substituents is, for example, 1 to 5, preferably 1 to 3, at substitutable position(s). When the number of the substituents is two or more, the respective substituents may be the same or different.

Preferable examples of the "substituent" of the "optionally substituted $C_{1-6}$ alkyl group" represented by $R^{XIg1}$ or $R^{XIg2}$ include a $C_{1-6}$ alkyl group, a $C_{3-10}$ cycloalkyl group and a $C_{6-14}$ aryl group.

The "substituent" of the "optionally substituted $C_{3-10}$ cycloalkyl group" represented by $R^{XIg1}$ or $R^{XIg2}$ and a number thereof are similar to those exemplified in the above-mentioned "optionally substituted $C_{1-6}$ alkyl group" represented by $R^{XIg1}$ or $R^{XIg2}$. Preferred are a $C_{1-6}$ alkyl group, a $C_{3-10}$ cycloalkyl group and a $C_{6-14}$ aryl group.

The "substituent" of the "optionally substituted $C_{6-14}$ aryl group" represented by $R^{XIg1}$ or $R^{XIg2}$ and a number thereof are similar to those exemplified in the above-mentioned "optionally substituted $C_{1-6}$ alkyl group" represented by $R^{XIg1}$ or $R^{XIg2}$. Preferred are a halogen atom, a $C_{1-6}$ alkyl group, a $C_{3-10}$ cycloalkyl group and a $C_{6-14}$ aryl group.

Preferable examples of the "substituent" of the "optionally substituted $C_{6-14}$ aryl group" represented by $R^{XIh1}$ include a halogen atom, a $C_{1-6}$ alkyl group, a $C_{3-10}$ cycloalkyl group and a $C_{6-14}$ aryl group.

$R^{XIh1}$ is preferably a hydrogen atom or a halogen atom.

Preferable examples of the "substituent" of the "optionally substituted $C_{6-14}$ aryl group" represented by $R^{XIh2}$ include a halogen atom, a $C_{1-6}$ alkyl group, a $C_{3-10}$ cycloalkyl group and a $C_{6-14}$ aryl group.

$R^{XIh2}$ is preferably a hydrogen atom or a $C_{1-6}$ alkyl group.

Specific examples of the above-mentioned two phosphine ligands (the two monophosphine ligand, each monophosphine ligand is the same or different) represented by L include (3,5-dioxa-4-phosphacyclohepta[2,1-a;3,4-a']dinaphthalen-4-yl)dimethylamine (MonoPhos), (3,5-dioxa-4-phosphacyclohepta[2,1-a;3,4-a']dinaphthalen-4-yl)benzyl(methyl)amine, (3,5-dioxa-4-phosphacyclohepta[2,1-a;3,4-a']dinaphthalen-4-yl)-(1-phenylethyl)amine, (3,5-dioxa-4-phosphacyclohepta[2,1-a;3,4-a']dinaphthalen-4-yl)bis(1-phenylethyl)amine, (3,5-dioxa-4-phosphacyclohepta[2,1-a;3,4-a']dinaphthalen-4-yl)-2,5-diphenylpyrrolidine, (3,5-dioxa-4-phosphacyclohepta[2,1-a;3,4-a']dinaphthalen-4-yl)morpholine (Morfphos), (3,5-dioxa-4-phosphacyclohepta[2,1-a;3,4-a']dinaphthalen-4-yl)piperidine (PipPhos), 2-(diphenylphosphino)-2'-methoxy-1,1'-binaphthoyl (MOP), 1-(2-diphenylphosphino-1-naphthyl)isoquinoline (QUI-NAP), N-dimethyl-[1,1-spirobiindane-7,7'-diyl]phosphoramidite (SIPHOS), N-di[(1-phenylethyl]-[1,1-spirobiindane-7,7-diyl]phosphoramidite (SIPHOS-PE), (3aR,8aR)-(−)-(2,2-dimethyl-4,4,8,8-tetraphenyl-tetrahydro-[1,3]dioxolo[4,5-e][1,3,2]dioxaphosphepin-6-yl)dimethylamine, (3aS,8aS)-(−)-(2,2-dimethyl-4,4,8,8-tetraphenyl-tetrahydro-[1,3]dioxolo[4,5-e][1,3,2]dioxaphosphepin-6-yl)dimethylamine, 5-[(3aR,8aR)-tetrahydro-2,2-dimethyl-4,4,8,8-tetraphenyl-1,3-dioxolo[4,5-e][1,3,2]dioxaphosphepin-6-yl]-5H-dibenzo[b,f]azepine, 5-[(3aS,8aS)-tetrahydro-2,2-dimethyl-4,4,8,8-tetraphenyl-1,3-dioxolo[4,5-e][1,3,2]dioxaphosphepin-6-yl]-5H-dibenzo[b,f]azepine, N-[(2S,5S)-4,4-diphenyl-3-oxa-1-aza-2-phosphabicyclo[3.3.0]octan-2-yl]dibenzo[b,f]azepine and the like.

The two phosphine ligands (the two monophosphine ligand, each monophosphine ligand is the same or different) represented by L is preferably an optically active form.

Specific examples of the PN ligand represented by L include

2-[(6-(diphenylphosphino)spiro[4.4]nona-1,6-dien-1-yl]-4,5-dihydro-4-benzyloxazole (Bn-SpinPHOX), 2-(2-(diphenylphosphino)phenyl)-4-isopropyl-4,5-dihydrooxazole (iPr-Phox)

and the like.

The PN ligand represented by L is preferably an optically active form.

The "ligand" used for the "transition metal complex" is preferably an optically active ligand.

The "transition metal complex" can be prepared from a "ligand" and the other complex as a transition metal source according to a means known per se (preparation of rhodium complexes; Journal of the American Chemical Society (J. Am. Chem. Soc.), vol. 94, page 6429, 1972, Organic Synthesis (Org. Synth.), vol. 67, page 33, 1989: preparation of ruthenium complexes; Journal of Organic Chemistry (J. Org. Chem.), vol. 57, page 4053, 1992, Tetrahedron Asymmetry (Tetrahedron Asym.), vol. 2, page 43, 1991, Journal of Organic Chemistry (J. Org. Chem.), vol. 59, page 3064, 1994, Angewandte Chemie International Edition (Angew. Chem. Int. Ed.), vol. 37, page 1703, 1998: preparation of iridium complexes; Journal of Organometallic Chemistry (J. Organomet. Chem.), vol. 428, page 213, 1992: preparation of palladium complexes; Organometallics, vol. 12, page 4188, 1993, Journal of the American Chemical Society (J. Am. Chem. Soc.), vol. 121, page 5450, 1999: preparation of nickel complexes; "5th Ed., Jikken Kagaku Koza" edited by Japan Chemical Society (Maruzen), vol. 21, organic zo transition metal compound, Supermolecular Complex, pages 293-(2004): preparation of copper complexes; "5th Ed., Jikken Kagaku Koza" edited by Japan Chemical Society (Maruzen), vol. 21, organic transition metal compound, Supermolecular Complex, page 357 (2004), Journal of Organic Chemistry (J. Org. Chem.), vol. 63, page 6090, 1998), and can be isolated or purified according to a means known per se (e.g., concentration, solvent extraction, fractional distillation, crystallization, recrystallization, chromatography).

Among the "diphosphine ligand" represented by L, SKEWPHOS derivative having 1 to 5 substituents such as a $C_{1-6}$ alkyl group and the like on the one benzene ring bonded to the phosphorus atom of SKEWPHOS can be synthesized according to the method described in the Patent Document WO 2013/146987.

The two phosphine ligands (the two monophosphine ligand, each monophosphine ligand is the same or different) represented by L can be prepared according to a means known per se (Wiley, Phosphorus Ligands in Asymmetric Catalysis, vol. 1, pages 5-69, (2008)), and can be isolated or purified according to a means known per se (e.g., concentration, solvent extraction, fractional distillation, crystallization, recrystallization, chromatography).

The "transition metal complex" can also be prepared by adding a "ligand" and the other complex as a transition metal source to a reaction system. The "transition metal complex" may be directly added to a reaction container, or may be prepared by adding a "transition metal source" mentioned above and a "ligand" to a reaction container. When the "transition metal complex" is prepared by adding a "transition metal source" and a "ligand" to a container, the "ligand" is used in an amount of 1- to 100-fold by mole, preferably 1 to 5-fold by mole, further more preferably 1.01 to 2.02-fold by mole, relative to the theoretical mole required to prepare the "transition metal complex".

While the amount of the "transition metal complex" to be used varies depending on the reaction container, the style of the reaction, and the like, it is, for example, about 1.0-about 0.00001 mol, per 1 mol of the substrate compound (I) or a salt thereof.

In the "hydrogenation reaction" of Step A-3, hydrogen gas, metal hydride, isopropyl alcohol, formic acid, benzthiazoline, Hantzsch ester and the like can be used as a hydrogen donor. Among them, hydrogen gas is preferably used.

When hydrogen gas is used, the hydrogenation reaction can be carried out by batch process or continuous process. When the hydrogenation reaction is carried out in the presence of hydrogen gas, the hydrogen pressure is, for example, 0.001 to atm, preferably 0.1 to 15 atm.

In the "hydrogenation reaction" of Step A-3, an additive such as a base, an acid, a salt and the like may be added, if necessary. The additive may be used in a mixture of two or more kinds thereof. The additive may be added to a reaction container before or during the "hydrogenation reaction".

Examples of the base which may be added to the "hydrogenation reaction" system of Step A-3 include inorganic bases and organic bases.

Examples of the inorganic base include alkali metal hydroxides such as lithium hydroxide, potassium hydroxide, sodium hydroxide, cesium hydroxide and the like; alkali metal alkoxides having 1 to 6 carbon atoms such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide and the like; alkali metal thioalkoxides having 1 to 6 carbon atoms such as sodium thiomethoxide and the like; carbonates such as sodium carbonate, potassium carbonate, cesium carbonate and the like; hydrogencarbonates such as sodium hydrogencarbonate, potassium hydrogencarbonate and the like; acetates such as sodium acetate, potassium acetate and the like; phosphates such as tripotassium phosphate, sodium phosphate and the like; and monohydrogen phosphates such as potassium monohydrogen phosphate, sodium monohydrogen phosphate and the like.

Examples of the organic base include aliphatic amine as such as trimethylamine, triethylamine, N-methylmorpholine, N,N-diisopropylethylamine, diethylamine, diisopropylamine, cyclohexylamine, ethylenediamine and the like; aromatic amines such as pyridine, picoline, N,N-dimethylaniline and the like; and basic amino acids such as arginine, lysine, ornithine and the like.

While the amount of the base to be used varies depending on the kind of the solvent and the other reaction condition, it is generally about 0.01 mol or more, per 1 mol of the substrate compound (I) or a salt thereof. The base can also be used as a solvent.

Examples of the acid which may be added to the "hydrogenation reaction" system of Step A-3 include mineral acids (specifically hydrofluoric acid, hydrochloric acid, hydrobromic acid, hydriodic acid, nitric acid, sulfuric acid, sulfurous acid, phosphoric acid, phosphorous acid, carbonic acid, bicarbonic acid and the like); carboxylic acids (i.e., compounds having one or more carboxy groups; specifically formic acid, acetic acid, trifluoroacetic acid, benzoic acid, phthalic acid, fumaric acid, oxalic acid, tartaric acid, maleic acid, citric acid, succinic acid, malic acid and the like); acidic amino acids (specifically aspartic acid, glutamic acid and the like); and sulfonic acids (i.e., compounds having one or more sulfo groups; specifically methanesulfonic acid, trifluoromethanesulfonic acid, benzenesulfonic acid, p-toluenesulfonic acid, camphorsulfonic acid and the like). Where necessary, the acid may be used in a mixture of two or more kinds thereof.

While the amount of the acid to be used varies depending on the kind of the solvent and the other reaction condition, it is generally about 0.01 mol or more, per 1 mol of the substrate compound (I) or a salt thereof. The acid can also be used as a solvent.

Examples of the salt which may be added to the "hydrogenation reaction" system of Step A-3 include salts which contain the above-mentioned "acid" as an acid component, in addition to salts exemplified as the above-mentioned "inorganic base".

While the amount of the salt to be used varies depending on the kind of the solvent and the other reaction condition, it is generally about 0.01 to 100 mol, per 1 mol of the substrate compound (I) or a salt thereof.

The "hydrogenation reaction" of Step A-3 is generally carried out in a solvent. The solvent is not particularly limited as long as it does not inhibit the reaction and can dissolve the raw material compound, organic metal complex and additive, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, isopropyl alcohol, n-butanol, 2-butanol, t-butyl alcohol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; esters such as ethyl acetate, isopropyl acetate, n-propyl acetate, n-butyl acetate, isobutyl acetate, methyl acetate, ethyl formate and the like; nitromethane; water and the like. These solvents may be used in a mixture in an appropriate ratio.

The amount of the solvent to be used is appropriately determined depending on the solubility of the substrate compound (I) or a salt thereof, and the like. The reaction can be carried out nearly without a solvent or in a solvent in an amount of 100 parts by weight or less per 1 part by weight of the substrate compound (I) or a salt thereof, preferably in a solvent in an amount of about 2-about 100 parts by weight per part by weight of the substrate compound (I) or a salt thereof.

The temperature in the "hydrogenation reaction" of Step A-3 is generally −30 to 160° C., preferably 0 to 120° C., more preferably 10 to 80° C. The reaction time is generally 0.1 to hr, preferably 1 to 72 hr.

Compound (II) or a salt thereof obtained in the "hydrogenation reaction" may be purified according to a means known per se (e.g., fractional recrystallization method, chiral column method, diastereomer salt method).

Alternatively, Compound (II) or a salt thereof obtained in the "hydrogenation reaction" may be treated according to a means known per se (e.g., concentration, solvent extraction, chromatography) if necessary, and then the obtained solution may be directly used in the next Step A-4, without isolation.

[Step A-4]

Step A-4 is a step of producing compound (III) or a salt thereof by subjecting compound (II) or a salt thereof to a deprotection reaction.

When PG is a group represented by the formula (VI-1), the deprotection reaction can be carried out according to a method known per se (e.g., the method described in Synthetic Communications, vol 10, page 253, 1980; Tetrahedron, vol. 50, page 4399, 1994).

When PG is a group represented by the formula (VI), the deprotection reaction can be carried out according to a method known per se (e.g., the method described in Protective Group in Organic Synthesis, the 3rd edition, pages 579-583, 1999).

In case of preferable embodiment wherein compound (I) or a salt thereof is compound (VII) or a salt thereof, and compound (II) or a salt thereof is compound (VIII) or a salt thereof, Step A-3 and Step A-4 in the production method of compound (III) or a salt thereof are explained below in detail.

The "transition metal complex" used in the "hydrogenation reaction" of Step A-3 in the preferable embodiment is particularly preferably an iridium complex.

The ligand for the "iridium complex" is preferably a monophosphine ligand, more preferably the compound represented by the formula (XI) or the compound represented by the formula (XII), further more preferably the compound represented by the formula (XII), particularly preferably the compound having the cyclic structural moiety represented by the formula (XI-b). Specific examples thereof include, (3,5-dioxa-4-phosphacyclohepta[2,1-a;3,4-a']dinaphthalen-4-yl)dimethylamine (MonoPhos);
(3,5-dioxa-4-phosphacyclohepta[2,1-a;3,4-a']dinaphthalen-4-yl)benzyl(methyl)amine;
(3,5-dioxa-4-phosphacyclohepta[2,1-a;3,4-a']dinaphthalen-4-yl)-(1-phenylethyl)amine;
(3,5-dioxa-4-phosphacyclohepta[2,1-a;3,4-a']dinaphthalen-4-yl)bis(1-phenylethyl)amine;
(3,5-dioxa-4-phosphacyclohepta[2,1-a;3,4-a']dinaphthalen-4-yl)-2,5-diphenylpyrrolidine;
(3,5-dioxa-4-phosphacyclohepta[2,1-a;3,4-a']dinaphthalen-4-yl)morpholine (Morfphos); and
(3,5-dioxa-4-phosphacyclohepta[2,1-a;3,4-a']dinaphthalen-4-yl)piperidine (PipPhos).

Preferred are
(3,5-dioxa-4-phosphacyclohepta[2,1-a;3,4-a']dinaphthalen-4-yl)dimethylamine (MonoPhos);
(3,5-dioxa-4-phosphacyclohepta[2,1-a;3,4-a']dinaphthalen-4-yl)morpholine (Morfphos); and
(3,5-dioxa-4-phosphacyclohepta[2,1-a;3,4-a']dinaphthalen-4-yl)piperidine (PipPhos),
particularly preferred is (3,5-dioxa-4-phosphacyclohepta[2,1-a;3,4-a']dinaphthalen-4-yl)dimethylamine (MonoPhos).

The "iridium complex" is preferably prepared by adding a "ligand" and the other iridium complex as an iridium metal source to a reaction system.

The "other iridium complex as an iridium metal source" is particularly preferably bis(cyclooctadiene)iridium(I) tetrakis(3,5-bis(trifluoromethyl)phenyl)borate.

Preferable examples of the solvent used in the "hydrogenation reaction" include toluene and dichloromethane, and particularly preferred is dichloromethane.

The "deprotection reaction" of Step A-4 in the preferable embodiment can be carried out according to a method known per se (i.e., the method described in Synthesis, vol. 4, page 570, 2003; Organic Letters, vol. 1, page 1395, 1999; Tetrahedron, vol. 52, page 10685, 1996; Tetrahedron Letters, vol. 32, page 5865, 1991).

The "deprotection reaction" is preferably carried out by reacting compound (VIII) or a salt thereof with triethylsilane in the presence of an acid.

Examples of the "acid" include mineral acids (specifically hydrofluoric acid, hydrochloric acid, hydrobromic acid, hydroiodic acid, nitric acid, sulfuric acid, sulfurous acid, phosphoric acid, phosphorous acid, carbonic acid, bicarbonic acid and the like); carboxylic acids (i.e., compounds having one or more carboxy groups; specifically formic acid, acetic acid, trifluoroacetic acid, benzoic acid, phthalic acid, fumaric acid, oxalic acid, tartaric acid, maleic acid, citric acid, succinic acid, malic acid and the like); acidic amino acids (specifically aspartic acid, glutamic acid and the like); sulfonic acids (i.e., compounds having one or more sulfo groups; specifically methanesulfonic acid, trifluoromethanesulfonic acid, benzenesulfonic acid, p-toluenesulfonic acid, camphorsulfonic acid and the like); and Lewis acids (specifically aluminium chloride, tin chloride, zinc chloride, zinc bromide, titanium tetrachloride, boron trifluoride-ethyl ether complex and the like). Where necessary, the acid may be used in a mixture of two or more kinds thereof. Preferred are trifluoroacetic acid and Lewis acids, more preferred are Lewis acids, and particularly preferred is aluminium chloride.

While the amount of the triethylsilane to be used in the "method reacting with triethylsilane" varies depending on the kind of the solvent and the other reaction condition, it is generally 0.1 to 30 mol, preferably 1.5 to 10 mol, per 1 mol of the substrate compound (VIII) or a salt thereof.

While the amount of the acid to be used in the "method reacting with triethylsilane" varies depending on the kind of the solvent and the other reaction condition, it is generally 0.1 to 30 mol, preferably 1.5 to 10 mol, per 1 mol of the substrate compound (VIII) or a salt thereof.

While the "method reacting with triethylsilane" may be carried out without a solvent, it is generally carried out in a solvent. The solvent is not particularly limited as long as it does not inhibit the reaction and can dissolve the raw material compound and additive, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, 2-propanol, n-butanol, 2-butanol, t-butyl alcohol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; esters such as ethyl acetate, isopropyl acetate, n-propyl acetate, n-butyl acetate, isobutyl acetate, methyl acetate, ethyl formate and the like; nitromethane; water and the like. These solvents may be used in a mixture in an appropriate ratio. As the solvent used in the above-mentioned "method reacting with triethylsilane", halogenated hydrocarbons and aromatic hydrocarbons are preferable, toluene, dichloromethane and 1,2-dichloroethane are more preferable, and 1,2-dichloroethane is particularly preferable.

The amount of the solvent to be used is appropriately determined depending on the solubility of the substrate compound (VIII) or a salt thereof, and the like. For example, when a halogenated hydrocarbon (preferably 1,2-dichloroethane) is used as a solvent, the reaction can be carried out nearly without a solvent or in a solvent in an amount of 100 parts by weight or less per 1 part by weight of the substrate compound (VIII) or a salt thereof, preferably in a solvent in an amount of 1 to 30 parts by weight per 1 part by weight of the substrate compound (VIII) or a salt thereof.

The temperature in the above-mentioned "method reacting with triethylsilane" is generally 10 to 180° C., preferably 30 to 120° C. The reaction time is generally 0.1 to 96 hr, preferably 0.5 to 48 hr.

Compound (III) wherein $R^2$ is a chlorine atom and $R^3$ is trifluoromethyl or a salt thereof, which is obtained in the above-mentioned "method reacting with triethylsilane", may be purified according to a means known per se (e.g., fractional recrystallization method, chiral column method, diastereomer salt method).

In order to obtain the above-mentioned compound (III) or a salt thereof with high optical purity, it is preferably purified by a fractional recrystallization method or a diastereomer salt method, preferably crystallization of the diastereomer salt with optically active di-p-toluoyl-tartaric acid (preferably di-p-toluoyl-(D)-tartaric acid when the above-mentioned compound (III) is (R)-form) or optically active mandelic acid (preferably (S)-mandelic acid when the above-mentioned compound (III) is (R)-form), particularly preferably crystallization of the diastereomer salt with optically active mandelic acid (preferably (S)-mandelic acid when the above-mentioned compound (III) is (R)-form).

The "deprotection reaction" is also preferably carried out by reacting compound (VIII) or a salt thereof with an oxidizing agent.

Preferable examples of the "oxidizing agent" include N-bromosuccinimide and N-chlorosuccinimide, and particularly preferred is N-bromosuccinimide.

While the amount of the "oxidizing agent" to be used varies depending on the kinds of the oxidizing agent and solvent and the other reaction condition, it is generally 0.8 to 30 mol, preferably 0.9 to 2 mol, per 1 mol of the substrate compound (VIII) or a salt thereof.

An additive is preferably used in the reaction by the "method reacting with an oxidizing agent". As the "additive", water and an acid are preferable.

Examples of the "acid" include mineral acids (specifically hydrofluoric acid, hydrochloric acid, hydrobromic acid, hydriodic acid, nitric acid, sulfuric acid, sulfurous acid, phosphoric acid, phosphorous acid, carbonic acid, bicarbonic acid and the like); carboxylic acids (i.e., compounds having one or more carboxy groups; specifically formic acid, acetic acid, trifluoroacetic acid, benzoic acid, phthalic acid, fumaric acid, oxalic acid, tartaric acid, maleic acid, citric acid, succinic acid, malic acid and the like); acidic amino acids (specifically aspartic acid, glutamic acid and the like); and sulfonic acids (i.e., compounds having one or more sulfo groups; specifically methanesulfonic acid, trifluoromethanesulfonic acid, benzenesulfonic acid, p-toluenesulfonic acid, camphorsulfonic acid and the like). Where necessary, the acid may be used in a mixture of two or more kinds thereof.

As the additive used in the reaction by the "method reacting with an oxidizing agent", water, acetic acid, citric acid and hydrochloric acid are preferable, and water is particularly preferable.

While the amount of the "additive" to be used varies depending on the kinds of the additive and solvent and the other reaction condition, it is generally 0.8 to 100 mol, preferably 5 to 50 mol, per 1 mol of the substrate compound (VIII) or a salt thereof.

While the reaction by the "method reacting with an oxidizing agent" may be carried out without a solvent, it is generally carried out in a solvent. The solvent is not particularly limited as long as it does not inhibit the reaction and can dissolve the raw material compound and additive, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, 2-propanol, n-butanol, 2-butanol, t-butyl alcohol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; esters such as ethyl acetate, isopropyl acetate, n-propyl acetate, n-butyl acetate, isobutyl acetate, methyl acetate, ethyl formate and the like; nitromethane; water and the like. These solvents may be used in a mixture in an appropriate ratio. As the solvent used in the reaction by the "method reacting with an oxidizing agent", acetonitrile is preferable.

The amount of the solvent to be used is appropriately determined depending on the solubility of the substrate compound (VIII) or a salt thereof, and the like. For example, when water is used as an additive and acetonitrile is used as a solvent, the reaction can be carried out nearly without a solvent or in a solvent in an amount of 100 parts by weight or less per 1 part by weight of the substrate compound (VIII) or a salt thereof, preferably in a solvent in an amount of 1 to 20 parts by weight per 1 part by weight of the substrate compound (VIII) or a salt thereof.

The temperature in the reaction by the "method reacting with an oxidizing agent" is generally −10 to 120° C., preferably to 60° C. The reaction time is generally 0.1 to 96 hr, preferably 0.5 to 48 hr.

Compound (III) wherein $R^2$ is a chlorine atom and $R^3$ is trifluoromethyl or a salt thereof, which is obtained by the above-mentioned "method reacting with an oxidizing agent", may be purified according to a means known per se (e.g., fractional recrystallization method, chiral column method, diastereomer salt method).

In order to obtain compound (III) or a salt thereof with high optical purity, it is preferably purified by a fractional recrystallization method or a diastereomer salt method.

While the undesired enantiomer may be removed as a crystal by a fractional recrystallization method, compound (III) or a salt thereof is preferably purified by crystallization of the diastereomer salt with optically active di-p-toluoyl-tartaric acid (preferably di-p-toluoyl-(D)-tartaric acid when the above-mentioned compound (III) is (R)-form) or optically active mandelic acid (preferably (S)-mandelic acid when the above-mentioned compound (III) is (R)-form), particularly preferably crystallization of the diastereomer salt with optically active mandelic acid (preferably (S)-mandelic acid when the above-mentioned compound (III) is (R)-form).

[Production Method (AX)]

Compound (III) or a salt thereof can also be directly synthesized by subjecting compound (A-c) or a salt thereof to an asymmetric reductive amination reaction according to Production Method (AX) shown in the following scheme.

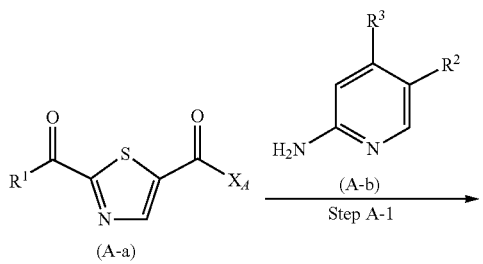

Production Method (AX)

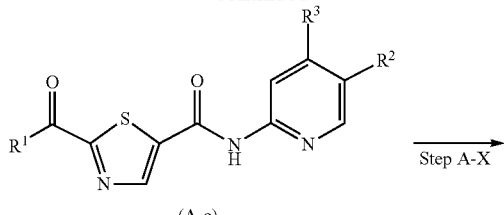

(A-c)

Step A-X →

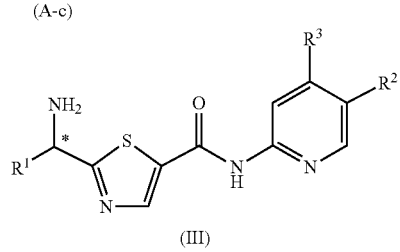

(III)

wherein each symbol is as defined above.

The reagent and condition used in Step A-X are explained in detail.

[Step (A-X)]

Step A-X is a step of producing compound (III) or a salt thereof by subjecting compound (A-c) or a salt thereof to an asymmetric reductive amination reaction.

The "asymmetric reductive amination reaction" is preferably carried out by reacting compound (A-c) or a salt thereof with an amine source and a reducing agent in the presence of an organic metal complex.

As the "reducing agent", a hydrogen donor is used. As a hydrogen donor, hydrogen gas, a metal hydride, isopropyl alcohol, formic acid, benzthiazoline, Hantzsch ester and the like can be used. Among them, hydrogen gas is preferably used.

When hydrogen gas is used, the reaction can be carried out by batch process or continuous process. When the "asymmetric reductive amination reaction" is carried out in the presence of hydrogen gas, the hydrogen pressure is, for example, 0.001 to 200 atm, preferably 0.1 to 80 atm.

The "amine source" is preferably an ammonium salts. Preferable examples of the acid to be used for forming an ammonium salt include an optionally substituted salicylic acid, an optionally substituted nicotinic acid, carbonic acid, formic acid, acetic acid, trifluoroacetic acid and benzoic acid.

Examples of the substituent of the optionally substituted salicylic acid include the above-mentioned "substituents". The number of the substituent is, for example, 1 to 4, preferably 1, at substitutable position(s).

Preferable examples of the optionally substituted salicylic acid include compounds shown below.

salicylic acid

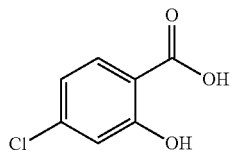
(XIII-1)

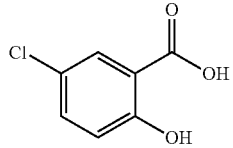
(XIII-2)

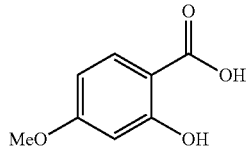
(XIII-3)

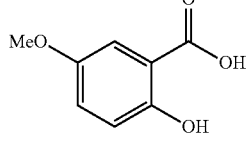
(XIII-4)

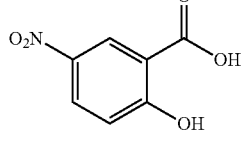
(XIII-5)

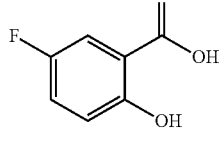
(XIII-6)

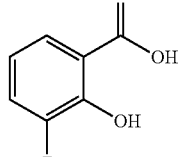
(XIII-7)

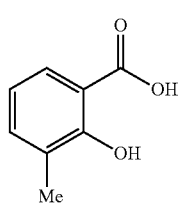
(XIII-8)

Examples of the substituent of the optionally substituted nicotinic acid include the above-mentioned "substituents". The number of the substituent is, for example, 1 to 4, preferably 1, at substitutable position(s).

Examples of the "organic metal complex" include those similar to the "organic metal complex" used in the above-mentioned "Step (A-3)".

The "organic metal complex" is preferably a "transition metal complex (an organic transition metal complex)".

Examples of the "transition metal complex" include compounds prepared by coordinating a "ligand" (preferably an optically active "ligand") to a "transition metal" which have the ability to catalyze an asymmetric hydrogenation reaction. Examples of the "ligand" include monophosphine ligands, diphosphine ligands, amine ligands, diamine ligands, phosphine amine ligands and the like, and include specific examples described herein and optical isomers thereof. The valence of the "transition metal" is, for example, 0 to 6, preferably 0 to 4, particularly preferably 0 to 3.

Preferable examples of the "transition metal complex" include rhodium complexes, ruthenium complexes, iridium complexes, palladium complexes, nickel complexes, copper complexes, osmium complexes, platinum complexes, iron complexes, gold complexes, silver complexes, zinc complexes, titanium complexes, cobalt complexes, zirconium complexes, samarium complexes and the like; more preferred are rhodium complexes, ruthenium complexes, iridium complexes, palladium complexes, nickel complexes and copper complexes; further more preferred are rhodium complexes, ruthenium complexes, palladium complexes and iridium complexes; still more preferred are rhodium complexes and iridium complexes; and particularly preferred are iridium complexes.

Among the "transition metal complexes", specific examples of the rhodium complexes, ruthenium complexes, iridium complexes, palladium complexes, nickel complexes and copper complexes include those similar to the specific examples of the "organic metal complex" used in the above-mentioned "Step (A-3)".

The "transition metal complex" can also be prepared by adding a "ligand" and the other complex as a transition metal source to a reaction system. The "transition metal complex" may be directly added to a reaction container, or may be prepared by adding a "transition metal source" mentioned above and a "ligand" to a reaction container. When the "transition metal complex" is prepared by adding a "transition metal source" and a "ligand" to a reaction container, the "ligand" is used in an amount of 1- to 100-fold by mole, preferably 1 to 5-fold by mole, further more preferably 1.01 to 2.02-fold by mole, relative to the theoretical mole required to prepare the "transition metal complex".

While the amount of the "transition metal complex" to be used varies depending on the reaction container, the style of the reaction, and the like, it is, for example, about 1.0-about 0.00001 mol, per 1 mol of the substrate compound (I) or a salt thereof.

In the "asymmetric reductive amination reaction" of Step A-X, an additive such as a base, an acid, a salt and the like may be added, if necessary. The additive may be used in a mixture of two or more kinds thereof. The additive may be added to a reaction container before or during the "asymmetric reductive amination reaction".

Examples of the base which may be added to the "asymmetric reductive amination reaction" system of Step A-X include inorganic bases and organic bases.

Examples of the inorganic base include alkali metal hydroxides such as lithium hydroxide, potassium hydroxide, sodium hydroxide, cesium hydroxide and the like; alkali metal alkoxides having 1 to 6 carbon atoms such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide and the like; alkali metal thioalkoxides having 1 to 6 carbon atoms such as sodium thiomethoxide and the like; carbonates such as sodium carbonate, potassium carbonate, cesium carbonate and the like; hydrogencarbonates such as sodium hydrogencarbonate, potassium hydrogencarbonate and the like; acetates such as sodium acetate, potassium acetate and the like; phosphates such as tripotassium phosphate, sodium phosphate and the like; and monohydrogen phosphates such as potassium monohydrogen phosphate, sodium monohydrogen phosphate and the like.

Examples of the organic base include aliphatic amine as such as trimethylamine, triethylamine, N-methylmorpholine, N,N-diisopropylethylamine, diethylamine, diisopropylamine, cyclohexylamine, ethylenediamine and the like; aromatic amines such as pyridine, picoline, N,N-dimethylaniline and the like; and basic amino acids such as arginine, lysine, ornithine and the like.

While the amount of the base to be used varies depending on the kind of the solvent and the other reaction condition, it is generally about 0.01 mol or more, per 1 mol of the substrate compound (A-c) or a salt thereof. The base can also be used as a solvent.

Examples of the acid which may be added to the "asymmetric reductive amination reaction" system of Step A-X include mineral acids (specifically hydrofluoric acid, hydrochloric acid, hydrobromic acid, hydriodic acid, nitric acid, sulfuric acid, sulfurous acid, phosphoric acid, phosphorous acid, carbonic acid, bicarbonic acid and the like); carboxylic acids (i.e., compounds having one or more carboxy groups; specifically formic acid, acetic acid, trifluoroacetic acid, benzoic acid, salicylic acid, phthalic acid, fumaric acid, oxalic acid, tartaric acid, maleic acid, citric acid, succinic acid, malic acid and the like); acidic amino acids (specifically aspartic acid, glutamic acid and the like); and sulfonic acids (i.e., compounds having one or more sulfo groups; specifically methanesulfonic acid, trifluoromethanesulfonic acid, benzenesulfonic acid, p-toluenesulfonic acid, camphorsulfonic acid and the like). Where necessary, the acid may be used in a mixture of two or more kinds thereof.

While the amount of the acid to be used varies depending on the kind of the solvent and the other reaction condition, it is generally about 0.01 mol or more, per 1 mol of the substrate compound (A-c) or a salt thereof. The acid can also be used as a solvent.

Examples of the salt which may be added to the "asymmetric reductive amination reaction" system of Step A-X include salts which contain the above-mentioned "acid" as an acid component, in addition to salts exemplified as the above-mentioned "inorganic base".

While the amount of the salt to be used varies depending on the kind of the solvent and the other reaction condition, it is generally about 0.01 to 100 mol, per 1 mol of the substrate compound (I) or a salt thereof.

The "asymmetric reductive amination reaction" of Step A-X is generally carried out in a solvent. The solvent is not particularly limited as long as it does not inhibit the reaction and can dissolve the raw material compound, organic metal complex and additive, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, isopropyl alcohol, n-butanol, 2-butanol, t-butyl alcohol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; esters such as ethyl acetate, isopropyl acetate, n-propyl acetate, n-butyl acetate, isobutyl acetate, methyl acetate, ethyl formate and the like; nitromethane; water and the like. These solvents may be used in a mixture in an appropriate ratio.

The amount of the solvent to be used is appropriately determined depending on the solubility of the substrate compound (A-c) or a salt thereof, and the like. The reaction can be carried out nearly without a solvent or in a solvent in an amount of 100 parts by weight or less per 1 part by weight of the substrate compound (A-c) or a salt thereof, preferably in a solvent in an amount of about 2-about 100 parts by weight per 1 part by weight of the substrate compound (A-c) or a salt thereof.

The temperature in the "asymmetric reductive amination reaction" of Step A-X is generally −30 to 160° C., preferably 0 to 120° C., more preferably 10 to 80° C. The reaction time is generally 0.1 to 120 hr, preferably 1 to 72 hr.

Compound (III) or a salt thereof obtained in the "asymmetric reductive amination reaction" may be purified according to a means known per se (e.g., fractional recrystallization method, chiral column method, diastereomer salt method).

As the most preferable embodiment, a compound represented by the formula (A-c) is 2-acetyl-N-(5-chloro-4-(trifluoromethyl)pyridin-2-yl)-1,3-thiazole-5-carboxamide; and an optically active form of a compound represented by the formula (III) is 2-((1R)-1-aminoethyl)-N-(5-chloro-4-(trifluoromethyl)pyridin-2-yl)-1,3-thiazole-5-carboxamide.

Step A-X in Production Method (AX) in the most preferable embodiment are explained in detail below.

The "transition metal complex" used as a catalyst in "asymmetric reductive amination reaction" of Step A-X in the most preferable embodiment is particularly preferably an iridium complex.

The ligand for the "iridium complex" is preferably a diphosphine ligand; more preferred are 2,4-bis(diphenylphosphino)pentane (SKEWPHOS), SKEWPHOS derivative having 1 to 5 substituents such as a $C_{1-6}$ alkyl group and the like on the benzene ring(s) bonded to the phosphorus atom of SKEWPHOS, 4,12-bis(diphenylphosphino)-[2,2]-paracyclophane (PhanePHOS), substituted-1,1'-bisphosphoranoferrocene (Ferrocelane) and 1-[2-(disubstituted-phosphino)ferrocenyl]ethyl-disubstituted-phosphine (Josiphos); further more preferred are 2,4-bis(diphenylphosphino)pentane (SKEWPHOS) and SKEWPHOS derivative having 1 to 5 substituents such as a $C_{1-6}$ alkyl group and the like on the benzene ring(s) bonded to the phosphorus atom of SKEWPHOS; and particularly preferred is pentane-2,4-diylbis(bis(4-(tert-butyl)phenyl)phosphine), and use of the optically active form thereof, i.e., (R,R)-pentane-2,4-diylbis(bis(4-(tert-butyl)phenyl)phosphine) leads to production of the optically active form in the most preferable embodiment (compound (III) is (R)-form).

The "iridium complex" is preferably prepared just before using, by mixing a "ligand" and the other iridium complex as a iridium metal source in a solvent, before addition of hydrogen gas. During preparing just before using, the iridium complex is preferably coexistent with the substrate compound (A-c) or a salt thereof and an ammonium salt as an amine source. The solvent used in the preparation just before using is preferably the same solvent as used in the subsequent "asymmetric reductive amination reaction". The temperature of the preparation of the "iridium complex" just before using is generally 10 to 80° C.; more preferably 30 to 60° C.: particularly preferably 35 to 55° C. The time of the preparation of the "iridium complex" just before using is generally 30 to 360 min; more preferably 60 to 120 min. The procedure of the preparation of the "iridium complex" just before using is preferably carried out under an inert gas atmosphere such as argon or nitrogen.

Preferable examples of the "other iridium complex as a iridium metal source" include bis(1,5-cyclooctadiene)iridium(I) tetrafluoroborate, chloro(1,5-cyclooctadiene)iridium(I) (dimer), bis(1,5-cyclooctadiene)iridium(I) tetrakis(3,5-bis(trifluoromethyl)phenyl)borate, iodo(1,5-cyclooctadiene)iridium(I) (dimer), (1,5-cyclooctadiene)(methoxy)iridium(I) (dimer) and (acetylacetonato) (1,5-cyclooctadiene)iridium(I); and particularly preferred is chloro (1,5-cyclooctadiene)iridium(I) (dimer).

The acid to be used for forming an ammonium salt used in the "asymmetric reductive amination reaction" is preferably an optionally substituted salicylic acid. The most preferable ammonium salt is ammonium salicylate. The amount of the ammonium salicylate to be added in the "asymmetric reductive amination reaction" is preferably 1.1 to 5 equivalent, more preferably 2 to 4 equivalent, relative to the substrate compound (A-c) or a salt thereof.

Preferable examples of the solvent in the "asymmetric reductive amination reaction" include tetrahydrofuran, 1,4-dioxane, methanol, isopropyl alcohol, 2-methyl-2-butanol and toluene, and particularly preferred is tetrahydrofuran.

In the "asymmetric reductive amination reaction", an additive may be added. Preferable examples of the additive include water, zinc chloride, lithium chloride and terpyridine, and particular preferred is water.

When water is added to the "asymmetric reductive amination reaction" system, the amount is limited to small amount so that the water concentration in the reaction solution is 4000 ppm or less, preferably 1000 to 3000 ppm; most preferably 1500 to 2500 ppm.

In the "asymmetric reductive amination reaction", the hydrogen pressure is preferably 8 to 80 atm, more preferably 4 to 80 atm.

In the "asymmetric reductive amination reaction", the reaction temperature is preferably 30 to 60° C., more preferably 35 to 55° C.

In the "asymmetric reductive amination reaction", the reaction time is preferably 12 to 50 hr; more preferably 20 to hr.

Compound (III) or a salt thereof in the most preferable embodiment may be purified according to a means known per se (e.g., fractional recrystallization method, chiral column method, diastereomer salt method).

In order to obtain the above-mentioned compound (III) or a salt thereof with high optical purity, it is preferably purified by a fractional recrystallization method or a diastereomer salt method. Particularly, compound (III) or a salt thereof is preferably purified by crystallization of the diastereomer salt with optically active di-p-toluoyl-tartaric acid (preferably di-p-toluoyl-(D)-tartaric acid when the above-mentioned compound (III) is (R)-form) or optically active mandelic acid (preferably (S)-mandelic acid when the above-mentioned compound (III) is (R)-form), particularly preferably crystallization of the diastereomer salt with optically active mandelic acid (preferably (S)-mandelic acid when the above-mentioned compound (III) is (R)-form).

[Production Method (B)]

Compound (V) or a salt thereof can be produced by reacting compound (III) or a salt thereof obtained in Production Method (A) with compound (IV) or a salt thereof, in order to form an amide bond, according to Production Method (B) shown in the following scheme.

Production Method (B)

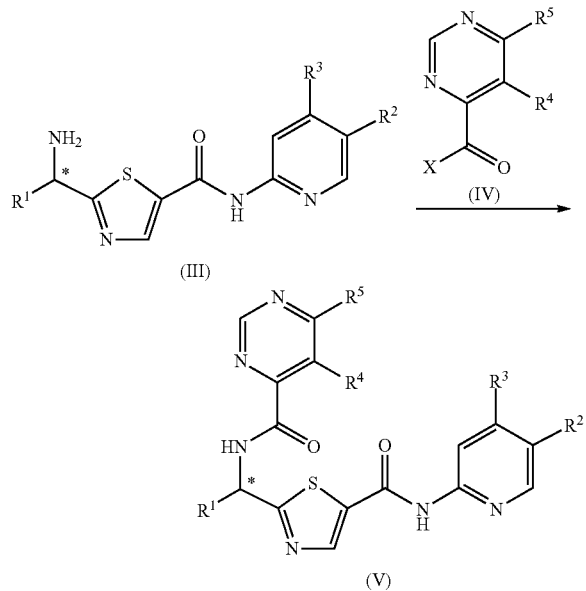

wherein each symbol is as defined above.

Compound (IV) or a salt thereof can be produced, for example, according to the method described in WO 2009-006389.

While the amount of compound (IV) or a salt thereof to be used in the method "forming an amide bond" in the Production Method (B) varies depending on the reaction condition, it is generally 0.5 to 30 mol, preferably 0.9 to 2 mol, per 1 mol of compound (III) or a salt thereof.

In the above-mentioned Production Method (B), while the salt of compound (III) obtained in Production Method (A) may be directly used in the condensation reaction, it is preferably converted to the free form by reacting with a base. Examples of the base include inorganic bases and organic bases.

Examples of the inorganic base include alkali metal hydroxides such as lithium hydroxide, potassium hydroxide, sodium hydroxide, cesium hydroxide and the like; alkali metal alkoxides having 1 to 6 carbon atoms such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide and the like; alkali metal thioalkoxides having 1 to 6 carbon atoms such as sodium thiomethoxide and the like; carbonates such as sodium carbonate, potassium carbonate, cesium carbonate and the like; hydrogencarbonates such as sodium hydrogencarbonate, potassium hydrogencarbonate and the like; acetates such as sodium acetate, potassium acetate and the like; phosphates such as tripotassium phosphate, sodium phosphate and the like; and monohydrogen phosphates such as potassium monohydrogen phosphate, sodium monohydrogen phosphate and the like.

Examples of the organic base include aliphatic amines such as trimethylamine, triethylamine, N-methylmorpholine, N,N-diisopropylethylamine, diethylamine, diisopropylamine, cyclohexylamine, ethylenediamine, 1,8-diazabicyclo[5.4.0]undecene and the like; aromatic amines such as pyridine, picoline, N,N-dimethylaniline and the like; and basic amino acids such as arginine, lysine, ornithine and the like. These bases may be used in a mixture in an appropriate ratio.

As the base used in the reaction for the conversion of the salt of compound (III) to the free form, sodium hydrogencarbonate is particularly preferable.

While the amount of the base to be used varies depending on the kind of the solvent and the other reaction condition, it is generally 0.5 to 100 mol, preferably 1.0 to 10 mol, particularly preferably 1.5 to 4 mol, per 1 mol of the substrate salt of compound (III). When the base is a liquid, it can also be used as a solvent.

While the reaction for the conversion of the salt of compound (III) to the free form may be carried out without a solvent, it is generally carried out in a solvent. The solvent is not particularly limited as long as it does not inhibit the reaction and can dissolve the raw material compound and additive, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, 2-propanol, n-butanol, 2-butanol, t-butyl alcohol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; esters such as ethyl acetate, isopropyl acetate, n-propyl acetate, n-butyl acetate, isobutyl acetate, methyl acetate, ethyl formate and the like; nitromethane; water and the like. These solvents may be used in a mixture in an appropriate ratio. As the solvent used in the reaction for the conversion the salt of compound (III) to the free form, ethers, alcohols and nitriles are preferable, and acetonitrile is particularly preferable.

The solvent is preferably used as a mixed solvent. When a nitrile (preferably acetonitrile) is used as a solvent, it is particularly preferably mixed with water.

The amount of the solvent to be used is appropriately determined depending on the solubility of the substrate salt of compound (III), and the like. For example, when the salt of compound (III) is a salt with mandelic acid, and a nitrile (preferably acetonitrile) is used as a solvent, the reaction can be carried out nearly without a solvent or in a solvent in an amount of 100 parts by weight or less per 1 part by weight of the substrate salt of compound (III), preferably in a solvent in an amount of 5 to 30 parts by weight per 1 part by weight of the substrate salt of compound (III).

The temperature in the reaction for the conversion to the free form is generally −10 to 80° C., preferably 0 to 40° C. The reaction time is generally 0.01 to 2 hr, preferably 0.1 to 1 hr.

Compound (III) obtained in the reaction for the conversion to the free form may be isolated and purified according to a means known per se (concentration, concentration under reduced pressure, solvent extraction, crystallization, recrystallization, phase transfer, chromatography and the like). Alternatively, the reaction solution may be used directly in the condensation reaction with compound (IV) or a salt thereof.

The method "forming an amide bond" in the Production Method (B) can be carried out according to a method known per se such as the method described in Tetrahedoron, vol 61, page 10827, 2005.

The method "forming an amide bond" is preferably carried out by the method using compound (IV) wherein X is a hydroxy group and a condensing agent.

Examples of the "condensing agent" include
carbodiimide condensing agents (1-ethyl-3-(3-dimethylaminopropyl)carbodiimide;
1-ethyl-3-(3-dimethylaminopropyl)carbodiimide hydrochloride
N,N'-dicyclohexylcarbodiimide;
N,N'-diisopropylcarbodiimide);
imidazole condensing agents (N,N'-carbonyldiimidazole; 1,1'-carbonyldi(1,2,4-triazole);
triazine condensing agents (4-(4,6-dimethoxy-1,3,5-triazin-2-yl)-4-methylmorpholinium chloride n hydrate;
(4,6-dimethoxy-1,3,5-triazin-2-yl)-(2-octoxy-2-oxoethyl) dimethylammonium trifluoromethanesulfonate);
phosphonium condensing agents (1H-benzotriazol-1-yloxy-tris(dimethylamino)phosphonium hexafluorophosphate;
1H-benzotriazol-1-yloxytripyrrolidinophosphonium hexafluorophosphate;
(7-azabenzotriazol-1-yloxy)tripyrrolidinophosphonium hexafluorophosphate;
chlorotripyrrolidinophosphonium hexafluorophosphate;
bromotris(dimethylamino)phosphonium hexafluorophosphate;
3-(diethoxyphosphoryloxy)-1,2,3-benzotriazin-4(3H)-one);
uronium condensing agents (O-(benzotriazol-1-yl)-N,N,N',N'-tetramethyluronium hexafluorophosphate;
O-(7-azabenzotriazol-1-yl)-N,N,N',N'-tetramethyluronium hexafluorophosphate;
O—(N-succinimidyl)-N,N,N',N'-tetramethyluronium tetrafluoroborate;
O—(N-succinimidyl)-N,N,N',N'-tetramethyluronium hexafluorophosphate;
O-(3,4-dihydro-4-oxo-1,2,3-benzotriazin-3-yl)-N,N,N',N'-tetramethyluronium tetrafluoroborate;
S-(1-oxide-2-pyridyl)-N,N,N',N'-tetramethyluronium tetrafluoroborate;
O-[2-oxo-1(2H)-pyridyl]-N,N,N',N'-tetramethyluronium tetrafluoroborate;
{{[(1-cyano-2-ethoxy-2-oxoethylidene)amino]oxy}-4-morpholinomethylene}dimethylammonium hexafluorophosphate); and
halouronium condensing agents (2-chloro-1,3-dimethylimidazolinium hexafluorophosphate;
1-(chloro-1-pyrrolidinyl methylene)pyrrolidinium hexafluorophosphate;
2-fluoro-1,3-dimethylimidazolinium hexafluorophosphate;
fluoro-N,N,N',N'-tetramethylformamidinium hexafluorophosphate).

As the "condensing agent", carbodiimide condensing agents are preferable, 1-ethyl-3-(3-dimethylaminopropyl) carbodiimide hydrochloride and N,N'-dicyclohexylcarbodiimide are more preferable, and N,N'-dicyclohexylcarbodiimide is particularly preferable.

While the amount of the "condensing agent" to be used varies depending on the kinds of the condensing agent and solvent and the other reaction condition, it is generally 0.8 to 10 mol, preferably 0.9 to 2 mol, per 1 mol of compound (IV) or a salt thereof.

In the reaction by the method "forming an amide bond" in Production Method (B), an additive is preferably used.

Examples of the "additive" include 1-hydroxybenzotriazole, 1-hydroxy-7-azabenzotriazole, N-hydroxysuccinimide and carbonic acid N,N'-disuccinimidyl. Preferred is 1-hydroxybenzotriazole.

While the amount of the "additive" to be used varies depending on the kinds of the additive, condensing agent and solvent and the other reaction condition, it is generally 0.01 to 1.0 mol, preferably 0.05 to 0.5 mol, per 1 mol of compound (IV) or a salt thereof.

While the reaction by the method "forming an amide bond" in Production Method (B) may be carried out nearly without a solvent, it is generally carried out in a solvent. The solvent is not particularly limited as long as it does not inhibit the reaction and can dissolve the raw material compound and additive, and examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, anisole and the like; alcohols such as methanol, ethanol, n-propanol, 2-propanol, n-butanol, 2-butanol, t-butyl alcohol, 3-methyl-1-butanol, 2-methyl-1-propanol, 1-pentanol, benzyl alcohol, 2-methoxyethanol, 2-ethoxyethanol, ethylene glycol and the like; aromatic hydrocarbons such as benzene, toluene, xylene, cumene, chlorobenzene and the like; saturated hydrocarbons such as hexane, heptane, pentane, cyclohexane, methylcyclohexane, isooctane, petroleum ether and the like; amides such as N,N-dimethylformamide, N,N-dimethylacetamide, formamide, hexamethylphosphoramide, N-methylpyrrolidone, 1,3-dimethyl-2-imidazolidinone and the like; halogenated hydrocarbons such as chloroform, dichloromethane, carbon tetrachloride, 1,2-dichloroethane and the like; nitriles such as acetonitrile, propionitrile and the like; sulfoxides such as dimethyl sulfoxide and the like; sulfones such as dimethylsulfone, sulfolane and the like; ketones such as acetone, ethyl methyl ketone, methyl isopropyl ketone, methyl butyl ketone and the like; esters such as ethyl acetate, isopropyl acetate, n-propyl acetate, n-butyl acetate, isobutyl acetate, methyl acetate, ethyl formate and the like; nitromethane; water and the like. These solvents may be used in a mixture in an appropriate ratio. As the solvent used in the reaction by the method "forming an amide bond" in Production Method (B), amides are preferable, and N,N-dimethylacetamide is more preferable.

The amount of the solvent to be used is appropriately determined depending on the solubility of compound (III) or a salt thereof, and compound (IV) or a salt thereof, and the like. For example, when N,N-dimethylacetamide is used as a solvent, the reaction can be carried out nearly without a solvent or in a solvent in an amount of 100 parts by weight or less per 1 part by weight of compound (III) or a salt thereof, preferably in a solvent in an amount of 1 to 20 parts by weight per 1 part by weight of the substrate compound (III) or a salt thereof.

The temperature in the reaction by the method "forming an amide bond" is generally −10 to 120° C., preferably 0 to 60° C. The reaction time is generally 0.1 to 48 hr, preferably 0.5 to hr.

Compound (V) or a salt thereof obtained in the reaction by the method "forming an amide bond" in Production Method (B) may be isolated and purified according to a means known per se (concentration, concentration under reduced pressure, solvent so extraction, crystallization, recrystallization, phase transfer, chromatography and the like).

The "isolation and purification" means is preferably crystallization, particularly preferably crystallization from a mixed solvent of n-butanol and water.

The isolated and purified compound (V) or a salt thereof is preferably further purified by recrystallization to give the compound with high purity. The solvent for the "recrystallization" is particularly preferably dimethyl sulfoxide, 2-propanol, or a mixed solvent of the solvent and water.

[Production Method (C)]

The asymmetric hydrogenation reaction in the presence of a transition metal complex in the present invention can be applied to the production of an optically active amine compound, in addition to the production of compound (II) or a salt thereof.

Preferable examples of the production of an optically active amine compound are shown below.

A compound represented by the formula (B):

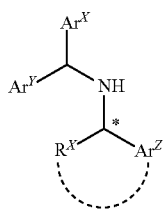

(B)

wherein
Ar$^X$ and Ar$^Y$ are each independently an optionally substituted C$_{6-14}$ aryl group;
Ar$^Z$ is an optionally substituted C$_{6-14}$ aryl group, or an optionally substituted heterocyclic group;
R$^x$ is an optionally substituted C$_{1-6}$ alkyl group;
R$^x$ and Ar$^Z$ in combination optionally form an optionally substituted 8-14-membered fused polycyclic together with the adjacent atom; and the carbon atom marked with * is an asymmetric carbon atom, or a salt thereof, can be obtained by subjecting a compound represented by the formula (A):

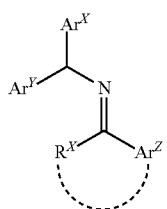

(A)

wherein each symbol is as defined above, or a salt thereof, to an asymmetric hydrogenation reaction in the presence of a transition metal complex having a trivalent phosphine ligand.

EXAMPLES

The present invention is explained in detail in the following by referring to Reference Examples and Examples, which are merely exemplified and not to be construed as limitative, and the invention may be changed within the scope of the present invention.

In the following Reference Examples and Examples, the "room temperature" generally means about 10° C. to about 35° C.

In the reaction scheme, s/c means substrate-catalyst ratio (substrate (mol)/catalyst (mol)), and s/s means substrate-solvent ratio (solvent (ml)/substrate (g)).

The chemical yield is an isolated yield (mol/mol %) or a yield measured by high-performance liquid chromatography. The optical purity (asymmetric yield) of an optically active form was evaluated by enantiomeric excess (% e.e.). The enantiomeric excess was calculated according to the following formula.

Enantiomeric excess (% e.e.)=100×[(R)−(S)]/[(R)+(S)] or 100×[(S)−(R)]/[(R)+(S)] wherein (R) and (S) are each an area of each enantiomer measured by high-performance liquid chromatography.

In addition, the amount of solvent used for chromatography is shown by % by volume, and the amount of the other is shown by % by weight.

Regarding enantiomer, the compound wherein the absolute configuration is determined is described as R or S. For the compound wherein the absolute configuration is not determined, the enantiomeric excess was calculated from the results of high-performance liquid chromatography (optical purity).

Enantiomeric excess (% e.e.)=100×[(front peak)−(back peak)]/[(front peak)+(back peak)]

In proton NMR spectrum, broad and unidentified protons such as OH and NH protons and the like are not described in data.

The abbreviations used in the specification mean the following technical term or the structure.
s: singlet
d: doublet
t: triplet
q: quartet
m: multiplet
br: broad
J: coupling constant
Hz: hertz)
CDCl$_3$: deuterochloroform
DMSO-d$_6$: deuterodimethyl sulfoxide
CD$_3$OD: deuteromethanol
$^1$H NMR: proton nuclear magnetic resonance
$^{13}$C NMR: $^{13}$Cnuclear magnetic resonance
$^{19}$F NMR: $^{19}$Fnuclear magnetic resonance
$^{31}$P NMR: $^{31}$Pnuclear magnetic resonance
[RhCl(cod)]$_2$: chloro(1,5-cyclooctadiene)rhodium(I) dimer
[Rh(cod)$_2$]OTf: bis(1,5-cyclooctadiene)rhodium(I) trifluoromethanesulfonate

[Rh(cod) (R)—(S)-josiphos]OTf: (1,5-cyclooctadiene){(R)-(−)-1-[(S)-2-(diphenylphosphino)ferrocenyl]ethyldicyclohexylphosphine}rhodium(I) trifluoromethanesulfonate

[Rh(nbd) (R)—(S)-josiphos]BF$_4$: {(R)-(−)-1-[(S)-2-(diphenylphosphino)ferrocenyl]ethyldicyclohexylphosphine}(norbornadiene)rhodium(I) tetrafluoroborate

[Rh(cod) (S,S)-skewphos]OTf: {(2S,4S)-(−)-2,4-bis(diphenylphosphino)pentane}(1,5-cyclooctadiene)rhodium(I) trifluoromethanesulfonate

[Rh(nbd) (S,S)-bisP*]BF$_4$: {(S,S)-1,2-bis-(t-butyl(methyl)phosphino)ethane}(norbornadiene)rhodium(I) tetrafluoroborate

[Rh(cod) (R,R)-dipamp]BF$_4$: (R,R)-1,2-bis[(2-methoxyphenyl)phenylphosphino]ethane(1,5-cyclooctadiene)rhodium(I) tetrafluoroborate

[Rh(cod) (S)-xyl-binap]OTf: {(S)-(−)-2,2'-bis[di(3,5-xylyl)phosphino]-1,1'-binaphthyl}(1,5-cyclooctadiene)rhodium(I) trifluoromethanesulfonate RuCl$_2${(R)-binap}: dichloro[(R)-2,2'-bis(diphenylphosphino)-1,1'-binaphthyl]ruthenium(II)

RuCl$_2${(R)-binap}{R,R-dpen}: dichloro[(R)-2,2'-bis(diphenylphosphino)-1,1'-binaphthyl]{(1R,2R)-(+)-1,2-diphenylmethanediamine}ruthenium(II)

RuCl$_2${(R)-binap}{R,R-dach}: dichloro[(R)-2,2'-bis(diphenylphosphino)-1,1'-binaphthyl]{(1R,2R)-(+)-1,2-diaminocyclohexane}ruthenium(II)

RuCl$_2${(R)-binap}{R-daipen}: dichloro{(R)-2,2'-bis(diphenylphosphino)-1,1'-binaphthyl}[(2R)-(−)-1,1-bis(4-methoxyphenyl)-3-methyl-1,2-butanediamine]ruthenium(II)

RuCl$_2${(R)-xyl-binap}{R,R-dpen}: dichloro{(R)-(+)-2,2'-bis[di(3,5-xylyl)phosphino]-1,1'-binaphthyl}{(1R,2R)-(+)-1,2-diphenylmethanediamine}ruthenium(II)

RuCl$_2${(R)-xyl-binap}{R,R-dach}:dichloro{(R)-(+)-2,2'-bis[di(3,5-xylyl)phosphino]-1,1'-binaphthyl}{(1R,2R)-(+)-1,2-diaminocyclohexane}ruthenium(II)

RuCl$_2${(R)-xyl-binap}{R-daipen}: dichloro{(R)-(+)-2,2'-bis[di(3,5-xylyl)phosphino]-1,1'-binaphthyl}[(2R)-(−)-1,1-bis(4-methoxyphenyl)-3-methyl-1,2-butanediamine]ruthenium(II)

[Ir(cod)$_2$]BARF: bis(1,5-cyclooctadiene)iridium(I) tetrakis[3,5-bis(trifluoromethyl)phenyl]borate

[Ir(cod)$_2$]BF$_4$: bis(1,5-cyclooctadiene)iridium(I) tetrafluoroborate

[IrCl(cod)]$_2$: chloro(1,5-cyclooctadiene)iridium(I) dimer

[IrOMe(cod)]$_2$: (1,5-cyclooctanediene)methoxyiridium(I) dimer

Ir(acac) (cod): (acetylacetonato) (1,5-cyclooctanediene) iridium(I)

Pd(OCOCF$_3$)$_2$: palladium (II) trifluoroacetate

Pd(OAC)$_2$: palladium(II) acetate (R)—(S)-Josiphos (SL-J001-1): (R)-(−)-1-[(S)-2-(diphenylphosphino)ferrocenyl]ethyldicyclohexylphosphine SL-M001-1: (αR,αR)-2,2'-bis(α-N,N-dimethylaminophenylmethyl)-(S,S)-1,1'-bis(diphenylphosphino)ferrocene SL-W001-1: (R)-1-[(R)-2-(2'-diphenylphosphinophenyl)ferrocenyl]ethyldi(bis-3,5-trifluoromethylphenyl)phosphine SL-W002-1: (R)-1-[(R)-2-(2'-diphenylphosphinophenyl)ferrocenyl]ethyldiphenylphosphine SL-W003-1: (R)-1-[(R)-2-(2'-diphenylphosphinophenyl)ferrocenyl]ethyldicyclohexylphosphine SL-T001-1: (S)-1-diphenylphosphino-2-[(R)-α-(N,N-dimethylamino)-o-diphenylphosphinophenyl-methyl]ferrocene SL-T002-1: (S)-1-dicyclohexylphosphino-2-[(R)-α-(N,N-dimethylamino)-o-dicyclohexylphosphinophenyl-methyl]ferrocene SL-J004-1: (R)-1-[(1S)-2-(dicyclohexylphosphino)ferrocenyl]ethyldiphenylphosphine (S) (R)-SL-J002-02: (S)-1-[(R)-2-(diphenylphosphino)ferrocenyl]ethyldi-t-butylphosphine (R) (S)-SL-J502-1: (R)-1-[(S)-2-(di-t-butylphosphino)ferrocenyl]ethyldiphenylphosphine (R) (S)-SL-J009-1: (R)-1-[(S)-2-(dicyclohexylphosphino)ferrocenyl]ethyldi-t-butylphosphine (R) (S)-SL-J005-1: (R)-1-[(S)-2-(diphenylphosphino)ferrocenyl]ethyldi-3,5-xylylphosphine (R) (S)-SL-J011-1: (R)-1-[(S)-2-[di-(4-trifluoromethylphenyl)phosphino]ferrocenyl]ethyldi-t-butylphosphine (R) (S)-SL-J013-1: (R)-1-[(S)-2-[di-(3,5-dimethyl-4-methoxyphenyl)phosphino]ferrocenyl]ethyldi-t-butylphosphine (R) (S)-SL-J014-1: (R)-1-[(S)-2-[di-(4-fluorophenyl)phosphino]ferrocenyl]ethyldi-t-butylphosphine (R) (S)-SL-J212-1: (R)-1-[(S)-2-(di-2-furylphosphino)ferrocenyl]ethyldi-t-butylphosphine (R) (S)-SL-J216-1: (R)-1-[(S)-2-(di-1-naphthylphosphino)ferrocenyl]ethyldi-t-butylphosphine (R) (S)-SL-J202-1: (R)-1-[(S)-2-[di-(4-methoxyphenyl)phosphino]ferrocenyl]ethyldi-t-butylphosphine (R) (S)-SL-J203-1: (R)-1-[(S)-2-[di-(3,5-di-t-butyl-4-methoxyphenyl)phosphino]ferrocenyl]ethyldi-t-butylphosphine (R) (S)-SL-J210-1: (R)-1-[(S)-2-[di-(3,5-di-trifluoromethylphenyl)phosphino]ferrocenyl]ethyldi-t-butylphosphine (S) (R)-SL-J210-2: (S)-1-[(R)-2-[di-(3,5-di-trifluoromethylphenyl)phosphino]ferrocenyl]ethyldi-t-butylphosphine (R,R)-Skewphos: (2R,4R)-(+)-2,4-bis(diphenylphosphino)pentane (R)-BINAP: (R)-2,2'-bis(diphenylphosphino)-1,1'-binaphthyl (R)-xylyl-BINAP: (R)-(+)-2,2'-bis[di(3,5-xylyl)phosphino]-1,1'-binaphthyl (S)-H8-BINAP: (S)-(−)-2,2'-bis(diphenylphosphino)-5,5',6,6',7,7',8,8'-octahydro-1,1'-binaphthyl (R,R)-Me-Duphos: (−)-1,2-bis[(2R,5R)-2,5-dimethylphosphorano]benzene (R,R)-Et-Duphos: (−)-1,2-bis[(2R,5R)-2,5-diethylphosphorano]benzene (R,R)-iPr-Duphos: (−)-1,2-bis[(2R,5R)-2,5-diisopropylphosphorano]benzene (R,R)-Ph-BPE: (−)-1,2-bis((2R,5R)-2,5-diphenylphosphorano)ethane (R)-Phanephos: (R)-(−)-4,12-bis(diphenylphosphino)-[2.2]-paracyclophane (S)-xyl-Phanephos: (S)-(+)-4,12-bis(di(3,5-xylyl)phosphino)-[2.2]-paracyclophane (S,S)-Et-Ferrotane: (−)-1,1'-bis[(2S,4S)-2,4-diethylphosphotano]ferrocene (R,R)-DIPAMP: (R,R)-1,2-bis[(2-methoxyphenyl)phenylphosphino]ethane (R,R)-Quinox-P*: (R,R)-(−)-2,3-bis(t-butylmethylphosphino)quinoxaline (S)-DTBM-Segphos: (S)-(+)-5,5'-bis[di(3,5-di-t-butyl-4-methoxyphenyl)phosphino]-4,4'-bi-1,3-benzodioxole (R)—C$_3$-Tunephos: (R)-(−)-1,13-bis(diphenylphosphino)-7,8-dihydro-6H-dibenzo[f,h][1,5]dioxonin (S)-MeO-BIPHEP: (S)-(−)-2,2'-bis(diphenylphosphino)-6,6'-dimethoxy-1,1'-biphenyl
(S)-ShiP: phenyl-[(S)-1,1-spirobiindane-7,7-diyl]phosphite
(S)-MOP: (S)-(−)-2-diphenylphosphino-2'-methoxy-1,1'-binaphthyl
(R)-QuINAP: (R)-1-[2-(diphenylphosphino)-1-naphthyl]isoquinoline
(S)-Monophos: (S)-(+)-(3,5-dioxa-4-phospha-cyclohepta[2,1-a;3,4-a']dinaphthalen-4-yl)dimethylamine
(S)-Me-Monophos: (S)-(+)-(2,6-dimethyl-3,5-dioxa-4-phospha-cyclohepta[2,1-a;3,4-a']dinaphthalen-4-yl)dimethylamine
(R,R)-Taddol-type: (3aR,8aR)-(−)-(2,2-dimethyl-4,4,8,8-tetraphenyl-tetrahydro-[1,3]dioxolo[4,5-e][1,3,2]dioxaphosphepin-6-yl)dimethylamine
(S)-BnMe: (S)-(+)-(3,5-dioxa-4-phospha-cyclohepta[2,1-a;3,4-a']dinaphthalen-4-yl)benzyl(methyl)amine
(S,R,R)-alpha-phenethyl: (S)-(+)-(3,5-dioxa-4-phospha-cyclohepta[2,1-a;3,4-a']dinaphthalen-4-yl)bis[(1R)-1-phenylethyl]amine
(S)-Et-Monophos: (S)-(+)-(2,6-dimethyl-3,5-dioxa-4-phospha-cyclohepta[2,1-a;3,4-a']dinaphthalen-4-yl)diethylamine
(S)-Morphos: (S)-(+)-(3,5-dioxa-4-phosphacyclohepta[2,1-a;3,4-a']dinaphthalen-4-yl)morpholine
(S)-alpha-phenethylH: (S)-(+)-(3,5-dioxa-4-phospha-cyclohepta[2,1-a;3,4-a']dinaphthalen-4-yl) [(1R)-1-phenylethyl]amine
(S)-Pipphos: (S)-(+)-(3,5-dioxa-4-phosphacyclohepta[2,1-a;3,4-a']dinaphthalen-4-yl)piperidine
(S)-H8-Monophos: (S)-(+)-(8,9,10,11,12,13,14,15-octahydro-3,5-dioxa-4-phospha-cyclohepta[2,1-a;3,4-a']dinaphthalen-4-yl)dimethylamine
(R,R)-cataciumM(R): (−)-2,3-bis[(2R,5R)-2,5-dimethylphosphorano]maleic anhydride cataASium T3: (+)-{4-[(1R,4S)-3-(diphenylphosphino)-1,7,7-trimethylbicyclo[2.2.1]heptenehept-2-en-2-yl]-2,5-dimethyl-3-thienyl}bis(3,5-dimethylphenyl)phosphine
(R,R)-Norphos: (2R,3R)-(−)-2,3-bis(diphenylphosphino) bicyclo[2.2.1]hept-5-ene
(R)-iPr-PHOX: (R)-(+)-2-[2-(diphenylphosphino)phenyl]-4-isopropyl-2-oxazoline
DMF: N,N-dimethylformamide
CPME: cyclopentyl methyl ether
DME: dimethyl ether
MeCN: acetonitrile
AcOH: acetic acid
EtOH: ethanol
NBS: N-bromosuccinimide
Et$_3$N: triethylamine
EDC: 1-[3-(dimethylamino)propyl]-3-ethylcarbodiimide hydrochloride
HOBT: 1-hydroxybenzotriazole
DMAc: N,N-dimethylacetamide
1-BuOH: n-butanol
IPA: 2-propanol
DMSO: dimethylsulfooxide
THF: tetrahydrofuran
DCM: dichloromethane
MeOH: methanol
p-TsOH: p-toluenesulfonic acid
TMSCl: chlorotrimethylsilane
DCE: 1,2-dichloroethane
Et$_3$SiH: triethylsilane
(S)-MA: (S)-mandelic acid
MS4A: molecular sieve 4A
TMEDA: tetramethylethylene diamine
AHN: ammonium 2-hydroxynicotinate
APC: ammonium picolinate
ATFA: ammonium trifluoroacetate
(−)-CSA: (−)-10-camphorsulfonic acid

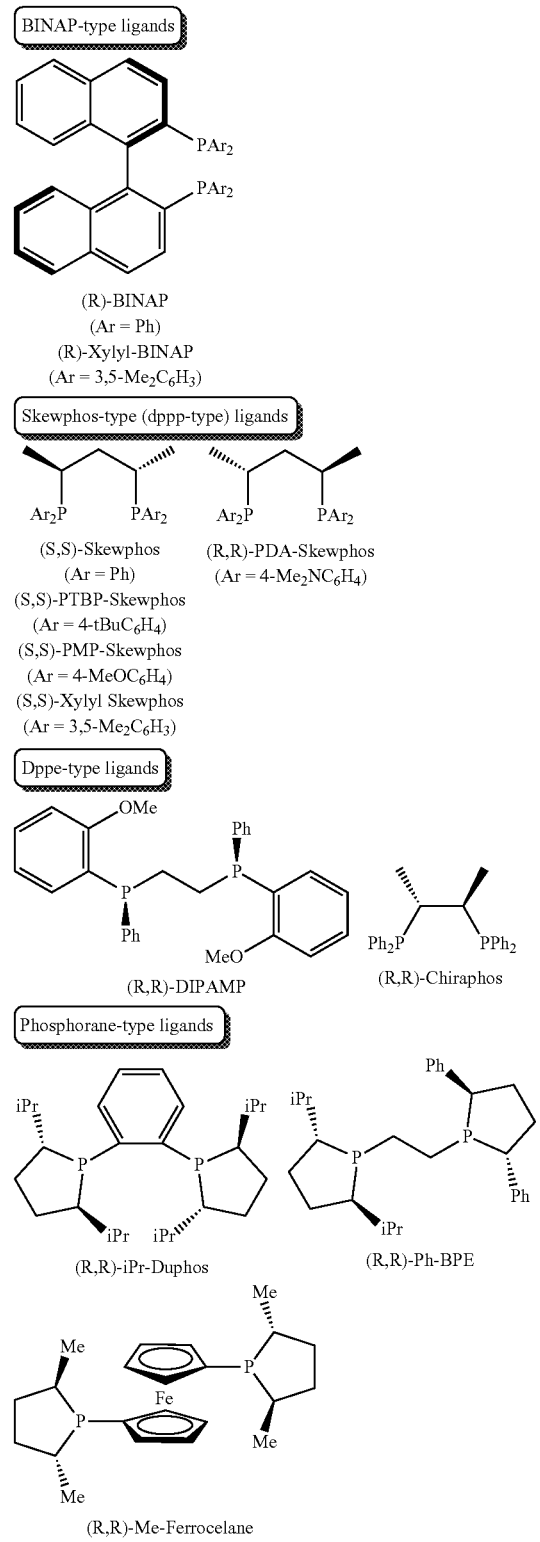

-continued

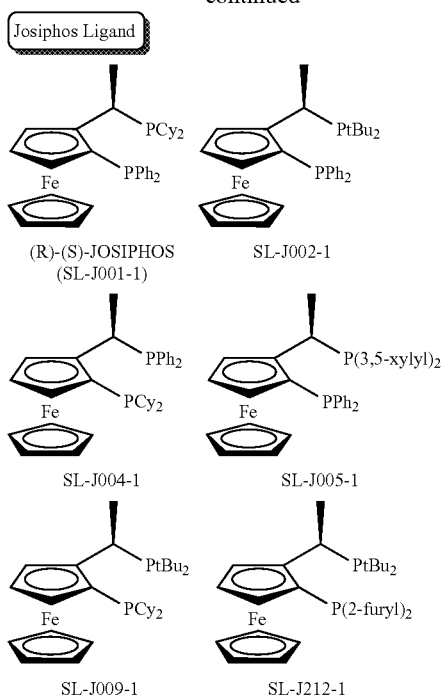

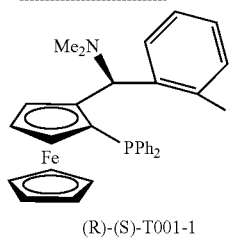

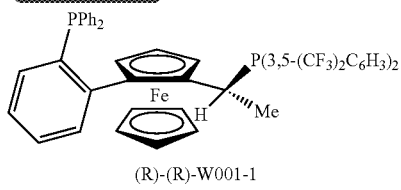

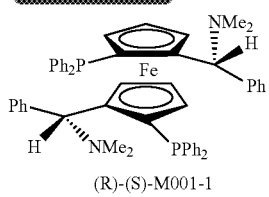

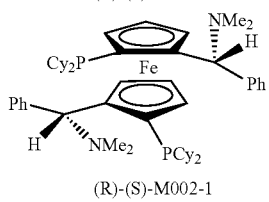

-continued

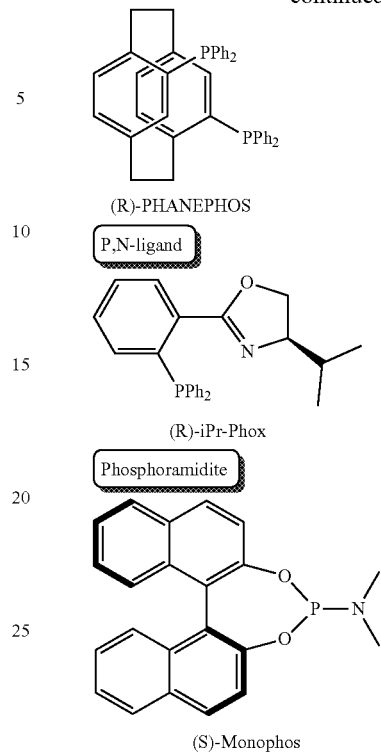

In the following Reference Examples and Examples, the nuclear magnetic resonance spectrum (NMR) was measured under the following conditions.

$^1$H nuclear magnetic resonance spectrum ($^1$H-NMR): BRUKER AVANCE (500 MHz) manufactured by Bruker Corporation, internal standard material: tetramethylsilane $^{13}$C nuclear magnetic resonance spectrum ($^{13}$C-NMR): BRUKER AVANCE 500 (125 MHz) manufactured by Bruker Corporation, internal standard material: CDCl$_3$ $^{19}$F nuclear magnetic resonance spectrum ($1^9$F-NMR): BRUKER AVANCE 500 (202 MHz) manufactured by Bruker Corporation, external standard material: trifluoroacetic acid $^{31}$P nuclear magnetic resonance spectrum ($^{31}$P-NMR): BRUKER AVANCE 500 (471 MHz) manufactured by Bruker Corporation, external standard material: 85%-H$_3$PO$_4$ aqueous solution Reference Example 1

Synthesis of 2-acetyl-N-(5-chloro-4-(trifluoromethyl)pyridin-2-yl)-1,3-thiazole-5-carboxamide

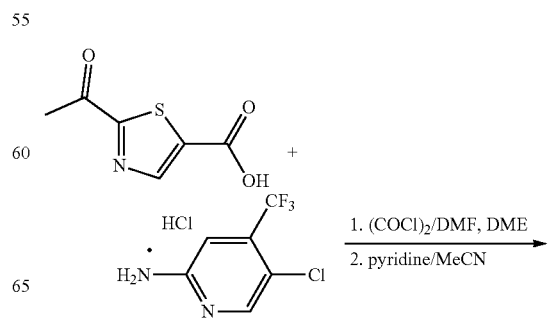

-continued

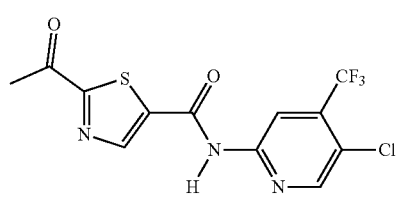

2-Acetyl-1,3-thiazole-5-carboxylic acid (24.7 g), 1,2-dimethoxyethane (43 mL), N,N-dimethylformamide (0.047 g) and oxalyl chloride (17.8 g) were put into a four-necked eggplant flask (100 mL), and the mixture was stirred at room temperature for 2 hr (Reaction Solution 1). Separately, 5-chloro-4-(trifluoromethyl)pyridin-2-amine hydrochloride (30.0 g), acetonitrile (96 mL) and pyridine (30.8 g) were put into a four-necked eggplant flask (500 mL), and the mixture was cooled to about 5° C. (Reaction Solution 2). Reaction Solution 1 was added to Reaction Solution 2 at 35° C. or lower, and 1,2-dimethoxyethane (15 mL) was added thereto. The mixture was stirred at room temperature for 1 hr, warmed to about 50° C., and stirred for 1 hr. Water (210 mL) was added thereto at about 50° C., and the mixture was cooled to room temperature, and was stirred for 30 min. The crystallized substance was collected by filtration, washed with a mixed solvent of acetonitrile (22.5 mL) and water (67.5 mL), washed with water (180 mL), and dried under reduced pressure at 50° C. to give the title compound. pale-brown powder, 43.4 g, yield 96%, purity 99.0% (HPLC).

Conditions for High-Performance Liquid Chromatography Analysis (Area Normalization)

column: Inertsil ODS-3 5 µm, 4.6 mm i.d.×150 mm

UV detection wavelength: 254 nm column temperature: 25° C.

mobile phase:

TABLE 1

|  | acetonitrile/0.025 mol/L aqueous potassium dihydrogenphosphate solution (6:4) | acetonitrile/0.025 mol/L aqueous potassium dihydrogenphosphate solution (8:2) |
| --- | --- | --- |
| 0.00 min. | 100% | 0% |
| 5.00 min. | 100% | 0% |
| 10.00 min. | 0% | 100% |
| 50.00 min. | 0% | 100% | flow rate: 1.0 mL/min retention time: 8.9 min (the title compound)

$^1$H NMR (DMSO-$d_6$) δ 2.67 (s, 3H), 8.58 (s, 1H), 8.80 (s, 1H), 9.00 (s, 1H), 12.00 (s, 1H). HRMS (ESI) calcd for $C_{12}H_8ClF_3N_3O_2S$ [(M+H)$^+$] 349.9972, found 349.9977. m.p. 165° C.

Reference Example 2

Synthesis of (E)-2-(1-(benzhydrylimino)ethyl)-N-(5-chloro-4-(trifluoromethyl)pyridin-2-yl)-1,3-thiazole-5-carboxamide

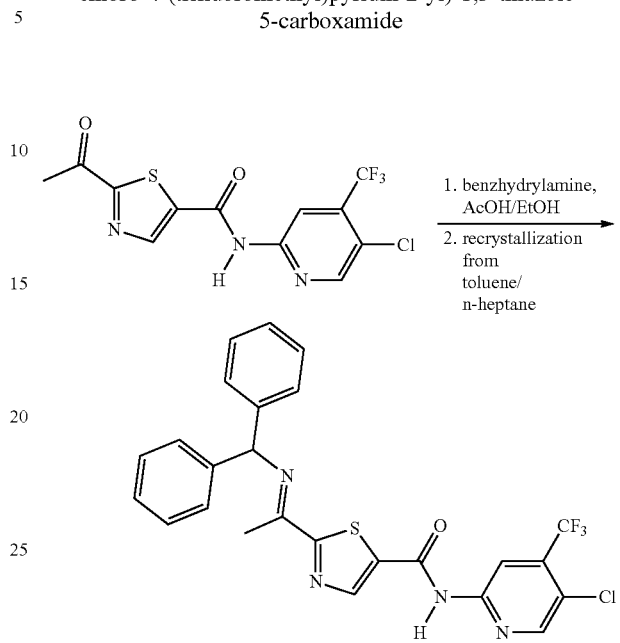

2-Acetyl-N-(5-chloro-4-(trifluoromethyl)pyridin-2-yl)-1,3-thiazole-5-carboxamide (40.0 g), ethanol (200 mL), benzhydrylamine (23.1 g) and acetic acid (1.96 mL) were put into a four-necked eggplant flask (300 mL) equipped with Dean-Stark trap, and the mixture was heated under reflux for 6.5 hr. The mixture was cooled to room temperature, and stirred for 1 hr. The crystallized substance was collected by filtration, washed with ethanol (100 mL), and dried under reduced pressure at 50° C. to give crystals. The obtained all crystals (59.4 g) and toluene (300 mL) were put into four-necked eggplant flask (2 L), and the mixture was heated under reflux until 60 mL of the solvent was evaporated. To the residue was added toluene (60 mL), and the mixture was heated under reflux until evaporation of 60 mL of the solvent. The procedure was performed three times in total. N-heptane (900 mL) was added thereto at about 80° C., and the mixture was cooled to room temperature, and stirred for 1 hr. The crystallized substance was collected by filtration, washed with a mixed solvent of toluene (40 mL) and n-heptane (200 mL), and dried under reduced pressure at 60° C. to give the title compound. white powder, 51.4 g, yield 87%, purity 99.7% (HPLC).

Conditions for High-Performance Liquid Chromatography Analysis (Area Normalization)

column: Inertsil C8-4, HP 3 µm, 4.6 mm i.d.×150 mm

UV detection wavelength: 254 nm column temperature: 25° C.

mobile phase:

TABLE 2

|  | 0.005 mol/L aqueous potassium dihydrogenphosphate solution/ 0.005 mol/L aqueous dipotassium hydrogenphosphate solution (1:1) | acetonitrile |
| --- | --- | --- |
| 0.00 min. | 45% | 55% |
| 2.00 min. | 45% | 55% |

TABLE 2-continued

| | 0.005 mol/L aqueous potassium dihydrogenphosphate solution/ 0.005 mol/L aqueous dipotassium hydrogenphosphate solution (1:1) | acetonitrile |
|---|---|---|
| 25.00 min. | 20% | 80% |
| 30.00 min. | 20% | 80% | flow rate: 1.0 mL/min
retention time: 20.8 min (the title compound)
$^1$H NMR (CDCl$_3$) δ 2.46 (s, 3H), 5.90 (s, 1H), 7.24 (m, 2H), 7.33 (m, 4H), 7.45 (m, 4H), 8.36 (s, 1H), 8.43 (brs, 1H), 8.44 (s, 1H), 8.69 (s, 1H). HRMS (ESI) calcd for C$_{25}$H$_{19}$ClF$_3$N$_4$OS [(M+H)$^+$]515.0915, found 515.0914. m.p. 175° C.

Example 1

Synthesis of 2-((1R)-1-aminoethyl)-N-(5-chloro-4-(trifluoromethyl)pyridin-2-yl)-1,3-thiazole-5-carboxamide (S)-mandelate

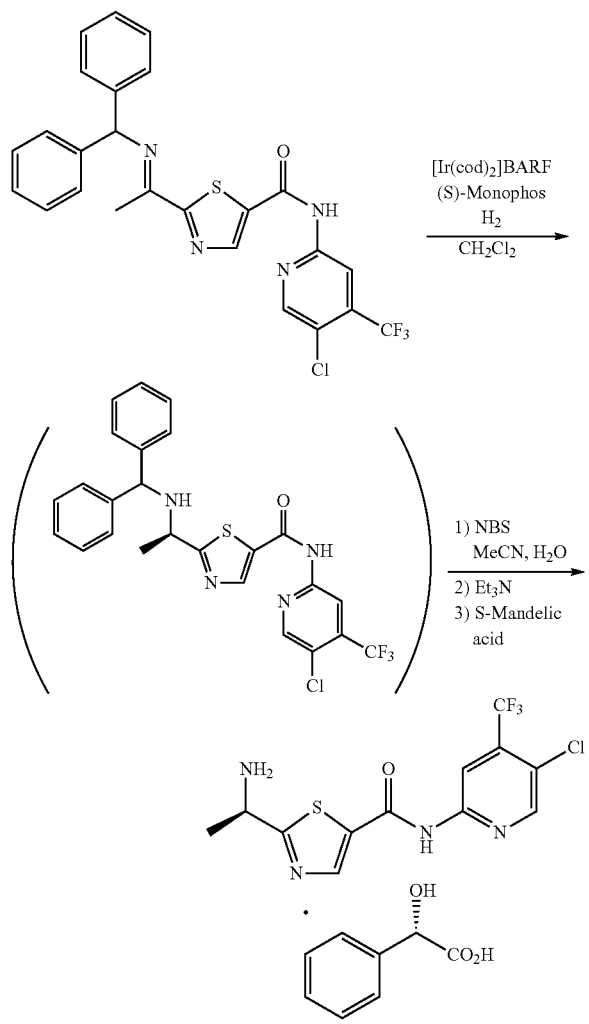

(E)-2-(1-(Benzhydrylimino)ethyl)-N-(5-chloro-4-(trifluoromethyl)pyridin-2-yl)-1,3-thiazole-5-carboxamide (45.0 g), [Ir(cod)$_2$]BARF (0.167 g) and (S)-Monophos (0.104 g) were put into an autoclave (1 L). The atmosphere in the autoclave was decompressed, and replaced with argon, and dehydrated dichloromethane (500 mL) was added thereto. The mixture was stirred at room temperature for 10 min, and hydrogen was fed into the autoclave until 0.65 MPa. The mixture was heated to about 50° C., hydrogen was fed into the autoclave until 0.80 MPa, and the mixture was stirred for 24 hr. The mixture was cooled to room temperature, the hydrogen was released, and the atmosphere was replaced with argon. The mixture was concentrated under reduced pressure, acetonitrile (135 mL) was added thereto, and the mixture was concentrated under reduced pressure. Acetonitrile (135 mL) and water (22.5 mL) were added thereto, and then N-bromosuccinimide (17.1 g) was added thereto at room temperature, and the mixture was stirred for 18 hr. Triethylamine (9.73 g) and acetonitrile (900 mL) were added thereto at room temperature, and then (S)-mandelic acid (16.0 g) dissolved in acetonitrile (270 mL) was added dropwise thereto at room temperature. The crystallized substance was collected by filtration, washed with acetonitrile (180 mL), and dried under reduced pressure at 50° C. to give the title compound. white powder, 32.9 g, yield 75%, purity 99.9% (HPLC), optical purity 98.6% de (chiral HPLC).
Conditions for High-Performance Liquid Chromatography Analysis (Area Normalization)
  column: L-column2 ODS, S-5 μm, 4.6 mm i.d.×250 mm
  UV detection wavelength: 220 nm
  column temperature: 25° C.
  mobile phase:

TABLE 3

| | 0.1 v/v % aqueous phosphoric acid solution | acetonitrile |
|---|---|---|
| 0.00 min. | 90% | 10% |
| 2.00 min. | 90% | 10% |
| 30.00 min. | 10% | 90% |
| 40.00 min. | 10% | 90% | flow rate: 1.0 mL/min
retention time: 14.9 min (the title compound)
Conditions for High-Performance Liquid Chromatography Analysis (Optical Purity)
  column: CROWNPAK CR-I(+), S-5 μm, 3.0 mm i.d.×150 mm
  UV detection wavelength: 305 nm
  column temperature: 25° C.
  mobile phase:

TABLE 4

| | 0.5% aqueous perchloric acid solution | acetonitrile |
|---|---|---|
| 0.00 min. | 60% | 40% |
| 2.00 min. | 60% | 40% |
| 15.00 min. | 40% | 60% |
| 16.00 min. | 10% | 90% |
| 20.00 min. | 10% | 90% | flow rate: 0.5 mL/min
retention time: 5.2 min (R), 8.1 min (S)
$^1$H NMR (DMSO-d$_6$) δ 1.43 (d, J=6.5 Hz, 3H), 4.33 (m, 1H), 4.91 (s, 1H), 7.25 (m, 1H), 7.32 (m, 1H), 7.40 (m, 1H), 8.59 (s, 1H), 8.73 (s, 1H), 8.77 (s, 1H), 11.66 (brs, 1H). m.p. 152° C.

Example 2

Synthesis of 2-((1R)-1-aminoethyl)-N-(5-chloro-4-(trifluoromethyl)pyridin-2-yl)-1,3-thiazole-5-carboxamide

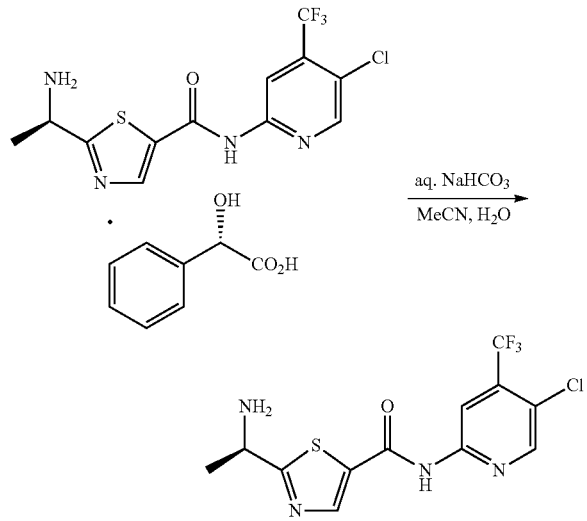

Water (145 mL), sodium hydrogencarbonate (8.35 g), acetonitrile (145 mL) and 2-((1R)-1-aminoethyl)-N-(5-chloro-4-(trifluoromethyl)pyridin-2-yl)-1,3-thiazole-5-carboxamide (S)-mandelate (25.0 g) were put into a four-necked eggplant flask (500 mL), and the mixture was stirred at room temperature for 15 min. Activated carbon SHIRASAGI A (2.5 g) was added thereto, and the mixture was stirred at room temperature for 15 min. The activated carbon was removed by filtration, and washed with a mixed solvent of acetonitrile (12.5 mL) and water (12.5 mL). To the filtrate and washing was added water (250 mL) at room temperature, and the mixture was stirred at room temperature for 1 hr. The crystallized substance was collected by filtration, washed with water (300 mL), and dried under reduced pressure at 50° C. to give the title compound. white powder, 15.1 g, yield 87%, purity 99.9% (HPLC). optical purity 98.6% ee (chiral HPLC).

Conditions for High-Performance Liquid Chromatography Analysis (Area Normalization)

column: L-column2 ODS, S-5 μm, 4.6 mm i.d.×250 mm
UV detection wavelength: 220 nm
column temperature: 25° C.
mobile phase:

TABLE 5

|  | 0.1 v/v % aqueous phosphoric acid solution | acetonitrile |
| --- | --- | --- |
| 0.00 min. | 90% | 10% |
| 2.00 min. | 90% | 10% |
| 30.00 min. | 10% | 90% |
| 40.00 min. | 10% | 90% | flow rate: 1.0 mL/min
retention time: 14.9 min (the title compound)

Conditions for High-Performance Liquid Chromatography Analysis (Optical Purity)

column: CROWNPAK CR-I(+), S-5 μm, 3.0 mm i.d.×150 mm
UV detection wavelength: 305 nm
column temperature: 25° C.
mobile phase:

TABLE 6

|  | 0.5% aqueous perchloric acid solution | acetonitrile |
| --- | --- | --- |
| 0.00 min. | 60% | 40% |
| 2.00 min. | 60% | 40% |
| 15.00 min. | 40% | 60% |
| 16.00 min. | 10% | 90% |
| 20.00 min. | 10% | 90% | flow rate: 0.5 mL/min
retention time: 5.2 min (R), 8.1 min (S)
$^1$H NMR (DMSO-$d_6$) δ 1.39 (d, J=7.0 Hz, 3H), 4.21 (q, J=7.0 Hz, 1H), 8.59 (s, 1H), 8.70 (s, 1H), 8.76 (s, 1H), 11.59 (brs, 1H). HRMS (ESI) calcd for $C_{12}H_{11}ClF_3N_4OS$ [(M+H)$^+$] 351.0289, found 351.0290. m.p. 154° C.

Example 3

Synthesis of 6-amino-5-chloro-N-((1R)-1-(5-((5-chloro-4-(trifluoromethyl)pyridin-2-yl)carbamoyl)-1,3-thiazol-2-yl)ethyl)pyrimidine-4-carboxamide

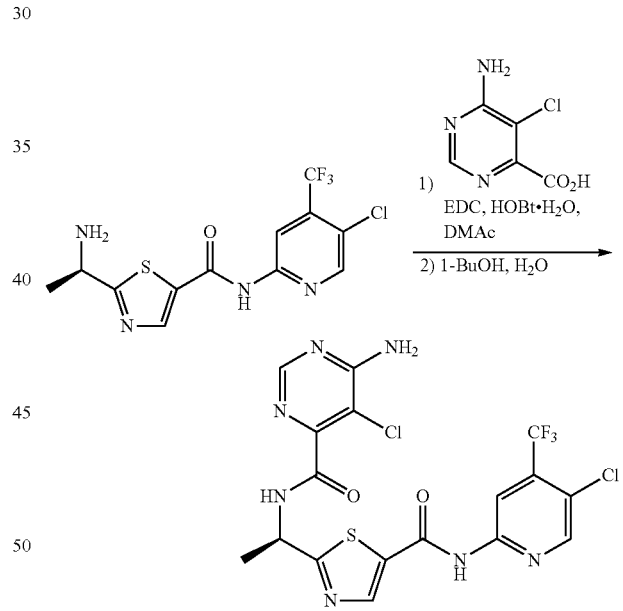

1-Hydroxybenzotriazole monohydrate (1.31 g), 6-amino-5-chloropyrimidine-4-carboxylic acid (8.16 g) and 2-((1R)-1-aminoethyl)-N-(5-chloro-4-(trifluoromethyl)pyridin-2-yl)-1,3-thiazole-5-carboxamide (15.0 g) and N,N-dimethylacetamide (75 mL) were put into a four-necked eggplant flask (500 mL), 1-ethyl-3-(3-dimethylaminopropyl)carbodiimide hydrochloride (8.61 g) was added thereto, and the mixture was stirred at room temperature for 4 hr. n-Butanol (75 mL) was added thereto at room temperature, and the mixture was heated to about 55° C. Water (180 mL) was added thereto, and the mixture was stirred for 40 min. Water (45 mL) was added thereto at about 55° C., and the mixture was cooled to room temperature, and stirred for 30 min. The crystallized substance was collected by filtration, washed with water (150 mL), and dried under reduced pressure at 60° C. to give the title compound. white powder, 19.1 g, yield 88%, purity 99.9% (HPLC). optical purity 96.1% ee (chiral HPLC).
Conditions for High-Performance Liquid Chromatography Analysis (Area Normalization)
   column: Waters XTerra RP18, 5 μm, 3.9×150 mm
   UV detection wavelength: 254 nm
   column temperature: 30° C.
   mobile phase:

TABLE 7

|  | 0.1 v/v % aqueous formic acid solution | 0.1 v/v % formic acid-containing acetonitrile |
| --- | --- | --- |
| 0.00 min. | 80% | 20% |
| 1.00 min. | 80% | 20% |
| 26.00 min. | 15% | 85% |
| 31.00 min. | 15% | 85% | flow rate: 0.6 mL/min
   retention time: 16.0 min (the title compound)
Conditions for High-Performance Liquid Chromatography Analysis (Optical Purity)
   column: CHIRALPAK IC-3, 3 μm, 4.6×150 mm
   UV detection wavelength: 277 nm
   column temperature: 40° C.
   mobile phase: aqueous formic acid solution (pH 2.0)/acetonitrile=6/4
   flow rate: 1.0 mL/min
   retention time: 14.1 min (R), 16.7 min (S)
   $^1$H NMR (DMSO-$d_6$) δ 1.59 (d, J=7.0 Hz, 3H), 5.35 (m, 1H), 7.41 (brs, 1H), 7.81 (brs, 1H), 8.37 (s, 1H), 8.58 (s, 1H), 8.76 (s, 1H), 8.78 (s, 1H), 9.51 (d, J=8.0 Hz, 3H), 11.76 (s, 1H). HRMS (ESI) calcd for $C_{17}H_{13}C_{12}F_3N_7O_2S$ [(M+H)$^+$] 506.0175, found 506.0175. m.p. 206° C.

Example 4

Purification of 6-amino-5-chloro-N-((1R)-1-(5-((5-chloro-4-(trifluoromethyl)pyridin-2-yl)carbamoyl)-1,3-thiazol-2-yl)ethyl)pyrimidine-4-carboxamide

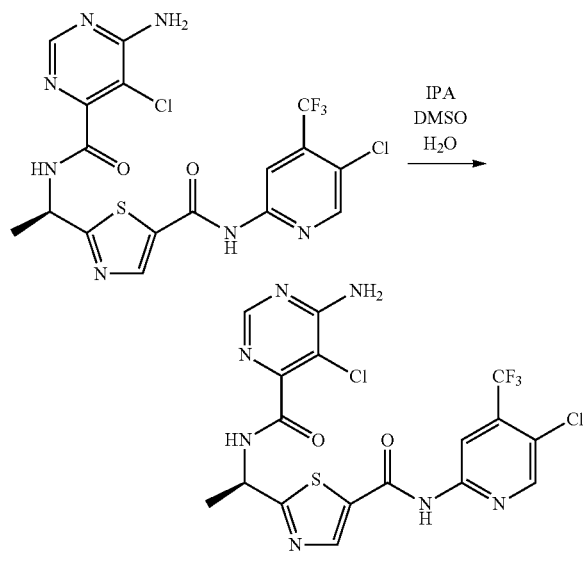

6-Amino-5-chloro-N-((1R)-1-(5-((5-chloro-4-(trifluoromethyl)pyridin-2-yl)carbamoyl)-1,3-thiazol-2-yl)ethyl)pyrimidine-4-carboxamide (15.0 g), dimethyl sulfoxide (25.5 mL) and 2-propanol (102 mL) were put into four-necked eggplant flask (200 mL), and the mixture was heated to about 75° C. The insoluble substance was removed by filtration, and washed with a mixed solvent of dimethyl sulfoxide (4.5 mL) and 2-propanol (18 mL). To the filtrate and washing was added water (45 mL) at about 75° C., and the seed crystals of 6-amino-5-chloro-N-((1R)-1-(5-((5-chloro-4-(trifluoromethyl)pyridin-2-yl)carbamoyl)-1,3-thiazol-2-yl)ethyl)pyrimidine-4-carboxamide (15.0 mg) was added thereto, and the mixture was stirred for 30 min. The mixture was cooled to about 45° C., and stirred for 1 hr. The mixture was heated to about 75° C., and water (90 mL) was added thereto. The mixture was cooled to room temperature, and stirred for 1 hr. The crystallized substance was collected by filtration, washed with 2-propanol (150 mL), and dried under reduced pressure at 60° C. to give the title compound. white powder, 13.8 g, yield 91%, purity 99.9% (HPLC). optical purity 97.5% ee (chiral HPLC).
Conditions for High-Performance Liquid Chromatography Analysis (Area Normalization)
   column: Waters XTerra RP18, 5 μm, 3.9×150 mm
   UV detection wavelength: 254 nm
   column temperature: 30° C.
   mobile phase:

TABLE 8

|  | 0.1 v/v % aqueous formic acid solution | 0.1 v/v % formic acid-containing acetonitrile |
| --- | --- | --- |
| 0.00 min. | 80% | 20% |
| 1.00 min. | 80% | 20% |
| 26.00 min. | 15% | 85% |
| 31.00 min. | 15% | 85% | flow rate: 0.6 mL/min
   retention time: 16.0 min (the title compound)
Conditions for High-Performance Liquid Chromatography Analysis (Optical Purity)
   column: CHIRALPAK IC-3, 3 μm, 4.6×150 mm
   UV detection wavelength: 277 nm
   column temperature: 40° C.
   mobile phase: aqueous formic acid solution (pH 2.0)/acetonitrile=6/4
   flow rate: 1.0 mL/min
   retention time: 14.1 min (R), 16.7 min (S)
   $^1$H NMR (DMSO-$d_6$) δ 1.59 (d, J=7.0 Hz, 3H), 5.35 (m, 1H), 7.41 (brs, 1H), 7.81 (brs, 1H), 8.37 (s, 1H), 8.58 (s, 1H), 8.76 (s, 1H), 8.78 (s, 1H), 9.51 (d, J=8.0 Hz, 3H), 11.76 (s, 1H). HRMS (ESI) calcd for $C_{17}H_{13}C_{12}F_3N_7O_2S$ [(M+H)$^+$] 506.0175, found 506.0175. m.p. 206° C.

Example 5

Synthesis of 2-((1R)-1-(benzhydrylamino)ethyl)-N-(5-chloro-4-(trifluoromethyl)pyridin-2-yl)-1,3-thiazole-5-carboxamide

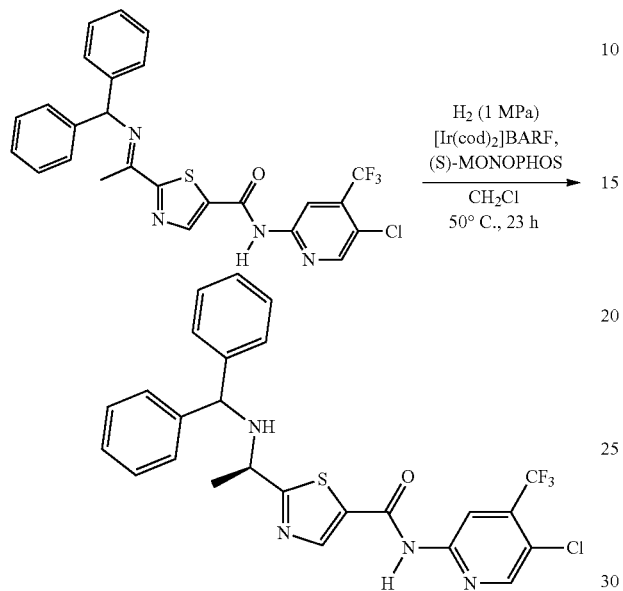

(E)-2-(1-(Benzhydrylimino)ethyl)-N-(5-chloro-4-(trifluoromethyl)pyridin-2-yl)-1,3-thiazole-5-carboxamide (290.66 g), [Ir(cod)$_2$]BARF (1.44 g) and (S)-MONOPHOS (0.89 g) were put into an autoclave (10 L). The atmosphere in the autoclave was decompressed until the pressure was decreased by −0.90 MPa or below, and the pressure was recovered to about 0.1 MPa with argon. The procedures were performed seven times in total. The pressure of the autoclave was recovered to normal pressure, and dehydrated dichloromethane (3 L) for organic synthesis was fed thereto by argon pressure. The mixture was stirred for 10 min. After stopping the stirring, hydrogen was fed into the autoclave until the pressure was increased by 0.1 MPa, and the pressure was recovered to normal pressure. The procedures were performed ten times in total. Hydrogen was fed into the autoclave until 0.90 MPa, and the mixture was stirred at the internal temperature of 50° C. for 23 hr. The mixture was cooled to the internal temperature of about 20° C., and the hydrogen was released. The atmosphere was replaced with argon, and the reaction solution was taken out. The reaction solution was concentrated under reduced pressure to give the title compound. brown oil, 304.77 g, yield 104.5%, HPLC area normalization 99.3%, optical purity 89.9% ee.

Conditions for High-Performance Liquid Chromatography Analysis (Area Normalization)
- column: YMC-Pack ODS-A (manufactured by YMC. CO., LTD.), 4.6*150 mm
- UV detection wavelength: 254 nm
- mobile phase: acetonitrile for high-performance liquid chromatography/0.025 mol/L aqueous potassium dihydrogenphosphate solution=8/2
- flow rate: 1.0 mL/min
- retention time: 6.9 min (the title compound), 9.3 min (the substrate)

Conditions for High-Performance Liquid Chromatography Analysis (Optical Purity)
- column: CHIRALCEL OJ-RH (manufactured by Daicel Chemical Industries), 4.6*150 mm
- UV detection wavelength: 254 nm
- mobile phase: acetonitrile for high-performance liquid chromatography/0.025 mol/L aqueous potassium dihydrogenphosphate solution=8/2
- flow rate: 1.0 mL/min
- retention time: 8.8 min (S), 14.3 min (R)

Example 6

Synthesis of 2-((1R)-1-aminoethyl)-N-(5-chloro-4-(trifluoromethyl)pyridin-2-yl)-1,3-thiazole-5-carboxamide hydrobromide

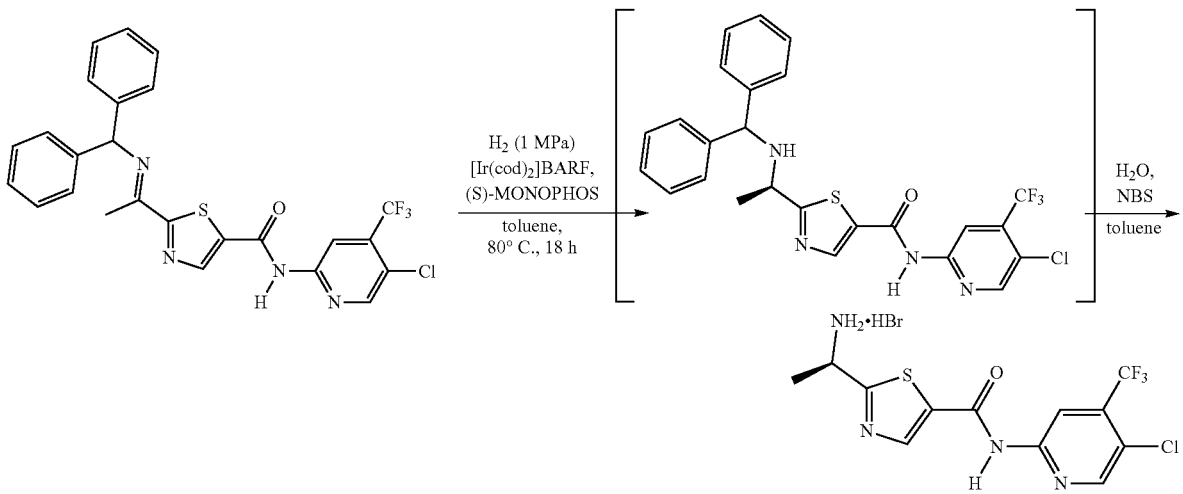

(E)-2-(1-(Benzhydrylimino)ethyl)-N-(5-chloro-4-(trifluoromethyl)pyridin-2-yl)-1,3-thiazole-5-carboxamide (5.00 g), [Ir(cod)$_2$]BARF (0.0247 g) and (S)-MONOPHOS (0.0154 g) were put into an autoclave (120 mL). The atmosphere in the autoclave was decompressed, and the pressure was recovered with argon. The procedures were performed seven times in total. The pressure of the autoclave was recovered to normal pressure, and dehydrated toluene (50 mL) for organic synthesis was fed thereto by argon pressure. Hydrogen was fed into the autoclave until the pressure was increased by 0.1 MPa, and the pressure was recovered to normal pressure. The procedures were performed ten times in total. Hydrogen was fed into the autoclave until 1.20 MPa, and the mixture was stirred at the internal temperature of 80° C. for 18 hr. The mixture was cooled to the internal temperature of about 20° C., the hydrogen was released, and the atmosphere was replaced with argon. The reaction solution was stirred at near room temperature for 2 hr, and the insoluble substance was removed by filtration, and washed with toluene (10 mL). To the filtrate and washing were added water (0.874 mL) and N-bromosuccinimide (1.73 g) at near room temperature, and the mixture was stirred for 19 hr. The crystallized substance was collected by filtration, washed with toluene (30 mL), and dried under reduced pressure at 60° C. to give the title compound. yellow powder, 3.86 g, yield 92.1%, purity 74.4%, optical purity 98.5% ee.

Conditions for High-Performance Liquid Chromatography Analysis (purity)
    column: YMC-Pack ODS-A (manufactured by YMC. CO., LTD.), 4.6*150 mm
    UV detection wavelength: 254 nm
    mobile phase: acetonitrile for high-performance liquid chromatography/0.025 mol/L aqueous potassium dihydrogenphosphate solution=8/2 flow rate: 1.0 mL/min
    retention time: 2.6 min (the title compound), 9.3 min (the raw material)

Conditions for High-Performance Liquid Chromatography Analysis (Optical Purity)
    column: CHIRALPAK IA (manufactured by Daicel Chemical Industries), 4.6*250 mm
    UV detection wavelength: 254 nm
    mobile phase: acetonitrile for high-performance liquid chromatography/methanol for high-performance liquid chromatography/distilled water for high-performance liquid chromatography=80/15/5
    flow rate: 2.0 mL/min
    retention time: 10.2 min (R), 14.4 min (S)

$^1$H NMR (DMSO-$d_6$) δ 1.67 (d, J=6.6 Hz, 3H), 5.01 (brs, 1H), 8.58 (s, 1H), 8.75 (brs, 3H), 8.80 (s, 1H), 8.90 (s, 1H), 11.88 (s, 1H).

Example 7

Synthesis of 2-((1R)-1-aminoethyl)-N-(5-chloro-4-(trifluoromethyl)pyridin-2-yl)-1,3-thiazole-5-carboxamide (S)-mandelate

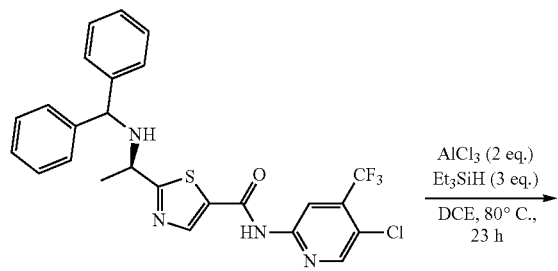

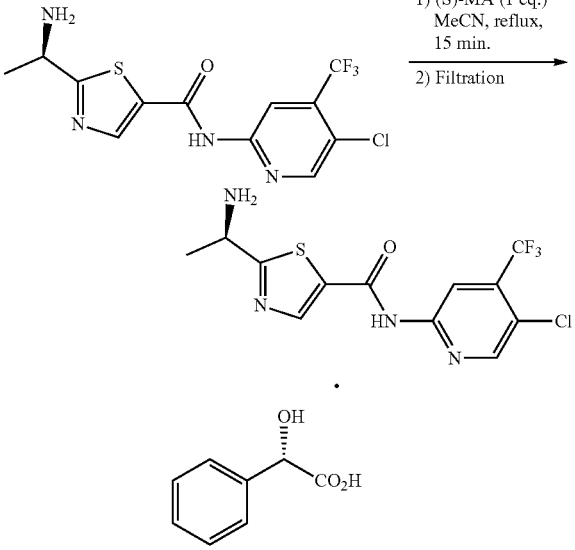

2-((1R)-1-((Benzhydrylamino)ethyl)-N-(5-chloro-4-(trifluoromethyl)pyridin-2-yl)-1,3-thiazole-5-carboxamide (1.00 g) and aluminium trichloride (0.516 g) were put into a Schlenk flask (50 mL). The atmosphere in the Schlenk flask was decompressed, and the pressure was recovered with argon. The procedures were performed three times in total.

Dichloromethane (20 mL) and triethylsilane (0.924 mL) were added thereto under argon atmosphere, and the reaction mixture was stirred at 80° C. for 23 hr. The reaction mixture was cooled to room temperature, and the reaction was quenched with 30 wt % aqueous sodium hydroxide solution (20 mL). The mixture was extracted three times with THF. The obtained organic layers were combined, washed with brine, dried over sodium sulfate, and concentrated under reduced pressure to give a pale yellow solid. This solid was suspended in acetonitrile (13.5 mL), and the suspension was heated to 50° C. (S)-Mandelic acid (0.294 g) was added thereto at 50° C., and the mixture was heated under reflux for 15 min. The mixture was cooled to room temperature, and stirred at the same temperature for 1.5 hr. The precipitate was collected by filtration using a glass filter, and the obtained white solid was washed with acetonitrile (3.5 mL), and dried at 50° C. for 2 hr under reduced pressure to give the title compound (0.655 g). yield 68%. HPLC area normalization 100%. 99.3% de.

Conditions for High-Performance Liquid Chromatography Analysis (HPLC Area Normalization)
    column: YMC-Pack ODS-A (manufactured by YMC. CO., LTD.), 4.6*150 mm
    UV detection wavelength: 254 nm
    mobile phase: acetonitrile for high-performance liquid chromatography/0.025 mol/L aqueous potassium dihydrogenphosphate solution=8/2
    flow rate: 1.4 mL/min
    retention time: 1.6 min. (the title compound); 5.5 min. (the raw material)

Conditions for High-Performance Liquid Chromatography Analysis (Optical Purity)
    column: IA (manufactured by Daicel Chemical Industries), 4.6*250 mm
    UV detection wavelength: 254 nm
    mobile phase: acetonitrile for high-performance liquid chromatography/methanol/water=80/15/5
flow rate: 2.0 mL/min
column temperature: 40° C.
retention time: 11.4 min. (R-form); 16.4 min. (S-form)
$^1$H NMR (DMSO-d$_6$) δ 1.40 (d, J=6.5 Hz, 3H), 4.26 (q, J=6.5 Hz, 1H), 4.72 (s, 1H), 7.18-7.22 (m, 1H), 7.25-7.29 (m, 2H), 7.36-7.40 (m, 2H), 8.59 (s, 1H), 8.72 (s, 1H), 8.77 (s, 1H).

Example 8

Synthesis of 2-((1R)-1-aminoethyl)-N-(5-chloro-4-(trifluoromethyl)pyridin-2-yl)-1,3-thiazole-5-carboxamide hydrochloride

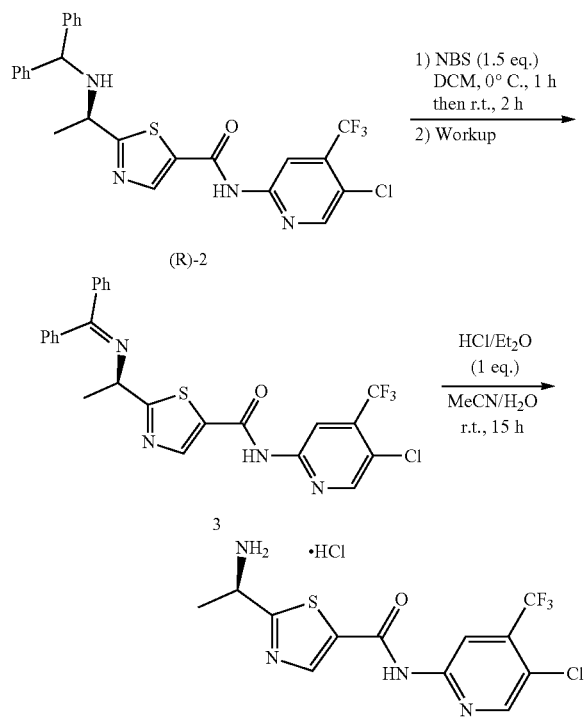

2-((1R)-1-((Benzhydrylamino)ethyl)-N-(5-chloro-4-(trifluoromethyl)pyridin-2-yl)-1,3-thiazole-5-carboxamide (0.80 g) was put into a Schlenk flask (50 mL). The atmosphere in the Schlenk flask was decompressed, and the pressure was recovered with argon. The procedures were performed three times in total. Dichloromethane (16 mL) was added thereto under argon atmosphere. This solution was cooled in an ice bath, and N-bromosuccinimide (0.414 g) was added thereto. The reaction mixture was stirred at 0° C. for 1 hr, and then at room temperature for 2 hr, and the reaction was quenched with 15 wt % aqueous sodium hydroxide solution (40 mL). The mixture was extracted three times with dichloromethane. The obtained organic layer was washed with brine, dried over sodium sulfate, and concentrated under reduced pressure to give a pale yellow solid. The solid was added to acetonitrile (6 mL), and the mixture was stirred at 0° C. for 30 min, and the resulting solid was collected by filtration to give the corresponding imine (0.524 g, yield 66%). The imine was suspended in acetonitrile/water=20/1 (3.78 mL), and 1 mol/L hydrogen chloride-ether solution (1.02 mL) was added thereto at room temperature. The mixture was stirred at room temperature for hr, and filtered using Hirsch funnel to give a white solid. The solid was washed with acetonitrile (2 mL), and dried at 50° C. for 8 hr under reduced pressure to give the title compound (two step yield 63%). The remaining benzophenone (2%) in the compound was confirmed by $^1$H NMR analysis.

Conditions for High-Performance Liquid Chromatography Analysis (HPLC Area Normalization)
 column: YMC-Pack ODS-A (manufactured by YMC. CO., LTD.), 4.6*150 mm
 UV detection wavelength: 254 nm
 mobile phase: acetonitrile for high-performance liquid chromatography/0.025 mol/L aqueous potassium dihydrogenphosphate solution=8/2
 flow rate: 1.4 mL/min
 retention time: 1.6 min. (the title compound); 2.3 min.(benzphenone); 5.5 min. (the raw material)

Conditions for High-Performance Liquid Chromatography Analysis (Optical Purity)
 column: IA (manufactured by Daicel Chemical Industries), 4.6*250 mm
 UV detection wavelength: 254 nm
 mobile phase: acetonitrile for high-performance liquid chromatography/methanol/water=80/15/5
 flow rate: 2.0 mL/min
 column temperature: 40° C.
 retention time: 11.4 min. (R-form); 16.4 min. (S-form)
$^1$H NMR (DMSO-d$_6$) δ 1.65 (d, J=6.5 Hz, 3H), 4.92 (q, J=6.5 Hz, 1H), 8.58 (s, 1H), 8.80 (s, 1H), 8.88 (s, 1H), 8.91 (br, 3H), 11.89 (s, 1H).

Examples 9-54

Synthesis of 2-((1R)-1-((benzhydrylamino)ethyl)-N-(5-chloro-4-(trifluoromethyl)pyridin-2-yl)-1,3-thiazole-5-carboxamide

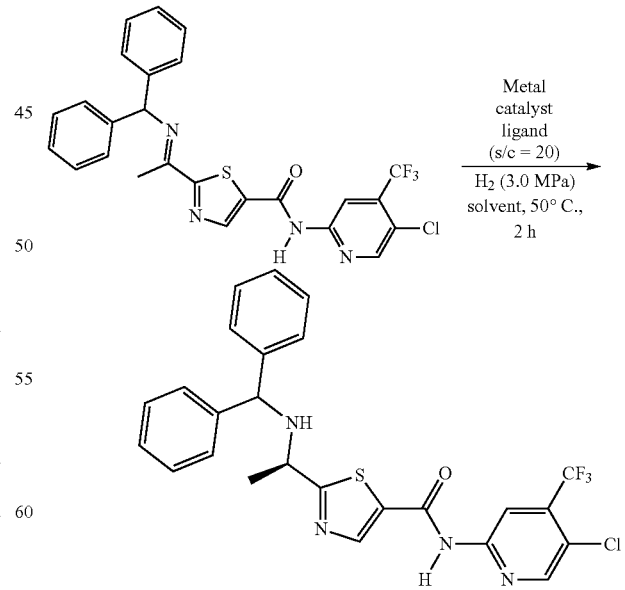

(E)-2-(1-(Benzhydrylimino)ethyl)-N-(5-chloro-4-(trifluoromethyl)pyridin-2-yl)-1,3-thiazole-5-carboxamide (0.0386 g), a catalyst (corresponding to s/c=20) and a ligand (1.1 or 2.2 equivalent relative to the iridium catalyst) were put into a test tube. The test tube was set in an autoclave. The atmosphere in the autoclave was decompressed, and the pressure was recovered with nitrogen. The procedures were performed three times in total. The pressure of the autoclave was recovered to normal pressure, and a solvent (0.75 mL) was added thereto. Hydrogen was fed into the autoclave until the pressure was increased by 0.1 MPa, and the pressure was recovered to normal pressure. The procedures were performed ten times in total. Hydrogen was fed into the autoclave until 3.0 MPa, and the mixture was stirred at the internal temperature of 50° C. for 2 hr. The mixture was cooled to the internal temperature of about 20° C., and the hydrogen was released. The conversion and enantiomeric excess were measured by HPLC. The results are shown in Table 9.

The conversion can be calculated by the following formula.

Conversion=100×the desired compound/(the desired compound+the raw material compound)

wherein the desired compound and raw material means each area in high-performance liquid chromatography.

Conditions for High-Performance Liquid Chromatography Analysis (HPLC Area Normalization)
   column: YMC-Pack ODS-A (manufactured by YMC. CO., LTD.), 4.6*150 mm
   UV detection wavelength: 254 nm
   mobile phase: acetonitrile for high-performance liquid chromatography/0.025 mol/L aqueous potassium dihydrogenphosphate solution=8/2
   flow rate: 1.4 mL/min
   retention time: 5.5 min. (the title compound), 7.2 min. (the raw material).

Conditions for High-Performance Liquid Chromatography Analysis (Optical Purity)
   column: OJ-RH (manufactured by Daicel Chemical Industries), 4.6*150 mm
   UV detection wavelength: 254 nm
   mobile phase: acetonitrile for high-performance liquid chromatography/0.025 mol/L aqueous potassium dihydrogenphosphate solution=8/2
   flow rate: 1.2 mL/min
   retention time: 8.3 min. (S-form), 13.6 min. (R-form).

$^1$H NMR (CDCl$_3$) δ 1.56 (d, J=6.5 Hz, 3H), 2.19 (s, 1H), 4.05 (q, J=6.5 Hz, 1H), 4.98 (s, 1H), 7.19-7.24 (m, 1H), 7.27-7.32 (m, 3H), 7.33-7.44 (m, 6H), 8.26 (s, 1H), 8.41 (s, 1H), 8.44 (s, 1H), 8.69 (s, 1H).

TABLE 9

| Ex. | catalyst or metal source | ligand | solvent | conversion (%) | % ee | stereo |
|---|---|---|---|---|---|---|
| 9 | [Rh(cod)(R)-(S)-josiphos] OTf | — | THF | 4.9 | 21.8 | R |
| 10 | [Rh(cod)(R)-(S)-josiphos] OTf | — | DCM | 3.8 | 23.1 | SR |
| 11 | Ir(cod)$_2$(BAr$_4^F$) | (R)-(S)-Josiphos | MeOH | 11.6 | 26.1 | S |
| 12 | Ir(cod)$_2$(BAr$_4^F$) | (R)-(S)-Josiphos | DCM | 59.7 | 28.9 | S |
| 13 | Ir(cod)$_2$(BAr$_4^F$) | (R)-BINAP | Toluene | 27.939.1 | 39.1 | S |
| 14 | Ir(cod)$_2$(BAr$_4^F$) | (R,R)-iPr-Duphos | Toluene | 97.1 | 10.5 | R |
| 15 | Ir(cod)$_2$(BAr$_4^F$) | (R)-(S)-Josiphos | Toluene | 69.4 | 38.8 | S |
| 16 | Ir(cod)$_2$(BAr$_4^F$) | (R)-Phanephos | Toluene | 79.3 | 52.5 | R |
| 17 | Ir(cod)$_2$(BAr$_4^F$) | (R)-xylyl-BINAP | Toluene | 47.2 | 62.9 | S |
| 18 | Ir(cod)$_2$(BAr$_4^F$) | (R,R)-DIPAMP | Toluene | 9.8 | 26.6 | S |
| 19 | Ir(cod)$_2$(BAr$_4^F$) | (R,R)-Quinox-P* | Toluene | 76.4 | 51.7 | S |
| 20 | Pd(OCOCF$_3$)$_2$ | (R)-BINAP | MeOH | 10.0 | 11.7 | S |
| 21 | Pd(OCOCF$_3$)$_2$ | (R)-BINAP | DCM | 2.1 | 33.7 | S |
| 22 | Pd(OCOCF$_3$)$_2$ | (R)-BINAP | Toluene | 1.6 | 28.1 | S |
| 23 | RuCl$_2${(R)-binap} | — | Toluene | 6.0 | 21.0 | R |
| 24 | RuCl$_2${(R)-binap}{R,R-dpen} | — | Toluene | 17.2 | 100.0 | S |
| 25 | (R,R)-Me-Duphos | (R,R)-Me-Duphos | Toluene | 7.2 | 43.9 | S |
| 26 | Ir(cod)$_2$(BAr$^F_4$) | (R,R)-Ph-BPE | Toluene | 7.4 | 48.1 | R |
| 27 | Ir(cod)$_2$(BAr$_4^F$) | (S,S)-Et-Ferrotne | Toluene | 4.0 | 33.4 | R |
| 28 | Ir(cod)$_2$(BAr$_4^F$) | (S)-H8-BINAP | Toluene | 62.8 | 18.0 | R |
| 29 | Ir(cod)$_2$(BAr$_4^F$) | (S)-DTBM-Segphos | Toluene | 8.5 | 23.0 | R |
| 30 | Ir(cod)$_2$(BAr$_4^F$) | (R)-C3-Tunephos | Toluene | 15.4 | 26.2 | S |
| 31 | Ir(cod)$_2$(BAr$_4^F$) | (S)-MeO-BIPHEP | Toluene | 16.1 | 19.5 | S |
| 32 | Ir(cod)$_2$(BAr$_4^F$) | SL-W001-1 | Toluene | 12.1 | 40.1 | R |
| 33 | Ir(cod)$_2$(BAr$_4^F$) | SL-J004-1 | Toluene | 43.3 | 11.1 | S |
| 34 | Ir(cod)$_2$(BAr$_4^F$) | (S)-ShiP | Toluene | 57.2 | 8.0 | R |
| 35 | Ir(cod)$_2$(BAr$_4^F$) | (S)-MOP | Toluene | 28.8 | 51.9 | S |
| 36 | Ir(cod)$_2$(BAr$_4^F$) | (R)-QuINAP | Toluene | 0.8 | 46.0 | R |
| 37 | Ir(cod)$_2$(BAr$_4^F$) | (R)-iPr-PHOX | Toluene | 6.3 | 0.9 | R |
| 38 | Ir(cod)$_2$(BAr$_4^F$) | (S)-Monophos | Toluene | 97.3 | 86.4 | R |
| 39 | Ir(cod)$_2$(BAr$_4^F$) | (S)-Me-Monophos | Toluene | 7.4 | 33.3 | R |
| 40 | Ir(cod)$_2$(BAr$_4^F$) | (R,R)-Taddol-type | Toluene | 30.3 | 16.2 | R |
| 41 | Ir(cod)$_2$(BAr$_4^F$) | (S)-BnMe | Toluene | 22.6 | 57.5 | R |
| 42 | Ir(cod)$_2$(BAr$_4^F$) | (S,R,R)-alpha-phenethyl | Toluene | 2.9 | 37.1 | R |
| 43 | Ir(cod)$_2$(BAr$_4^F$) | (S)-Et-Monophos | Toluene | 4.1 | 56.2 | R |
| 44 | Ir(cod)$_2$(BAr$_4^F$) | (S)-Morphos | Toluene | 52.6 | 92.9 | R |
| 45 | Ir(cod)$_2$(BAr$_4^F$) | (S)-alpha-phenethylH | Toluene | 1.7 | 27.1 | R |
| 46 | Ir(cod)$_2$(BAr$_4^F$) | (S)-Pipphos | Toluene | 98.1 | 62.5 | R |
| 47 | Ir(cod)$_2$(BAr$_4^F$) | (S)-H8-Monophos | Toluene | 20.2 | 12.4 | R |
| 48 | [Ir(cod)$_2$]BF$_4$ | (S)-Monophos | DCM | 15.6 | 70.9 | R |
| 49 | [Ir(cod)$_2$]BF$_4$ | (S)-Morphos | DCM | 3.3 | 43.5 | R |
| 50 | [Ir(cod)$_2$]BF$_4$ | (S)-Pipphos | DCM | 5.8 | 62.0 | R |
| 51 | [Ir(cod)$_2$]BF$_4$ | (R)-Phanephos | DCM | 82.7 | 47.1 | R |

TABLE 9-continued

| Ex. | catalyst or metal source | ligand | solvent | conversion (%) | % ee | stereo |
|---|---|---|---|---|---|---|
| 52 | Ir(cod)$_2$(BAr$_4^F$) | (S)-Monophos | DCM | 98.7 | 89.4 | R |
| 53 | Ir(cod)$_2$(BAr$_4^F$) | (S)-Morphos | DCM | 89.6 | 92.6 | R |
| 54 | Ir(cod)$_2$(BAr$_4^F$) | (S)-Pipphos | DCM | 72.2 | 83.4 | R |

Reference Example 3

Synthesis of (E)-2-(1-(bis(4-methoxyphenyl)methyl) ethyl)-N-(5-chloro-4-(trifluoromethyl)pyridin-2-yl)-1,3-thiazole-5-carboxamide

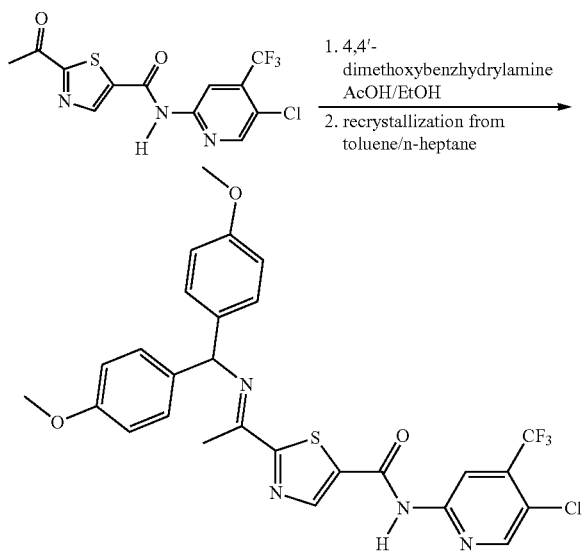

2-Acetyl-N-(5-chloro-4-(trifluoromethyl)pyridin-2-yl)-1,3-thiazole-5-carboxamide (13.00 g), 4,4'-dimethoxybenzhydrylamine (10.00 g), ethanol (65 mL) and acetic acid (0.642 mL) were put into a four-necked eggplant flask (200 mL), and the mixture was stirred for 8 hr with heating under reflux under nitrogen atmosphere. The reaction mixture was cooled to room temperature, ethanol (10 mL) was added thereto, and the mixture was filtered. The residual white solid was washed with ethanol (30 mL), and the filtrate and washing were combined, and concentrated under reduced pressure to give a solid. To the solid was added toluene (80 mL), and the mixture was heated to 99° C. Hexane (190 mL) was added dropwise thereto at 73 to 99° C., and the mixture was stirred at 73° C. (reflux temperature) for 10 min, and cooled to room temperature. The resulting crystals were aged at room temperature. The crystals were collected by filtration, washed with a mixed solvent (60 mL) of hexane and toluene (1:3), and dried under reduced pressure at 60° C. to give the title compound (16.57 g, yield 77%) as a pale-brown solid.

$^1$H NMR (CDCl$_3$) δ 2.45 (s, 3H), 3.78 (s, 6H), 5.82 (s, 1H), 6.86 (d, J=9.0 Hz, 4H), 7.33 (d, J=9.0 Hz, 4H), 8.36 (s, 1H), 8.44 (s, 1H), 8.57 (bs, 1H), 8.69 (s, 1H); $^{13}$C NMR (CDCl$_3$) δ 14.62, 55.26, 67.42, 111.89 (q, J=5.4 Hz), 114.01, 121.45 (q, J=275.2 Hz), 124.06, 128.30, 135.16, 135.91, 137.81 (q, J=32.7 Hz), 145.41, 149.48, 149.92, 158.68, 158.81, 159.67, 176.60.

Reference Example 4

Synthesis of (E)-2-(1-(2-benzoylhydrazono)ethyl)-N-(5-chloro-4-(trifluoromethyl)pyridin-2-yl)-1,3-thiazole-5-carboxamide

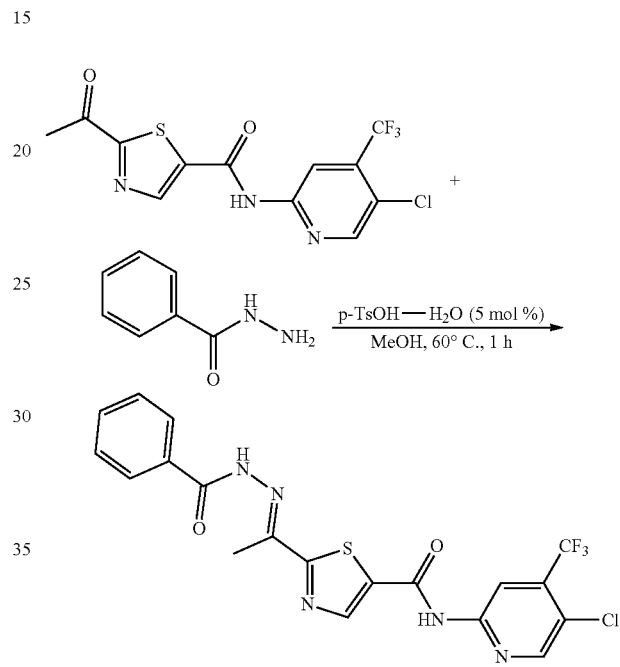

2-Acetyl-N-(5-chloro-4-(trifluoromethyl)pyridin-2-yl)-1,3-thiazole-5-carboxamide (1.00 g), benzoylhydrazine (0.408 g) and p-toluenesulfonic acid monohydrate (0.0272 g) were put into a four-necked eggplant flask (50 mL). Methanol (15 mL) was added thereto under nitrogen atmosphere, and the mixture was stirred at 60° C. for 1 hr. The reaction mixture was cooled in a water bath, and the precipitate was collected by filtration using a glass filter. The resulting white solid was washed with methanol (5 mL), and dried under reduced pressure at 50° C. to give the title compound (1.21 g). yield 91%, HPLC area normalization 99.3%. E/Z isomer ratio 11/1.

Conditions for High-Performance Liquid Chromatography Analysis (Area Normalization)
  column: YMC-Pack ODS-A (manufactured by YMC. CO., LTD.), 4.6*150 mm
  UV detection wavelength: 254 nm
  mobile phase: acetonitrile for high-performance liquid chromatography/0.025 mol/L aqueous potassium dihydrogenphosphate solution=8/2
  flow rate: 1.0 mL/min
  retention time: 1.47 min. (benzoylhydrazine), 4.36 min. (the title compound), 4.48 min. (the raw material)

$^1$H NMR (DMSO-d$_6$) δ 2.48 (s, 3H), 7.50-7.57 (m, 2H), 7.58-7.65 (m, 1H), 7.81-7.94 (m, 2H), 8.59 (s, 1H), 8.78 (s, 1H), 8.86 (s, 1H), 11.22 (bs, 1H), 11.81 (bs, 1H).

Reference Example 5

Synthesis of (E)-(S)-tert-butyl 2-(1-(5-((5-chloro-4-(trifluoromethyl)pyridin-2-yl)carbamoyl)-1,3-thiazol-2-yl)ethylidene)hydrazinecarboxylate

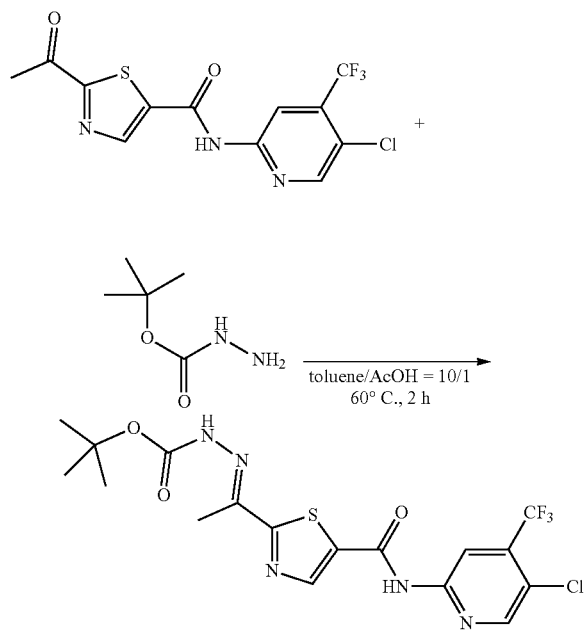

2-Acetyl-N-(5-chloro-4-(trifluoromethyl)pyridin-2-yl)-1,3-thiazole-5-carboxamide (6.00 g) was put into a four-necked eggplant flask (100 mL). The atmosphere in the container was decompressed, and the pressure was recovered with nitrogen. The procedures were performed three times in total. Toluene (18 mL), acetic acid (3.6 mL) and tert-butoxycarbonylhydrazine (0.408 g) were added thereto under nitrogen atmosphere, and the mixture was stirred at 60° C. for 2 hr. The reaction mixture was cooled in a water bath, and thereby the objective product was precipitated. The mixture was aged at room temperature, and then for 1 hr, and the precipitate was collected by filtration using a glass filter. The resulting white solid was washed with toluene/hexane=1/1 (50 mL), and dried under reduced pressure at 50° C. to give the title compound (7.18 g). yield 89%, HPLC area normalization 93.9%.

Conditions for High-Performance Liquid Chromatography Analysis (Area Normalization)
    column: YMC-Pack ODS-A (manufactured by YMC. CO., LTD.), 4.6*150 mm
    UV detection wavelength: 254 nm
    mobile phase: acetonitrile for high-performance liquid chromatography/0.025 mol/L aqueous potassium dihydrogenphosphate solution=7/3
    flow rate: 1.0 mL/min
    retention time: 4.48 min. (the raw material); 5.66 min. (the title compound)

$^1$H NMR (DMSO-d$_6$) δ 1.51 (s, 9H), 2.31 (s, 3H), 8.58 (s, 1H), 8.75 (s, 1H), 8.80 (s, 1H), 10.46 (s, 1H), 11.74 (s, 1H); $^{13}$C NMR (DMSO-d$_6$) δ 12.59, 27.95, 80.33, 111.81 (q, J=5.4 Hz), 121.58 (q, J=274.3 Hz), 121.62, 134.85, 135.32 (q, J=31.8 Hz), 145.51, 149.70, 151.33, 152.23, 159.69, 172.44; 19F NMR (DMSO-d$_6$) δ −63.81.

Reference Example 6

Synthesis of (E)-2-(1-(benzylimino)ethyl)-N-(5-chloro-4-(trifluoromethyl)pyridin-2-yl)-1,3-thiazole-5-carboxamide

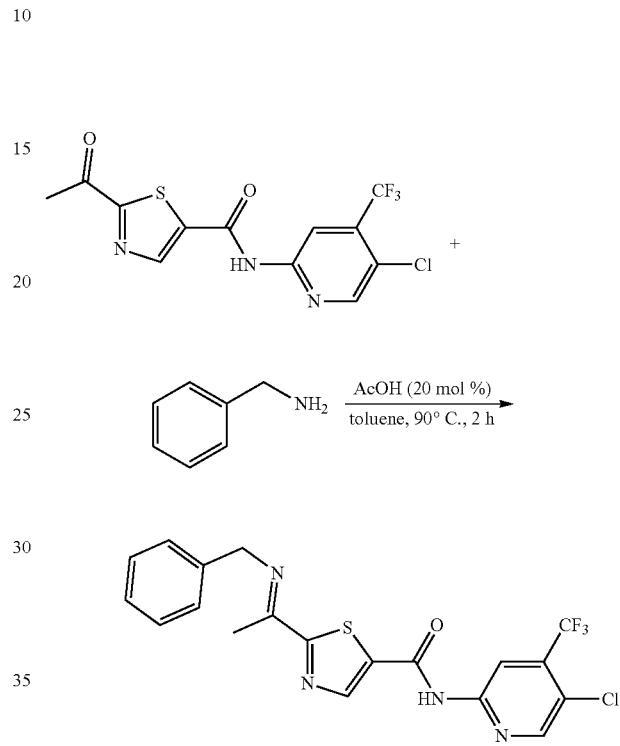

2-Acetyl-N-(5-chloro-4-(trifluoromethyl)pyridin-2-yl)-1,3-thiazole-5-carboxamide (6.00 g) was put into a four-necked eggplant flask (100 mL). Toluene (30 mL), benzyl alcohol (1.97 mL) and acetic acid (0.196 mL) were added thereto under nitrogen atmosphere, and the mixture was stirred at 90° C. for 2 hr. The reaction mixture was cooled to room temperature, and concentrated under reduced pressure. The crude objective product was suspended in hexane/ethyl acetate=9/1 (60 mL), and the suspension was dissolved with heating at 90° C., and the solution was cooled to 0° C. to precipitate crystals. The mixture was aged at 0° C. for 30 min, and the precipitate was collected by filtration using a glass filter. The resulting pale-orange solid was washed with hexane/ethyl acetate=9/1 (30 mL), and dried under reduced pressure at 50° C. to give the title compound (6.83 g). yield 91%, HPLC area normalization 84.7%.

Conditions for High-Performance Liquid Chromatography Analysis (Area Normalization)
    column: YMC-Pack ODS-A (manufactured by YMC. CO., LTD.), 4.6*150 mm
    UV detection wavelength: 254 nm
    mobile phase: acetonitrile for high-performance liquid chromatography/0.025 mol/L aqueous potassium dihydrogenphosphate solution=8/2
    flow rate: 1.0 mL/min
    retention time: 4.48 min. (the raw material), 16.4 min.(the title compound)

Reference Example 7

Synthesis of (E)-N-(5-chloro-4-(trifluoromethyl)pyridin-2-yl)-2-(1-((4-methoxybenzyl)imino)ethyl)-1,3-thiazole-5-carboxamide

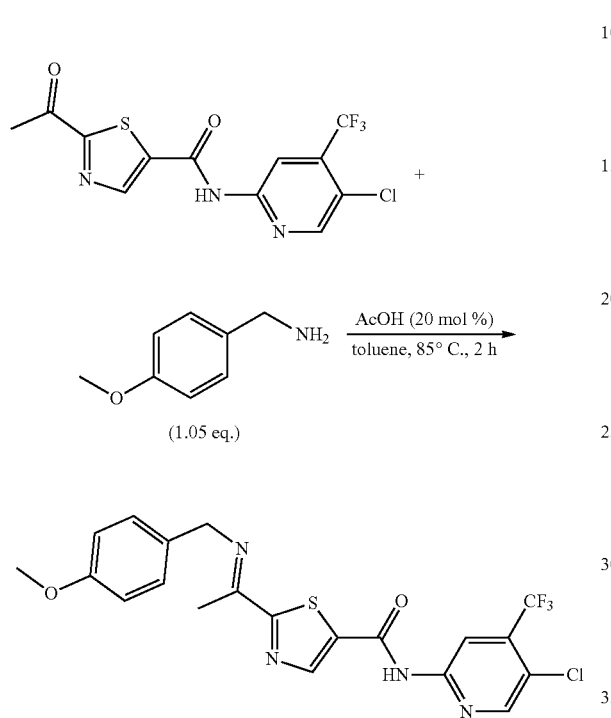

2-Acetyl-N-(5-chloro-4-(trifluoromethyl)pyridin-2-yl)-1,3-thiazole-5-carboxamide (6.00 g) was put into a four-necked eggplant flask (100 mL). Toluene (30 mL), 4-methoxybenzylamine (2.35 mL) and acetic acid (0.196 mL) were added thereto under nitrogen atmosphere, and the mixture was stirred at 85° C. for 2 hr. The reaction mixture was cooled to room temperature, and concentrated under reduced pressure. The crude objective product was suspended in ethanol (48 mL), and the suspension was dissolved with heating at 70° C., and the solution was cooled to room temperature to precipitate crystals. The precipitate was collected by filtration using a glass filter, washed with ethanol (20 mL), and dried under reduced pressure at 60° C. to give the title compound (5.64 g) as a single isomer. pale-orange solid, yield 70%, HPLC area normalization 99.4%.

Conditions for High-Performance Liquid Chromatography Analysis (HPLC Area Normalization)
- column: YMC-Pack ODS-A (manufactured by YMC. CO., LTD.), 4.6*150 mm
- UV detection wavelength: 254 nm
- mobile phase: acetonitrile for high-performance liquid chromatography/0.025 mol/L aqueous potassium dihydrogenphosphate solution=7/3
- flow rate: 1.0 mL/min
- retention time: 4.7 min (the raw material); 11.2 min. (the title compound).

$^1$H NMR (CDCl$_3$) δ 2.47 (s. 3H), 3.82 (s, 3H), 4.74 (s, 2H), 6.92 (d, J=8.5 Hz, 2H), 7.33 (d, J=8.5 Hz, 2H), 8.37 (s, 1H), 8.40 (s, 1H), 8.44 (s, 1H), 8.67 (s, 1H).

Synthesis of Reference Example 8

(E)-N-(5-chloro-4-(trifluoromethyl)pyridin-2-yl)-2-(1-((2,4-dimethoxybenzyl)imino)ethyl)-1,3-thiazole-5-carboxamide

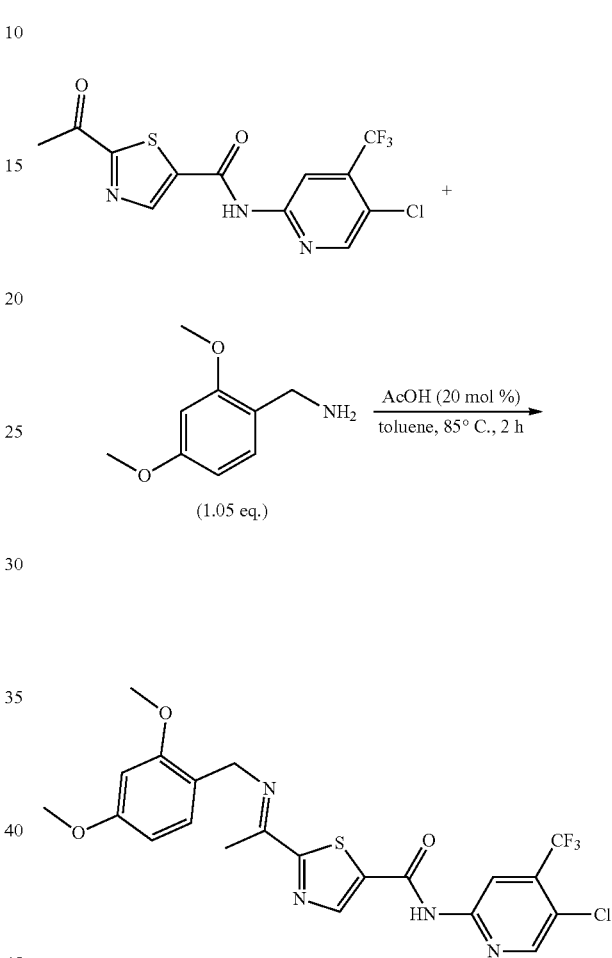

The title compound (6.81 g) was obtained as a single isomer in the same manner as in Reference Example 7. yellow solid, yield 75%, HPLC area normalization 96.2%.

Conditions for High-Performance Liquid Chromatography Analysis (HPLC Area Normalization)
- column: YMC-Pack ODS-A (manufactured by YMC. CO., LTD.), 4.6*150 mm
- UV detection wavelength: 254 nm
- mobile phase: acetonitrile for high-performance liquid chromatography/0.025 mol/L aqueous potassium dihydrogenphosphate solution=7/3
- flow rate: 1.0 mL/min
- retention time: 4.7 min (the raw material); 12.1 min. (the title compound).

$^1$H NMR (CDCl$_3$) δ 2.47 (s. 3H), 3.82 (s, 3H), 3.84 (s, 3H), 4.70 (s, 2H), 6.49 (d, J=2.5 Hz, 1H), 6.52 (dd, J=8.5, 2.5 Hz, 1H), 7.36 (d, J=8.5 Hz, 1H), 8.37 (s, 1H), 8.41 (s, 1H), 8.43 (s, 1H), 8.68 (s, 1H).

Reference Example 9

Synthesis of (E)-N-(5-chloro-4-(trifluoromethyl)pyridin-2-yl)-2-(1-((4-methoxyphenyl)imino)ethyl)-1,3-thiazole-5-carboxamide

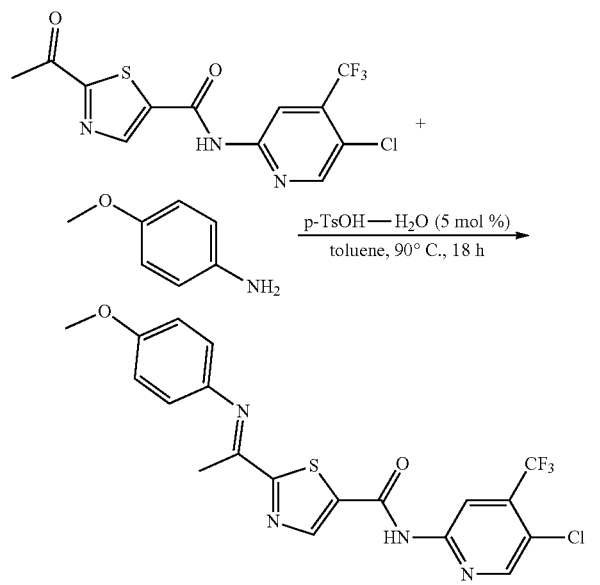

2-Acetyl-N-(5-chloro-4-(trifluoromethyl)pyridin-2-yl)-1,3-thiazole-5-carboxamide (1.00 g), p-toluenesulfonic acid monohydrate (0.0272 g) and p-anisidine (0.369 g) were put into a four-necked eggplant flask (50 mL). Toluene (6 mL) was added thereto under nitrogen atmosphere, and the mixture was stirred at 90° C. for 18 hr. The reaction mixture was cooled to room temperature, and concentrated under reduced pressure. The crude objective product was suspended in ethanol (10 mL), and the suspension was dissolved with heating at 65° C. Water (10 mL) was added dropwise thereto at the same temperature, and the mixture was cooled to room temperature. The obtained red-brown suspension was stirred at room temperature for 30 min, and the precipitate was collected by filtration using a glass filter, washed with ethanol/water=1/1 (10 mL), and dried under reduced pressure at 50° C. to give the title compound (1.08 g) as a single isomer. brown solid, yield 83%, HPLC area normalization 91.7%.

Conditions for High-Performance Liquid Chromatography Analysis (HPLC Area Normalization)
- column: YMC-Pack ODS-A (manufactured by YMC. CO., LTD.), 4.6*150 mm
- UV detection wavelength: 254 nm
- mobile phase: acetonitrile for high-performance liquid chromatography/0.025 mol/L aqueous potassium dihydrogenphosphate solution=7/3
- flow rate: 1.0 mL/min
- retention time: 4.7 min. (the raw material); 28.0 min. (the title compound).

$^1$H NMR (DMSO-$d_6$) δ 2.37 (s. 3H), 3.78 (s, 3H), 6.86-7.05 (m, 4H), 8.59 (s, 1H), 8.78 (s, 1H), 8.93 (s, 1H), 11.85 (s, 1H);

$^{13}$C NMR δ 16.18, 55.22, 111.89, 114.19, 122.08 (q, J=274.28 Hz), 121.79, 122.00, 135.36 (q, J=32.7 Hz), 136.93, 141.46, 146.01, 149.74, 151.27, 156.78, 159.61, 160.61, 174.22; $^{19}$F NMR δ −63.81.

Example 55

Synthesis of 2-((1R)-1-((bis(4-methoxyphenyl)methyl)amino)ethyl)-N-(5-chloro-4-(trifluoromethyl)pyridin-2-yl)-1,3-thiazole-5-carboxamide

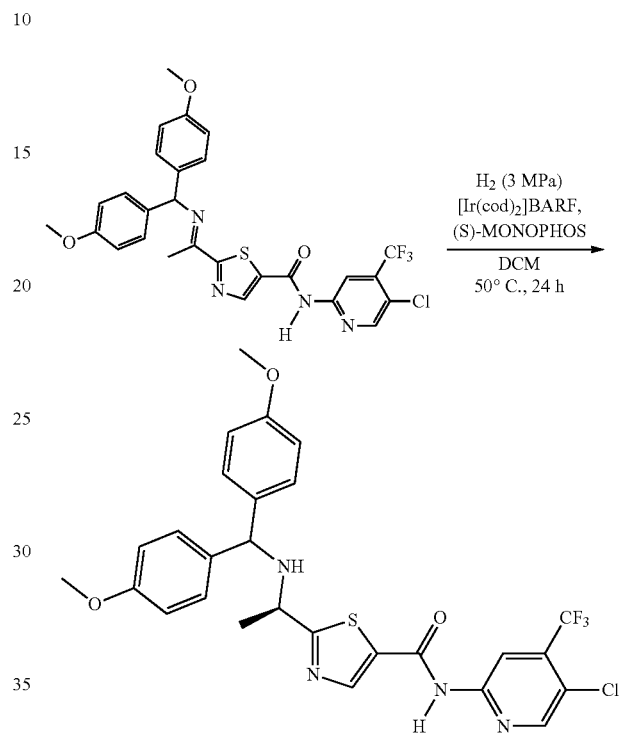

(E)-2-(1-((Bis(4-methoxyphenyl)methyl)imino)ethyl)-N-(5-chloro-4-(trifluoromethyl)pyridin-2-yl)-1,3-thiazole-5-carboxamide (3.00 g), [Ir(cod)$_2$]BARF (0.0664 g) and (S)-MONOPHOS (0.0412 g) were put into an autoclave (120 mL). The atmosphere in the autoclave was decompressed, and the pressure was recovered with argon. The procedures were performed five times in total. The pressure of the autoclave was recovered to normal pressure, and dehydrated dichloromethane (30 mL) for organic synthesis was fed thereto by argon pressure. Hydrogen was fed into the autoclave until the pressure was increased by 0.1 MPa, and the pressure was recovered to normal pressure. The procedures were performed ten times in total. Hydrogen was fed into the autoclave until 1.0 MPa, and the mixture was stirred at the internal temperature of 50° C. for 24 hr. The mixture was cooled to the internal temperature of about 20° C., the hydrogen was released, and the atmosphere was replaced with argon (conversion 73.7%, optical purity 93.7% ee). The reaction solution was concentrated under reduced pressure, and the residue was purified by silica gel column to give the title compound. pale-brown solid, 1.54 g, yield 50%, HPLC area normalization 96.2%.

Conditions for High-Performance Liquid Chromatography Analysis (Area Normalization)
- column: YMC-Pack ODS-A (manufactured by YMC. CO., LTD.), 4.6*150 mm
- UV detection wavelength: 254 nm
- mobile phase: acetonitrile for high-performance liquid chromatography/0.025 mol/L aqueous potassium dihydrogenphosphate solution=8/2 flow rate: 1.0 mL/min retention time: 2.4 min (the title compound)

$^1$H NMR (CDCl$_3$) δ 1.54 (d, J=6.6 Hz, 3H), 4.42 (q, J=6.6 Hz, 1H), 7.23 (d, J=3.2 Hz, 1H), 7.70 (d, J=3.2 Hz, 1H).

$^{13}$C NMR (CDCl$_3$) δ 24.66, 49.65, 118.36, 142.38, 178.38.

Example 56

Synthesis of 2-((1R)-1-aminoethyl)-N-(5-chloro-4-(trifluoromethyl)pyridin-2-yl)-1,3-thiazole-5-carboxamide hydrochloride

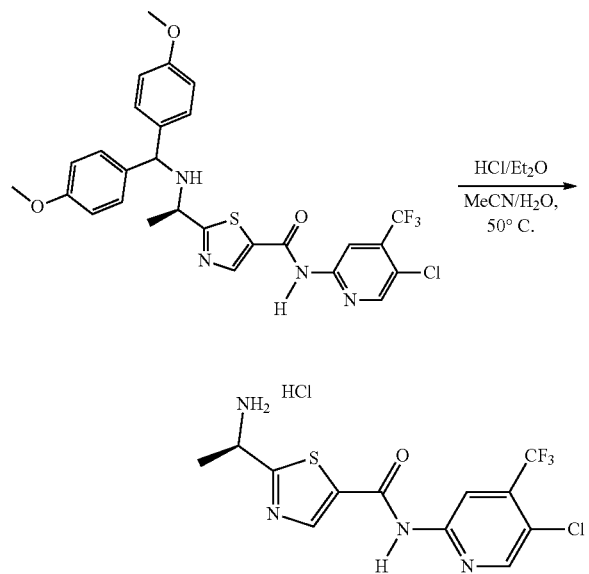

2-((1R)-1-((Bis(4-methoxyphenyl)methyl)amino)ethyl)-N-(5-chloro-4-(trifluoromethyl)pyridin-2-yl)-1,3-thiazole-5-carboxamide (0.150 g) was dissolved in a mixed solvent of acetonitrile and water (9:1, 3.0 mL), and to this solution was added dropwise 1 mol/L hydrogen chloride-diethyl ether solution (0.312 mL). The mixture was warmed to 50° C., and the mixture was stirred overnight at the same temperature. The mixture was cooled to room temperature, and the resulting crystals were collected by filtration to give the title compound. colorless solid, 0.0776 g, yield 77%.

Examples 57-101

Synthesis of 2-((1R)-1-(2-benzoylhydrazinyl)ethyl)-N-(5-chloro-4-(trifluoromethyl)pyridin-2-yl)-1,3-thiazole-5-carboxamide

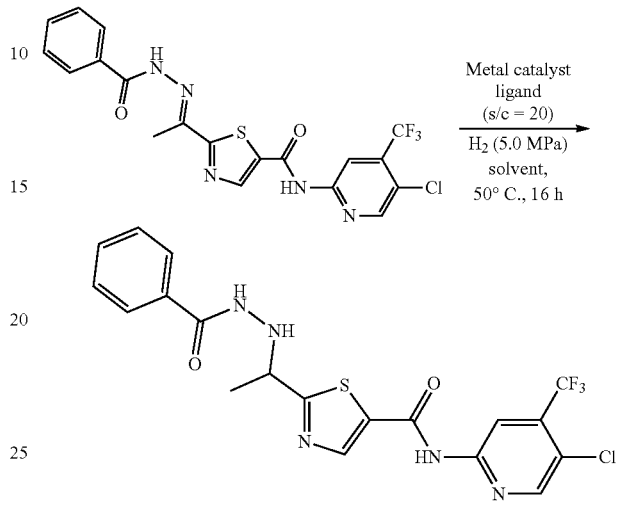

(E)-2-(1-(2-Benzoylhydrazono)ethyl)-N-(5-chloro-4-(trifluoromethyl)pyridin-2-yl)-1,3-thiazole-5-carboxamide (0.0702 g), a catalyst (corresponding to s/c=20), a ligand (1.1 or 2 equivalent relative to the catalyst) and an additive (potassium butoxide was used in an amount of 1 equivalent relative to the substrate in Examples 57-62, and the additive was not used in Examples 63-101) were put into a test tube. A solvent (1 mL) was added thereto under nitrogen atmosphere, the test tube was set in an autoclave, and the reaction system was purged with hydrogen. Hydrogen was fed into the autoclave until 5.0 MPa, and the mixture was stirred at 50° C. for 16 hr. The production of the title compound was confirmed by analyzing the reaction solution using HPLC. The results are shown in Table 10.

Conditions for High-Performance Liquid Chromatography Analysis (Optical Purity)

column: OJ-RH (manufactured by Daicel Chemical Industries), 4.6*150 mm

UV detection wavelength: 254 nm mobile phase: acetonitrile for high-performance liquid chromatography/0.025 mol/L aqueous potassium dihydrogenphosphate solution=1/1 flow rate: 1.0 mL/min retention time: 5.4 min. (S-form); 6.1 min. (R-form); 7.6 min. (the raw material)

TABLE 10

| Ex. | catalyst or metal source | ligand | solvent | conversion (%) | % ee | stereo |
|---|---|---|---|---|---|---|
| 57 | RuCl$_2$\{(R)-binap\}\{R,R-dpen\} | — | IPA | 25.9 | 75.1 | S |
| 58 | RuCl$_2$\{(R)-binap\}\{R,R-dach\} | — | IPA | 51.4 | 71.2 | S |
| 59 | RuCl$_2$\{(R)-binap\}\{R,R-daipen\} | — | IPA | 41.5 | 85.3 | S |
| 60 | RuCl$_2$\{(R)-xyl-binap\}\{R,R-dpen\} | — | IPA | 30.5 | 40.5 | S |
| 61 | RuCl$_2$\{(R)-xyl-binap\}\{R,R-dach\} | — | IPA | 28.9 | 38.3 | R |
| 62 | RuCl$_2$\{(R)-xyl-binap\}\{R,R-daipen\} | — | IPA | 28.0 | 62.6 | S |
| 63 | [IrCl(cod)]$_2$ | (R,R)-iPr-Duphos | DCM | 9.8 | 7.2 | R |
| 64 | [RhCl(cod)]$_2$ | (R,R)-iPr-Duphos | MeOH | 77.0 | 69.1 | R |
| 65 | [RhCl(cod)]$_2$ | (R)-(S)-Josiphos | MeOH | 98.5 | 17.1 | S |
| 66 | [RhCl(cod)]$_2$ | (R)-Phanephos | MeOH | 99.3 | 43.9 | R |
| 67 | [RhCl(cod)]$_2$ | (R,R)-Quinox-P* | MeOH | 24.5 | 13.9 | R |
| 68 | [Rh(cod)$_2$]OTf | (R)-BINAP | MeOH | 19.8 | 31.1 | S |

TABLE 10-continued

| Ex. | catalyst or metal source | ligand | solvent | conversion (%) | % ee | stereo |
|---|---|---|---|---|---|---|
| 69 | [Rh(cod)₂]OTf | (R,R)-iPr-Duphos | MeOH | 89.9 | 70.2 | R |
| 70 | [Rh(cod)₂]OTf | (R)-Phanephos | MeOH | 98.8 | 45.4 | R |
| 71 | [Rh(cod)(S)-skewphos]OTf | — | MeOH | 57.1 | 68.1 | S |
| 72 | [Rh(nbd)(R)-(S)-josiphos]BF₄ | — | MeOH | 58.9 | 16.4 | S |
| 73 | [Rh(nbd)(S,S)-bisP*]BF₄ | — | MeOH | 45.0 | 61.4 | S |
| 74 | [Rh(cod)₂]OTf | (R,R)-iPr-Duphos | MeOH | 14.6 | 68.2 | S |
| 75 | [Rh(cod){(R,R)-Et-duphos}]OTf | — | MeOH | 31.4 | 79.8 | S |
| 76 | [Rh(cod)₂]OTf | (R,R)-Ph-BPE | MeOH | 23.0 | 50.3 | R |
| 77 | [Rh(cod)₂]OTf | (R,R)-cataciumM(R) | MeOH | 27.3 | 54.8 | S |
| 78 | [Rh(cod)₂]OTf | (S,S)-Et-Ferrotne | MeOH | 99.4 | 26.4 | S |
| 79 | [Rh(cod){(S,S)-ptbp-skewphos}]OTf | — | MeOH | 48.4 | 70.5 | S |
| 80 | [Rh(cod)₂]OTf | (R,R)-Norphos | MeOH | 29.3 | 72.4 | S |
| 81 | [Rh(cod)₂]OTf | (S)-xyl-Phanephos | MeOH | 98.5 | 50.9 | S |
| 82 | [Rh(cod)₂]OTf | cataASium T3 | MeOH | 25.1 | 47.0 | R |
| 83 | [Rh(cod)₂]OTf | SL-J004-1 | MeOH | 57.6 | 25.1 | R |
| 84 | [Rh(cod)₂]OTf | (S)(R)-SL-J002-02 | MeOH | 99.2 | 81.9 | S |
| 85 | [Rh(cod)₂]OTf | (R)(S)-SL-J502-1 | MeOH | 98.7 | 58.5 | R |
| 86 | [Rh(cod)₂]OTf | (R)(S)-SL-J009-1 | MeOH | 99.6 | 16.0 | R |
| 87 | [Rh(cod)₂]OTf | (R)(S)-SL-J005-1 | MeOH | 38.6 | 8.6 | R |
| 88 | [Rh(cod)₂]OTf | (R)(S)-SL-J011-1 | MeOH | 99.2 | 90.7 | R |
| 89 | [Rh(cod)₂]OTf | (R)(S)-SL-J013-1 | MeOH | 98.7 | 86.0 | R |
| 90 | [Rh(cod)₂]OTf | (R)(S)-SL-J212-1 | MeOH | 99.2 | 67.1 | R |
| 91 | [Rh(cod)₂]OTf | (R)(S)-SL-J216-1 | MeOH | 24.5 | 49.5 | R |
| 92 | [Rh(cod)₂]OTf | (R)(S)-SL-J014-1 | MeOH | 98.8 | 87.8 | R |
| 93 | [Rh(cod)₂]OTf | (R)(S)-SL-J202-1 | MeOH | 99.2 | 82.7 | R |
| 94 | [Rh(cod)₂]OTf | (R)(S)-SL-J203-2 | MeOH | 99.6 | 67.6 | S |
| 95 | [Rh(cod)₂]OTf | (R)(S)-SL-J210-1 | MeOH | 98.9 | 91.8 | R |
| 96 | [Rh(cod)₂]OTf | SL-M001-1 | MeOH | 65.4 | 6.0 | R |
| 97 | [Rh(cod)₂]OTf | SL-W001-1 | MeOH | 98.5 | 37.0 | R |
| 98 | [Rh(cod)₂]OTf | SL-W002-1 | MeOH | 81.9 | 47.0 | R |
| 99 | [Rh(cod)₂]OTf | SL-W003-1 | MeOH | 99.4 | 22.6 | R |
| 100 | [Rh(cod)₂]OTf | SL-T001-1 | MeOH | 97.0 | 72.2 | S |
| 101 | [Rh(cod)₂]OTf | SL-T002-1 | MeOH | 23.2 | 62.9 | S |

Example 102

Synthesis of 2-((1S)-1-(2-benzoylhydrazinyl)ethyl)-N-(5-chloro-4-(trifluoromethyl)pyridin-2-yl)-1,3-thiazole-5-carboxamide

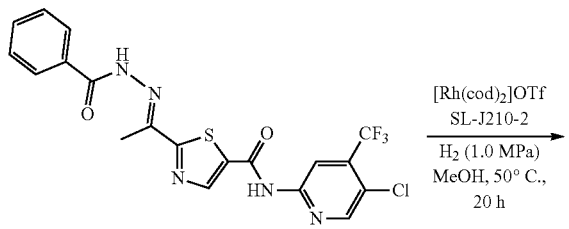

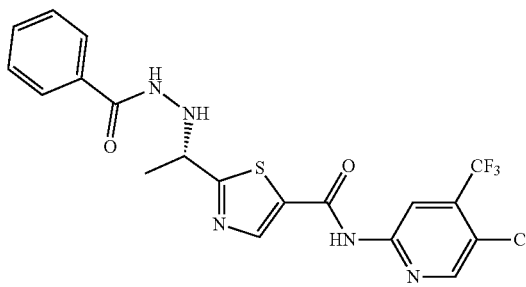

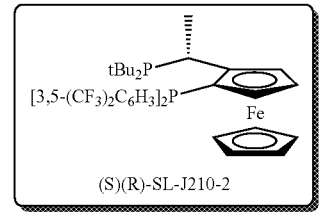

(S)(R)-SL-J210-2

[Rh(cod)₂]OTf (0.0020 g) and (S) (R)-SL-J210-2 (0.0037 g) were put into a Schlenk flask (20 mL). The atmosphere in the container was decompressed, and the pressure was recovered with argon. The procedures were performed five times in total. The pressure of the container was recovered to normal pressure, dehydrated methanol (20 mL) for organic synthesis was added thereto, and the mixture was stirred at room temperature for 1 hr. Separately, (E)-2-(1-(2-benzoylhydrazono)ethyl)-N-(5-chloro-4-(trifluoromethyl)pyridin-2-yl)-1,3-thiazole-5-carboxamide (2.00 g) was put into an autoclave. The atmosphere in the container was decompressed, and the pressure was recovered with argon. The procedures were performed seven times in total. The pressure of the container was recovered to normal pressure, and the rhodium catalyst methanol solution, which was prepared above, was fed thereto by argon pressure. The Schlenk container was washed with methanol (20 mL), and the washing was added by argon pressure. Hydrogen was fed into the container until 1.0 MPa, and the mixture was stirred at the internal temperature of 50° C. for 20 hr. The mixture was cooled to the internal temperature of about 20° C., and the hydrogen was released. The production of the title compound was confirmed by analyzing the reaction solution using HPLC (conversion 99% or more, 90% ee). The reaction mixture was concentrated to give a yellow solid. The solid was suspended in acetonitrile (4 mL)/diisopropyl ether (16 mL), and the suspension was stirred at 60° C. for 1 hr, cooled to room temperature and stirred overnight. The precipitate was collected by filtration using a glass filter, and washed with acetonitrile (2 mL)/diisopropyl ether (8 mL). The obtained solid was dried under reduced pressure at 60° C. to give the title compound (yield-86%, 91% ee). HPLC area normalization 98.3%.

Conditions for High-Performance Liquid Chromatography Analysis (Optical Purity)
   column: OJ-RH (manufactured by Daicel Chemical Industries), 4.6*150 mm
   UV detection wavelength: 254 nm
   mobile phase: acetonitrile for high-performance liquid chromatography/0.025 mol/L aqueous potassium dihydrogenphosphate solution=1/1
   flow rate: 1.0 mL/min
   retention time: 5.4 min. (S-form); 6.1 min. (R-form); 7.6 min. (the raw material)
$^1$H NMR (CDCl$_3$) δ 1.62 (d, J=6.5 Hz, 3H), 4.64 (qd, J=6.5, 2.0 Hz, 1H), 5.31 (dd, 1H), 7.43 (t, J=7.5 Hz, 2H), 7.53 (tt, J=8.0, 1.5 Hz, 1H), 7.71 (dd, J=8.0, 1.5 Hz, 2H), 7.84 (d, J=5.5 Hz, 1H), 8.29 (s, 1H), 8.43 (s, 1H), 8.67 (s, 2H); $^{19}$F NMR (CDCl$_3$) δ−64.77; $^{13}$C NMR (CDCl$_3$) δ 20.43, 59.12, 111.96 (q, J=5.4 Hz), 121.4 (q, J=275.2 Hz), 123.97, 126.96, 128.78, 132.16, 132.37, 133.55, 137.79 (q, J=33.6 Hz), 144.67, 149.42, 150.04, 158.94, 168.02, 180.68.

Example 103

Synthesis of 2-((1S)-1-aminoethyl)-N-(5-chloro-4-(trifluoromethyl)pyridin-2-yl)-1,3-thiazole-5-carboxamide hydrochloride

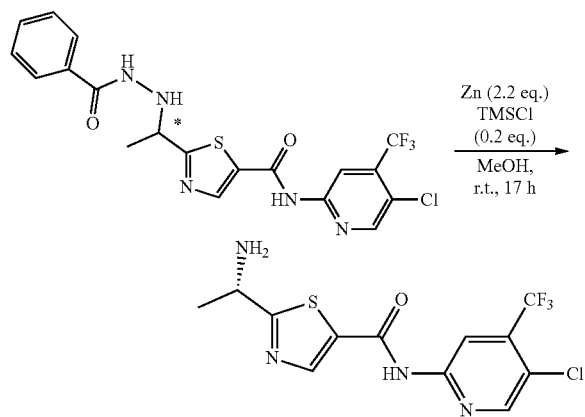

2-((1S)-1-(2-Benzoylhydrazinyl)ethyl)-N-(5-chloro-4-(trifluoromethyl)pyridin-2-yl)-1,3-thiazole-5-carboxamide (0.0500 g) and zinc powder (0.0152 g) were put into a Schlenk flask (10 mL). The atmosphere in the container was decompressed, and the pressure was recovered with argon. The procedures were performed three times in total. Methanol (2.0 mL) and chlorotrimethylsilane (0.002 mL) were added thereto at room temperature. After confirming that the reaction solution became gray, benzoic acid (0.029 g) was added thereto, and the reaction mixture was stirred at room temperature for 17 hr. The production of the title compound was confirmed by HPLC (55.8% ee)

Conditions for High-Performance Liquid Chromatography Analysis (Optical Purity)
   column: OJ-H (manufactured by Daicel Chemical Industries), 4.6*150 mm
   UV detection wavelength: 270 nm
   mobile phase: hexane for high-performance liquid chromatography/isopropyl alcohol/methanol/diethylamine=80/15/5/0.1
   flow rate: 1.0 mL/min
   retention time: 5.7 min.(S-form); 8.6 min. (R-form)

Examples 104-111

Synthesis of tert-butyl 2-((1S)-1-(5-((5-chloro-4-(trifluoromethyl)pyridin-2-yl)carbamoyl)-1,3-thiazol-2-yl)ethyl)hydrazinecarboxylate

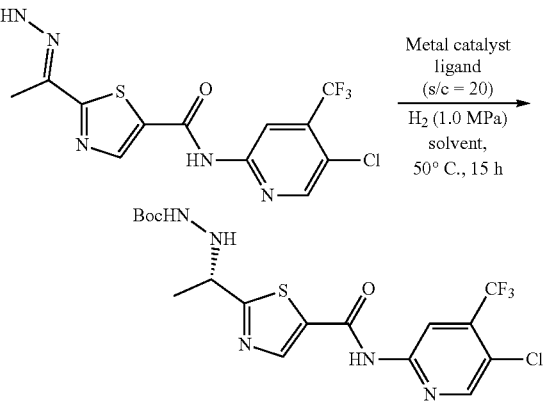

tert-Butyl 2-(1-(5-((5-chloro-4-(trifluoromethyl)pyridin-2-yl)carbamoyl)-1,3-thiazol-2-yl)ethylidene)hydrazinecarboxylate (0.0696 g), a catalyst (corresponding to s/c=20) and a ligand (1.1 equivalent relative to the catalyst) were put into a test tube. A solvent (1.5 mL) was added thereto under nitrogen atmosphere, the test tube was set in an autoclave, and the reaction system was purged with hydrogen. Hydrogen was fed into the autoclave until 1.0 MPa, and the mixture was stirred at 50° C. for 15 hr. The production of the title compound was confirmed by analyzing the reaction solution using HPLC. The results are shown in Table 11.

Conditions for High-Performance Liquid Chromatography Analysis (Optical Purity)
   column: OJ-RH (manufactured by Daicel Chemical Industries), 4.6*150 mm
   UV detection wavelength: 254 nm
   mobile phase: acetonitrile for high-performance liquid chromatography/0.025 mol/L aqueous potassium dihydrogenphosphate solution=1/1
   flow rate: 0.5 mL/min
   retention time: 12.8 min. (enantiomer-A); 14.6 min. (the raw material); 16.1 min. (enantiomer-B)

TABLE 11

| Ex. | catalyst or metal source | ligand | solvent | conversion (%) | % ee |
|---|---|---|---|---|---|
| 104 | [Rh(cod)$_2$]OTf | (S,S)-Et-Ferrotne | IPA | 77.2 | 61.0 |
| 105 | [Rh(cod)$_2$]OTf | (R,R)-iPr-Duphos | IPA | 20.7 | −66.3 |
| 106 | [Rh(cod)$_2$]OTf | (S)-xyl-Phanephos | IPA | 78.5 | 94.9 |
| 107 | [Rh(cod)$_2$]OTf | SL-T001-1 | IPA | 27.2 | 46.7 |

TABLE 11-continued

| Ex. | catalyst or metal source | ligand | solvent | conversion (%) | % ee |
|---|---|---|---|---|---|
| 108 | [Rh(cod)₂]OTf | (S)(R)-SL-J002-02 | IPA | 98.9 | 11.0 |
| 109 | [Rh(cod)₂]OTf | (R)(S)-SL-J011-1 | IPA | 97.5 | 37.2 |
| 110 | [Rh(cod)₂]OTf | (R)(S)-SL-J014-1 | DCM | 98.9 | 3.3 |
| 111 | [RhCl(cod)]₂ | (R)(S)-SL-J210-2 | MeOH | 85.5 | −24.6 |

Examples 112-149

Synthesis of 2-(1-(benzylamino)ethyl)-N-(5-chloro-4-(trifluoromethyl)pyridin-2-yl)-1,3-thiazole-5-carboxamide

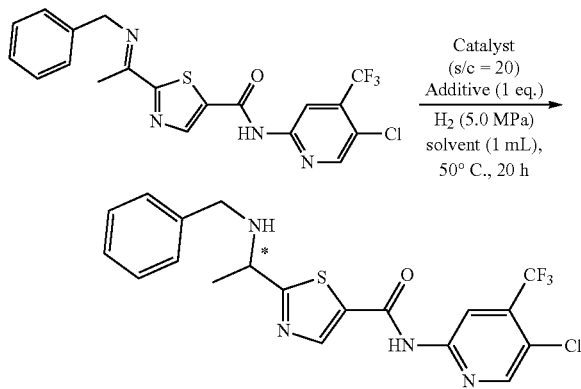

(E)-2-(1-(Benzylimino)ethyl)-N-(5-chloro-4-(trifluoromethyl)pyridin-2-yl)-1,3-thiazole-5-carboxamide (0.0658 g), a catalyst (corresponding to s/c=20), a ligand (1.1 or 2 equivalent relative to the catalyst) and an additive (potassium butoxide was used in an amount of 1 equivalent relative to the substrate in Examples 113-118, and the additive was not used in Examples 119-149) were put into a test tube. A solvent (1 mL) was added thereto under nitrogen atmosphere, the test tube was set in an autoclave, and the reaction system was purged with hydrogen. Hydrogen was fed into the autoclave until 5.0 MPa, and the mixture was stirred at 50° C. for 20 hr. The production of the title compound was confirmed by analyzing the reaction solution using HPLC. The results are shown in Table 12.

Conditions for High-Performance Liquid Chromatography Analysis (HPLC Area Normalization)
 column: YMC-Pack ODS-A (manufactured by YMC. CO., LTD.), 4.6*150 mm
 UV detection wavelength: 254 nm
 mobile phase: acetonitrile for high-performance liquid chromatography/0.025 mol/L aqueous potassium dihydrogenphosphate solution=7/3
 flow rate: 1.4 mL/min
 retention time: 7.2 min. (the title compound); 12.0 min. (the raw material).

Conditions for High-Performance Liquid Chromatography Analysis (Optical Purity)
 column: OJ-RH (manufactured by Daicel Chemical Industries), 4.6*150 mm
 UV detection wavelength: 254 nm
 mobile phase: acetonitrile for high-performance liquid chromatography/0.025 mol/L aqueous potassium dihydrogenphosphate solution=7/3
 flow rate: 1.0 mL/min
 retention time: 4.8 min. (the title compound); 7.2 min. (the raw material); 11.9 min. (the title compound)

TABLE 12

| Ex. | catalyst ormetal source | ligand | solvent | conversion (%) | % ee |
|---|---|---|---|---|---|
| 112 | RuCl₂{(R)-binap} | — | IPA | 47.9 | −6.2 |
| 113 | RuCl₂{(R)-binap}{R,R-dpen} | — | IPA | 20.7 | −8.8 |
| 114 | RuCl₂{(R)-binap}{R,R-dach} | — | IPA | 22.7 | 2.9 |
| 115 | RuCl₂{(R)-binap}(R,R-daipen} | — | IPA | .35.9 | 8.1 |
| 116 | RuCl₂{(R)-xyl-binap}{R,R-dpen} | — | IPA | 23.1 | −9.0 |
| 117 | RuCl₂{(R)-xyl-binap}{R,R-dach} | — | IPA | 8.8 | 17.6 |
| 118 | RuCl₂{(R)-xyl-binap}[R,R-daipen} | — | IPA | 19.7 | −14.9 |
| 119 | [IrCl(cod)]₂ | (R)-BINAP | Toluene | 55.7 | 4.0 |
| 120 | [IrCl(cod)]₂ | (R,R)-iPr-Duphos | Toluene | 57.5 | 1.4 |
| 121 | [IrCl(cod)]₂ | (R,R)-Skewphos | Toluene | 28.7 | 3.6 |
| 122 | [IrCl(cod)]₂ | (R)-(S)-Josiphos | Toluene | 59.7 | 6.8 |
| 123 | [IrCl(cod)]₂ | (R)-Phanephos | Toluene | 65.0 | 4.0 |
| 124 | [IrCl(cod)]₂ | (R)-iPr-PHOX | Toluene | 61.5 | 2.2 |
| 125 | Ir(cod)₂(BAr₄$^F$) | (R)-(S)-Josiphos | Toluene | 42.8 | 22.2 |
| 126 | Ir(cod)₂(BAr₄$^F$) | (R)-Phanephos | Toluene | 23.5 | −6.6 |
| 127 | Ir(cod){(S,S)-Ph₂PThrePHOX}(BAr₄$^F$) | — | Toluene | 5.0 | 33.1 |
| 128 | Ir(cod){(S,S)-Cy₂PThrePH0X}(BAr₄$^F$) | — | Toluene | 26.7 | 2.0 |
| 129 | [RhCl(cod)]₂ | (R)-BINAP | MeOH | 21.9 | 10.1 |
| 130 | [RhCl(cod)]₂ | (R,R)-iPr-Duphos | MeOH | 39.5 | 7.3 |
| 131 | [RhCl(cod)]₂ | (R,R)-Skewphos | MeOH | 78.8 | 3.5 |
| 132 | [RhCl(cod)]₂ | (R)-(S)-Josiphos | MeOH | 75.8 | −0.1 |
| 133 | [RhCl(cod)]₂ | (R)-Phanephos | MeOH | 62.1 | −9.0 |
| 134 | [RhCl(cod)]₂ | (R,R)-DIPAMP | MeOH | 66.9 | 5.4 |
| 135 | [RhCl(cod)]₂ | (R,R)-Quinox-P* | MeOH | 89.9 | 12.1 |
| 136 | [Rh(cod)₂]OTf | (R)-BINAP | MeOH | 36.0 | 7.3 |
| 137 | [Rh(cod)₂]OTf | (R,R)-iPr-Duphos | MeOH | 71.4 | 2.6 |
| 138 | [Rh(cod)₂]OTf | (R)-Phanephos | MeOH | 60.0 | −10.2 |

TABLE 12-continued

| Ex. | catalyst or metal source | ligand | solvent | conversion (%) | % ee |
|---|---|---|---|---|---|
| 139 | [Rh(cod)(S)-skewphos]OTf | — | MeOH | 87.8 | 3.3 |
| 140 | [Rh(nbd)(R)-(S)-josiphos]BF$_4$ | — | MeOH | 93.9 | 2.4 |
| 141 | [Rh(nbd)(S,S)-bisP*]BF$_4$ | — | MeOH | 92.1 | 2.1 |
| 142 | [Rh(cod)(R,R)-dipamp]BF$_4$ | — | MeOH | 68.0 | 3.3 |
| 143 | [Rh(cod)(S)-xyl-binap]OTf | — | MeOH | 77.1 | 2.9 |
| 144 | [IrCl(cod)]$_2$ | (R)-(S)-Josiphos | DCM | 99.4 | 3.7 |
| 145 | [IrCl(cod)]$_2$ | (R)-iPr-PHOX | DCM | 98.9 | 3.2 |
| 146 | Ir(cod)$_2$(BAr$_4^F$) | (R)-(S)-Josiphos | DCM | 34.9 | 9.5 |
| 147 | Ir(cod)$_2$(BAr$_4^F$) | (R)-iPr-PHOX | MeOH | 30.7 | −5.6 |
| 148 | Ir(cod)$_2$(BAr$_4^F$) | (R)-iPr-PHOX | DCM | 51.2 | 2.6 |
| 149 | Ir(cod)$_2$(BAr$_4^F$) | (S)-Monophos | Toluene | 57.6 | −78.8 |

Examples 150-156

Synthesis of N-(5-chloro-4-(trifluoromethyl)pyridin-2-yl)-2-(1-((4-methoxybenzyl)amino)ethyl)-1,3-thiazole-5-carboxamide

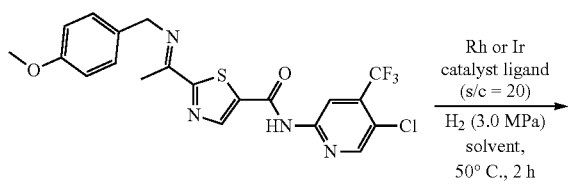

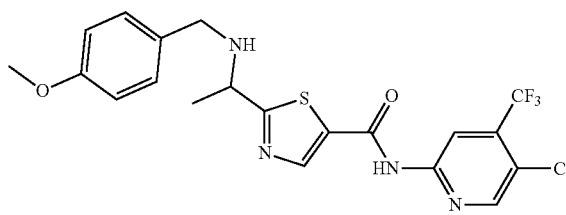

N-(5-Chloro-4-(trifluoromethyl)pyridin-2-yl)-2-(1-((4-methoxybenzyl)imino)ethyl)-1,3-thiazole-5-carboxamide (0.0351 g), a catalyst (corresponding to s/c=20) and a ligand (1.1 or 2 equivalent relative to the catalyst) were put into a test tube. A solvent (0.75 mL) was added thereto under nitrogen atmosphere, the test tube was set in an autoclave, and the reaction system was purged with hydrogen. Hydrogen was fed into the autoclave until 3.0 MPa, and the mixture was stirred at 50° C. for 2 hr. The production of the title compound was confirmed by analyzing the reaction solution using HPLC. The results are shown in Table 13.

Conditions for High-Performance Liquid Chromatography Analysis (HPLC Area Normalization)
  column: YMC-Pack ODS-A (manufactured by YMC. CO., LTD.), 4.6*150 mm
  UV detection wavelength: 254 nm
  mobile phase: acetonitrile for high-performance liquid chromatography/0.025 mol/L aqueous potassium dihydrogenphosphate solution=7/3
  flow rate: 1.0 mL/min
  retention time: 6.9 min. (the title compound); 11.2 min. (the raw material).

Conditions for High-Performance Liquid Chromatography Analysis (Optical Purity)
  column: OJ-RH (manufactured by Daicel Chemical Industries), 4.6*150 mm
  UV detection wavelength: 254 nm
  mobile phase: acetonitrile for high-performance liquid chromatography/0.025 mol/L aqueous potassium dihydrogenphosphate solution=7/3
  flow rate: 1.0 mL/min
  retention time: 5.0 min. (the title compound); 6.0 min. (the title compound); 7.4 min. (the raw material)

TABLE 13

| Ex. | catalyst or metal source | ligand | solvent | conversion (%) | % ee |
|---|---|---|---|---|---|
| 150 | [Rh(cod)(R)-(S)-josiphos]OTf | — | MeOH | 14.0 | −9.7 |
| 151 | [Rh(cod)(R)-(S)-josiphos]OTf | — | THF | 5.4 | −22.1 |
| 152 | Ir(cod)$_2$(BAr$_4^F$) | (R)-(S)-Josiphos | MeOH | 31.4 | 17.2 |
| 153 | Ir(cod)$_2$(BAr$_4^F$) | (R)-(S)-Josiphos | THF | 26.8 | 24.4 |
| 154 | Ir(cod)$_2$(BAr$_4^F$) | (R)-(S)-Josiphos | DCM | 99.4 | 17.1 |
| 155 | Ir(cod)$_2$(BAr$_4^F$) | (R)-(S)-Josiphos | Toluene | 65.2 | 21.6 |
| 156 | Ir(cod)$_2$(BAr$_4^F$) | (S)-Monophos | Toluene | 74.6 | −74.0 |

Examples 157-162

Synthesis of N-(5-chloro-4-(trifluoromethyl)pyridin-2-yl)-2-(1-((2,4-dimethoxybenzyl)amino)ethyl)-1,3-thiazole-5-carboxamide

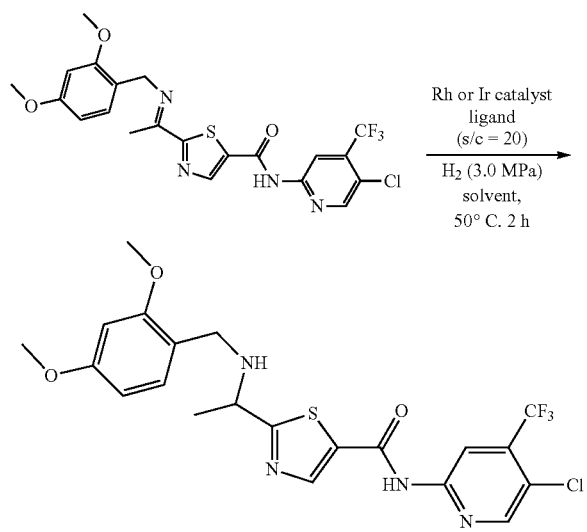

N-(5-Chloro-4-(trifluoromethyl) pyridin-2-yl)-2-(1-((2,4-dimethoxybenzyl)imino)ethyl)-1,3-thiazole-5-carboxamide (0.0351 g), a catalyst (corresponding to s/c=20) and a ligand (1.1 or 2 equivalent relative to the catalyst) were put into a test tube. A solvent (0.75 mL) was added thereto under nitrogen atmosphere, the test tube was set in an autoclave, and the reaction system was purged with hydrogen. Hydrogen was fed into the autoclave until 3.0 MPa, and the mixture was stirred at 50° C. for 2 hr. The production of the title compound was confirmed by analyzing the reaction solution using HPLC. The results are shown in Table 15.

Conditions for High-Performance Liquid Chromatography Analysis (HPLC Area Normalization)

column: YMC-Pack ODS-A (manufactured by YMC. CO., LTD.), 4.6*150 mm

UV detection wavelength: 254 nm mobile phase: acetonitrile for high-performance liquid chromatography/0.025 mol/L aqueous potassium dihydrogenphosphate solution=7/3 flow rate: 1.0 mL/min retention time: 6.3 min. (the title compound); 12.1 min. (the raw material).

Conditions for High-Performance Liquid Chromatography Analysis (Optical Purity)

column: OJ-RH (manufactured by Daicel Chemical Industries), 4.6*150 mm

UV detection wavelength: 254 nm

TABLE 14

| mobile phase: | | |
|---|---|---|
| | acetonitrile for high-performance liquid chromatography | 0.025 mol/L aqueous potassium dihydrogenphosphate solution |
| 0.0-10.0 min. | 40% | 60% |
| 10.1-20.0 min. | 80% | 20% | acetonitrile for high-performance liquid chromatography/0.025 mol/L aqueous potassium dihydrogenphosphate solution=4/6, 10 min flow rate: 1.2 mL/min retention time: 6.0 min. (the title compound); 6.5 min. (the title compound); 10.8 min. (the raw material)

TABLE 15

| Ex. | catalyst or metal source | ligand | solvent | conversion (%) | % ee |
|---|---|---|---|---|---|
| 157 | [Rh(cod)(R)-(S)-josiphos]OTf | — | THF | 1.3 | −10.5 |
| 158 | [Rh(cod)(R)-(S)-josiphos]OTf | — | DCM | 4.4 | — |
| 159 | Ir(cod)$_2$(BAr$_4^F$) | (R)-(S)-Josiphos | THF | 24.1 | 17.5 |
| 160 | Ir(cod)$_2$(BAr$_4^F$) | (R)-(S)-Josiphos | DCM | 68.6 | 11.5 |
| 161 | Ir(cod)$_2$(BAr$_4^F$) | (R)-(S)-Josiphos | Toluene | 93.1 | 18.5 |
| 162 | Ir(cod)$_2$(BAr$_4^F$) | (S)-Monophos | Toluene | 45.6 | −80.0 |

Reference Example 10

Synthesis of (E)-1,1-diphenyl-N-(1-phenylethylidene)methanamine

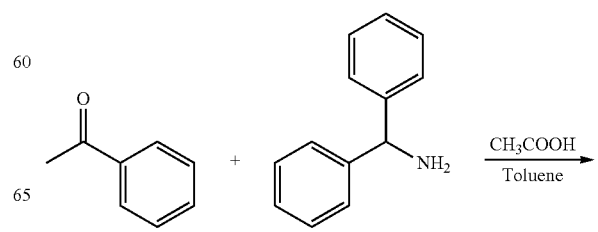

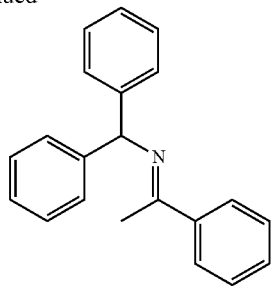

Acetophenone (4.92 g), toluene (50 mL), benzhydrylamine (7.88 g) and acetic acid (0.5 mL) were put into a four-necked eggplant flask (100 mL) equipped with Dean-Stark trap, and the mixture was stirred at the external temperature of 135° C. for 6 hr. The reaction mixture was cooled to room temperature, and concentrated under reduced pressure to give an oil. To the oil was added normal hexane, and the mixture was stirred at 0° C. for hr. The resulting solid was collected by filtration, washed with normal hexane (20 mL), and dried under reduced pressure at 50° C. to give the title compound (4.13 g, yield 35%) as a white solid.

$^1$H NMR (CDCl$_3$) δ 2.26 (s, 3H), 5.84 (s, 1H), 7.12-7.21 (m, 2H), 7.24-7.30 (m, 4H), 7.33-7.39 (m, 3H), 7.42-7.50 (m, 4H), 7.88-7.96 (m, 2H); $^{13}$C NMR (CDCl$_3$) δ 16.03, 68.52, 126.81, 127.08, 127.70, 128.25, 128.52, 129.73, 141.33, 144.97, 164.51.

Reference Example 11

Synthesis of (E)-N-(1-(4-methoxyphenyl)ethylidene)-1,1-diphenylmethanamine

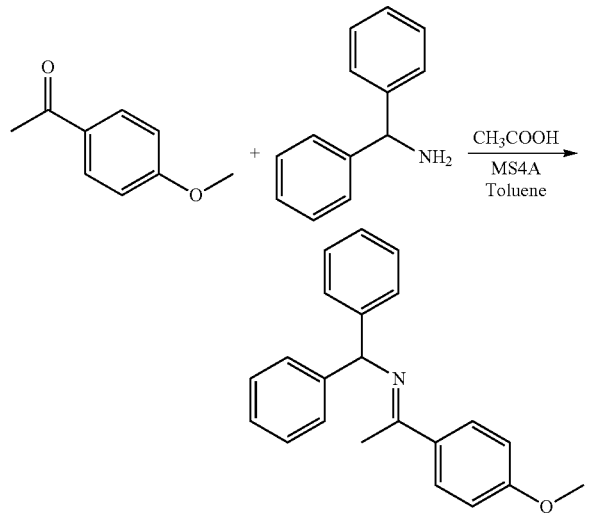

Molecular sieve 4A (5.00 g) was put into a four-necked eggplant flask (100 mL), and dried under reduced pressure at 100° C. for 30 min, and the reaction system was purged with nitrogen. The flask was cooled to room temperature, toluene (30 mL), 4'-methoxyacetophenone (5.00 g), benzhydrylamine (6.03 mL) and acetic acid (0.38 mL) were added thereto, and the mixture was stirred for at the internal temperature of 90° C. for hr. The reaction mixture was cooled to room temperature, and filtered using Hirsch funnel, and the filtrate was concentrated under reduced pressure to give an oil. To the oil was added normal hexane (30 mL), and the oil was dissolved at 90° C. The mixture was cooled to room temperature, and stirred for 1 hr. The resulting solid was collected by filtration, washed with normal hexane (20 mL), and dried under reduced pressure at 40° C. The obtained white solid (5.55 g) was again dissolved with heating in normal hexane (20 mL) at 90° C., and the solution was cooled to room temperature, and stirred overnight at room temperature. The resulting solid was collected by filtration, washed with normal hexane (10 mL), and dried under reduced pressure at 40° C. to give the title compound (4.81 g, yield 46%) as a white solid.

$^1$H NMR (CDCl$_3$) δ 2.27 (s, 3H), 3.82 (s, 3H), 5.83 (s, 1H), 6.90 (d, J=9.0 Hz, 2H), 7.19 (t, J=7.5 Hz, 2H), 7.29 (t, J=7.5 Hz, 4H), 7.46 (d, J=7.5 Hz, 4H), 7.92 (d, J=9.0 Hz, 2H);

$^{13}$C NMR (CDCl$_3$) δ 15.60, 55.31, 68.23, 113.40, 126.60, 127.56, 128.35, 128.44, 133.98, 145.08, 160.92, 163.47.

Reference Example 12

Synthesis of (E)-N-(1-(4-chlorophenyl)ethylidene)-1,1-diphenylmethanamine

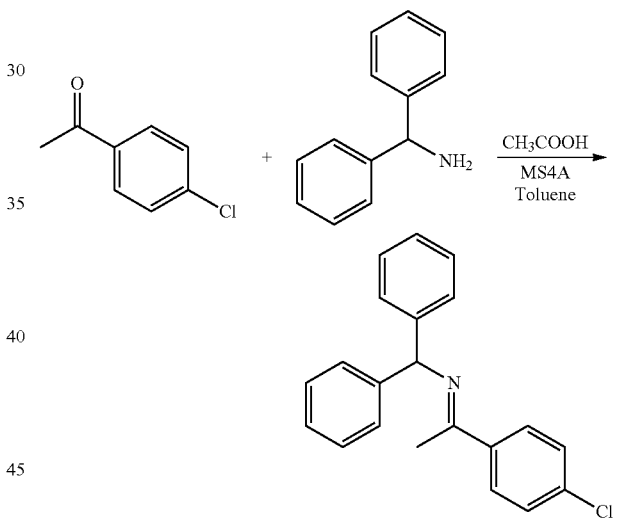

Molecular sieve 4A (5.00 g) was put into a four-necked eggplant flask (100 mL), and dried under reduced pressure at 100° C. for 30 min, and the reaction system was purged with nitrogen. The flask was cooled to room temperature, toluene (30 mL), 4'-chloroacetophenone (5.00 mL), benzhydrylamine (7.97 mL) and acetic acid (0.44 mL) were added thereto, and the mixture was stirred at the internal temperature of 100° C. for 25 hr. 7 hr after the beginning of the stirring, additional benzhydrylamine (1.3 mL) was added thereto. The reaction mixture was cooled to room temperature, and filtered using Hirsch funnel, and the filtrate was concentrated under reduced pressure to give a white solid. To the solid was added normal hexane (50 mL), and the mixture was heated under reflux for 20 min, cooled to 0° C., and stirred at the same temperature for 1 hr. The resulting solid was collected by filtration, washed with normal hexane (30 mL) cooled to 0° C., and dried under reduced pressure at 40° C. to give the title compound (8.25 g, yield 67%) as a white solid.

¹H NMR (CDCl₃) δ 2.29 (s, 3H), 5.85 (s, 1H), 7.20 (t, J=7.5 Hz, 2H), 7.30 (t, J=7.5 Hz, 4H), 7.35 (d, J=8.5 Hz, 2H), 7.44 (d, J=7.5 Hz, 4H), 7.88 (d, J=8.5 Hz); ¹³C NMR (CDCl₃) δ15.75, 68.50, 126.79, 127.51, 128.31, 128.45, 135.75, 139.52, 144.64, 163.16 (two peaks are duplicated in one of the underlined peaks).

Reference Example 13

Synthesis of (E)-1,1-diphenyl-N-(1-(4-trifluoromethylphenyl)ethylidene)methanamine

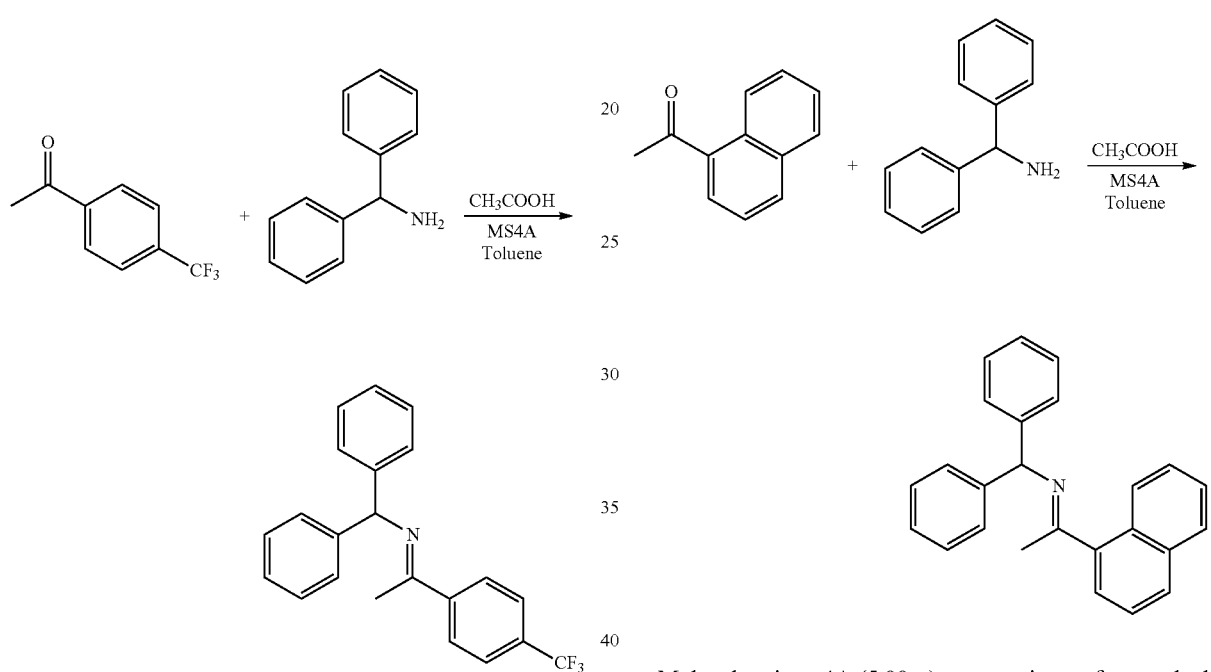

Molecular sieve 4A (5.00 g) was put into a four-necked eggplant flask (100 mL), and dried under reduced pressure at 100° C. for 30 min, and the reaction system was purged with nitrogen. The flask was cooled to room temperature, toluene (30 mL), 4'-trifluoromethylacetophenone (5.00 g), benzhydrylamine (5.72 mL) and acetic acid (0.31 mL) were added thereto, and the mixture was stirred at the internal temperature of 100° C. for 16 hr. The reaction mixture was cooled to room temperature, and filtered using Hirsch funnel, and the filtrate was concentrated under reduced pressure to give a white solid. To the solid was added normal hexane (30 mL), and the mixture was stirred at 90° C., cooled to 0° C., and stirred at the same temperature for 1 hr. The resulting solid was collected by filtration, washed with normal hexane (20 mL) cooled to 0° C., and dried under reduced pressure at 40° C. to give the title compound (4.68 g, yield 50%) as a white solid. The residual filtrate was concentrated under reduced pressure, and the residue was recrystallized from normal hexane (15 mL) at −20° C. to give the title compound (1.45 g, yield 15%) as a white solid.

¹H NMR (CDCl₃) δ 2.33 (s, 3H), 5.88 (s, 1H), 7.21 (t, J=7.5 Hz, 2H), 7.31 (d, J=7.5 Hz, 4H), 7.45 (d, J=7.5 Hz, 4H), 7.64 (d, J=8.5 Hz, 2H), 8.03 (d, J=8.5 Hz, 2H); ¹⁹F NMR (CDCl₃) δ −62.65; ¹³C NMR (CDCl₃) δ 15.99, 68.67, 124.13 (q, J=272.4 Hz), 125.13 (q, J=4.5 Hz), 126.89, 127.28, 127.49, 128.51, 131.41 (q, J=31.8 Hz), 144.30, 144.43, 163.23.

Reference Example 14

Synthesis of (E)-N-(1-(naphthalen-1-yl)ethylidene)-1,1-diphenylmethanamine

Molecular sieve 4A (5.00 g) was put into a four-necked eggplant flask (100 mL), and dried under reduced pressure at 100° C. for 30 min, and the reaction system was purged with nitrogen. The flask was cooled to room temperature, toluene (25 mL), 1-acetonaphthone (5.00 mL), benzhydrylamine (5.95 mL) and acetic acid (0.38 mL) were added thereto, and the mixture was stirred at the internal temperature of 100° C. for 28 hr. The reaction mixture was cooled to 90° C., and filtered using Hirsch funnel, and the filtrate was concentrated under reduced pressure to give a brown solid. To the solid was added normal hexane (60 mL), and the mixture was heated under reflux for 10 min, cooled to −20° C., and stirred at the same temperature for 1 hr. The resulting solid was collected by filtration, washed with normal hexane (40 mL) cooled to −20° C., and dried under reduced pressure at 40° C. to give the title compound (7.82 g, yield 71%) as a white solid.

¹H NMR (CDCl₃) δ 2.50 (s, 3H), 5.22 (s, 1H), 7.02-7.05 (m, 1H), 7.06-7.11 (m, 2H), 7.13-7.21 (m, 6H), 7.22-7.27 (m, 2H), 7.30-7.36 (m, 1H), 7.40-7.44 (m, 1H), 7.46-7.51 (m, 2H), 7.82-7.86 (m, 1H), 7.87-7.90 (m, 1H); ¹³C NMR (CDCl₃) δ 29.61, 70.19, 123.13, 125.12, 125.20, 126.31, 126.47, 126.56, 126.59, 127.52, 127.74, 128.00, 128.09, 128.22, 128.45, 129.09, 133.43, 137.91, 144.04, 144.48, 168.46.

Reference Example 15

Synthesis of (E)-N-(1-(furan-2-yl)ethylidene)-1,1-diphenylmethanamine

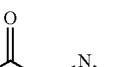

Molecular sieve 4A (4.00 g) was put into a four-necked eggplant flask (100 mL), and dried under reduced pressure at 100° C. for 30 min, and the reaction system was purged with nitrogen. The flask was cooled to room temperature, toluene (20 mL), 2-acetylfuran (3.44 mL), benzhydrylamine (6.20 mL) and acetic acid (0.39 mL) were added thereto, and the mixture was stirred at the internal temperature of 90° C. for 4 hr. The reaction mixture was cooled to 60° C., and filtered using Hirsch funnel, and the filtrate was concentrated under reduced pressure to give a mixture of brown liquid and white solid. To the residue was added toluene (20 mL), and the mixture was heated to 90° C., cooled to 0° C., and stirred at the same temperature for 1 hr. The resulting solid was collected by filtration, and washed with toluene (20 mL) cooled to 0° C. The obtained filtrate was concentrated under reduced pressure, toluene (10 mL) was added thereto, and the mixture was heated to 90° C., cooled, and stirred at −20° C. for 1 hr. The resulting solid was collected by filtration, washed with toluene (8 mL) cooled to −20° C., and dried under reduced pressure at 40° C. to give the title compound (1.50 g, yield 16%) as a white solid.

$^1$H NMR (CDCl$_3$) δ 2.24 (s, 3H), 5.83 (s, 1H), 6.45 (dd, J=3.5, 2.0 Hz, 1H), 6.89 (d, J=3.5 Hz, 1H), 7.20 (t, J=7.0 Hz, 2H), 7.29 (t, J=7.0 Hz, 4H), 7.41 (d, J=7.0 Hz, 4H), 7.50 (d, J=2.0 Hz, 1H); $^{13}$C NMR (CDCl$_3$) δ 15.22, 67.91, 111.13, 111.45, 126.75, 127.68, 128.42, 143.90, 144.43, 156.22 (two peaks are duplicated in one of the underlined peaks).

Reference Example 16

Synthesis of (E)-1,1-diphenyl-N-(1-(pyridin-2-yl)ethylidene)methanamine

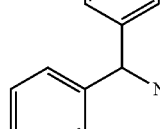

Toluene (50 mL), 2-acetylpyridine (5.00 mL), benzhydrylamine (8.07 mL) and acetic acid (0.51 mL) were put into a four-necked eggplant flask (100 mL) which was purged with nitrogen, and the mixture was stirred at the internal temperature of 80° C. for 4 hr. The reaction mixture was cooled to room temperature, concentrated under reduced pressure to give an oil. To the residue was added normal hexane (50 mL), and the mixture was stirred at 85° C. for 15 min, cooled to room temperature, and stirred at the same temperature for 1.5 hr. The resulting solid was collected by filtration, and washed with normal hexane (20 mL). The obtained filtrate was concentrated under reduced pressure until the volume was reduced to about 40 mL, and left standing at −5° C. for 1 hr in a freezer. The resulting solid was washed with normal hexane (40 mL) cooled to −5° C., dried under reduced pressure at 50° C. to give the title compound (7.22 g, yield 57%) as pale-brown crystals.

$^1$H NMR (CDCl$_3$) δ 2.46 (s, 3H), 5.93 (s, 1H), 7.21 (t, J=7.5 Hz, 2H), 7.26-7.33 (m, 5H), 7.46 (d, J=7.5 Hz, 4H), 7.73 (td, J=8.0, 2.0 Hz, 1H), 8.37 (d, J=7.5 Hz, 1H), 8.56-8.60 (m, 1H); $^{13}$C NMR (CDCl$_3$) δ 14.38, 68.72, 121.39, 124.19, 126.80, 127.57, 128.43, 136.17, 144.46, 148.14, 157.83, 166.06.

Reference Example 17

Synthesis of (E)-1,1-diphenyl-N-(1-(pyridin-3-yl)ethylidene)methanamine

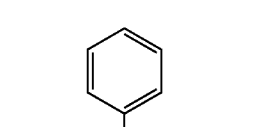

-continued

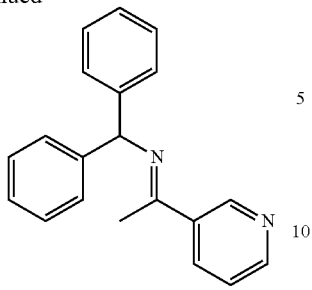

Molecular sieve 4A (5.00 g) was put into a four-necked eggplant flask (100 mL), and dried under reduced pressure at 100° C. for 30 min, and the reaction system was purged with nitrogen. The flask was cooled to room temperature, toluene (25 mL), 3-acetylpyridine (5.00 mL), benzhydrylamine (8.72 mL) and acetic acid (0.52 mL) were added thereto, and the mixture was stirred at the internal temperature of 100° C. for 2 hr. The reaction mixture was cooled to 80° C., and filtered using Hirsch funnel, and the filtrate was concentrated under reduced pressure to give an oil. To the residue was added toluene (20 mL), and the mixture was stirred at 100° C. for 10 min, cooled to −20° C., and stirred at the same temperature for 1 hr. The resulting solid was collected by filtration, and washed with toluene (20 mL) cooled to −20° C. The obtained filtrate was concentrated under reduced pressure, and solvent substitution was performed with by normal hexane. The residue was dissolved in a mixed solvent (15 mL) of normal hexane:toluene=1:2, and the solution was cooled to −78° C., and stirred for 5 hr. The resulting solid was collected by filtration, washed with a mixed solvent (15 mL) of normal hexane:toluene=10:1, which was cooled to −78° C., and dried under reduced pressure at 40° C. to give the title compound (4.85 g, yield 37%) as a white solid.

$^1$H NMR (CDCl$_3$) δ 2.33 (s, 3H), 5.88 (s, 1H), 7.21 (tt, J=7.5, 1.5 Hz, 2H), 7.28-7.33 (m, 5H), 7.46 (dd, J=8.0, 1.5 Hz, 4H), 8.26 (dt, J=8.0, 2.0 Hz, 1H), 8.62 (dd, J=4.5, 2.0 Hz, 1H), 9.11 (d, J=2.0 Hz, 1H); 13C NMR (CDCl$_3$) δ 5.72, 68.49, 123.07, 126.87, 127.46, 128.49, 134.27, 136.26, 144.39, 148.56, 150.58, 162.23.

Reference Example 18

Synthesis of (E)-1,1-diphenyl-N-(1-(thiazol-2-yl)ethylidene)methanamine

-continued

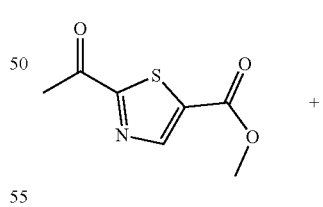

Molecular sieve 4A (5.00 g) was put into a four-necked eggplant flask (100 mL), and dried under reduced pressure at 100° C. for 30 min, and the reaction system was purged with nitrogen. The flask was cooled to room temperature, toluene (25 mL), 2-acetylthiazole (5.00 mL), benzhydrylamine (8.72 mL) and acetic acid (0.55 mL) were added thereto, and the mixture was stirred at the internal temperature of 100° C. for 4 hr. The reaction mixture was cooled to 70° C., and filtered using Hirsch funnel, and the filtrate was concentrated under reduced pressure to give an oil. To the residue was added normal hexane (50 mL), and the mixture was stirred at 50° C. for 10 min, cooled to −11° C., and stirred at the same temperature for 30 min. The resulting solid was collected by filtration, washed with normal hexane (40 mL) cooled to −11° C., and dried under reduced pressure at 40° C. to give the title compound (10.64 g, yield 75%) as a white solid.

$^1$H NMR (CDCl$_3$) δ 2.46 (s, 3H), 5.89 (s, 1H), 7.22 (t, J=7.0 Hz, 2H), 7.31 (t, J=7.0 Hz, 4H), 7.38 (d, J=3.0 Hz, 1H), 7.45 (d, J=7.0 Hz, 4H), 7.84 (d, J=3.0 Hz, 1H); $^{13}$C NMR (CDCl$_3$) δ 15.08, 68.29, 122.39, 126.97, 127.43, 128.52, 143.29, 143.95, 160.62, 172.10.

Reference Example 19

Synthesis of (E)-methyl 2-((1-benzhydrylimino)ethyl)-1,3-thiazole-5-carboxylate

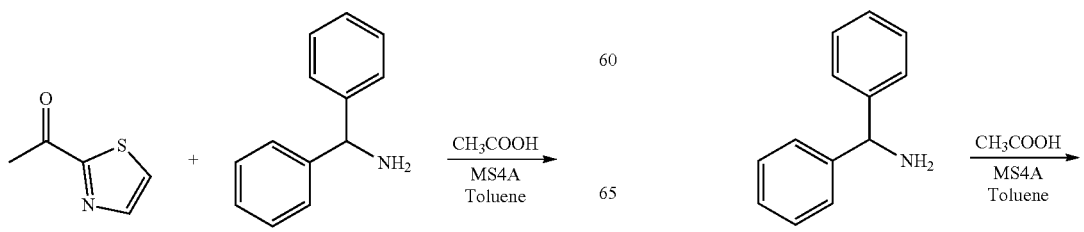

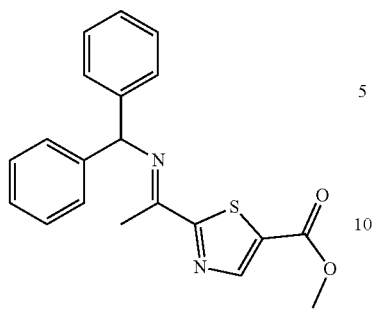

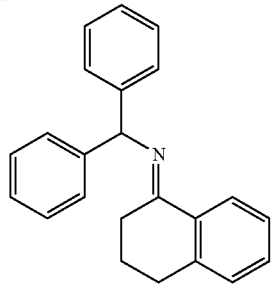

Molecular sieve 4A (5.00 g) was put into a four-necked eggplant flask (100 mL), and dried under reduced pressure at 100° C. for 30 min, and the reaction system was purged with nitrogen. The flask was cooled to room temperature, toluene (30 mL), methyl 2-acetyl-5-thiazolecarboxylate (5.00 g), benzhydrylamine (4.90 mL) and acetic acid (0.31 mL) were added thereto, and the mixture was stirred at the internal temperature of 100° C. for 22 hr. 4 hr after the beginning of the stirring, additional benzhydrylamine (0.70 mL) was added thereto. The reaction mixture was cooled to 70° C., and filtered using Hirsch funnel, and the filtrate was concentrated under reduced pressure to give an oil. To the residue was added a mixed solvent (30 mL) of normal hexane:toluene=2:1, cooled to −78° C., warmed to −20° C., and stirred for 1 hr. The resulting solid was collected by filtration, washed with a mixed solvent (20 mL) of normal hexane:toluene=2:1, which was cooled to −20° C., and dried under reduced pressure at 40° C. to give the title compound (4.78 g, yield 51%) as a pale-brown solid. The residual filtrate was concentrated under reduced pressure, and the residue was recrystallized from a mixed solvent of normal hexane:toluene=6:1(14 mL) at 0° C. The resulting solid was collected by filtration, washed with a mixed solvent of normal hexane:toluene=10:1, which was cooled to 0° C., and dried under reduced pressure at 40° C. to give the title compound (2.51 g, yield 26%) as a pale-brown solid.

$^1$H NMR (CDCl$_3$) δ 2.44 (s, 3H), 3.92 (s, 3H), 5.88 (s, 1H), 7.23 (t, J=7.5 Hz, 2H), 7.32 (t, J=7.5 Hz, 4H), 7.44 (d, J=7.5 Hz, 4H), 8.39 (s, 1H); $^{13}$C NMR (CDCl$_3$) δ 14.73, 52.49, 68.59, 127.14, 127.35, 128.60, 131.41, 143.55, 148.62, 160.55, 161.94, 176.52.

Reference Example 20

Synthesis of (E)-N-(3,4-dihydronaphthalen-1(2H)-ylidene)-1,1-diphenylmethanamine

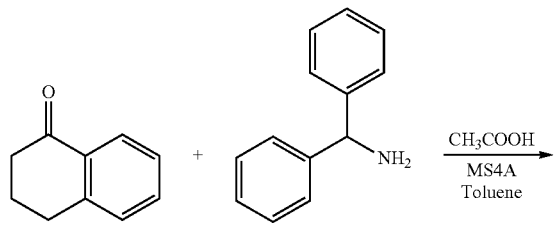

Molecular sieve 4A (5.00 g) was put into a four-necked eggplant flask (100 mL), and dried under reduced pressure at 100° C. for 30 min, and the reaction system was purged with nitrogen. The flask was cooled to room temperature, toluene (30 mL), α-tetralone (5.00 mL), benzhydrylamine (8.10 mL) and acetic acid (0.43 mL) were added thereto, and the mixture was stirred at the internal temperature of 100° C. for 18 hr. The reaction mixture was cooled to 70° C., and filtered using Hirsch funnel, and the filtrate was concentrated under reduced pressure to give a brown oil. To the residue was added normal hexane (30 mL), and the mixture was heated under reflux, cooled to 0° C., and stirred for 2.5 hr. The resulting solid was collected by filtration, washed with normal hexane (35 mL) cooled to 0° C., and dried under reduced pressure at 40° C. to give the title compound (5.90 g, yield 50%) as a white solid.

$^1$H NMR (CDCl$_3$) δ 1.90 (quint, J=6.5 Hz, 2H), 2.64 (t, J=6.5 Hz, 2H), 2.78 (t, J=6.5 Hz, 2H), 5.88 (s, 1H), 7.12 (d, J=7.5 Hz, 1H), 7.18 (t, J=7.5 Hz, 2H), 7.25-7.32 (m, 6H), 7.47 (d, J=7.5 Hz, 4H), 8.50 (d, J=8.0 Hz, 1H); $^{13}$C NMR (CDCl$_3$) δ 22.65, 28.28, 29.77, 67.05, 126.27, 126.34, 126.61, 127.56, 128.27, 128.35, 129.72, 135.10, 140.59, 145.11, 163.73.

Reference Example 21

Synthesis of (E)-N-(chroman-4-ylidene)-1,1-diphenylmethanamine

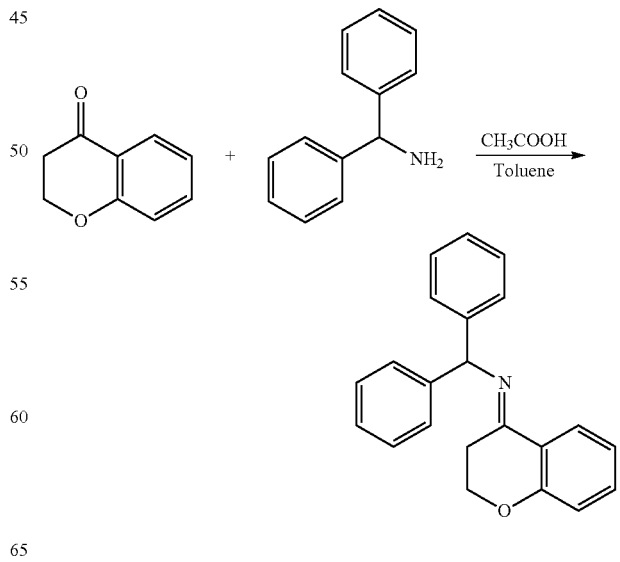

Four-necked eggplant flask (100 mL) equipped with Dean-Stark trap was purged with nitrogen, toluene (30 mL), 4-chromanone (5.00 g), benzhydrylamine (7.27 mL) and acetic acid (0.39 mL) were added thereto, and the mixture was heated under reflux at the external temperature 140° C. for 16 hr. The reaction mixture was cooled to room temperature, and concentrated under reduced pressure, and solvent substitution was performed with ethanol to give an oil. To the residue was added ethanol (30 mL), and the mixture was stirred at 50° C., cooled to room temperature, and stirred at the same temperature for 1 hr. The resulting solid was collected by filtration, washed with ethanol (50 mL), and dried under reduced pressure at 50° C. to give the title compound (3.71 g, yield 35%) as a white solid.

$^1$H NMR (CDCl$_3$) δ 2.79 (t, J=6.0 Hz, 2H), 4.26 (t, J=6.0 Hz, 2H), 5.81 (s, 1H), 6.85-6.90 (m, 1H), 6.97-7.03 (m, 1H), 7.17-7.22 (m, 2H), 7.26-7.32 (m, 5H), 7.42-7.48 (m, 4H), 8.34-8.79 (m, 1H); $^{13}$C NMR (CDCl$_3$) δ 27.75, 65.68, 67.09, 117.27, 121.22, 122.92, 126.36, 126.78, 127.47, 128.44, 131.85, 144.66, 158.09, 158.13.

Reference Example 22

Synthesis of
N-benzhydryl-(1R)-1-phenylethanamine

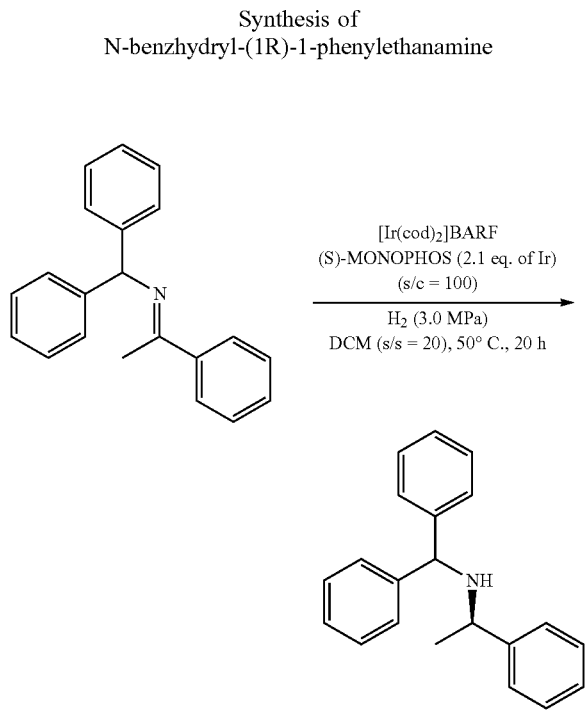

(E)-1,1-Diphenyl-N-(1-phenylethylidene)methanamine (0.075 g), [Ir(cod)$_2$]BARF (0.0033 g) and (S)-MONOPHOS (0.0020 g) were charade in a sample tube for an 24-hole autoclave, and the tube was set in an autoclave. The autoclave was put in a glove box, and dichloromethane (1.5 mL) was added thereto under nitrogen atmosphere. The autoclave was sealed, and taken out of the glove box, and the reaction system was purged ten times with hydrogen. Hydrogen was fed into the autoclave until 3.0 MPa, and the mixture was stirred at 50° C. for 20 hr. The reaction solution was cooled to room temperature, and the hydrogen was released. The production of the title compound was confirmed by analyzing the reaction solution using high-performance liquid chromatography and $^1$H NMR (conversion 100%, 79.4% ee).

Conditions for High-Performance Liquid Chromatography Analysis
  column: CHIRALCEL OJ-RH (manufactured by Daicel Chemical Industries), 4.6*150 mm
  UV detection wavelength: 254 nm
  mobile phase: acetonitrile for high-performance liquid chromatography/0.025 mol/L aqueous potassium dihydrogenphosphate solution=8/2
  flow rate: 1.0 mL/min
  retention time: 5.1 min (enantiomer-A), 5.9 min (enantiomer-B)

$^1$H NMR (CDCl$_3$) δ 1.36 (d, J=7.0 Hz, 3H), 3.67 (q, J=7.0 Hz, 1H), 4.63 (s, 1H), 7.15-7.19 (m, 1H), 7.22-7.29 (m, 8H), 7.31-7.36 (m, 6H) (the protons derived from NH were not detected).

Reference Example 23

Synthesis of
N-benzhydryl-(1R)-1-(4-methoxyphenyl)ethanamine

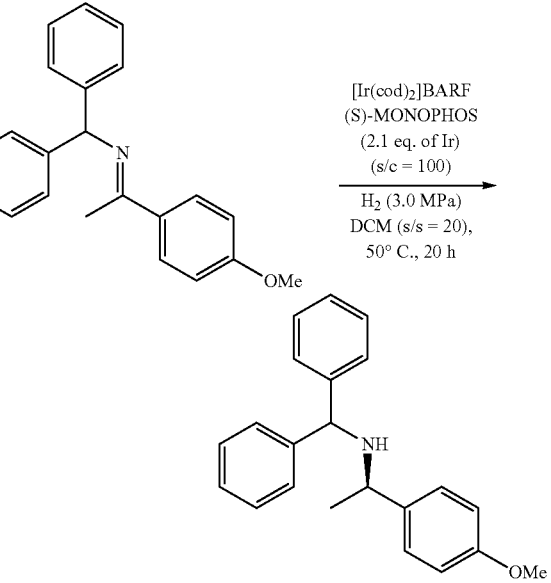

(E)-N-(1-(4-Methoxyphenyl)ethylidene)-1,1-diphenylmethanamine (0.075 g), [Ir(cod)$_2$]BARF (0.0030 g) and (S)-MONOPHOS (0.0018 g) were put into a sample tube for an 24-hole autoclave, and the tube was set in an autoclave. The autoclave was put in a glove box, and dichloromethane (1.5 mL) was added thereto under nitrogen atmosphere. The autoclave was sealed, and taken out of the glove box, and the reaction system was purged ten times with hydrogen. Hydrogen was fed into the autoclave until 3.0 MPa, and the mixture was stirred at 50° C. for hr. The reaction solution was cooled to room temperature, and the hydrogen was released. The production of the title compound was confirmed by analyzing the reaction solution using high-performance liquid chromatography and $^1$H NMR (conversion 100%, 87.9% ee).

Conditions for High-Performance Liquid Chromatography Analysis
  column: CHIRALCEL OJ-RH (manufactured by Daicel Chemical Industries), 4.6*150 mm
  UV detection wavelength: 254 nm
  mobile phase: acetonitrile for high-performance liquid chromatography/0.025 mol/L aqueous potassium dihydrogenphosphate solution=8/2
flow rate: 1.2 mL/min
retention time: 4.7 min (enantiomer-A), 5.5 min (enantiomer-B)

$^1$H NMR (CDCl$_3$) δ1.34 (d, J=6.5 Hz, 3H), 3.63 (q, J=6.5 Hz, 1H), 3.82 (s, 3H), 4.62 (s, 1H), 6.87 (d, J=8.5 Hz, 2H), 7.14-7.19 (m, 3H), 7.21-7.29 (m, 5H), 7.30-7.34 (m, 4H) (the protons derived from NH were not detected).

Reference Example 24

Synthesis of N-benzhydryl-(1R)-1-(4-chlorophenyl)ethanamine

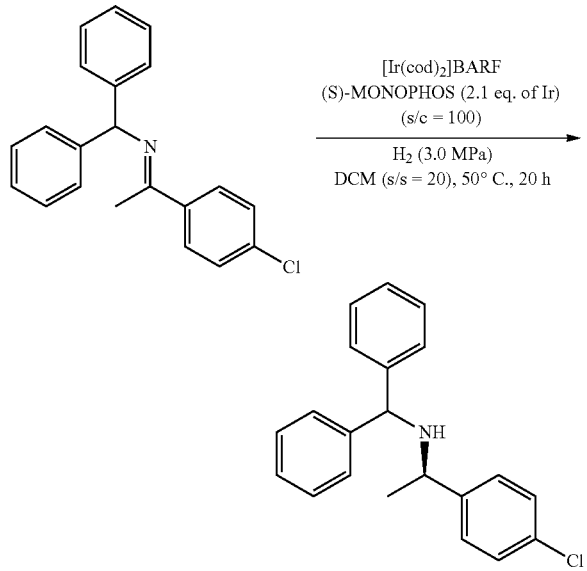

(E)-N-(1-(4-Chlorophenyl)ethylidene)-1,1-diphenylmethanamine (0.075 g), [Ir(cod)$_2$]BARF (0.0030 g) and (S)-MONOPHOS (0.0018 g) were put into a sample tube for an 24-hole autoclave, and the tube was set in an autoclave. The autoclave was put in a glove box, and dichloromethane (1.5 mL) was added thereto under nitrogen atmosphere. The autoclave was sealed, and taken out of the glove box, and the reaction system was purged ten times with hydrogen. Hydrogen was fed into the autoclave until 3.0 MPa, and the mixture was stirred at 50° C. for hr. The reaction solution was cooled to room temperature, and the hydrogen was released. The production of the title compound was confirmed by analyzing the reaction solution using high-performance liquid chromatography and $^1$H NMR (conversion 100%, 96.0% ee).

Conditions for High-Performance Liquid Chromatography Analysis column: CHIRALCEL OJ-RH (manufactured by Daicel Chemical Industries), 4.6*150 mm
UV detection wavelength: 254 nm
mobile phase: acetonitrile for high-performance liquid chromatography/0.025 mol/L aqueous potassium dihydrogenphosphate solution=8/2
flow rate: 1.2 mL/min
retention time: 7.6 min. (enantiomer-A), 8.8 min. (enantiomer-B)

$^1$H NMR (CDCl$_3$) δ 1.34 (d, J=7.0 Hz, 3H), 3.66 (q, J=7.0 Hz, 1H), 4.58 (s, 1H), 7.16-7.21 (m, 3H), 7.22-7.35 (m, 11H) (the protons derived from NH were not detected).

Reference Example 25

Synthesis of N-benzhydryl-(1R)-1-(4-trifluoromethylphenyl)ethanamine

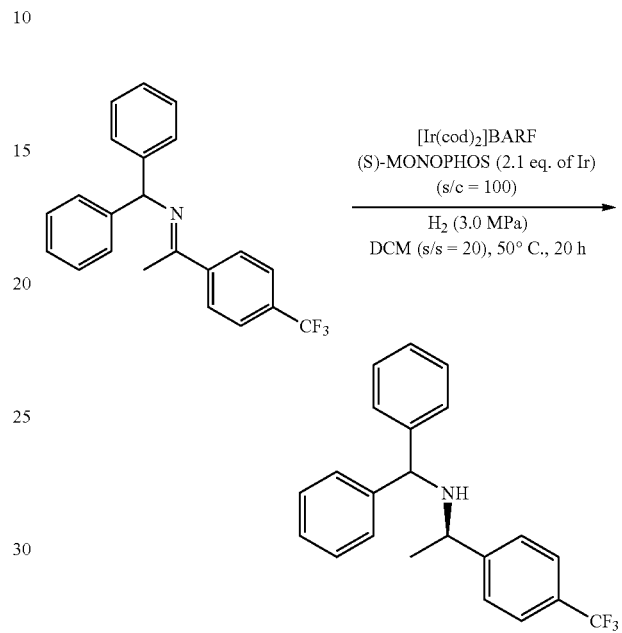

(E)-1,1-Diphenyl-N-(1-(4-trifluoromethylphenyl)ethylidene)methanamine (0.075 g), [Ir(cod)$_2$]BARF (0.0027 g) and (S)-MONOPHOS (0.0016 g) were put into a sample tube for an 24-hole autoclave, and the tube was set in an autoclave. The autoclave was put in a glove box, and dichloromethane (1.5 mL) was added thereto under nitrogen atmosphere. The autoclave was sealed, and taken out of the glove box, and the reaction system was purged ten times with hydrogen. Hydrogen was fed into the autoclave until 3.0 MPa, and the mixture was stirred at 50° C. for 20 hr. The reaction solution was cooled to room temperature, and the hydrogen was released. The production of the title compound was confirmed by analyzing the reaction solution using high-performance liquid chromatography and $^1$H NMR (conversion 100%, 95.5% ee).

Conditions for High-Performance Liquid Chromatography Analysis column: CHIRALCEL OJ-RH (manufactured by Daicel Chemical Industries), 4.6*150 mm
UV detection wavelength: 254 nm
mobile phase: acetonitrile for high-performance liquid chromatography/0.025 mol/L aqueous potassium dihydrogenphosphate solution=8/2
flow rate: 1.2 mL/min
retention time: 4.0 min (enantiomer-A), 5.4 min (enantiomer-B)

$^1$H NMR (CDCl$_3$) δ 1.36 (d, J=7.0 Hz, 3H), 3.75 (q, J=7.0 Hz, 1H), 4.58 (s, 1H), 7.18 (tt, J=7.0, 1.5 Hz, 1H), 7.22-7.35 (m, 9H), 7.38 (d, J=8.5 Hz, 2H), 7.58 (d, J=8.5 Hz, 2H) (the protons derived from NH were not detected).

Reference Example 26

Synthesis of
N-benzhydryl-(1R)-1-(naphthalen-1-yl)ethanamine

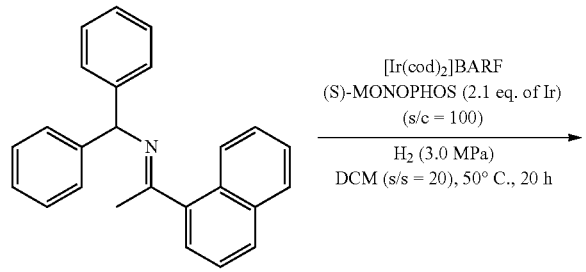

[Ir(cod)₂]BARF
(S)-MONOPHOS (2.1 eq. of Ir)
(s/c = 100)
H₂ (3.0 MPa)
DCM (s/s = 20), 50° C., 20 h

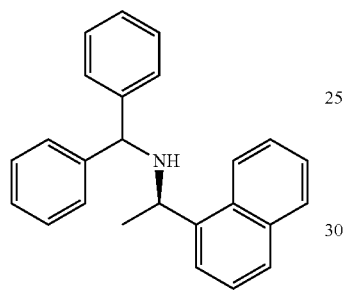

(E)-N-(1-(Naphthalen-1-yl)ethylidene)-1,1-diphenylmethanamine (0.075 g), [Ir(cod)₂]BARF (0.0028 g) and (S)-MONOPHOS (0.0017 g) were put into a sample tube for an 24-hole autoclave, and the tube was set in an autoclave. The autoclave was put in a glove box, and dichloromethane (1.5 mL) was added thereto under nitrogen atmosphere. The autoclave was sealed, and taken out of the glove box, and the reaction system was purged ten times with hydrogen. Hydrogen was fed into the autoclave until 3.0 MPa, and the mixture was stirred at 50° C. for hr. The reaction solution was cooled to room temperature, and the hydrogen was released. The production of the title compound was confirmed by analyzing the reaction solution using high-performance liquid chromatography and ¹H NMR (conversion 100%, 70.1% ee).

Conditions for High-Performance Liquid Chromatography Analysis
- column: CHIRALCEL OJ-RH (manufactured by Daicel Chemical Industries), 4.6*150 mm
- UV detection wavelength: 254 nm
- mobile phase: acetonitrile for high-performance liquid chromatography/0.025 mol/L aqueous potassium dihydrogenphosphate solution=8/2
- flow rate: 1.0 mL/min
- retention time: 7.4 min (enantiomer-A), 9.0 min (enantiomer-B)

¹H NMR (CDCl₃) δ 1.49 (d, J=7.0 Hz, 3H), 4.56 (q, J=7.0 Hz, 1H), 4.74 (s, 1H), 7.16-7.35 (m, 10H), 7.36-7.41 (m, 1H), 7.42-7.47 (m, 1H), 7.47-7.52 (m, 1H), 7.66-7.70 (m, 1H), 7.74-7.78 (m, 1H), 7.84-7.91 (m, 2H) (the protons derived from NH were not detected).

Reference Example 27

Synthesis of
N-benzhydryl-(1R)-1-(furan-2-yl)ethanamine

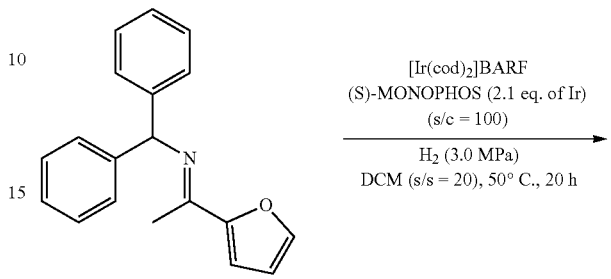

[Ir(cod)₂]BARF
(S)-MONOPHOS (2.1 eq. of Ir)
(s/c = 100)
H₂ (3.0 MPa)
DCM (s/s = 20), 50° C., 20 h

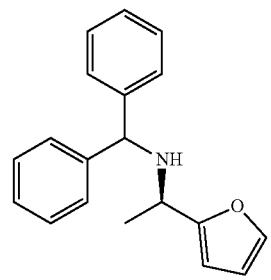

(E)-N-(1-(Furan-2-yl)ethylidene)-1,1-diphenylmethanamine (0.075 g), [Ir(cod)₂]BARF (0.0035 g) and (S)-MONOPHOS (0.0021 g) were put into a sample tube for an 24-hole autoclave, and the tube was set in an autoclave. The autoclave was put in a glove box, and dichloromethane (1.5 mL) was added thereto under nitrogen atmosphere. The autoclave was sealed, and taken out of the glove box, and the reaction system was purged ten times with hydrogen. Hydrogen was fed into the autoclave until 3.0 MPa, and the mixture was stirred at 50° C. for 20 hr. The reaction solution was cooled to room temperature, and the hydrogen was released. The production of the title compound was confirmed by analyzing the reaction solution using high-performance liquid chromatography and ¹H NMR (conversion 100%, 70.0% ee).

Conditions for High-Performance Liquid Chromatography Analysis
- column: CHIRALCEL OJ-RH (manufactured by Daicel Chemical Industries), 4.6*150 mm
- UV detection wavelength: 254 nm
- mobile phase: acetonitrile for high-performance liquid chromatography/0.025 mol/L aqueous potassium dihydrogenphosphate solution=7/3
- flow rate: 1.0 mL/min
- retention time: 5.6 min (enantiomer-A), 6.5 min (enantiomer-B)

¹H NMR (CDCl₃) δ 1.42 (d, J=7.0 Hz, 3H), 3.73 (q, J=7.0 Hz, 1H), 4.75 (s, 1H), 6.06 (d, J=3.5 Hz, 1H), 6.31 (dd, J=3.5, 1.5 Hz, 1H), 7.15-7.19 (m, 1H), 7.20-7.27 (m, 3H), 7.29-7.33 (m, 4H), 7.36 (d, J=1.5 Hz, 1H), 7.40-7.44 (m, 2H) (the protons derived from NH were not detected).

Reference Example 28

Synthesis of N-benzhydryl-(1R)-1-(pyridin-2-yl)ethanamine

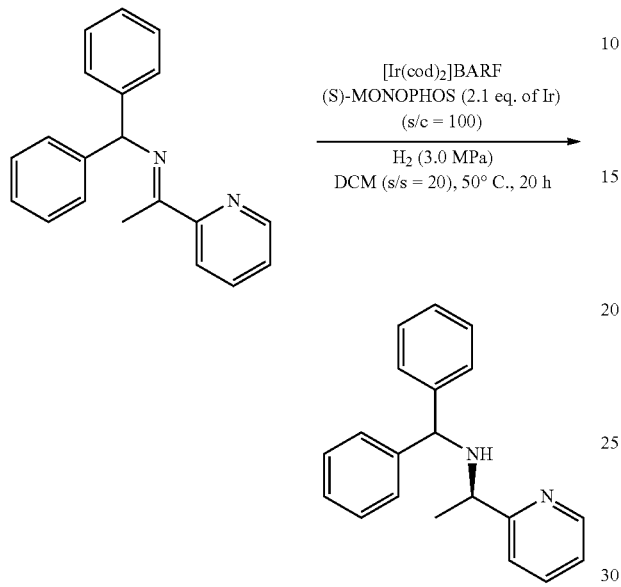

(E)-1,1-Diphenyl-N-(1-(pyridin-2-yl)ethylidene)methanamine (0.075 g), [Ir (cod) 2]BARF (0.0033 g) and (S)-MONOPHOS (0.0020 g) were put into a sample tube for an 24-hole autoclave, and the tube was set in an autoclave. The autoclave was put in a glove box, and dichloromethane (1.5 mL) was added thereto under nitrogen atmosphere. The autoclave was sealed, and taken out of the glove box, and the reaction system was purged ten times with hydrogen. Hydrogen was fed into the autoclave until 3.0 MPa, and the mixture was stirred at 50° C. for hr. The reaction solution was cooled to room temperature, and the hydrogen was released. The production of the title compound was confirmed by analyzing the reaction solution using high-performance liquid chromatography and $^1$H NMR (conversion 55%, 76.7% ee).

Conditions for High-Performance Liquid Chromatography Analysis column: CHIRALCEL OJ-RH (manufactured by Daicel Chemical Industries), 4.6*150 mm UV detection wavelength: 254 nm mobile phase: acetonitrile for high-performance liquid chromatography/0.025 mol/L aqueous potassium dihydrogenphosphate solution=1/1 flow rate: 1.0 mL/min retention time: 6.5 min (enantiomer-A), 8.0 min (enantiomer-B)

$^1$H NMR (CDCl$_3$) δ 1.39 (d, J=6.5 Hz, 3H), 3.78 (q, J=6.5 Hz, 1H), 4.60 (s, 1H), 7.13-7.18 (m, 3H), 7.20-7.33 (m, 7H), 7.38 (d, J=7.5 Hz, 2H), 7.61 (td, J=7.5, 2.0 Hz, 1H), 8.57-8.60 (m, 1H) (the protons derived from NH were not detected).

Reference Example 29

Synthesis of N-benzhydryl-(1R)-1-(pyridin-3-yl)ethanamine

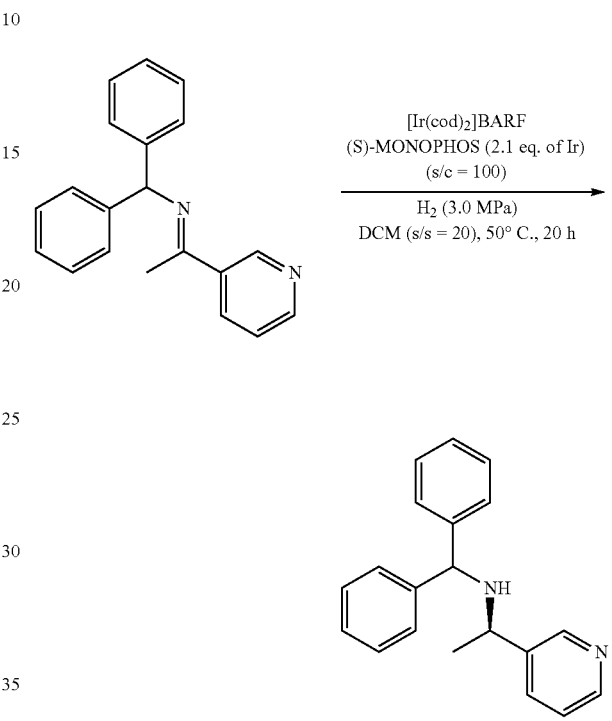

(E)-1,1-Diphenyl-N-(1-(pyridin-3-yl)ethylidene)methanamine (0.075 g), [Ir (cod)$_2$]BARF (0.0033 g) and (S)-MONOPHOS (0.0020 g) were put into a sample tube for an 24-hole autoclave, and the tube was set in an autoclave. The autoclave was put in a glove box, and dichloromethane (1.5 mL) was added thereto under nitrogen atmosphere. The autoclave was sealed, and taken out of the glove box, and the reaction system was purged ten times with hydrogen. Hydrogen was fed into the autoclave until 3.0 MPa, and the mixture was stirred at 50° C. for hr. The reaction solution was cooled to room temperature, and the hydrogen was released. By analyzing the reaction solution using high-performance liquid chromatography and $^1$H NMR, it was confirmed that the conversion was 0%.

Conditions for High-Performance Liquid Chromatography Analysis column: CHIRALCEL OD-RH(manufactured by Daicel Chemical Industries), 4.6*150 mm UV detection wavelength: 254 nm mobile phase: acetonitrile for high-performance liquid chromatography/0.025 mol/L aqueous potassium dihydrogenphosphate solution=3/7, 35 min-.acetonitrile for high-performance liquid chromatography/0.025 mol/L aqueous potassium dihydrogenphosphate solution=8/2, 10 min flow rate: 1.2 mL/min retention time: 25.1 min (enantiomer-A), 27.6 min (enantiomer-B)

Reference Example 30

Synthesis of N-benzhydryl-(1R)-1-(thiazol-2-yl)ethanamine

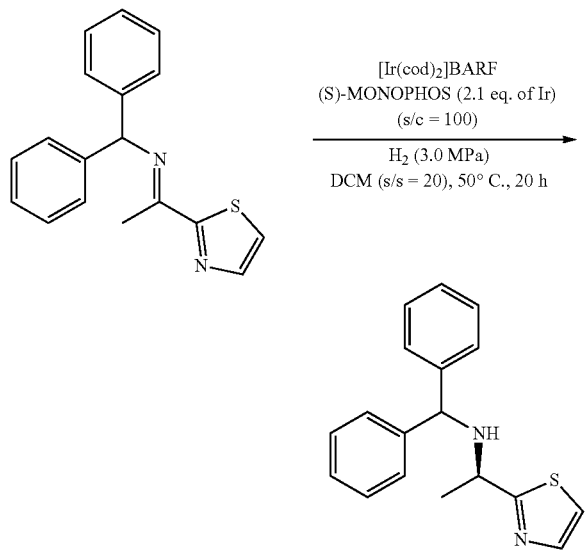

(E)-1,1-Diphenyl-N-(1-(thiazol-2-yl)ethylidene)methanamine (0.075 g), [Ir(cod)₂]BARF (0.0033 g) and (S)-MONOPHOS (0.0019 g) were put into a sample tube for an 24-hole autoclave, and the tube was set in an autoclave. The autoclave was put in a glove box, and dichloromethane (1.5 mL) was added thereto under nitrogen atmosphere. The autoclave was sealed, and taken out of the glove box, and the reaction system was purged ten times with hydrogen. Hydrogen was fed into the autoclave until 3.0 MPa, and the mixture was stirred at 50° C. for hr. The reaction solution was cooled to room temperature, and the hydrogen was released. The production of the title compound was confirmed by analyzing the reaction solution using high-performance liquid chromatography and $^1$H NMR (conversion 100%, 82.8% ee).

Conditions for High-Performance Liquid Chromatography Analysis column: CHIRALCEL OD-RH(manufactured by Daicel Chemical Industries), 4.6*150 mm UV detection wavelength: 254 nm mobile phase: acetonitrile for high-performance liquid chromatography/0.025 mol/L aqueous potassium dihydrogenphosphate solution=4/6, 35 min→acetonitrile for high-performance liquid chromatography/0.025 mol/L aqueous potassium dihydrogenphosphate solution=8/2, 10 min flow rate: 1.2 mL/min retention time: 31.3 min (enantiomer-A), 33.2 min (enantiomer-B)

$^1$H NMR (CDCl₃) δ 1.53 (d, J=6.5 Hz, 3H), 4.07 (q, J=6.5 Hz, 1H), 4.92 (s, 1H), 7.17-7.21 (m, 1H), 7.23-7.29 (m, 4H), 7.33 (t, J=7.5 Hz, 2H), 7.36-7.40 (m, 4H), 7.73 (d, J=2.5 Hz, 1H) (the protons derived from NH were not detected).

Reference Example 31

Synthesis of methyl 2-((1R)-1-(benzhydrylamino)ethyl)-1,3-thiazole-5-carboxylate

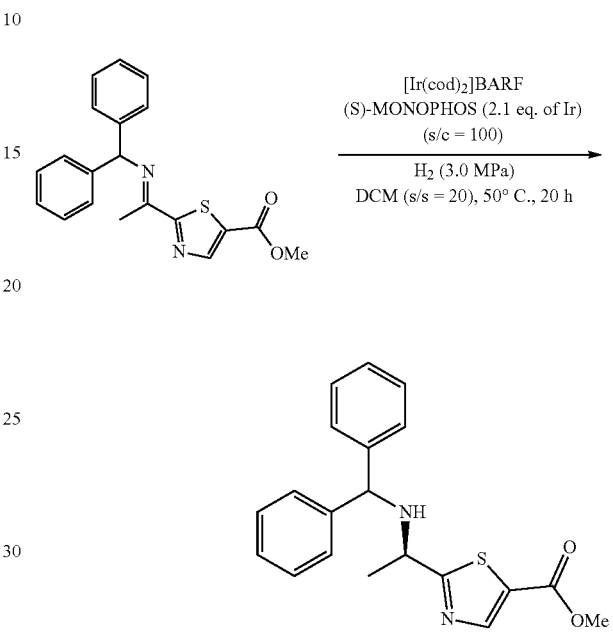

(E)-Methyl 2-((1-Benzhydrylimino)ethyl)-1,3-thiazole-5-carboxylate (0.075 g), [Ir(cod)₂]BARF (0.0027 g) and (S)-MONOPHOS (0.0016 g) were put into a sample tube for an 24-hole autoclave, and the tube was set in an autoclave. The autoclave was put in a glove box, and dichloromethane (1.5 mL) was added thereto under nitrogen atmosphere. The autoclave was sealed, and taken out of the glove box, and the reaction system was purged ten times with hydrogen. Hydrogen was fed into the autoclave until 3.0 MPa, and the mixture was stirred at 50° C. for hr. The reaction solution was cooled to room temperature, and the hydrogen was released. The production of the title compound was confirmed by analyzing the reaction solution using high-performance liquid chromatography and $^1$H NMR (conversion 100%, 79.7% ee).

Conditions for High-Performance Liquid Chromatography Analysis column: CHIRALCEL OJ-RH (manufactured by Daicel Chemical Industries), 4.6*150 mm UV detection wavelength: 254 nm mobile phase: acetonitrile for high-performance liquid chromatography/0.025 mol/L aqueous potassium dihydrogenphosphate solution=8/2 flow rate: 1.0 mL/min retention time: 4.4 min (enantiomer-A), 5.1 min (enantiomer-B)

$^1$H NMR (CDCl₃) δ 1.53 (d, J=6.5 Hz, 3H), 3.91 (s, 3H), 4.01 (q, J=6.5 Hz, 1H), 4.95 (s, 1H), 7.18-7.23 (m, 1H), 7.23-7.30 (m, 3H), 7.32-7.36 (m, 2H), 7.36-7.42 (m, 4H), 8.31 (s, 1H) (the protons derived from NH were not detected).

Reference Example 32

Synthesis of N-benzhydryl-1,2,3,4-tetrahydronaphthalene-(1R)-1-amine

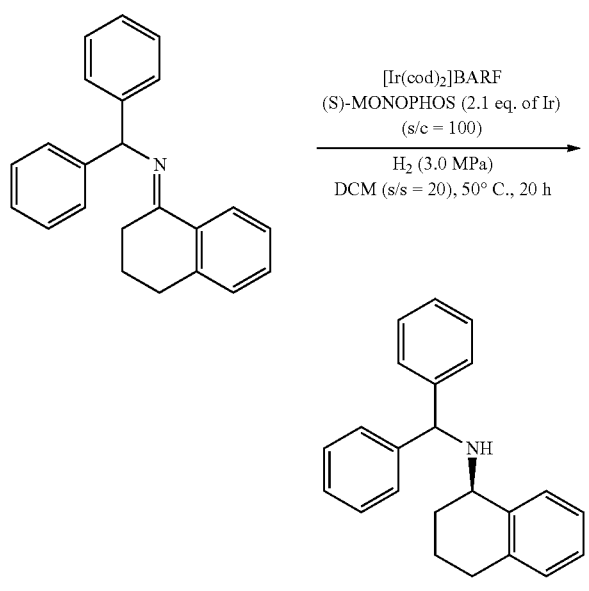

(E)-N-(3,4-Dihydronaphthalen-1(2H)-ylidene)-1,1-diphenylmethanamine (0.075 g), [Ir(cod)₂]BARF (0.0031 g) and (S)-MONOPHOS (0.0018 g) were put into a sample tube for an 24-hole autoclave, and the tube was set in an autoclave. The autoclave was put in a glove box, and dichloromethane (1.5 mL) was added thereto under nitrogen atmosphere. The autoclave was sealed, and taken out of the glove box, and the reaction system was purged ten times with hydrogen. Hydrogen was fed into the autoclave until 3.0 MPa, and the mixture was stirred at 50° C. for hr. The reaction solution was cooled to room temperature, and the hydrogen was released. The production of the title compound was confirmed by analyzing the reaction solution using high-performance liquid chromatography and $^1$H NMR (conversion 100%, 23.0% ee).

Conditions for High-Performance Liquid Chromatography Analysis
  column: CHIRALCEL OJ-RH (manufactured by Daicel Chemical Industries), 4.6*150 mm
  UV detection wavelength: 254 nm
  mobile phase: acetonitrile for high-performance liquid chromatography/0.025 mol/L aqueous potassium dihydrogenphosphate solution=8/2
  flow rate: 1.2 mL/min
  retention time: 5.5 min (enantiomer-A), 8.1 min (enantiomer-B)

$^1$H NMR (CDCl₃) δ 1.66-1.75 (m, 1H), 1.81-2.01 (m, 3H), 2.66-2.74 (m, 1H), 2.77-2.84 (m, 1H), 3.67-3.72 (m, 1H), 5.11 (s, 1H), 7.03-7.08 (m, 1H), 7.11-7.24 (m, 4H), 7.25-7.30 (m, 2H), 7.30-7.36 (m, 2H), 7.43-7.49 (m, 3H), 7.49-7.53 (m, 2H) (the protons derived from NH were not detected).

Reference Example 33

Synthesis of N-benzhydrylchroman-(4R)-4-amine

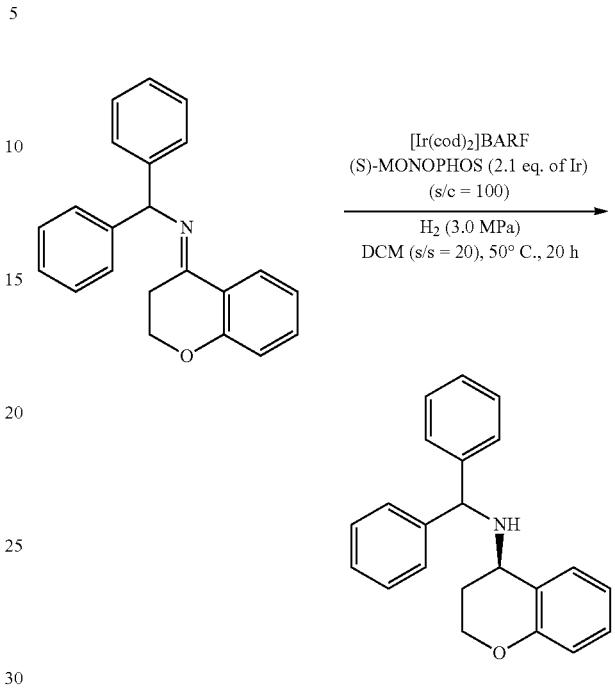

(E)-N-(Chroman-4-ylidene)-1,1-diphenylmethanamine (0.075 g), [Ir(cod)₂]BARF (0.0031 g) and (S)-MONOPHOS (0.0018 g) were put into a sample tube for an 24-hole autoclave, and the tube was set in an autoclave. The autoclave was put in a glove box, and dichloromethane (1.5 mL) was added thereto under nitrogen atmosphere. The autoclave was sealed, and taken out of the glove box, and the reaction system was purged ten times with hydrogen. Hydrogen was fed into the autoclave until 3.0 MPa, and the mixture was stirred at 50° C. for 20 hr. The reaction solution was cooled to room temperature, and the hydrogen was released. The production of the title compound was confirmed by analyzing the reaction solution using high-performance liquid chromatography and $^1$H NMR (conversion 100%, 16.1% ee).

Conditions for High-Performance Liquid Chromatography Analysis
  column: CHIRALCEL OJ-RH (manufactured by Daicel Chemical Industries), 4.6*150 mm
  UV detection wavelength: 254 nm
  mobile phase: acetonitrile for high-performance liquid chromatography/0.025 mol/L aqueous potassium dihydrogenphosphate solution=8/2
  flow rate: 1.2 mL/min
  retention time: 4.0 min (enantiomer-A), 4.8 min (enantiomer-B)

$^1$H NMR (CDCl₃) δ 1.90-1.98 (m, 1H), 2.00-2.09 (m, 1H), 3.76 (t, J=5.0 Hz, 1H), 4.15-4.21 (m, 1H), 4.36 (td, J=10.5, 3.0 Hz, 1H), 5.09 (s, 1H), 6.79 (d, J=8.0 Hz, 1H), 6.87 (td, J=7.5, 1.5 Hz, 1H), 7.13 (td, J=7.5, 1.0 Hz, 1H), 7.18-7.32 (m, 5H), 7.35 (t, J=7.5 Hz, 2H), 7.42-7.50 (m, 4H) (the protons derived from NH were not detected).

Reference Example 34

Synthesis of (1R)-1-(thiazol-2-yl)ethanamine

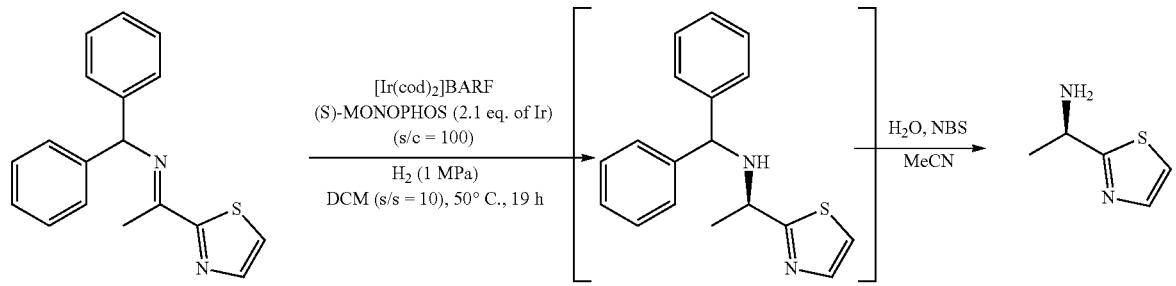

(E)-1,1-Diphenyl-N-(1-(thiazol-2-yl)ethylidene)methanamine (2.00 g), [Ir(cod)₂]BARF (0.0870 g) and (S)-MONOPHOS (0.0540 g) were put into an autoclave (120 mL). The atmosphere in the autoclave was decompressed, and the pressure was recovered with argon. The procedures were performed seven times in total. The pressure of the autoclave was recovered to normal pressure, and dehydrated dichloromethane (20 mL) for organic synthesis was fed thereto by argon pressure. Hydrogen was fed into the autoclave until the pressure was increased by 0.1 MPa, and the pressure was recovered to normal pressure. The procedures were performed ten times in total. Hydrogen was fed into the autoclave until 1.10 MPa, and the mixture was stirred at the internal temperature of 50° C. for 19 hr. The mixture was cooled to the internal temperature of about 20° C., the hydrogen was released, and the atmosphere was replaced with argon (conversion 100%, optical purity 82.7% ee). The reaction solution was concentrated under reduced pressure, and acetonitrile (18 mL) and water (2 mL) were added thereto. N-Bromosuccinimide (1.83 g) was added thereto at near room temperature, and the mixture was stirred for 7 hr. The mixture was concentrated under reduced pressure, and the residue was partitioned with 1 mol/L hydrochloric acid (10 mL) and ethyl acetate (20 mL) (organic layer (1) and aqueous layer (1)). The aqueous layer (1) was adjusted to pH 5 with 5 mol/L aqueous sodium hydroxide solution (about 3 mL), and extracted with ethyl acetate (20 mL) (organic layer (2) and aqueous layer (2)). The aqueous layer (2) was partitioned with 5 mol/L aqueous sodium hydroxide solution (1 mL) and ethyl acetate (20 mL) (organic layer (3) and aqueous layer (3)). The organic layer (3) was washed with saturated brine (10 mL) (organic layer (4) and aqueous layer (4)). The organic layer (1) was washed with saturated brine (10 mL) (organic layer (5) and aqueous layer (5)). The aqueous layer (4) and aqueous layer (5) were combined, and extracted with ethyl acetate (30 mL) (organic layer (6) and aqueous layer (6)) The organic layer (4), organic layer (5) and organic layer (6) were combined, and dried over magnesium sulfate. The magnesium sulfate was removed by filtration, and the filtrate was concentrated under reduced pressure to give the title compound. brown oil, 0.61 g, yield 70.1%, HPLC area normalization 89.7%.

Conditions for High-Performance Liquid Chromatography Analysis (Area Normalization)

column: YMC-Pack ODS-A (manufactured by YMC. CO., LTD.), 4.6*150 mm
  UV detection wavelength: 254 nm
  mobile phase: acetonitrile for high-performance liquid chromatography/0.025 mol/L aqueous potassium dihydrogenphosphate solution=8/2
  flow rate: 1.0 mL/min
  retention time: 2.4 min (the title compound)
  ¹H NMR (CDCl₃) δ 1.54 (d, J=6.6 Hz, 3H), 4.42 (q, J=6.6 Hz, 1H), 7.23 (d, J=3.2 Hz, 1H), 7.70 (d, J=3.2 Hz, 1H).
  ¹³C NMR (CDCl₃) δ 24.66, 49.65, 118.36, 142.38, 178.38.

Reference Example 35

Synthesis of (R)-methyl-2-(1-aminoethyl)-1,3-thiazole-5-carboxylate p-toluenesulfonate

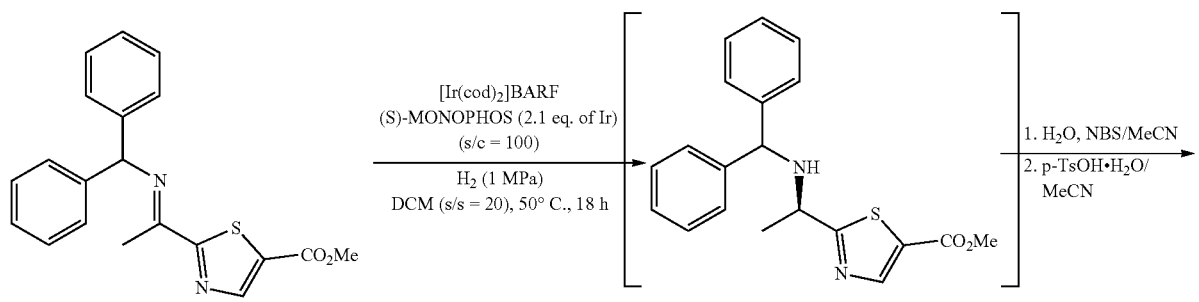

(E)-Methyl 2-((1-benzhydrylimino)ethyl)-1,3-thiazole-5-carboxylate (1.00 g), [Ir(cod)₂]BARF (0.0363 g) and (S)-MONOPHOS (0.0226 g) were put into an autoclave (120 mL). The atmosphere in the autoclave was decompressed, and the pressure was recovered with argon. The procedures were performed seven times in total. The pressure of the autoclave was recovered to normal pressure, and dehydrated dichloromethane (20 mL) for organic synthesis was fed thereto by argon pressure. Hydrogen was fed into the autoclave until the pressure was increased by 0.1 MPa, and the pressure was recovered to normal pressure. The procedures were performed ten times in total. Hydrogen was fed into the autoclave until 1.0 MPa, and the mixture was stirred at the internal temperature of 50° C. for 18 hr. The mixture was cooled to the internal temperature of about 20° C., the hydrogen was released, and the atmosphere was replaced with argon (conversion 100%, optical purity 80.1% ee). The reaction solution was concentrated under reduced pressure, and acetonitrile (9 mL), water (1 mL) and N-bromosuccinimide (0.61 g) were thereto at near room temperature, and the mixture was stirred for 23 hr. The mixture was concentrated under reduced pressure, and the residue was partitioned with water (3 mL) and ethyl acetate (10 mL) (organic layer (1) and aqueous layer (1)). The aqueous layer (1) was partitioned with 1 mol/L aqueous sodium hydroxide solution (3 mL) and ethyl acetate (15 mL) (organic layer (2) and aqueous layer (2)). The aqueous layer (2) was partitioned with 1 mol/L aqueous sodium hydroxide solution (1 mL) and ethyl acetate (10 mL) (organic layer (3) and aqueous layer (3)). The organic layer (2) and organic layer (3) were combined, and p-toluenesulfonic acid monohydrate (0.56 g) was added thereto. The mixture was concentrated under reduced pressure, acetonitrile (10 mL) was added thereto, and the mixture was stirred at the temperature of near room temperature for 1 hr. The crystallized substance was collected by filtration, and washed with acetonitrile, and dried under reduced pressure at 50° C. to give the title compound. pale yellow powder, 0.6412 g, yield 62.7%, HPLC area normalization 100%, optical purity 80.3% ee.
Conditions for High-Performance Liquid Chromatography Analysis (HPLC Area Normalization)
  column: YMC-Pack ODS-A (manufactured by YMC. CO., LTD.), 4.6*150 mm
  UV detection wavelength: 254 nm
  mobile phase: acetonitrile for high-performance liquid chromatography/0.025 mol/L aqueous potassium dihydrogenphosphate solution=8/2
  flow rate: 1.0 mL/min
  retention time: 2.2 min (the title compound) conditions for high-performance liquid chromatography analysis (optical purity)
  column: CHIRALPAK IA (manufactured by Daicel Chemical Industries), 4.6*250 mm
  UV detection wavelength: 254 nm
  mobile phase: acetonitrile for high-performance liquid chromatography/methanol for high-performance liquid chromatography/distilled water for high-performance liquid chromatography=80/15/5
  flow rate: 1.0 mL/min
  retention time: 4.5 min (enantiomer-A), 5.7 min (enantiomer-B)
¹H NMR (DMSO-d₆) δ 1.61 (d, J=6.9 Hz, 3H), 2.29 (s, 3H), 3.87 (s, 3H), 4.95 (q, J=6.8 Hz, 1H), 7.12 (d, J=7.9 Hz, 2H), 7.48 (d, J=7.9 Hz, 2H), 8.51 (s, 1H), 8.64 (brs, 3H).
¹³C NMR (DMSO-d₆) δ 19.76, 20.74, 47.62, 52.79, 125.45, 128.04, 130.01, 137.73, 145.44, 147.56, 160.80, 172.89.

Examples 163-368

Synthesis of 2-((1R)-1-aminoethyl)-N-(5-chloro-4-(trifluoromethyl)pyridin-2-yl)-1,3-thiazole-5-carboxamide

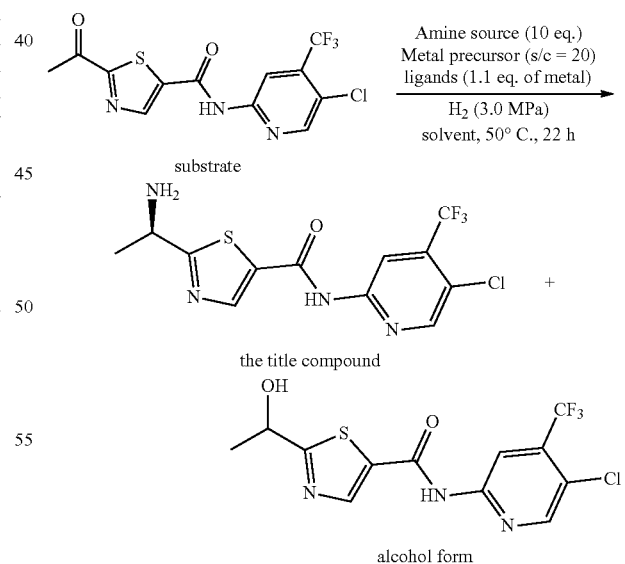

2-Acetyl-N-(5-chloro-4-(trifluoromethyl)pyridin-2-yl)-1,3-thiazole-5-carboxamide (substrate, 0.0350 g), an ammonium salt (amine source, 10 equivalent relative to the substrate), a metal source (0.05 equivalent relative to the substrate) and a ligand (1.1 equivalent relative to the metal source) were each weighed, and they were put into a test tube for a 24-hole autoclave. A solvent (1.5 mL) was added thereto under nitrogen atmosphere, and the atmosphere in the autoclave was purged with hydrogen. Hydrogen was fed into the autoclave until 3.0 MPa, and the mixture was stirred at 50° C. for 22 hr. After the completion of the reaction, the autoclave was cooled, and the hydrogen gas was released. The selectivity of the title compound (containing R-form and S-form) and the enantiomeric excess (ee) of the title compound (R-form) were calculated from HPLC. The results are shown in Table 16-Table 20. The structure of the ligand used above is shown above. In Examples 348-355 and 359-361, (−)-CSA is used in an amount of 0.1 equivalent relative to the substrate, as an additive.

Conditions for High-Performance Liquid Chromatography Analysis (Area Normalization)
  column: YMC-Pack ODS-A (manufactured by YMC. CO., LTD.), 4.6*150 mm
  UV detection wavelength: 254 nm
  mobile phase: acetonitrile for high-performance liquid chromatography/0.025 mol/L aqueous potassium dihydrogenphosphate solution=8/2
  flow rate: 1.0 mL/min
  retention time: 2.3 min. (the title compound (containing R-form and S-form)), 2.9 min. (alcohol form), 4.8 min. (substrate)

Conditions for High-Performance Liquid Chromatography Analysis (Optical Purity)
  column: IA (manufactured by Daicel Chemical Industries), 4.6*250 mm
  UV detection wavelength: 254 nm
  mobile phase: acetonitrile for high-performance liquid chromatography/methanol/water=80/15/5
  flow rate: 1.0 mL/min
  column temperature: 40° C.
  retention time: 4.6 min. (substrate), 5.8 min. (alcohol form), 11.6 min. (alcohol form), 16.2 min. (the title compound (R-form)), 24.2 min. (enantiomer (S-form) of the title compound).

TABLE 16

| Ex. | metal source | ligand | amine source | solvent | title compound (%)* | alcohol form (%) | % ee | Stereo | selectivity (%)** |
|---|---|---|---|---|---|---|---|---|---|
| 163 | [Rh(cod)₂]OTf | (R)-BINAP | Ammonium acetate | MeOH | 42.1 | 26.1 | 5.4 | S | 92.1 |
| 164 | [Rh(cod)₂]OTf | (R)-Xylyl-BINAP | Ammonium acetate | MeOH | 49.7 | 20.5 | 4.2 | S | 94.5 |
| 165 | [Rh(cod)₂]OTf | (R,R)-DIPAMP | Ammonium acetate | MeOH | 16.3 | 31.5 | 3.3 | S | 49.8 |
| 166 | [Rh(cod)₂]OTf | (R,R)-Skewphos | Ammonium acetate | MeOH | 63.7 | 25.1 | 1.0 | S | 76.1 |
| 167 | [Rh(cod)₂]OTf | (S,S)-PTBP-SKEWPHOS | Ammonium acetate | MeOH | 56.4 | 33.4 | 1.0 | S | 64.5 |
| 168 | [Rh(cod)₂]OTf | (R)(S)-JOSIPHOS | Ammonium acetate | MeOH | 70.0 | 17.5 | 1.4 | S | 90.8 |
| 169 | [Rh(cod)₂]OTf | (R,R)-iPr-DUPHOS | Ammonium acetate | MeOH | 21.8 | 32.8 | 0.6 | S | 55.2 |
| 170 | [Rh(cod)₂]OTf | (R)-PHANEPHOS | Ammonium acetate | MeOH | 73.7 | 17.7 | 1.2 | R | 86.5 |
| 171 | [Rh(cod)₂]OTf | (R,R)-Me-Ferrocelane | Ammonium acetate | MeOH | 45.4 | 48.0 | 10.4 | S | 49.4 |
| 172 | [RhCl(cod)]₂ | (R)-BINAP | Ammonium acetate | MeOH | 41.7 | 19.7 | 4.2 | S | 94.2 |
| 173 | [RhCl(cod)]₂ | (R)-Xylyl-BINAP | Ammonium acetate | MeOH | 52.6 | 20.1 | 3.8 | S | 95.1 |
| 174 | [RhCl(cod)]₂ | (R,R)-DIPAMP | Ammonium acetate | MeOH | 23.4 | 30.8 | 4.1 | S | 62.6 |
| 175 | [RhCl(cod)]₂ | (R,R)-Skewphos | Ammonium acetate | MeOH | 62.3 | 26.5 | 0.6 | S | 74.3 |
| 176 | [RhCl(cod)]₂ | (S,S)-PTBP-SKEWPHOS | Ammonium acetate | MeOH | 54.6 | 34.2 | 4.6 | S | 63.6 |
| 177 | [RhCl(cod)]₂ | (R)(S)-JOSIPHOS | Ammonium acetate | MeOH | 53.7 | 21.7 | 6.2 | S | 87.2 |
| 178 | [RhCl(cod)]₂ | (R,R)-iPr-DUPHOS | Ammonium acetate | MeOH | 14.5 | 29.9 | 3.0 | R | 43.3 |
| 179 | [RhCl(cod)]₂ | (R)-PHANEPHOS | Ammonium acetate | MeOH | 72.0 | 18.7 | 0.8 | R | 85.4 |
| 180 | [RhCl(cod)]₂ | (R,R)-Me-Ferrocelane | Ammonium acetate | MeOH | 59.7 | 31.4 | 9.5 | S | 69.1 |
| 181 | [RH(cod)₂]OTf | (R)-Xylyl-BINAP | Ammonium salicylate | MeOH | 9.4 | 6.6 | 11.1 | S | nd |
| 182 | [Rh(cod)₂]OTf | (R,R)-CHIRAPHOS | Ammonium salicylate | MeOH | 35.4 | 21.4 | 1.5 | S | 58.0 |
| 183 | [Rh(cod)₂]OTf | (R,R)-DIPAMP | Ammonium salicylate | MeOH | 24.1 | 26.5 | 8.2 | S | 39.3 |
| 184 | [Rh(cod)₂]OTf | (R,R)-Skewphos | Ammonium salicylate | MeOH | 54.4 | 15.1 | 6.3 | R | 76.6 |
| 185 | [Rh(cod)₂]OTf | (S,S)-PTBP-SKEWPHOS | Ammonium salicylate | MeOH | 55.0 | 17.5 | 10.7 | S | 74.4 |
| 186 | [Rh(cod)₂]OTf | (R)(S)-JOSIPHOS | Ammonium salicylate | MeOH | 41.3 | 8.7 | 9.2 | S | 86.4 |
| 187 | [Rh(cod)₂]OTf | (R,R)-iPr-DUPHOS | Ammonium salicylate | MeOH | 14.9 | 24.4 | 10.3 | S | 28.6 |
| 188 | [Rh(cod)₂]OTf | (R)-PHANEPHOS | Ammonium salicylate | MeOH | 65.4 | 4.5 | 3.2 | R | 96.0 |

TABLE 16-continued

| Ex. | metal source | ligand | amine source | solvent | title compound (%)* | alcohol form (%) | % ee | Stereo | selectivity (%)** |
|---|---|---|---|---|---|---|---|---|---|
| 189 | [Rh(cod)₂]OTf | (R,R)-Me-Ferrocelane | Ammonium salicylate | MeOH | 32.8 | 34.8 | 11.5 | S | 41.0 |
| 190 | [RhCl(cod)]₂ | (R)-Xylyl-BINAP | Ammonium salicylate | MeOH | 11.6 | 6.5 | 25.7 | S | nd |
| 191 | [RhCl(cod)]₂ | (R,R)-CHIRAPHOS | Ammonium salicylate | MeOH | 27.3 | 28.7 | 9.3 | S | 40.1 |
| 192 | [RhCl(cod)]₂ | (R,R)-DIPAMP | Ammonium salicylate | MeOH | 26.0 | 24.9 | 8.4 | S | 43.0 |
| 193 | [RhCl(cod)]₂ | (R,R)-Skewphos | Ammonium salicylate | MeOH | 55.5 | 16.1 | 8.3 | R | 74.7 |
| 194 | [RhCl(cod)]₂ | (S,S)-PTBP-SKEWPHOS | Ammonium salicylate | MeOH | 54.1 | 18.7 | 21.6 | S | 71.3 |
| 195 | [RhCl(cod)]₂ | (R)(S)-JOSIPHOS | Ammonium salicylate | MeOH | 42.3 | 11.8 | 4.3 | S | 77.6 |
| 196 | [RhCl(cod)]₂ | (R,R)-Ph-BPE | Ammonium salicylate | MeOH | 20.9 | 4.0 | 10.7 | S | nd |
| 197 | [RhCl(cod)]₂ | (R,R)-iPr-DUPHOS | Ammonium salicylate | MeOH | 16.9 | 25.5 | 9.7 | S | 30.4 |
| 198 | [RhCl(cod)]₂ | (R)-PHANEPHOS | Ammonium salicylate | MeOH | 67.0 | 4.6 | 7.5 | R | 95.9 |
| 199 | [RhCl(cod)]₂ | (R,R)-Me-Ferrocelane | Ammonium salicylate | MeOH | 37.6 | 15.5 | 9.2 | S | 69.4 |
| 200 | [Rh(cod)₂]OTf | (R,R)-Skewphos | Ammonium salicylate | IPA | 57.2 | 9.6 | 23.7 | R | 85.6 |
| 201 | [Rh(cod)₂]OTf | (R)(S)-JOSIPHOS | Ammonium salicylate | IPA | 45.2 | 4.2 | 8.2 | S | 93.9 |
| 202 | [Rh(cod)₂]OTf | (R)-PHANEPHOS | Ammonium salicylate | IPA | 59.3 | 6.0 | 3.1 | R | 90.2 |
| 203 | [Rh(cod)₂]OTf | (R,R)-Me-Ferrocelane | Ammonium salicylate | IPA | 21.1 | 9.9 | 10.6 | S | 63.5 |
| 204 | [Rh(cod)₂]OTf | (R,R)-Skewphos | Ammonium salicylate | TFE | 7.0 | 3.5 | 6.9 | R | 78.7 |
| 205 | [Rh(cod)₂]OTf | (R)(S)-JOSIPHOS | Ammonium salicylate | TFE | 6.4 | 20.7 | 4.4 | S | 19.1 |
| 206 | [Rh(cod)₂]OTf | (R)-PHANEPHOS | Ammonium salicylate | TFE | 5.2 | 2.8 | 0.4 | R | 60.2 |
| 207 | [Rh(cod)₂]OTf | (R,R)-Skewphos | Ammonium salicylate | THF | 72.8 | 2.2 | 8.0 | S | 97.4 |
| 208 | [Rh(cod)₂]OTf | (R)(S)-JOSIPHOS | Ammonium salicylate | THF | 64.1 | 2.3 | 19.0 | S | 98.6 |
| 209 | [Rh(cod)₂]OTf | (R)-PHANEPHOS | Ammonium salicylate | THF | 75.4 | 1.2 | 13.9 | S | 100.0 |
| 210 | [Rh(cod)₂]OTf | (R,R)-Me-Ferrocelane | Ammonium salicylate | THF | 72.3 | 4.1 | 22.6 | S | 97.0 |
| 211 | [Rh(cod)₂]OTf | (R,R)-Skewphos | Ammonium salicylate | EtOAc | 52.0 | 9.7 | 5.2 | S | 82.7 |
| 212 | [Rh(cod)₂]OTf | (R)(S)-JOSIPHOS | Ammonium salicylate | EtOAc | 37.8 | 9.9 | 23.6 | S | 76.6 |
| 213 | [Rh(cod)₂]OTf | (R)-PHANEPHOS | Ammonium salicylate | EtOAc | 58.2 | 4.8 | 11.8 | S | 91.8 |
| 214 | [Rh(cod)₂]OTf | (R,R)-Me-Ferrocelane | Ammonium salicylate | EtOAc | 34.4 | 31.5 | 18.6 | S | 45.4 |
| 215 | [Rh(cod)₂]OTf | (R)-PHANEPHOS | Ammonium salicylate | DCM | 11.7 | 12.4 | 9.7 | S | 37.9 |
| 216 | [Rh(cod)₂]OTf | (R,R)-Me-Ferrocelane | Ammonium salicylate | DCM | 2.6 | 72.3 | 6.8 | S | 2.2 |
| 217 | [Rh(cod)₂]OTf | (R,R)-Skewphos | Ammonium salicylate | Toluene | 5.0 | 4.2 | 17.2 | R | 47.9 |
| 218 | [Rh(cod)₂]OTf | (R)(S)-JOSIPHOS | Ammonium salicylate | Toluene | 4.7 | 19.7 | 38.0 | S | 4.3 |
| 219 | [Rh(cod)₂]OTf | (R)-PHANEPHOS | Ammonium salicylate | Toluene | 5.6 | 5.7 | 30.8 | R | 31.9 |
| 220 | [Rh(cod)₂]OTf | (R,R)-Me-Ferrocelane | Ammonium salicylate | Toluene | 3.6 | 25.9 | 17.3 | S | 9.8 |
| 221 | [Rh(cod)₂]OTf | (S,S)-PTBP-SKEWPHOS | Ammonium salicylate | IPA | 50.3 | 9.3 | 8.2 | S | 84.5 |
| 222 | [Rh(cod)₂]OTf | (S,S)-Xylyl-Skewphos | Ammonium salicylate | MeOH | 50.2 | 21.5 | 1.1 | S | 70.0 |
| 224 | [Rh(cod)₂]OTf | SL-J002-1 | Ammonium salicylate | MeOH | 40.4 | 11.8 | 0.3 | S | 82.3 |
| 225 | [Rh(cod)₂]OTf | SL-J004-1 | Ammonium salicylate | MeOH | 42.3 | 10.9 | 0.3 | S | 81.3 |
| 226 | [Rh(cod)₂]OTf | SL-J005-1 | Ammonium salicylate | MeOH | 49.7 | 6.5 | 0.8 | S | 91.4 |
| 227 | [Rh(cod)₂]OTf | SL-J009-1 | Ammonium salicylate | MeOH | 26.3 | 49.3 | 18.2 | R | 33.9 |

TABLE 16-continued

| Ex. | metal source | ligand | amine source | solvent | title compound (%)* | alcohol form (%) | % ee | Stereo | selectivity (%)** |
|---|---|---|---|---|---|---|---|---|---|
| 228 | [Rh(cod)₂]OTf | SL-J212-1 | Ammonium salicylate | MeOH | 44.5 | 5.9 | 1.7 | S | 93.2 |
| 229 | [Rh(cod)₂]OTf | SL-T001-1 | Ammonium salicylate | MeOH | 54.1 | 13.9 | 2.5 | R | 81.8 |
| 230 | [Rh(cod)₂]OTf | SL-W001-1 | Ammonium salicylate | MeOH | 58.7 | 6.6 | 17.0 | S | 97.2 |
| 231 | [Rh(cod)₂]OTf | SL-M001-1 | Ammonium salicylate | MeOH | 59.3 | 5.5 | 38.3 | S | 91.6 |
| 232 | [Rh(cod)₂]OTf | SL-M002-1 | Ammonium salicylate | MeOH | 40.7 | 17.3 | 9.8 | S | 71.6 |
| 233 | [Rh(cod)₂]OTf | (S,S)-PTBP-SKEWPHOS | Ammonium salicylate | THF | 73.1 | 3.0 | 9.3 | S | 95.5 |
| 234 | [Rh(cod)₂]OTf | (S,S)-Xylyl-Skewphos | Ammonium salicylate | THF | 57.2 | 16.3 | 16.2 | S | 81.7 |
| 236 | [Rh(cod)₂]OTf | SL-J002-1 | Ammonium salicylate | THF | 72.1 | 2.8 | 44.5 | S | 92.4 |
| 237 | [Rh(cod)₂]OTf | SL-J004-1 | Ammonium salicylate | THF | 32.1 | 1.9 | 65.6 | S | 100.0 |
| 238 | [Rh(cod)₂]OTf | SL-J005-1 | Ammonium salicylate | THF | 57.8 | 1.5 | 4.7 | S | 96.9 |
| 239 | [Rh(cod)₂]OTf | SL-J009-1 | Ammonium salicylate | THF | 53.3 | 19.7 | 47.9 | S | 69.6 |
| 240 | [Rh(cod)₂]OTf | SL-J212-1 | Ammonium salicylate | THF | 65.6 | 1.3 | 15.5 | R | 100.0 |
| 241 | [Rh(cod)₂]OTf | SL-T001-1 | Ammonium salicylate | THF | 73.2 | 1.3 | 4.0 | S | 100.0 |
| 242 | [Rh(cod)₂]OTf | SL-W001-1 | Ammonium salicylate | THF | 73.1 | 3.9 | 13.3 | S | 100.0 |
| 243 | [Rh(cod)₂]OTf | SL-M001-1 | Ammonium salicylate | THF | 73.9 | 0.7 | 7.7 | S | 100.0 |
| 244 | [Rh(cod)₂]OTf | SL-M002-1 | Ammonium salicylate | THF | 62.2 | 3.3 | 22.3 | S | 96.0 |

*the title compound (containing R-form and S-form)
**selectivity (%) = 100 × the title compound (R form + S-form)/(alcohol form + the title compound (R form + S-form))

TABLE 17

| Ex. | metal source | ligand | amine source | solvent | title compound (%)* | alcohol form (%) | % ee | Stereo | selectivity (%)** |
|---|---|---|---|---|---|---|---|---|---|
| 245 | [Ir(cod)₂]BARF | (R)-BINAP | Ammonium acetate | MeOH | 20.1 | 71.4 | 3.9 | S | 23.1 |
| 246 | [Ir(cod)₂]BARF | (R)-Xylyl-BINAP | Ammonium acetate | MeOH | 56.0 | 31.5 | 0.7 | S | 70.1 |
| 247 | [Ir(cod)₂]BARF | (R,R)-CHIRAPHOS | Ammonium acetate | MeOH | 10.8 | 24.9 | 0.4 | S | 47.8 |
| 248 | [Ir(cod)₂]BARF | (R,R)-Skewphos | Ammonium acetate | MeOH | 46.6 | 43.9 | 1.7 | R | 55.1 |
| 249 | [Ir(cod)₂]BARF | (S,S)-PTBP-SKEWPHOS | Ammonium acetate | MeOH | 57.8 | 35.5 | 1.0 | S | 68.3 |
| 250 | [Ir(cod)₂]BARF | (R)(S)-JOSIPHOS | Ammonium acetate | MeOH | 44.4 | 45.6 | 0.5 | R | 54.1 |
| 251 | [Ir(cod)₂]BARF | (R,R)-iPr-DUPHOS | Ammonium acetate | MeOH | 27.0 | 47.1 | 0.7 | R | 43.3 |
| 252 | [Ir(cod)₂]BARF | (R)-PHANEPHOS | Ammonium acetate | MeOH | 5.7 | 59.0 | 14.4 | S | 5.0 |
| 253 | [Ir(cod)₂]BARF | (R,R)-Me-Ferrocelane | Ammonium acetate | MeOH | 36.1 | 51.6 | 2.5 | R | 45.6 |
| 254 | [IrCl(cod)]₂ | (R)-BINAP | Ammonium acetate | MeOH | 20.2 | 66.0 | 6.9 | S | 24.0 |
| 255 | [IrCl(cod)]₂ | (R)-Xylyl-BINAP | Ammonium acetate | MeOH | 29.8 | 44.1 | 4.0 | S | 45.2 |
| 256 | [IrCl(cod)]₂ | (R,R)-CHIPAPHOS | Ammonium acetate | MeOH | 30.7 | 52.4 | 1.7 | R | 37.5 |
| 257 | [IrCl(cod)]₂ | (R,R)-DIPAMP | Ammonium acetate | MeOH | 52.0 | 35.1 | 1.0 | R | 64.0 |
| 258 | [IrCl(cod)]₂ | (R,R)-Skewphos | Ammonium acetate | MeOH | 49.2 | 41.6 | 1.8 | R | 57.4 |
| 259 | [IrCl(cod)]₂ | (S,S)-PTBP-SKEWPHOS | Ammonium acetate | MeOH | 60.2 | 32.2 | 2.6 | S | 71.7 |
| 260 | [IrCl(cod)]₂ | (R)(S)-JOSIPHOS | Ammonium acetate | MeOH | 28.8 | 58.6 | 1.3 | R | 34.7 |
| 261 | [IrCl(cod)]₂ | (R)-iPr-PHOX | Ammonium acetate | MeOH | 3.8 | 48.9 | 2.4 | S | 3.1 |

TABLE 17-continued

| Ex. | metal source | ligand | amine source | solvent | title compound (%)* | alcohol form (%) | % ee | Stereo | selectivity (%)** |
|---|---|---|---|---|---|---|---|---|---|
| 262 | [IrCl(cod)]$_2$ | (R,R)-iPr-DUPHOS | Ammonium acetate | MeOH | 32.8 | 44.5 | 1.4 | R | 51.2 |
| 263 | [IrCl(cod)]$_2$ | (R)-PHANEPHOS | Ammonium acetate | MeOH | 27.3 | 64.5 | 2.0 | S | 29.2 |
| 264 | [IrCl(cod)]$_2$ | (R,R)-Me-Ferrocelane | Ammonium acetate | MeOH | 39.1 | 49.3 | 0.2 | S | 46.2 |
| 265 | [IrCl(cod)]$_2$ | (R)-MONOPHOS | Ammonium acetate | MeOH | 3.5 | 55.5 | 0.9 | S | 2.3 |
| 266 | [Ir(cod)$_2$]BARF | (R)-BINAP | Ammonium salicylate | MeOH | 25.4 | 35.3 | 0.4 | S | 39.5 |
| 267 | [Ir(cod)$_2$]BARF | (R)-Xylyl-BINAP | Ammonium salicylate | MeOH | 35.1 | 24.4 | 0.2 | R | 58.7 |
| 268 | [Ir(cod)$_2$]BARF | (R,R)-CHIRAPHOS | Ammonium salicylate | MeOH | 29.2 | 33.2 | 1.4 | R | 45.7 |
| 269 | [Ir(cod)$_2$]BARF | (R,R)-DIPAMP | Ammonium salicylate | MeOH | 38.5 | 13.1 | 1.1 | R | 75.9 |
| 270 | [Ir(cod)$_2$]BARF | (R,R)-Skewphos | Ammonium salicylate | MeOH | 36.0 | 15.5 | 0.1 | S | 70.2 |
| 271 | [Ir(cod)$_2$]BARF | (S,S)-PTBP-SKEWPHOS | Ammonium salicylate | MeOH | 36.2 | 16.8 | 0.6 | S | 68.0 |
| 272 | [Ir(cod)$_2$]BARF | (R)(S)-JOSIPHOS | Ammonium salicylate | MeOH | 51.9 | 13.8 | 1.1 | R | 81.3 |
| 273 | [Ir(cod)$_2$]BARF | (R)-iPr-PHOX | Ammonium salicylate | MeOH | 4.3 | 9.0 | 1.4 | R | 23.9 |
| 274 | [Ir(cod)$_2$]BARF | (R,R)-iPr-DUPHOS | Ammonium salicylate | MeOH | 25.1 | 35.2 | 1.0 | S | 41.0 |
| 275 | [Ir(cod)$_2$]BARF | (R)-PHANEPHOS | Ammonium salicylate | MeOH | 14.6 | 24.0 | 0.8 | S | 36.6 |
| 276 | [Ir(cod)$_2$]BARF | (R,R)-Me-Ferrocelane | Ammonium salicylate | MeOH | 38.0 | 19.7 | 0.4 | S | 69.2 |
| 277 | [Ir(cod)$_2$]BARF | (R)-MONOPHOS | Ammonium salicylate | MeOH | 38.0 | 18.1 | 0.5 | S | 68.4 |
| 278 | [IrCl(cod)]$_2$ | (R)-BINAP | Ammonium salicylate | MeOH | 49.7 | 15.5 | 8.2 | S | 78.0 |
| 279 | [IrCl(cod)]$_2$ | (R)-Xylyl-BINAP | Ammonium salicylate | MeOH | 20.4 | 40.7 | 0.9 | S | 29.8 |
| 280 | [IrCl(cod)]$_2$ | (R,R)-CHIRAPHOS | Ammonium salicylate | MeOH | 11.8 | 16.8 | 3.0 | S | 41.2 |
| 281 | [IrCl(cod)]$_2$ | (R,R)-DIPAMP | Ammonium salicylate | MeOH | 20.0 | 13.4 | 2.4 | S | 60.9 |
| 282 | [IrCl(cod)]$_2$ | (R,R)-Skewphos | Ammonium salicylate | MeOH | 64.5 | 9.6 | 22.6 | R | 89.1 |
| 283 | [IrCl(cod)]$_2$ | (S,S)-PTBP-SKEWPHOS | Ammonium salicylate | MeOH | 62.6 | 10.7 | 32.1 | S | 87.0 |
| 284 | [IrCl(cod)]$_2$ | (R)(S)-JOSIPHOS | Ammonium salicylate | MeOH | 36.3 | 28.8 | 2.0 | S | 55.2 |
| 285 | [IrCl(cod)]$_2$ | (R)-iPr-PHOX | Ammonium salicylate | MeOH | 36.4 | 10.6 | 4.4 | S | 72.1 |
| 286 | [IrCl(cod)]$_2$ | (R,R)-iPr-DUPHOS | Ammonium salicylate | MeOH | 21.6 | 27.0 | 9.5 | S | 44.6 |
| 287 | [IrCl(cod)]$_2$ | (R)-PHANEPHOS | Ammonium salicylate | MeOH | 18.5 | 11.9 | 8.9 | S | 64.3 |
| 288 | [IrCl(cod)]$_2$ | (R,R)-Me-Ferrocelane | Ammonium salicylate | MeOH | 39.9 | 12.2 | 2.3 | S | 82.4 |
| 289 | [IrCl(cod)]$_2$ | (R)-MONOPHOS | Ammonium salicylate | MeOH | 8.3 | 13.0 | 9.9 | S | 37.4 |
| 290 | [IrCl(cod)]$_2$ | (R,R)-Skewphos | Ammonium salicylate | MeOH | 51.0 | 14.9 | 0.1 | R | 76.6 |
| 291 | [IrCl(cod)]$_2$ | (S,S)-PTBP-SKEWPHOS | Ammonium salicylate | MeOH | 63.6 | 10.9 | 16.1 | S | 86.5 |
| 292 | [IrCl(cod)]$_2$ | (S,S)-Xylyl-Skewphos | Ammonium salicylate | MeOH | 61.4 | 10.7 | 3.1 | S | 86.2 |
| 293 | [IrCl(cod)]$_2$ | (R,R)-Skewphos | Ammonium salicylate | IPA | 66.4 | 5.4 | 74.6 | R | 92.6 |
| 294 | [IrCl(cod)]$_2$ | (S,S)-PTBP-SKEWPHOS | Ammonium salicylate | IPA | 67.9 | 2.8 | 87.4 | S | 96.3 |
| 295 | [IrCl(cod)]$_2$ | (S,S)-Xylyl-Skewphos | Ammonium salicylate | IPA | 64.3 | 3.9 | 27.0 | S | 94.7 |
| 296 | [IrCl(cod)]$_2$ | (R,R)-Skewphos | Ammonium salicylate | THF | 70.8 | 4.4 | 35.4 | R | 93.8 |
| 297 | [IrCl(cod)]$_2$ | (S,S)-PTBP-SKEWPHOS | Ammonium salicylate | THF | 73.6 | 3.6 | 59.9. | S | 96.0 |
| 298 | [IrCl(cod)]$_2$ | (S,S)-Xylyl-Skewphos | Ammonium salicylate | THF | 53.0 | 7.2 | 19.2 | S | 86.7 |
| 299 | [IrCl(cod)]$_2$ | (R,R)-Skewphos | Ammonium salicylate | DCM/MeOH = 2/1 | 70.3 | 5.9 | 7.0 | R | 93.3 |

TABLE 17-continued

| Ex. | metal source | ligand | amine source | solvent | title compound (%)* | alcohol form (%) | % ee | Stereo | selectivity (%)** |
|---|---|---|---|---|---|---|---|---|---|
| 300 | [IrCl(cod)]$_2$ | (S,S)-PTBP-SKEWPHOS | Ammonium salicylate | DCM/MeOH = 2/1 | 61.7 | 5.5 | 14.9 | S | 92.2 |
| 301 | [IrCl(cod)]$_2$ | (S,S)-Xylyl-Skewphos | Ammonium salicylate | DCM/MeOH = 2/1 | 46.1 | 7.8 | 1.0 | S | 84.7 |
| 302 | [IrCl(cod)]$_2$ | (R,R)-Skewphos | Ammonium salicylate | Toulene/MeOH = 2/1 | 33.1 | 3.0 | 23.9 | R | nd |
| 303 | [IrCl(cod)]$_2$ | (S,S)-PTBP-SKEWPHOS | Ammonium salicylate | Toulene/MeOH = 2/1 | 35.0 | 1.8 | 43.5 | S | 96.0 |
| 304 | [IrCl(cod)]$_2$ | (S,S)-Xylyl-Skewphos | Ammonium salicylate | Toulene/MeOH = 2/1 | 31.3 | 4.0 | 6.2 | S | 88.2 |
| 305 | [IrCl(cod)]$_2$ | (R,R)-Skewphos | Ammonium salicylate | TFE | 11.0 | 26.5 | 6.4 | S | 26.6 |
| 306 | [IrCl(cod)]$_2$ | (S,S)-PTBP-SKEWPHOS | Ammonium salicylate | TFE | 6.5 | 38.1 | 4.5 | S | 11.6 |
| 307 | [IrCl(cod)]$_2$ | (S,S)-PTBP-SKEWPHOS | Ammonium salicylate | IPA | 70.0 | 2.0 | 75.9 | S | 97.8 |
| 308 | [IrCl(cod)]$_2$ | (S,S)-PMP-SKEWPHOS | Ammonium salicylate | IPA | 63.9 | 1.9 | 71.6 | S | 96.8 |
| 309 | [IrCl(cod)]$_2$ | (R,R)-PDA-Skewphos | Ammonium salicylate | IPA | 43.8 | 5.2 | 35.0 | R | 89.1 |
| 310 | [IrCl(cod)]$_2$ | (S,S)-PTBP-SKEWPHOS | Ammonium salicylate | IPA | 68.1 | 1.9 | 78.3 | S | 98.1 |
| 311 | [IrCl(cod)]$_2$ | (S,S)-PMP-SKEWPHOS | Ammonium salicylate | IPA | 62.1 | 1.8 | 73.0 | S | 96.9 |
| 312 | [IrCl(cod)]$_2$ | (R,R)-PDA-Skewphos | Ammonium salicylate | IPA | 32.0 | 5.5 | 29.9 | R | 84.2 |
| 313 | [IrCl(cod)]$_2$ | SL-J002-1 | Ammonium salicylate | IPA | 6.6 | 7.7 | 11.6 | R | 39.1 |
| 314 | [IrCl(cod)]$_2$ | SL-J003-1 | Ammonium salicylate | IPA | 6.6 | 7.9 | 2.1 | R | 36.5 |
| 315 | [IrCl(cod)]$_2$ | SL-J004-1 | Ammonium salicylate | IPA | 37.5 | 3.9 | 3.7 | R | 90.3 |
| 316 | [IrCl(cod)]$_2$ | SL-J009-1 | Ammonium salicylate | IPA | 9.2 | 11.1 | 0.0 | R | 61.3 |
| 317 | [IrCl(cod)]$_2$ | SL-J502-1 | Ammonium salicylate | IPA | 3.6 | 14.0 | 0.0 | R | 8.3 |
| 318 | [IrCl(cod)]$_2$ | SL-J005-1 | Ammonium salicylate | IPA | 52.8 | 3.3 | 39.6 | R | 94.7 |
| 319 | [IrCl(cod)]$_2$ | SL-J006-1 | Ammonium salicylate | IPA | 9.7 | 4.9 | 0.6 | R | 60.7 |
| 320 | [IrCl(cod)]$_2$ | SL-J007-1 | Ammonium salicylate | IPA | 26.1 | 5.5 | 0.2 | R | 82.2 |
| 321 | [IrCl(cod)]$_2$ | SL-J011-1 | Ammonium salicylate | IPA | 5.5 | 8.2 | 0.3 | S | 31.7 |
| 322 | [IrCl(cod)]$_2$ | SL-J212-1 | Ammonium salicylate | IPA | 4.6 | 9.0 | 2.0 | S | 26.4 |
| 323 | [IrCl(cod)]$_2$ | SL-J202-1 | Ammonium salicylate | IPA | 8.7 | 6.1 | 0.8 | S | 69.6 |
| 324 | [IrCl(cod)]$_2$ | SL-J013-1 | Ammonium salicylate | IPA | 7.9 | 7.9 | 1.8 | S | 47.0 |
| 325 | [IrCl(cod)]$_2$ | SL-J216-1 | Ammonium salicylate | IPA | 37.4 | 3.9 | 1.4 | S | 90.5 |
| 326 | [IrCl(cod)]$_2$ | SL-J210-1 | Ammonium salicylate | IPA | 2.2 | 7.8 | 3.9 | S | 21.7 |
| 327 | [IrCl(cod)]$_2$ | SL-J203-2 | Ammonium salicylate | IPA | 9.0 | 8.1 | 2.2 | S | 37.5 |
| 328 | [IrCl(cod)]$_2$ | R-Bophoz | Ammonium salicylate | IPA | 36.1 | 5.1 | 2.7 | S | 89.0 |

*the title compound (containing R-form and S-form)
**selectivity (%) = 100 × the title compound (R form + S-form)/(alcohol form + the title compound (R form + S-form))

TABLE 18

| Ex. | metal source | ligand | amine source | solvent | title compound (%)* | alcohol form (%) | % ee | Stereo | selectivity (%)** |
|---|---|---|---|---|---|---|---|---|---|
| 329 | [Ir(cod)$_2$]BARF | (R,R)-Skewphos | Ammonium salicylate | IPA | 42.5 | 11.4 | 2.6 | R | 78.2 |

TABLE 18-continued

| Ex. | metal source | ligand | amine source | solvent | title compound (%)* | alcohol form (%) | % ee | Stereo | selectivity (%)** |
|---|---|---|---|---|---|---|---|---|---|
| 330 | [Ir(cod)₂]BARF | (S,S)-PTBP-SKEWPHOS | Ammonium salicylate | IPA | 0.3 | 55.0 | 4.3 | S | 83.2 |
| 331 | [IrCl(cod)]₂ | (R,R)-Skewphos | Ammonium salicylate | IPA | 0.3 | 63.8 | 67.8 | R | 94.7 |
| 332 | [IrCl(cod)]₂ | (S,S)-PTBP-SKEWPHOS | Ammonium salicylate | IPA | 0.3 | 70.8 | 80.1 | S | 97.9 |
| 333 | [RhCl(cod)]₂ | (R,R)-Skewphos | Ammonium salicylate | IPA | 0.3 | 8.7 | 5.5 | S | 58.1 |
| 334 | [RhCl(cod)]₂ | (S,S)-PTBP-SKEWPHOS | Ammonium salicylate | IPA | 0.5 | 71.0 | 32.7 | S | 83.4 |
| 335 | [Rh(cod)₂]OTf | (R,R)-Skewphos | Ammonium salicylate | IPA | 0.2 | 49.2 | 4.7 | R | 88.6 |
| 336 | [Rh(cod)₂]OTf | (S,S)-PTBP-SKEWPHOS | Ammonium salicylate | IPA | 0.3 | 58.1 | 24.7 | S | 81.3 |
| 337 | [Ir(cod)₂]BARF | (R,R)-Skewphos | Ammonium salicylate | THF | 0.2 | 73.8 | 35.1 | R | 93.4 |
| 338 | [Ir(cod)₂]BARF | (S,S)-PTBP-SKEWPHOS | Ammonium salicylate | THF | 0.2 | 76.8 | 38.9 | S | 95.9 |
| 339 | [IrCl(cod)]₂ | (R,R)-Skewphos | Ammonium salicylate | THF | 0.2 | 74.1 | 35.4 | R | 92.3 |
| 340 | [IrCl(cod)]₂ | (S,S)-PTBP-SKEWPHOS | Ammonium salicylate | THF | 0.2 | 77.0 | 62.1 | S | 95.6 |
| 341 | [RhCl(cod)]₂ | (R,R)-Skewphos | Ammonium salicylate | THF | 0.1 | 72.4 | 7.4 | S | 96.1 |
| 342 | [RhCl(cod)]₂ | (S,S)-PTBP-SKEWPHOS | Ammonium salicylate | THF | 0.2 | 77.0 | 22.0 | S | 96.8 |
| 343 | [Rh(cod)₂]OTf | (R,R)-Skewphos | Ammonium salicylate | THF | 0.2 | 75.4 | 1.6 | S | 96.7 |
| 344 | [Rh(cod)₂]OTf | (S,S)-PTBP-SKEWPHOS | Ammonium salicylate | THF | 0.2 | 76.7 | 2.4 | S | 96.2 |

*the title compound (containing R-form and S-form)

**selectivity (%) = 100 × the title compound (R form + S-form)/(alcohol form + the title compound (R form + S-form))

TABLE 19

| Ex. | metal source | ligand | amine source | solvent | Additive | title compound (%)* | alcohol form (%) | % ee | Stereo | selectivity (%)** |
|---|---|---|---|---|---|---|---|---|---|---|
| 345 | Pd(OAc)₂ | (R)-BINAP | Ammonium salicylate | MeOH | — | 52.6 | 2.8 | 4.0 | R | 96.5 |
| 346 | Pd(OAc)₂ | (R,R)-Skewphos | Ammonium salicylate | MeOH | — | 11.9 | 3.7 | 1.1 | S | nd |
| 347 | Pd(OAc)₂ | (R)(S)-JOSIPHOS | Ammonium salicylate | MeOH | — | 28.5 | 2.6 | 1.2 | S | 97.1 |
| 348 | Pd(OAc)₂ | (R)-BINAP | Ammonium salicylate | MeOH | (−)-CSA 0.1 eq. | 50.3 | 2.2 | 10.8 | S | nd |
| 349 | Pd(OAc)₂ | (R,R)-Skewphos | Ammonium salicylate | MeOH | (−)-CSA 0.1 eq. | 12.9 | 4.3 | 25.2 | S | nd |
| 350 | Pd(OAc)₂ | (R)(S)-JOSIPHOS | Ammonium salicylate | MeOH | (−)-CSA 0.1 eq. | 20.7 | 3.7 | 18.4 | S | nd |
| 351 | Pd(OAc)₂ | (R)-PHANEPHOS | Ammonium salicylate | MeOH | (−)-CSA 0.1 eq. | 8.7 | 3.8 | 10.4 | R | nd |
| 352 | Pd(OAc)₂ | (R)-BINAP | Ammonium salicylate | MeOH | (−)-CSA 1.0 eq. | 41.5 | 1.8 | 12.5 | R | nd |
| 353 | Pd(OAc)₂ | (R,R)-Skewphos | Ammonium salicylate | MeOH | (−)-CSA 1.0 eq. | 40.7 | 2.5 | 9.5 | R | nd |
| 354 | Pd(OAc)₂ | (R)(S)-JOSIPHOS | Ammonium salicylate | MeOH | (−)-CSA 1.0 eq. | 10.8 | 2.8 | 15.2 | R | nd |
| 355 | Pd(OAc)₂ | (R)-PHANEPHOS | Ammonium salicylate | MeOH | (−)-CSA 1.0 eq. | 44.3 | 1.8 | 12.7 | R | nd |
| 356 | Pd(OAc)₂ | (R)-BINAP | Ammonium salicylate | THF | — | 16.0 | 0.4 | 7.1 | S | nd |
| 357 | Pd(OAc)₂ | (R,R)-Skewphos | Ammonium salicylate | THF | — | 3.9 | 0.7 | 2.8 | S | nd |
| 358 | Pd(OAc)₂ | (R)-PHANEPHOS | Ammonium salicylate | THF | — | 19.7 | 0.3 | 2.4 | S | nd |
| 359 | Pd(OAc)₂ | (R)-BINAP | Ammonium salicylate | THF | (−)-CSA 0.1 eq. | 27.9 | 0.4 | 22.5 | S | nd |
| 360 | Pd(OAc)₂ | (R)-PHANEPHOS | Ammonium salicylate | THF | (−)-CSA 0.1 eq. | 38.7 | 0.2 | 22.9 | S | nd |

TABLE 19-continued

| Ex. | metal source | ligand | amine source | solvent | Additive | title compound (%)* | alcohol form (%) | % ee | Stereo | selectivity (%)** |
|---|---|---|---|---|---|---|---|---|---|---|
| 361 | Pd(OAc)$_2$ | (R)-PHANEPHOS | Ammonium salicylate | THF | (−)-CSA 0.1 eq. | 13.8 | 0.3 | 34.5 | R | nd |

*the title compound (containing R-form and S-form)
**selectivity (%) = 100 × the title compound (R form + S-form)/(alcohol form + the title compound (R form + S-form))

TABLE 20

| Ex. | metal source | ligand | amine source | solvent | title compound (%)* | alcohol form (%) | % ee | Stereo | selectivity (%)** |
|---|---|---|---|---|---|---|---|---|---|
| 362 | [IrCl(cod)]$_2$ | (R,R)-PTBP-SKEWPHOS | Ammonium salicylate | IPA | 68.1 | 2.5 | 77.5 | R | 98.2 |
| 363 | [IrCl(cod)]$_2$ | (R,R)-PTBP-SKEWPHOS | Ammonium carbonate | IPA | 40.5 | 45.3 | 32.5 | R | 44.7 |
| 364 | [IrCl(cod)]$_2$ | (R,R)-PTBP-SKEWPHOS | Ammonium formate | IPA | 27.0 | 71.5 | 6.8 | R | 25.9 |
| 365 | [IrCl(cod)]$_2$ | (R,R)-PTBP-SKEWPHOS | Ammonium trifluoroacetate | IPA | 20.4 | 45.6 | 26.8 | R | 27.8 |
| 366 | [IrCl(cod)]$_2$ | (R,R)-PTBP-SKEWPHOS | Ammonium benzoate | IPA | 31.0 | 34.7 | 63.3 | R | 41.8 |
| 367 | [IrCl(cod)]$_2$ | (R,R)-PIBP-SKEWPHOS | Ammonium MeO-salicylate | IPA | 21.9 | 26.6 | 43.3 | R | 42.0 |
| 368 | [IrCl(cod)]$_2$ | (R,R)-PTBP-SKEWPHOS | Ammonium nicotinate | IPA | 36.0 | 10.4 | 22.2 | R | 76.0 |

*the title compound (containing R-form and S-form)
**selectivity (%) = 100 × the title compound (R form + S-form)/(alcohol form + the title compound (R form + S-form))

Examples 369-380

Synthesis of 2-((1R)-1-aminoethyl)-N-(5-chloro-4-(trifluoromethyl)pyridin-2-yl)-1,3-thiazole-5-carboxamide

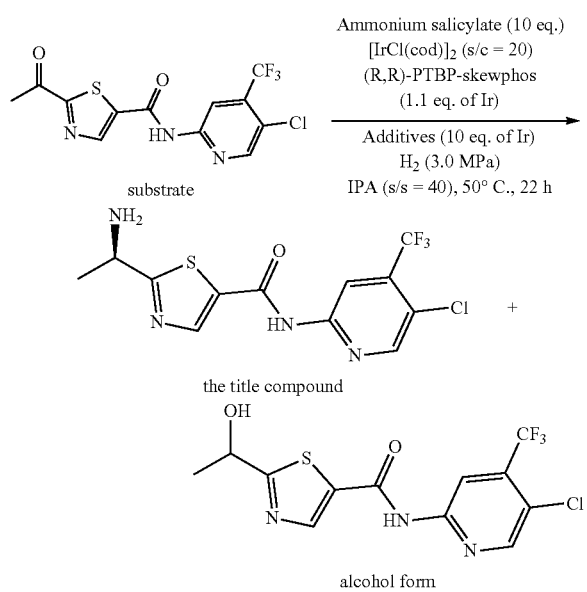

The reaction was carried out in the same manner as in Examples 163-368, except that ammonium salicylate (0.155 g) was used as an amine source, [IrCl(cod)]$_2$ (0.0017 g) was used as a metal source, (R,R)-PTBP-Skewphos (0.0037 g) was used as a ligand, and IPA (1.4 mL) was used as a solvent, and an additive (10 equivalent relative to the iridium catalyst) was added to the test tube for the 24-hole autoclave. The selectivity of the title compound (containing R-form and S-form) and the enantiomeric excess of the title compound (R-form) were calculated from HPLC under the same condition as in Examples 163-368. The results are shown in Table 21.

TABLE 21

| Ex. | Additive | title compound (%)* | alcohol form (%) | % ee | selectivity (%)** |
|---|---|---|---|---|---|
| 369 | NH$_4$Cl | 65.3 | 1.8 | 65.1 | 98.2 |
| 370 | NH$_4$Br | 67.4 | 1.6 | 64.2 | 97.9 |
| 371 | BnEt$_3$NCl | 66.6 | 1.6 | 66.2 | 98.4 |
| 372 | Et$_4$NBr | 66.9 | 1.8 | 61.0 | 97.7 |
| 373 | Et4NI | 63.9 | 1.6 | 64.5 | 98.1 |
| 374 | LiCl | 66.2 | 1.8 | 62.3 | 98.2 |
| 375 | LiBr•H$_2$O | 68.6 | 1.9 | 58.0 | 97.5 |
| 376 | LiI | 66.3 | 1.9 | 65.5 | 97.8 |
| 377 | NaBr | 66.0 | 1.7 | 60.8 | 98.0 |
| 378 | NaI | 63.3 | 2.1 | 61.1 | 96.5 |
| 379 | KCl | 66.3 | 2.0 | 63.2 | 97.9 |
| 380 | KBr | 66.3 | 1.7 | 65.2 | 98.3 |

*the title compound (containing R-form and S-form)
**selectivity (%) = 100 × the title compound (R form + S-form)/(alcohol form + the title compound (R form + S-form))

Examples 381-385

Synthesis of 2-((1R)-1-aminoethyl)-N-(5-chloro-4-(trifluoromethyl)pyridin-2-yl)-1,3-thiazole-5-carboxamide

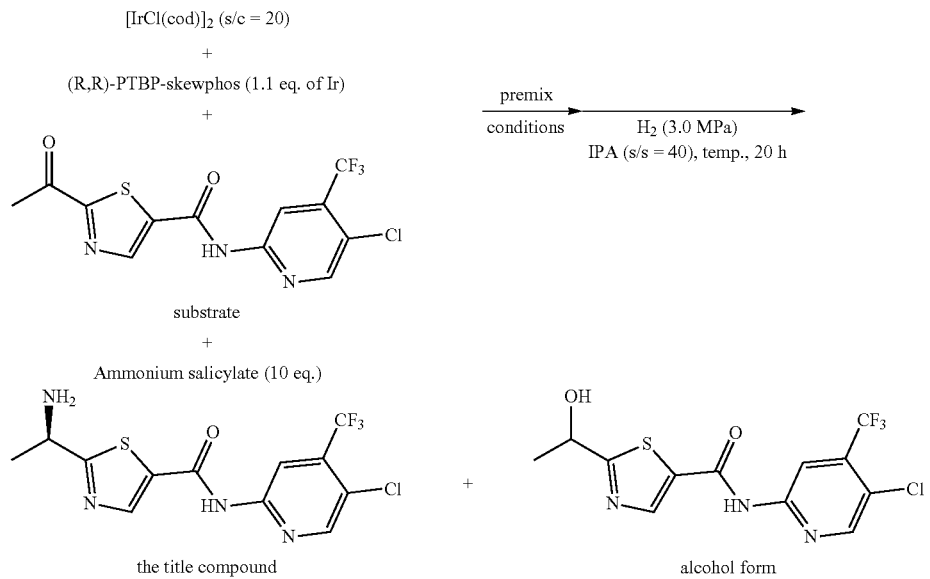

2-Acetyl-N-(5-chloro-4-(trifluoromethyl)pyridin-2-yl)-1,3-thiazole-5-carboxamide (substrate, 0.100 g), ammonium salicylate (0.444 g), [IrCl(cod)]$_2$ (0.0048 g) and (R,R)-PTBP-Skewphos (0.0105 g) were each weighed, and they were put into an autoclave (120 mL). The atmosphere in the autoclave was decompressed, and the pressure was recovered under argon atmosphere. The procedures were performed five times in total. Under argon atmosphere, dehydrated isopropyl alcohol (4.0 mL) was added thereto using a syringe, and the mixture was stirred under given premixing conditions (temperature and time). After the completion of stirring, the atmosphere in the autoclave was purged with hydrogen. Hydrogen was fed into the autoclave until 3.0 MPa, and the mixture was stirred under hydrogen pressure at a given temperature for 20 hr. After the completion of the reaction, the autoclave was cooled, and the hydrogen gas was released. The enantiomeric excess of the title compound (R-form) was calculated from HPLC. The results are shown in Table 22. The HPLC conditions were the same as in Examples 163-368.

TABLE 22

| Ex. | premixing conditions | hydrogenation temperature | HPLC area % title compound (%)* | alcohol form (%) | % ee |
|---|---|---|---|---|---|
| 381 | 50° C., 5 h | 50° C. | 55.5 | 9.6 | 71.3 |
| 382 | 50° C., 1 h | 50° C. | 68.3 | 6.7 | 64.9 |
| 383 | 50° C., 2 h | 50° C. | 60.1 | 7.7 | 82.1 |
| 384 | 30° C., 5 h | 50° C. | 71.3 | 3.5 | 36.8 |
| 385 | 30° C., 5 h | 30° C. | 27.5 | 2.0 | 24.3 |

*the title compound (containing R-form and S-form)

Examples 386-400

Synthesis of 2-((1R)-1-aminoethyl)-N-(5-chloro-4-(trifluoromethyl)pyridin-2-yl)-1,3-thiazole-5-carboxamide

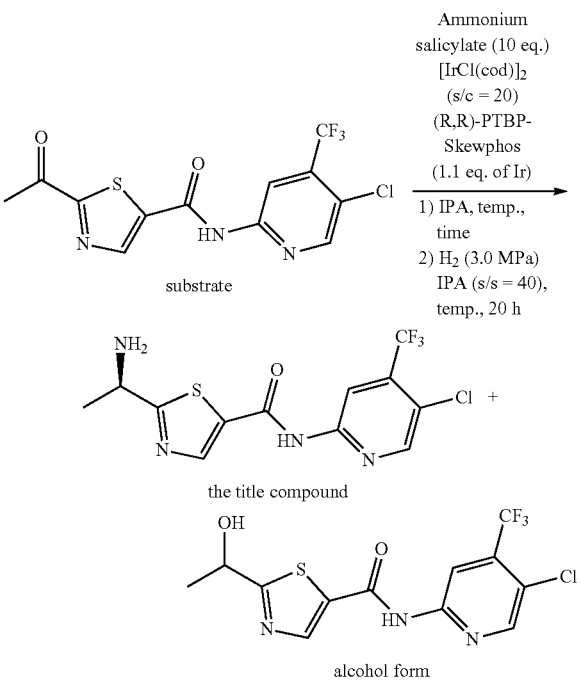

The amount of each reactant to be used was as follows. 2-acetyl-N-(5-chloro-4-(trifluoromethyl)pyridin-2-yl)-1,3-thiazole-5-carboxamide (0.100 g), ammonium salicylate (0.444 g), [IrCl(cod)]$_2$ (0.0048 g) and (R,R)-PTBP-Skewphos (0.0105 g). The reactants marked with ○ in Table 23 were put into Schlenk flask (10 mL). Separately, the reactants marked with ⊚ (when exist) were put into another Schlenk flask (10 mL). To each Schlenk flask containing the reactants was added isopropyl alcohol under argon atmosphere, and each mixture was stirred at a given temperature for a given time to prepare the reaction solutions. The reactants not marked with ○ nor ⊚ in the table were put into an autoclave (120 mL), the atmosphere in the autoclave was replaced with argon, and the reaction solutions previously heated under stirring were fed thereto. The atmosphere in the autoclave was purged with hydrogen, and hydrogen was fed into the autoclave until 3.0 MPa, and the mixture was stirred under hydrogen pressure at a given temperature for 20 hr. After the completion of the reaction, the autoclave was cooled, and the hydrogen gas was released. The enantiomeric excess of the title compound (R-form) was calculated from HPLC. The results are shown in Table 23. The HPLC conditions were the same as in Examples 163-368. Special procedures were described in the note of Table 23.

Examples 401-412

Synthesis of 2-((1R)-1-aminoethyl)-N-(5-chloro-4-(trifluoromethyl)pyridin-2-yl)-1,3-thiazole-5-carboxamide

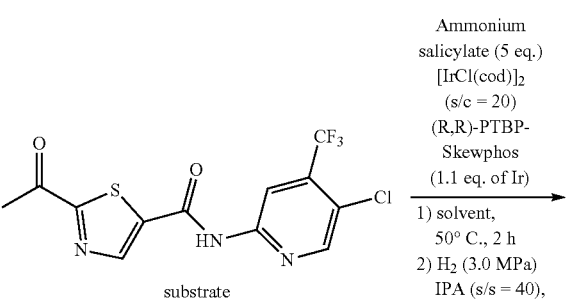

TABLE 23

| | Premix | | | | | HPLC area % | | |
|---|---|---|---|---|---|---|---|---|
| Ex. | substrate | Ammonium Salicylate (AS) | [IrCl(cod)]$_2$ | ligand | temp., time | hydrogenation temp. | title compound * | alcohol form | % ee |
| 386 | ○ | ○ | | | 50° C., 5 h | 50° C. | 60.6 | 4.0 | 22.0 |
| 387 | ○ | | ○ | ○ | 50° C., 5 h | 50° C. | 59.9 | 3.3 | 17.8 |
| 388 | | ○ | ○ | ○ | 50° C., 5 h | 50° C. | 69.0 | 3.6 | 39.4 |
| 389 | ○ | ○ | ○ | ○ | 50° C., 5 h | 50° C. | 55.5 | 9.6 | 71.3 |
| 390 | ○ | ○ | ○ | ○ | 50° C., 1 h | 50° C. | 68.3 | 6.7 | 64.9 |
| 391 | ○ | ○ | ○ | ○ | 50° C., 2 h | 50° C. | 60.1 | 7.7 | 82.1 |
| 392 | ○ | ○ | ○ | ○ | 50° C., 2 h | 50° C. | 61.3 | 9.5 | 63.7 |
| 393 | ○ | ○ | ○ | ○ | 50° C., 2 h | 50° C. | 54.5 | 9.2 | 77.5 |
| 394[1)] | | ○ | ○ | ○ (+AS 10 eq) | 50° C., 2 h | 50° C. | 68.3 | 3.4 | 20.2 |
| 395[2)] | | | ○ | ○ (+substrate (2 eq.), AS (10 eq.)) | 50° C., 2 h | 50° C. | 60.7 | 3.5 | 23.1 |
| 396[3)] | ○ | ○ | ⊚ | ⊚ (+substrate (2 eq.), AS (10 eq.)) | 50° C., 2 h | 50° C. | 55.0 | 2.8 | 47.2 |
| 397[4)] | ○ | ○ | ⊚ | ⊚ (rt) | 50° C., 2 h | 50° C. | 58.2 | 3.9 | 48.0 |
| 398 | ○ | ○ | ○ | ○ | 30° C., 5 h | 50° C. | 71.3 | 3.5 | 36.8 |
| 399 | ○ | ○ | ○ | ○ | 50° C., 2 h | 30° C. | 49.6 | 16.7 | 81.9 |
| 400 | ○ | ○ | ○ | ○ | 30° C., 5 h | 30° C. | 27.5 | 2.0 | 24.3 |

* the title compound (containing R-form and S-form)
[1)] Ammonium salicylate (10 equivalent relative to the iridium catalyst) was stirred together with [IrCl(cod)]$_2$ and (R,R)-PTBP-Skewphos (1.1 equivalent relative to the iridium catalyst).
[2)] The substrate (2 equivalent relative to the iridium catalyst) and ammonium salicylate (10 equivalent relative to the iridium catalyst) were stirred together with [IrCl(cod)]$_2$ and (R,R)-PTBP-Skewphos.
[3)] The isopropyl alcohol solution of the substrate and ammonium salicylate, and the isopropyl alcohol solution of [IrCl(cod)]$_2$, (R,R)-PTBP-Skewphos, the substrate (2 equivalent relative to the iridium catalyst) and ammonium salicylate (10 equivalent relative to the iridium catalyst) were separately put into Schlenk flasks, and each mixture was stirred at 50° C. for 2 hr.
[4)] The isopropyl alcohol solution of the substrate and ammonium salicylate was stirred at 50° C. for 2 hr, and [IrCl(cod)]$_2$ and (R,R)-PTBP-Skewphos were stirred at room temperature for 2 hr.

-continued

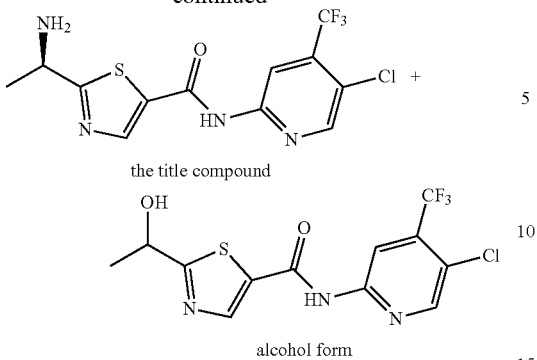

the title compound alcohol form

The reaction was carried out in the same manner as in Examples 381-385, except that ammonium salicylate was used in an amount of 5 equivalent (0.222 g) relative to the substrate, and the solvent shown in Table 24 was used as a dehydrated solvent used after recovering under argon atmosphere. The selectivity of the title compound (containing R-form and S-form) and the enantiomeric excess of the title compound (R-form) were calculated from HPLC. The results are shown in Table 24.

TABLE 24

| | | assay yield (%) | | | |
|---|---|---|---|---|---|
| Ex. | solvent | title compound * | alcohol form | selectivity** | % ee |
| 401 | IPA (10 eq. of AS) | 56 | 10 | 85.0 | 68.9 |
| 402 | IPA (5 eq. of AS) | 51 | 28 | 65.0 | 79.6 |
| 403 | IPA (2 eq. of AS) | 39 | 49 | 44.0 | 52.4 |
| 404 | THF | 74 | 10 | 88.0 | 74.4 |
| 405 | MeOH | 44 | 23 | 66.0 | 10.7 |
| 406 | EtOH | 60 | 16 | 79.0 | 27.9 |
| 407 | IPA/toluene = 10/1 | 46 | 27 | 63.0 | 74.9 |
| 408 | IPA/toluene = 1/1 | 56 | 20 | 74.0 | 84.4 |
| 409 | THF/toluene = 10/1 | 71 | 9 | 89.0 | 73.3 |
| 410 | THF/toluene = 1/1 | 69 | 19 | 78.0 | 45.9 |
| 411 | IPA/H$_2$O = 10/1 | 7 | 31 | 18.0 | 13.1 |
| 412 | THF/H$_2$O = 10/1 | 11 | 32 | 26.0 | 9.7 |

\* the title compound (containing R-form and S-form)
\*\*selectivity (%) = 100 × the title compound (R form + S-form)/(alcohol form + the title compound (R form + S-form))
AS: Ammonium salicylate

Examples 413-415

Synthesis of 2-((1R)-1-aminoethyl)-N-(5-chloro-4-(trifluoromethyl)pyridin-2-yl)-1,3-thiazole-5-carboxamide

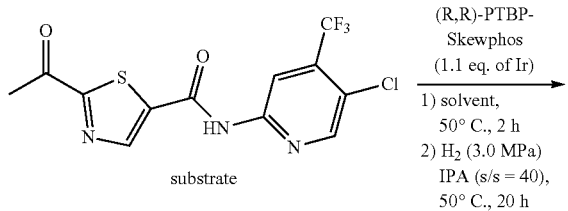

substrate

Ammonium salicylate (5 eq.)
[IrCl(cod)]$_2$
(R,R)-PTBP-Skewphos
(1.1 eq. of Ir)

1) solvent, 50° C., 2 h
2) H$_2$ (3.0 MPa)
IPA (s/s = 40), 50° C., 20 h

-continued

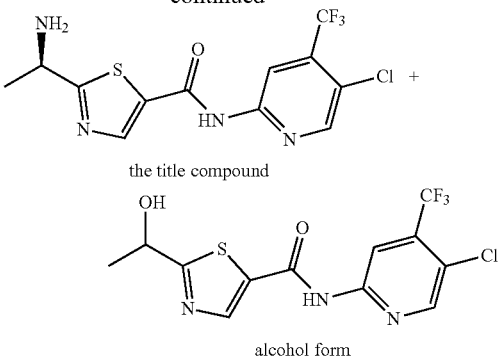

the title compound alcohol form

The reaction was carried out in the same manner as in Examples 401-412, except that the S/C of [IrCl(cod)]$_2$ was 50 or 100. The results are shown in Table 25.

TABLE 25

| | | | assay yield (%) | | | |
|---|---|---|---|---|---|---|
| Ex. | solvent | [IrCl(cod)]$_2$ s/c | title compound * | alcohol form | Amine Ratio** | % ee |
| 413 | IPA | 50 | 64 | 9 | 0.88 | 37.4 |
| 414 | THF | 50 | 74 | 9 | 0.89 | 71.2 |
| 415[1)] | THF | 100 | 80 | 5 | 0.94 | 67.1 |

[1)]The substrate (0.300 g) and ammonium salicylate (0.600 g) were used.
\* the title compound (containing R-form and S-form)
\*\*Amine ratio = the title compound (R form + S-form)/(alcohol form + the title compound (R form + S-form))

Example 416

Synthesis of 2-((1R)-1-aminoethyl)-N-(5-chloro-4-(trifluoromethyl)pyridin-2-yl)-1,3-thiazole-5-carboxamide (S)-mandelate

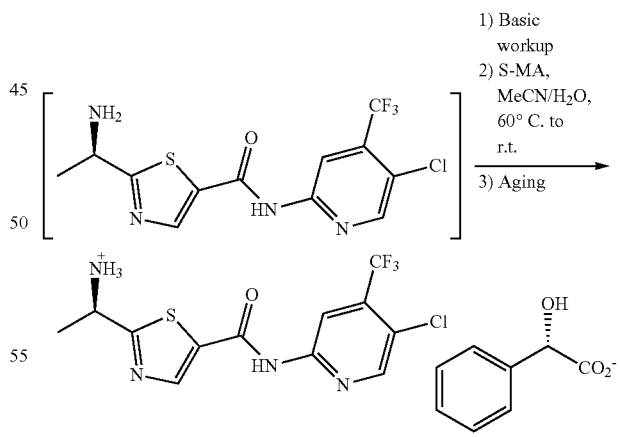

1) Basic workup
2) S-MA, MeCN/H$_2$O, 60° C. to r.t.
3) Aging

The hydrogenation reaction solution containing 2-((1R)-1-aminoethyl)-N-(5-chloro-4-(trifluoromethyl)pyridin-2-yl)-1,3-thiazole-5-carboxamide (2.82 mmol, 59.6% ee) was concentrated under reduced pressure, and the residue was partitioned between a mixed solvent (30 mL) of toluene/ethyl acetate=1/1 and aqueous triethylamine solution (prepared by diluting triethylamine (5.26 mL) with water (40 mL)). The organic layer was separated, and the aqueous layer was washed twice with a mixed solvent (30 mL) of toluene/ethyl acetate=1/1. The three organic layers were combined, and washed with aqueous triethylamine solution (prepared by diluting triethylamine (0.478 mL) with water (40 mL)). The organic layer was separated, dried over sodium sulfate, and concentrated under reduced pressure. The residue was subjected to solvent replacement with acetonitrile, to the residue were added acetonitrile (27.8 mL) and water (0.96 mL), and the residue was dissolved under heating at 60° C. (S)-Mandelic acid (0.399 g) was added thereto at 60° C., and the mixture was cooled to room temperature. The resulting crystals were aged at room temperature for 3 hr. The crystals were collected by filtration using Hirsch funnel, washed with acetonitrile (4.0 mL), and dried overnight under reduced pressure at 50° C. to give 2-((1R)-1-aminoethyl)-N-(5-chloro-4-(trifluoromethyl)pyridin-2-yl)-1,3-thiazole-5-carboxamide (S)-mandelate (93.4 HPLC area % and 98.9% de). To the obtained wet crystals was added acetonitrile (72 mL), and the mixture was heated under reflux for 30 min, and cooled again to room temperature. The resulting crystals were collected by filtration using Hirsch funnel, washed with acetonitrile (18 mL), and dried overnight under reduced pressure at 50° C. to give 2-((1R)-1-aminoethyl)-N-(5-chloro-4-(trifluoromethyl)pyridin-2-yl)-1,3-thiazole-5-carboxamide (S)-mandelate (1.01 g). yield 77%, 94.4% de.

Example 417

Synthesis of 2-((1R)-1-aminoethyl)-N-(5-chloro-4-(trifluoromethyl)pyridin-2-yl)-1,3-thiazole-5-carboxamide (S)-mandelate

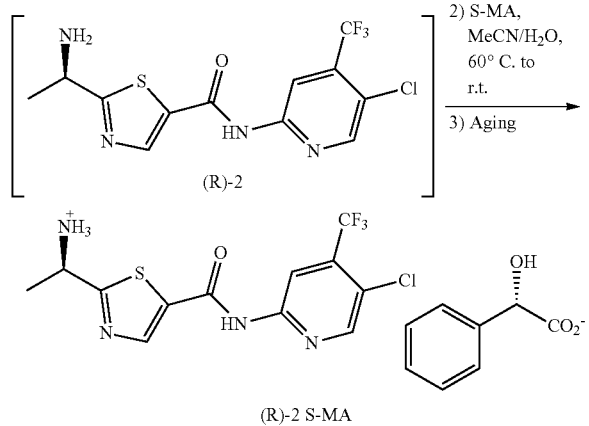

The hydrogenation reaction solution containing 2-((1R)-1-aminoethyl)-N-(5-chloro-4-(trifluoromethyl)pyridin-2-yl)-1,3-thiazole-5-carboxamide (2.21 mmol, 80.5% ee) was concentrated under reduced pressure, and the residue was partitioned between a mixed solvent (30 mL) of toluene/ethyl acetate=1/1 and aqueous triethylamine solution (prepared by diluting triethylamine (5.38 mL) with water (40 mL)). The organic layer was separated, and the aqueous layer was washed twice with a mixed solvent (30 mL) of toluene/ethyl acetate=1/1. The three organic layers were combined, dried over sodium sulfate, and concentrated under reduced pressure. The residue was subjected to solvent replacement with acetonitrile, to the residue were added acetonitrile (22.1 mL) and water (0.76 mL), and the residue was dissolved under heating at 60° C. (S)-Mandelic acid (0.361 g) was added thereto at 60° C., and the mixture was cooled to room temperature. The resulting crystals were aged at room temperature for 3 hr. The crystals were collected by filtration using Hirsch funnel, washed with acetonitrile (4.0 mL), and dried overnight under reduced pressure at 50° C. to give (R)-2-(1-aminoethyl)-N-(5-chloro-4-(trifluoromethyl)pyridin-2-yl)thiazole-5-carboxamide (S)-mandelate (93.4 HPLC area % and 98.9% de). To the obtained wet crystals was added acetonitrile (72 mL), and the mixture was heated under reflux for 30 min, and cooled again to room temperature. The resulting crystals were collected by filtration using Hirsch funnel, washed with acetonitrile (18 mL), and dried overnight under reduced pressure at 50° C. to give 2-((1R)-1-aminoethyl)-N-(5-chloro-4-(trifluoromethyl)pyridin-2-yl)-1,3-thiazole-5-carboxamide (S)-mandelate (0.87 g). yield 79%, 97.1% de.

Example 418

Synthesis of 2-((1R)-1-aminoethyl)-N-(5-chloro-4-(trifluoromethyl)pyridin-2-yl)-1,3-thiazole-5-carboxamide (S)-mandelate

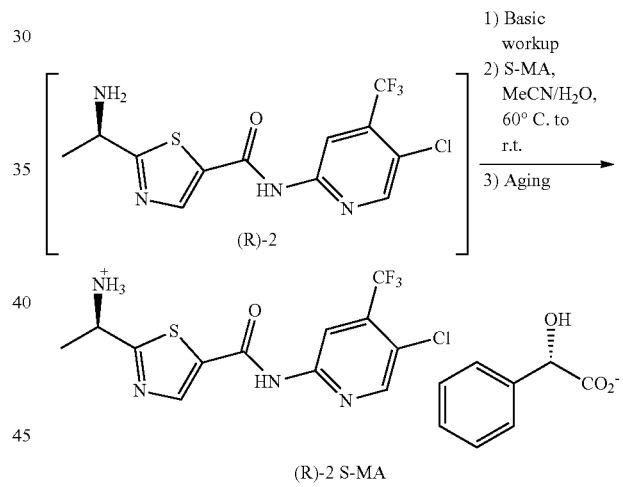

The hydrogenation reaction solution containing 2-((1R)-1-aminoethyl)-N-(5-chloro-4-(trifluoromethyl)pyridin-2-yl)-1,3-thiazole-5-carboxamide (2.79 mmol, 63.6% ee) was concentrated under reduced pressure, and the residue was partitioned between a mixed solvent (30 mL) of toluene/ethyl acetate=1/1 and 1 mol/L aqueous sodium hydroxide solution (40 mL). The organic layer was separated, and the aqueous layer was washed twice with a mixed solvent (30 mL) of toluene/ethyl acetate=1/1. The three organic layers were combined, and washed with 0.1 mol/L aqueous sodium hydroxide solution (40 mL). The three organic layers were combined, dried over sodium sulfate, and concentrated under reduced pressure. The residue was subjected to solvent replacement with acetonitrile, to the residue were added acetonitrile (22.2 mL) and water (0.77 mL), and the residue was dissolved under heating at 60° C. (S)-Mandelic acid (0.327 g) was added thereto at 60° C., and the mixture was cooled to room temperature. The resulting crystals were aged overnight at room temperature. The crystals were collected by filtration using Hirsch funnel, washed with acetonitrile (4.0 mL), and dried overnight under reduced pressure at 50° C. to give 2-((1R)-1-aminoethyl)-N-(5-chloro-4-(trifluoromethyl)pyridin-2-yl)-1,3-thiazole-5-carboxamide (S)-mandelate (0.81 g). yield 57%, 96.0% de.

Example 419

Synthesis of 2-((1R)-1-aminoethyl)-N-(5-chloro-4-(trifluoromethyl)pyridin-2-yl)-1,3-thiazole-5-carboxamide (S)-mandelate

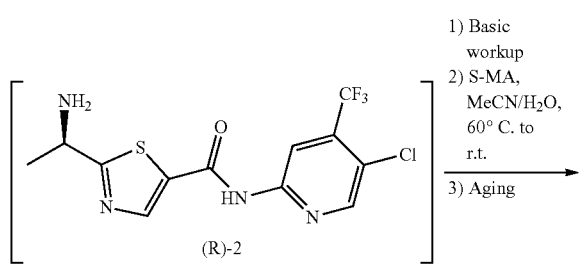

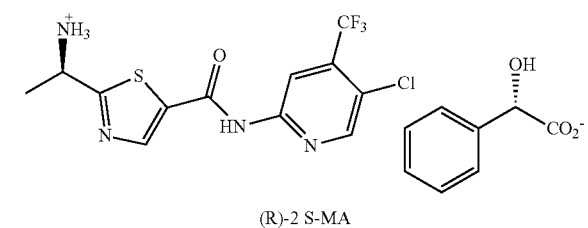

The hydrogenation reaction solution containing 2-((1R)-1-aminoethyl)-N-(5-chloro-4-(trifluoromethyl)pyridin-2-yl)-1,3-thiazole-5-carboxamide (2.94 mmol, 64.6% ee) was concentrated under reduced pressure, and the residue was partitioned between a mixed solvent (30 mL) of toluene/ethyl acetate=1/1 and 0.5 mol/L aqueous sodium hydroxide solution (80 mL). The organic layer was separated, and the aqueous layer was washed twice with a mixed solvent (30 mL) of toluene/ethyl acetate=1/1. The three organic layers were combined, and washed with 0.05 mol/L aqueous sodium hydroxide solution (80 mL). The three organic layers were combined, dried over sodium sulfate, and concentrated under reduced pressure. The residue was subjected to solvent replacement with acetonitrile, to the residue were added acetonitrile (27.9 mL) and water (0.96 mL), and the residue was dissolved under heating at 60° C. (S)-Mandelic acid (0.415 g) was added thereto at 60° C., and the mixture was cooled to room temperature. The resulting crystals were aged overnight at room temperature. The crystals were collected by filtration using Hirsch funnel, washed with acetonitrile (4.0 mL), and dried overnight under reduced pressure at 50° C. to give 2-((1R)-1-aminoethyl)-N-(5-chloro-4-(trifluoromethyl)pyridin-2-yl)-1,3-thiazole-5-carboxamide (S)-mandelate (1.04 g). yield 70%, 95.3% de.

Example 420

Synthesis of 2-((1R)-1-aminoethyl)-N-(5-chloro-4-(trifluoromethyl)pyridin-2-yl)-1,3-thiazole-5-carboxamide (S)-mandelate

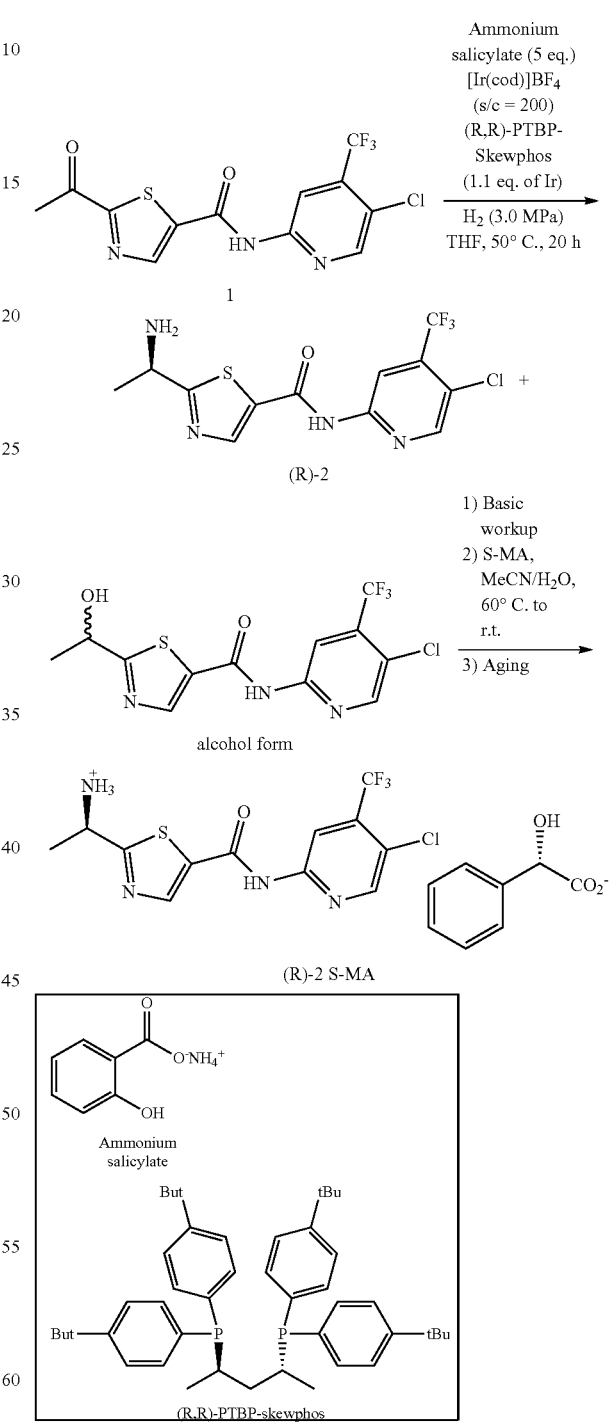

2-Acetyl-N-(5-chloro-4-(trifluoromethyl)pyridin-2-yl)-1,3-thiazole-5-carboxamide (3.50 g), ammonium salicylate (7.76 g), [Ir(cod)$_2$]BF$_4$ (0.0248 g) and (R,R)-PTBP-skewphos (0.0366 g) were put into Schlenk flask (200 mL). The atmosphere in the Schlenk flask was decompressed, and the pressure was recovered under argon atmosphere. The procedures were performed five times in total. Under argon atmosphere, super-dehydrated THF (120 mL) was added thereto, and the mixture was stirred at 50° C. for 2 hr. After the completion of stirring, the reaction solution was fed to an autoclave (300 mL) under argon atmosphere. The inside of the Schienk flask was washed with THF (20 mL), and the washing was also fed to the autoclave. The atmosphere in the autoclave was purged with hydrogen. Hydrogen was fed into the autoclave until 3.0 MPa, and the mixture was stirred under hydrogen pressure at 50° C. for 2 hr. After the completion of the reaction, the autoclave was cooled, and the hydrogen gas was released. The yields of 2-((1R)-1-aminoethyl)-N-(5-chloro-4-(trifluoromethyl)pyridin-2-yl)-1,3-thiazole-5-carboxamide and the alcohol form, and the enantiomeric excess of 2-((1R)-1-aminoethyl)-N-(5-chloro-4-(trifluoromethyl)pyridin-2-yl)-1,3-thiazole-5-carboxamide were calculated from HPLC. The production of 2-((1R)-1-aminoethyl)-N-(5-chloro-4-(trifluoromethyl)pyridin-2-yl)-1,3-thiazole-5-carboxamide (yield 81%, 85% ee) and the alcohol form (2%) was confirmed. Toluene (10 mL) was added thereto, and the reaction mixture was concentrated under reduced pressure. To the residue were added a mixed solvent (80 mL) of toluene/ethyl acetate=1/1 and aqueous ammonia solution (the solution (80 mL) prepared by diluting 25% aqueous ammonia solution (7.49 g) with water), and the mixture was stirred at room temperature for 10 min. The organic layer was separated, and the aqueous layer was washed twice with a mixed solvent (20 mL) of toluene/ethyl acetate=1/1. The three organic layers were combined, and washed with aqueous ammonia solution (the solution (80 mL) prepared by diluting 25% aqueous ammonia solution (0.68 g) with water). The organic layer was separated, dried over sodium sulfate, and concentrated under reduced pressure. The residue was subjected to solvent replacement with acetonitrile, to the residue were added acetonitrile (84 mL) and water (2.9 mL), and the residue was dissolved under heating at 60° C. (S)-Mandelic acid (1.39 g) was added thereto at 60° C., and the mixture was cooled to room temperature. The resulting crystals were aged overnight at room temperature. The crystals were collected by filtration using Hirsch funnel, washed with acetonitrile (11.6 mL), and dried under reduced pressure at 50° C. for 3 hr to give (R)-2-(1-aminoethyl)-N-(5-chloro-4-(trifluoromethyl)pyridin-2-yl)thiazole-5-carboxamide (S)-mandelate (93.4 HPLC area %, 98.9% de). To the obtained wet crystals was added acetonitrile (72 mL), and the mixture was heated under reflux for 30 min, and cooled again to room temperature. The resulting crystals were collected by filtration using Hirsch funnel, washed with acetonitrile (18 mL), and dried overnight under reduced pressure at 50° C. to give 2-((1R)-1-aminoethyl)-N-(5-chloro-4-(trifluoromethyl)pyridin-2-yl)-1,3-thiazole-5-carboxamide (S)-mandelate (3.46 g). yield 69%, 99.8% de.

Conditions for High-Performance Liquid Chromatography Analysis (Area Normalization)
  column: YMC-Pack ODS-A (manufactured by YMC. CO., LTD.), 4.6*150 mm
  UV detection wavelength: 254 nm
  mobile phase: acetonitrile for high-performance liquid chromatography/0.025 mol/L aqueous potassium dihydrogenphosphate solution=8/2
  flow rate: 1.0 mL/min
  retention time: 2.3 min. (the title compound (containing R-form and S-form)), 2.9 min. (alcohol form), 4.8 min. (substrate) conditions for high-performance liquid chromatography analysis (optical purity)
  column: IA (manufactured by Daicel Chemical Industries), 4.6*250 mm
  UV detection wavelength: 254 nm
  mobile phase: acetonitrile for high-performance liquid chromatography/methanol/water=80/15/5
  flow rate: 1.0 mL/min
  column temperature: 40° C.
  retention time: 4.6 min. (substrate), 5.8 min. (alcohol form), 11.6 min. (alcohol form), 16.2 min. (the title compound (R-form)), 24.2 min. (enantiomer (S-form) of the title compound).

Examples 421-428

Synthesis of 2-((1R)-1-aminoethyl)-N-(5-chloro-4-(trifluoromethyl)pyridin-2-yl)-1,3-thiazole-5-carboxamide

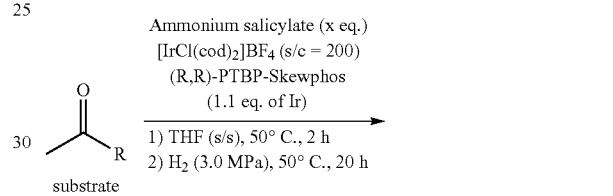

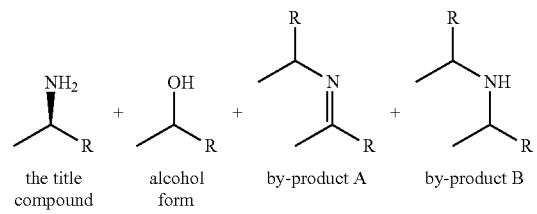

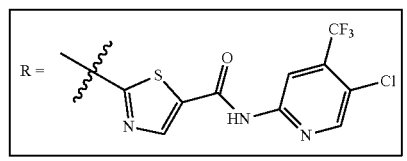

2-Acetyl-N-(5-chloro-4-(trifluoromethyl)pyridin-2-yl)-1,3-thiazole-5-carboxamide (0.400 g), ammonium salicylate, [Ir(cod)$_2$]BF$_4$ (0.0028 g) and (R,R)-PTBP-Skewphos (0.0042 g) were each weighed, and they were put into a test tube for Endeavor (registered trademark). The test tube was set in the apparatus. The atmosphere in the apparatus was decompressed, and the pressure was recovered under argon atmosphere. The procedures were performed five times in total. Under argon atmosphere, super-dehydrated THE was added thereto using a syringe, and the mixture was stirred at 50° C. for 2 hr. After the completion of stirring, the atmosphere in the apparatus was purged with hydrogen. Hydrogen was fed into the apparatus until 3.0 MPa, and the mixture was stirred under hydrogen pressure at 50° C. for 2 hr. The reaction solution was cooled to room temperature, and the hydrogen gas was released. The yield of each product and the enantiomic excess of the title compound were calculated from HPLC. The results are shown in Table 27.

Conditions for High-Performance Liquid Chromatography Analysis (Area Normalization)
    column: YMC-Pack ODS-A (manufactured by YMC. CO., LTD.), 4.6*150 mm
    UV detection wavelength: 254 nm
    mobile phase A: acetonitrile for high-performance liquid chromatography/0.010 mol/L aqueous potassium dihydrogenphosphate solution=6/4
    mobile phase B: acetonitrile for high-performance liquid chromatography/0.010 mol/L aqueous potassium dihydrogenphosphate solution=8/2
    flow rate: 1.0 mL/min
    gradient program:

TABLE 26

|  | Mobile phase A | Mobile phase B |
|---|---|---|
| 0.00 min | 100% | 0% |
| 8.00 min | 100% | 0% |
| 10.00 min | 0% | 100% |
| 25.00 min | 0% | 100% |
| 25.01 min | 100% | 0% |
| 35.00 min | 100% | 0% | retention time: 2.2 min. (the title compound (containing R-form and S-form)), 3.6 min. (alcohol form), 7.0 min. (substrate), 19.8 min. (by-product B)

Conditions for High-Performance Liquid Chromatography Analysis (Optical Purity)
    column: IA (manufactured by Daicel Chemical Industries), 4.6*250 mm
    UV detection wavelength: 254 nm
    mobile phase: acetonitrile for high-performance liquid chromatography/methanol/water=80/15/5
    flow rate: 1.0 mL/min
    column temperature: 40° C.
    retention time: 4.6 min. (substrate), 5.8 min. (alcohol form), 11.6 min. (alcohol form), 16.2 min. (the title compound (R-form)), 24.2 min. (enantiomer (S-form) of the title compound).

Examples 429-442

Synthesis of 2-((1R)-1-aminoethyl)-N-(5-chloro-4-(trifluoromethyl)pyridin-2-yl)-1,3-thiazole-5-carboxamide

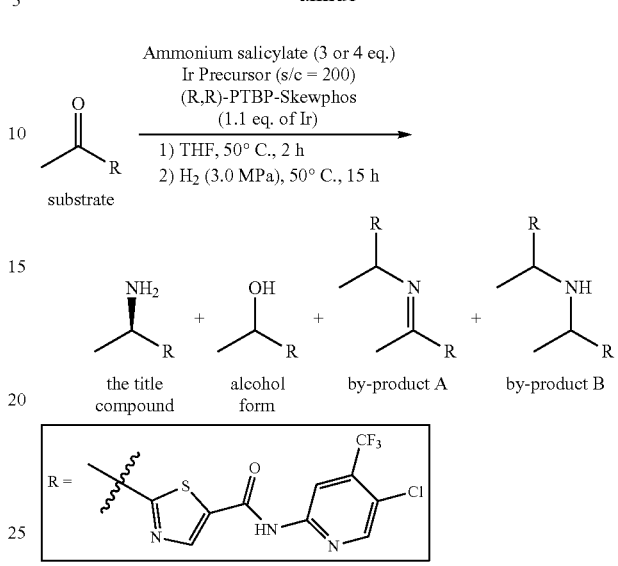

2-Acetyl-N-(5-chloro-4-(trifluoromethyl)pyridin-2-yl)-1,3-thiazole-5-carboxamide (substrate, 0.400 g), ammonium salicylate, an iridium precursor (0.005 equivalent relative to the substrate) and (R,R)-PTBP-Skewphos (0.0042 g) were each weighed, and they were put into a test tube for Endeavor (registered trademark) The test tube was set in the apparatus. The atmosphere in the apparatus was decompressed, and the pressure was recovered under argon atmosphere. The procedures were performed five times in total. Under argon atmosphere, super-dehydrated THF (8.0 mL) was added thereto using a syringe, and the mixture was stirred at 50° C. for 2 hr. After the completion of stirring, the atmosphere in the apparatus was purged with hydrogen. Hydrogen was fed into the apparatus until 3.0 MPa, and the mixture was stirred under hydrogen pressure at 50° C. for 15 hr. The reaction solution was cooled to room temperature, and the hydrogen gas was released. The yield of each product and the enantiomic excess of the title compound were calculated from HPLC. The results are shown in Table 28. The HPLC conditions were the same as in Examples 421-428.

TABLE 27

| | | | HPLC assay (%) | | | | | | |
|---|---|---|---|---|---|---|---|---|---|
| Ex. | amount of AS | s/s | title compound yield | % ee | alcohol form yield | substrate yield | by-product B yield | by-product A yield | total yield | Amine ratio* |
| 421 | 1.2 | 20 | 67 | 83.6 | 12 | 1 | 0 | 8 | 96 | 0.85 |
| 422 | 2.0 | 20 | 80 | 73.6 | 7 | 0 | 0 | 4 | 95 | 0.92 |
| 423 | 3.0 | 20 | 83 | 81.9 | 5 | 0 | 0 | 2 | 92 | 0.94 |
| 424 | 4.0 | 20 | 84 | 87.2 | 4 | 0 | 0 | 1 | 90 | 0.95 |
| 425 | 1.2 | 10 | 66 | 77.9 | 14 | 1 | 0 | 4 | 89 | 0.83 |
| 426 | 2.0 | 10 | 71 | 80.9 | 9 | 1 | 0 | 2 | 85 | 0.89 |
| 427 | 3.0 | 10 | 74 | 80.7 | 6 | 1 | 0 | 1 | 83 | 0.93 |
| 428 | 4.0 | 10 | 71 | 76.7 | 4 | 1 | 0 | 3 | 82 | 0.95 |

*Amine ratio = the title compound (R form + S-form)/(alcohol form + the title compound (R form + S-form))
AS: Ammonium salicylate

TABLE 28

| | | amount of AS | title compound | | alcohol form yield | substrate yield | by-product B yield | by-product A yield | total yield | Amine ratio* |
|---|---|---|---|---|---|---|---|---|---|---|
| Ex. | Ir precursor | | yield | % ee | | | | | | |
| 429 | [Ir(cod)$_2$]BF$_4$ | 3.0 | 57 | 83.7 | 3 | 4 | 0 | 15 | 94 | 0.95 |
| 430 | [Ir(cod)$_2$]BF$_4$ | 4.0 | 55 | 85.1 | 3 | 5 | 0 | 15 | 93 | 0.95 |
| 431 | [IrCl(cod)]$_2$ | 3.0 | 68 | 85.2 | 4 | 2 | 0 | 11 | 96 | 0.94 |
| 432 | [IrCl(cod)]$_2$ | 4.0 | 73 | 85.8 | 4 | 2 | 0 | 8 | 95 | 0.95 |
| 433 | [IrCl(cod)]$_2$ + NaBF$_4$ | 3.0 | 66 | 84.8 | 4 | 3 | 0 | 11 | 95 | 0.94 |
| 434 | [IrCl(cod)]$_2$ + NaBF$_4$ | 4.0 | 65 | 84.5 | 3 | 3 | 0 | 11 | 93 | 0.96 |
| 435 | [Ir(cod)$_2$]BARF | 3.0 | 73 | 86.4 | 5 | 1 | 0 | 8 | 95 | 0.94 |
| 436 | [Ir(cod)$_2$]BARF | 4.0 | 67 | 67.9 | 4 | 2 | 0 | 9 | 91 | 0.94 |
| 437 | [IrI(cod)]$_2$ | 3.0 | 37 | 84.7 | 3 | 10 | 0 | 22 | 94 | 0.93 |
| 438 | [IrI(cod)]$_2$ | 4.0 | 38 | 84.4 | 3 | 10 | 0 | 20 | 91 | 0.93 |
| 439 | [IrOMe(cod)]$_2$ | 3.0 | 74 | 86.5 | 5 | 2 | 0 | 7 | 95 | 0.94 |
| 440 | [IrOMe(cod)]$_2$ | 4.0 | 71 | 85.5 | 4 | 2 | 0 | 8 | 93 | 0.95 |
| 441 | Ir(acac)(cod) | 3.0 | 75 | 87.2 | 5 | 1 | 0 | 6 | 93 | 0.94 |
| 442 | Ir(acac)(cod) | 4.0 | 77 | 86.9 | 4 | 1 | 0 | 6 | 94 | 0.95 |

*Amine ratio = the title compound (R form + S-form)/(alcohol form + the title compound (R form + S-form))
AS: Ammonium salicylate

Examples 443-450

Synthesis of 2-((1R)-1-aminoethyl)-N-(5-chloro-4-(trifluoromethyl)pyridin-2-yl)-1,3-thiazole-5-carboxamide

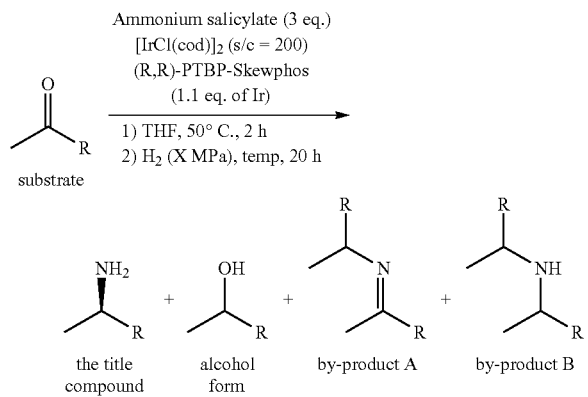

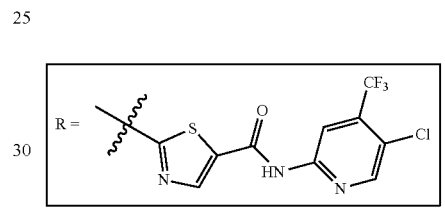

2-Acetyl-N-(5-chloro-4-(trifluoromethyl)pyridin-2-yl)-1,3-thiazole-5-carboxamide (0.400 g), ammonium salicylate (0.532 g), [IrCl(cod)]$_2$ (0.0019 g) and (R,R)-PTBP-Skewphos (0.0042 g) were each weighed, and they were put into a test tube for Endeavor (registered trademark). The reaction was carried out in the same manner as in Examples 421-428. The yield of each product and the enantiomeric excess of the title compound were calculated from HPLC. The results are shown in Table 29.

TABLE 29

| | H$_2$ | | title compound | | alcohol form | substrate | by-product B | by-product A | total | Amine |
|---|---|---|---|---|---|---|---|---|---|---|
| Ex. | pressure | temperature | yield | % ee | yield | yield | yield | yield | yield | ratio* |
| 443 | 3.0 | 30 | 23 | 95.4 | 2 | 15 | 0 | 26 | 92 | 0.92 |
| 444 | 3.0 | 50 | 73 | 81.0 | 3 | 1 | 0 | 7 | 91 | 0.96 |
| 445 | 3.0 | 80 | 91 | 37.3 | 2 | 0 | 0 | 0 | 93 | 0.98 |
| 446 | 3.0 | 100 | 81 | 2.6 | 3 | 0 | 0 | 0 | 84 | 0.96 |
| 447 | 1.0 | 30 | 6 | 94.8 | 1 | 36 | 0 | 22 | 87 | 0.86 |
| 448 | 1.0 | 50 | 34 | 78.7 | 1 | 8 | 0 | 23 | 89 | 0.97 |
| 449 | 1.0 | 80 | 76 | 16.5 | 2 | 0 | 0 | 5 | 88 | 0.97 |
| 450 | 1.0 | 100 | 54 | 2.3 | 3 | 5 | 1 | 13 | 90 | 0.95 |

*Amine ratio = the title compound (R form + S-form)/(alcohol form + the title compound (R form + S-form))

Examples 451-457

Synthesis of 2-((1R)-1-aminoethyl)-N-(5-chloro-4-(trifluoromethyl)pyridin-2-yl)-1,3-thiazole-5-carboxamide

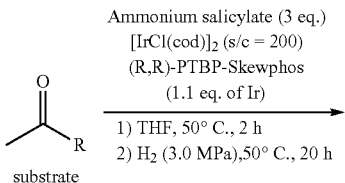
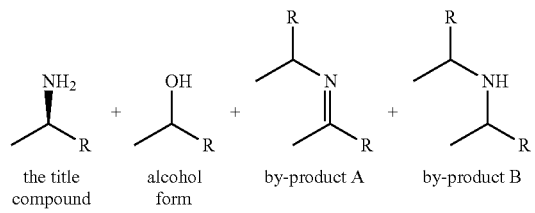
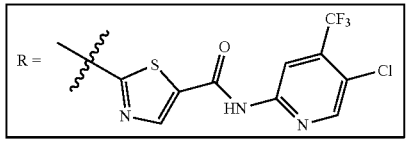

Examples 458-464

Synthesis of 2-((1R)-1-aminoethyl)-N-(5-chloro-4-(trifluoromethyl)pyridin-2-yl)-1,3-thiazole-5-carboxamide

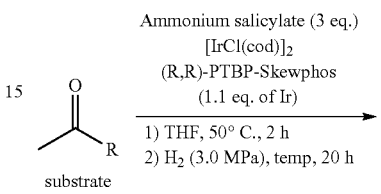
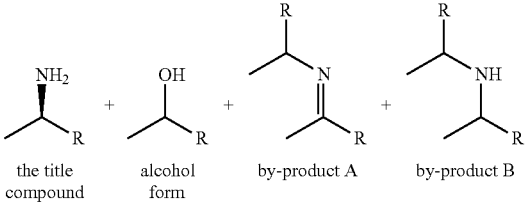
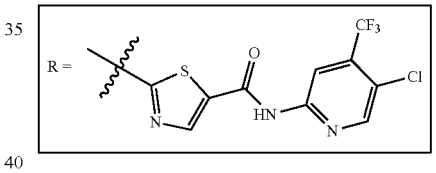

2-Acetyl-N-(5-chloro-4-(trifluoromethyl)pyridin-2-yl)-1,3-thiazole-5-carboxamide (0.400 g), ammonium salicylate (0.532 g), [IrCl(cod)]$_2$ (0.0019 g) and (R,R)-PTBP-Skewphos were each weighed, and they were put into a test tube for Endeavor (registered trademark). The reaction was carried out in the same manner as in Examples 421-428. The yield of each product and the enantiomic excess of the title compound were calculated from HPLC. The results are shown in Table 30.

2-Acetyl-N-(5-chloro-4-(trifluoromethyl)pyridin-2-yl)-1,3-thiazole-5-carboxamide (0.400 g), ammonium salicylate (0.532 g), [IrCl(cod)]$_2$ and (R,R)-PTBP-Skewphos were each weighed, and they were put into a test tube for Endeavor (registered trademark). The reaction was carried out in the same manner as in Examples 421-428. The yield of each product and the enantiomic excess of the title compound were calculated from HPLC. The results are shown in Table 31.

TABLE 30

| | | HPLC assay (%) | | | | | | |
|---|---|---|---|---|---|---|---|---|
| | | title compound | | alcohol form | substrate | by-product B | by-product A | total | Amine |
| Ex. | ligand/Ir | yield | % ee | yield | yield | yield | yield | yield | ratio* |
| 451 | 0.20 | 37 | 78.0 | 1 | 7 | 0 | 23 | 91 | 0.97 |
| 452 | 0.40 | 72 | 80.7 | 2 | 1 | 0 | 10 | 95 | 0.97 |
| 453 | 0.50 | 77 | 83.3 | 3 | 1 | 0 | 7 | 95 | 0.96 |
| 454 | 0.30 | 89 | 86.5 | 5 | 0 | 0 | 2 | 98 | 0.95 |
| 455 | 1.10 | 88 | 87.1 | 5 | 0 | 0 | 1 | 95 | 0.95 |
| 456 | 2.00 | 88 | 85.3 | 4 | 0 | 0 | 2 | 96 | 0.96 |
| 457 | 3.00 | 88 | 87.3 | 5 | 0 | 0 | 1 | 95 | 0.95 |

*Amine ratio = the title compound (R form + S-form)/(alcohol form + the title compound (R form + S-form))

TABLE 31

| | | HPLC assay (%) | | | | | | |
|---|---|---|---|---|---|---|---|---|
| | s/c | title compound | | alcohol form | substrate | by-product B | by-product A | total | Amine |
| Ex. | (initial) | yield | % ee | yield | yield | yield | yield | yield | ratio* |
| 458 | 5 | 63 | 74.3 | 16 | 0 | 0 | 0 | 79 | 0.80 |
| 459 | 10 | 73 | 84.3 | 13 | 0 | 0 | 0 | 86 | 0.85 |
| 460 | 50 | 82 | 89.0 | 9 | 0 | 0 | 1 | 93 | 0.90 |
| 461 | 100 | 83 | 89.2 | 8 | 0 | 0 | 0 | 91 | 0.91 |
| 462 | 200 | 85 | 86.7 | 5 | 0 | 0 | 1 | 92 | 0.94 |
| 463 | 400 | 66 | 78.8 | 3 | 2 | 0 | 10 | 91 | 0.96 |
| 464 | 600 | 33 | 78.2 | 1 | 9 | 0 | 23 | 89 | 0.97 |

*Amine ratio = the title compound (R form + S-form)/(alcohol form + the title compound (R form + S-form))

Examples 465-472

Synthesis of 2-((1R)-1-aminoethyl)-N-(5-chloro-4-(trifluoromethyl)pyridin-2-yl)-1,3-thiazole-5-carboxamide

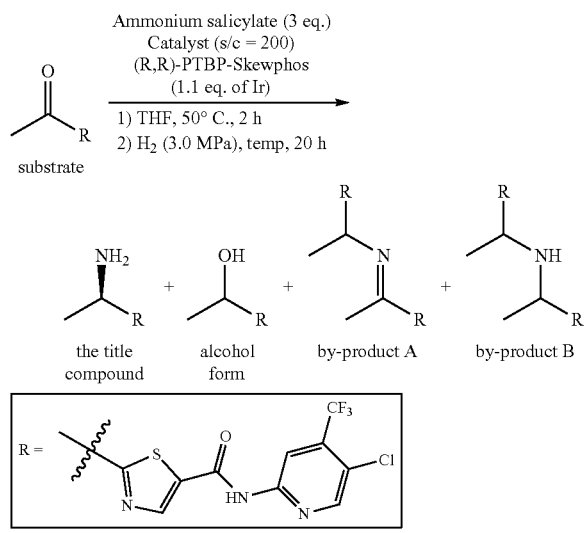

Catalyst A ([IrCl(cod)]$_2$ (0.0019 g), (R,R)-PTBP-Skewphos (0.0042 g)) or catalyst B ([IrCl(cod){(R,R)-PTBP-skewphos}] (0.0057 g)), and the reactants marked with ○ in the table (2-acetyl-N-(5-chloro-4-(trifluoromethyl)pyridin-2-yl)-1,3-thiazole-5-carboxamide (0.400 g), ammonium salicylate (0.532 g)) were each weighed, and they are put into Schlenk flask. The atmosphere in the Schlenk flask was decompressed, and the pressure was recovered under argon atmosphere. The procedures were performed five times in total. Under argon atmosphere, super-dehydrated THF (8.0 mL) was added thereto using a syringe, and the mixture was stirred at 50° C. for 2 hr. Separately, the remaining reactant (not marked with ○ in the table) was weighed, and put into a test tube for Endeavor (registered trademark), and the atmosphere in the apparatus was replaced with argon. After the completion of stirring, the reaction solution was fed to the Endeavor, and the atmosphere in the apparatus was purged with hydrogen. Hydrogen was fed into the apparatus until 3.0 MPa, and the mixture was stirred under hydrogen pressure at 50° C. for 2 hr. The reaction solution was cooled to room temperature, and the hydrogen gas was released. The yield of each product and the enantiomeric excess of the title compound were calculated from HPLC. The results are shown in Table 32. The HPLC conditions were the same as in Examples 421-428. In Example 467, the hydrogenation reaction was carried out without premixing.

TABLE 32

| | | | | | HPLC assay (%) | | | | | | |
|---|---|---|---|---|---|---|---|---|---|---|---|
| | | | | | title compound | | alcohol form | substrate | by-product B | by-product A | total | Amine |
| Ex. | catalyst | substrate | Ammonium salycylate | premix | yield | % ee | yield | yield | yield | yield | yield | ratio* |
| 465 | A | ○ | ○ | ○ | 88 | 87.1 | 5 | 0 | 0 | 1 | 95 | 0.95 |
| 466 | B | ○ | ○ | ○ | 84 | 84.7 | 4 | 0 | 0 | 2 | 92 | 0.95 |
| 467 | A | ○ | ○ |   | 42 | 79.2 | 2 | 5 | 0 | 23 | 95 | 0.95 |
| 468 | B | ○ | ○ | ○ | 41 | 80.2 | 2 | 5 | 0 | 23 | 94 | 0.95 |
| 469 | A | ○ |   | ○ | 53 | 76.4 | 2 | 4 | 0 | 18 | 95 | 0.96 |
| 470 | B | ○ |   | ○ | 48 | 77.1 | 1 | 4 | 0 | 20 | 93 | 0.98 |
| 471 | A |   | ○ | ○ | 59 | 75.5 | 2 | 3 | 0 | 16 | 96 | 0.97 |
| 472 | B |   | ○ | ○ | 50 | 77.0 | 1 | 5 | 0 | 19 | 94 | 0.98 |

*Amine ratio = the title compound (R form + S-form)/(alcohol form + the title compound (R form + S-form))

Reference Example 36

Synthesis of iridium catalyst

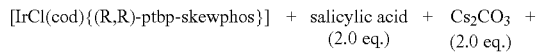

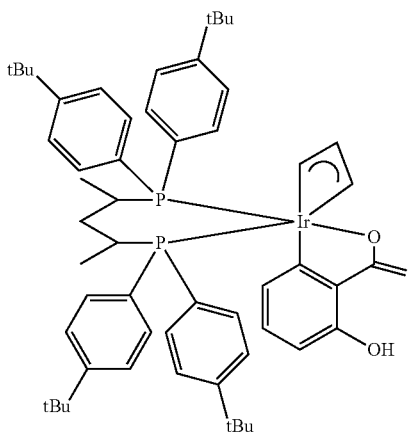

Chemical Formula: $C_{55}H_{71}IrO_3P_2$
Molecular Weight: 1034.32

[IrCl(cod){(R,R)-ptbp-skepwhos}] (0.600 g), salicylic acid (0.166 g) and cesium carbonate (0.391 g) were each weighed, and they are put into Schlenk flask. The atmosphere in the Schlenk flask was decompressed, and the pressure was recovered under argon atmosphere. The procedures were performed five times in total. Under argon atmosphere, super-dehydrated THF (20.0 mL) and allyl acetate (0.161 mL) were added thereto using a syringe, and the mixture was stirred at room temperature for 10 min, and then stirred under heating with reflux for 3 hr. The reaction solution was cooled to room temperature, dichloromethane (15 mL) was added thereto, and the mixture was filtered through Celite. The Celite was washed with dichloromethane (15 mL), and the filtrate and washing were concentrated under reduced pressure to give a yellow solid. The solid was purified by silica gel column chromatography (developing solvent: hexane/ethyl acetate=10/1) to give a yellow solid (0.65 g). Hexane (15 mL) was added thereto, and the mixture was heated under reflux, ice-cooled, and stirred for 30 min. The resulting solid was filtered, and washed with ice-cooled hexane, and the filtrate was concentrated under reduced pressure to give the desired compound as a mixture of two diastereomers (0.47 g). yield 47%.

$^{31}$P NMR (202 MHz, CDCl$_3$) δ: −15.58 (d, J=32.3 Hz, 1P), −14.80 (d, J=29.9 Hz, 1P), −9.75 (d, J=32.3 Hz, two peaks merge)

Example 473

Synthesis of 2-((1R)-1-aminoethyl)-N-(5-chloro-4-(trifluoromethyl)pyridin-2-yl)-1,3-thiazole-5-carboxamide

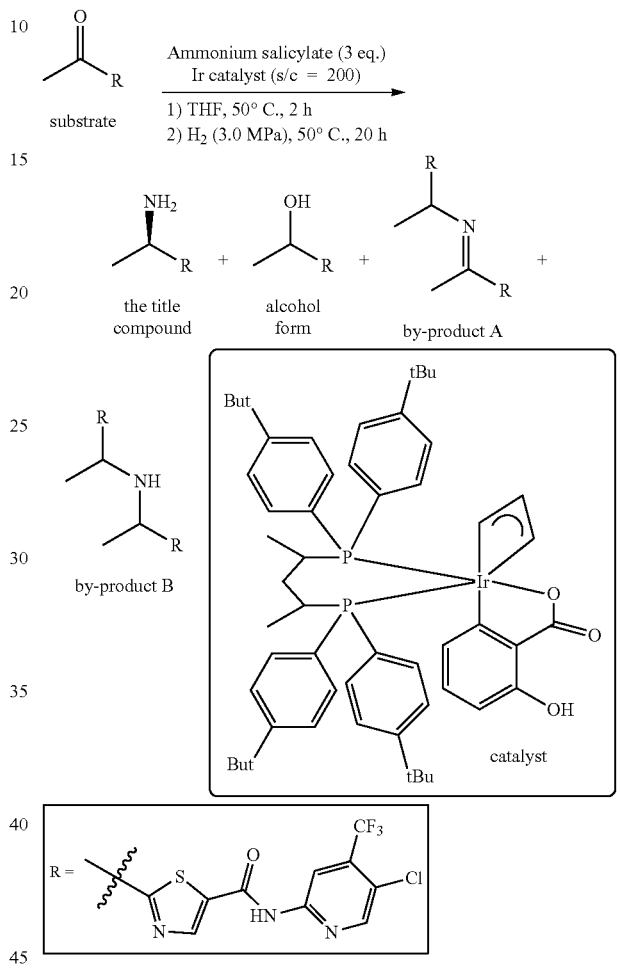

2-Acetyl-N-(5-chloro-4-(trifluoromethyl)pyridin-2-yl)-1,3-thiazole-5-carboxamide (0.400 g), ammonium salicylate (0.532 g), and the iridium catalyst (0.0059 g) synthesized in Reference Example 36 were each weighed, and they were put into a test tube for Endeavor (registered trademark). The test tube was set in the apparatus. The atmosphere in the apparatus was decompressed, and the pressure was recovered under argon atmosphere. The procedures were performed five times in total. Under argon atmosphere, super-dehydrated THF (8.0 mL) was added thereto using a syringe, and the mixture was stirred at 50° C. for 2 hr. After the completion of stirring, the atmosphere in the apparatus was purged with hydrogen. Hydrogen was fed into the apparatus until 3.0 MPa, and the mixture was stirred under hydrogen pressure at 50° C. for 2 hr. The reaction solution was cooled to room temperature, and the hydrogen gas was released. The yield of each product and the enantiomic excess of the title compound were calculated from HPLC. the title compound: yield 84%, 85.9% ee; alcohol form: yield 4%; by-product A: yield 0%; by-product B yield 2%.

Examples 474-499

Synthesis of 2-((1R)-1-aminoethyl)-N-(5-chloro-4-(trifluoromethyl)pyridin-2-yl)-1,3-thiazole-5-carboxamide

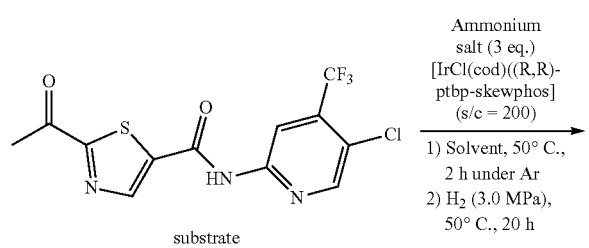

substrate

Ammonium salt (3 eq.)
[IrCl(cod)((R,R)-ptbp-skewphos]
(s/c = 200)

1) Solvent, 50° C., 2 h under Ar
2) H$_2$ (3.0 MPa), 50° C., 20 h

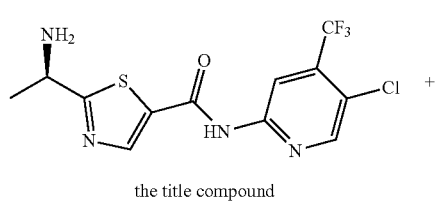

the title compound

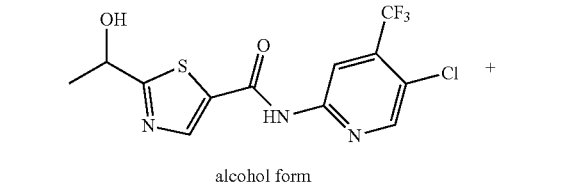

alcohol form

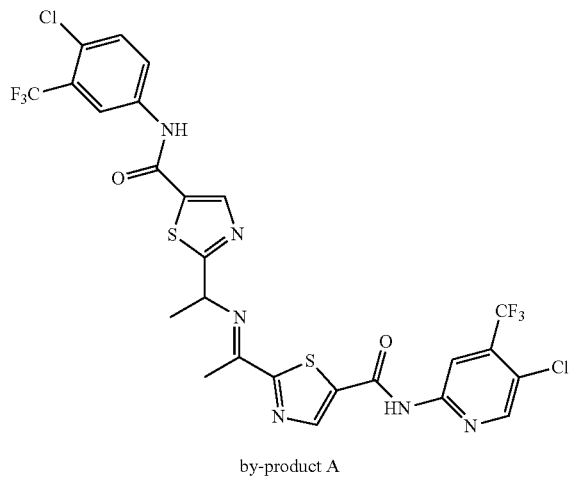

by-product A

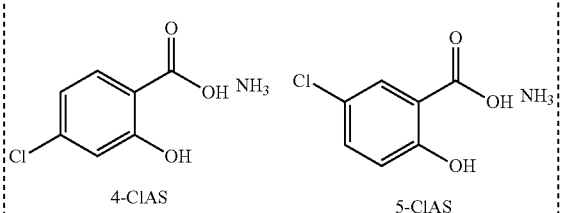

4-ClAS    5-ClAS

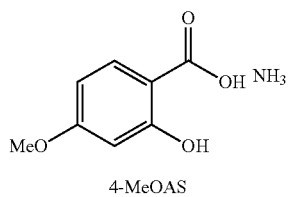

4-MeOAS

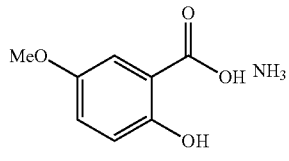

5-MeOAS

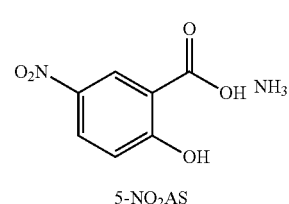

5-NO$_2$AS

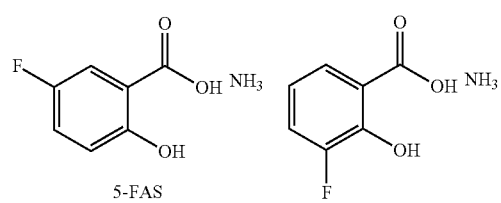

5-FAS    3-FAS

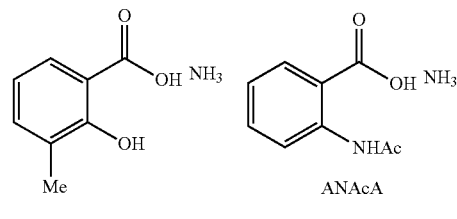

3-MeAS    ANAcA

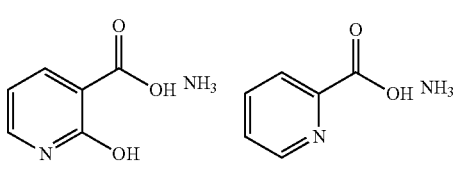

AHN    APC

CF$_3$CO$_2$H  NH$_3$

ATFA

2-Acetyl-N-(5-chloro-4-(trifluoromethyl)pyridin-2-yl)-1,3-thiazole-5-carboxamide (substrate) (0.400 g), an ammonium salicylate derivative (amine source, 3 equivalent relative to the substrate) and [IrCl(cod){(R,R)-ptbp-Skewphos}] (0.0057 g) were each weighed, and they were put into a test tube for Endeavor (registered trademark). The reaction was carried out in the same manner as in Examples 421-428. The yield of each product and the enantiomic excess of the title compound were calculated from HPLC. The results are shown in Table 33.

TABLE 33

| | | | HPLC assay (%) | | | | |
|---|---|---|---|---|---|---|---|
| Ex. | amine source | solvent | title compound yield | % ee | alcohol form yield | substrate yield | by-product A yield | total yield |
| 474 | AS | THF | 85 | 83.1 | 5 | 0 | 1 | 92 |
| 475 | AS | THF/MeOH = 3/1 | 76 | 71.8 | 3 | 1 | 6 | 92 |
| 476 | AS | THF/IPA = 3/1 | 86 | 86.4 | 5 | 0 | 2 | 95 |
| 477 | 4-ClAS | THF | 82 | 87.2 | 3 | 1 | 3 | 92 |
| 478 | 5-ClAS | THF | 90 | 88.7 | 2 | 0 | 1 | 94 |
| 479 | 5-ClAS | IPA | 22 | 23.5 | 2 | 28 | 24 | 100 |
| 480 | 5-ClAS | IPA/THF = 3/1 | 77 | 68.4 | 3 | 2 | 7 | 96 |
| 481 | 5-ClAS | THF/IPA = 3/1 | 87 | 86.9 | 3 | 1 | 3 | 97 |
| 482 | 5-ClAS | THF/MeOH = 3/1 | 37 | 72.5 | 1 | 11 | 21 | 91 |
| 483 | 5-ClAS (1.2 eq.) | THF | 58 | 86.2 | 3 | 5 | 14 | 94 |
| 484 | 5-NO$_2$AS | THF | 3 | 61.4 | 1 | 72 | 11 | 98 |
| 485 | 5-NO$_2$AS | THF/MeOH = 3/1 | 13 | 71.5 | 1 | 50 | 17 | 98 |
| 486 | 5-FAS | THF | 77 | 86.1 | 2 | 1 | 4 | 88 |
| 487 | 3-FAS | THF | 54 | 50.8 | 4 | 6 | 17 | 98 |
| 488 | 3-MeAS | THF | 65 | 79.9 | 5 | 2 | 11 | 94 |
| 489 | 3-MeAS | THF/MeOH = 3/1 | 18 | 69.0 | 2 | 9 | 26 | 81 |
| 490 | Ammonium | THF | 9 | 95.6 | 4 | 48 | 18 | 97 |
| 491 | N-acethylanthranate | THF/MeOH = 3/1 | 20 | 53.8 | 2 | 10 | 28 | 88 |
| 492 | 4-MeOAS | THF | 42 | 76.9 | 8 | 5 | 21 | 97 |
| 493 | 5-MeOAS | THF | 82 | 86.5 | 5 | 0 | 1 | 89 |
| 494 | 5-MeOAS | THF/MeOH = 3/1 | 74 | 73.9 | 4 | 1 | 4 | 87 |
| 495 | AHN | IPA | 0.1 | nd | 1 | 79 | 0 | 80 |
| 496 | AHN | THF/IPA | 0.1 | nd | 1 | 111 | 0 | 112 |
| 497 | APC | IPA | 0.1 | nd | 1 | 98 | 0 | 99 |
| 498 | APC | THF/IPA | 0.1 | nd | 0 | 97 | 0 | 97 |
| 499 | ATFA | THF | 19 | 77.6 | 1 | 64 | 6 | 96 |

Examples 500-508

Synthesis of 2-((1R)-1-aminoethyl)-N-(5-chloro-4-(trifluoromethyl)pyridin-2-yl)-1,3-thiazole-5-carboxamide

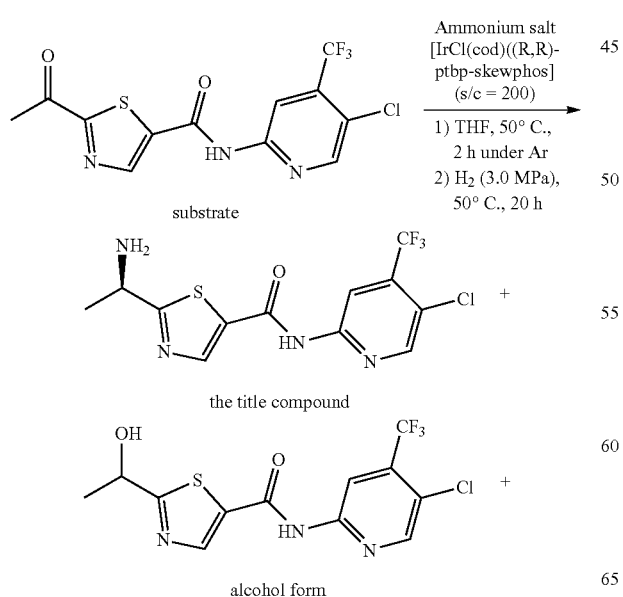

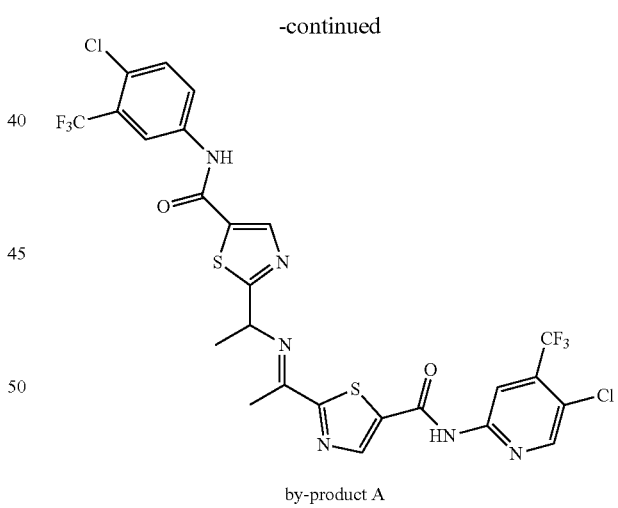

2-Acetyl-N-(5-chloro-4-(trifluoromethyl)pyridin-2-yl)-1,3-thiazole-5-carboxamide (0.400 g), ammonium salicylate and/or ammonium salt (amine source) and [IrCl (cod) {(R,R)-ptbp-Skewphos}] (0.0057 g) were each weighed, and they were put into a test tube for Endeavor (registered trademark). The reaction was carried out in the same manner as in Examples 421-428. The yield of each product and the enantiomeric excess of the title compound were calculated from HPLC. The results are shown in Table 34.

TABLE 34

| | | Eq of ammonium | HPLC assay (%) | | | | | |
| | | | title compound | | alcohol form | substrate | by-product A | total |
| Ex. | amine source | salt | yield | % ee | yield | yield | yield | yield |
|---|---|---|---|---|---|---|---|---|
| 500 | Ammonium salicylate | 1.2 | 67 | 83.6 | 12 | 1 | 8 | 96 |
| 501 | Ammonium salicylate | 2.0 | 80 | — | 7 | 0 | 4 | 95 |
| 502 | Ammonium salicylate | 3.0 | 85 | 83.1 | 5 | 0 | 1 | 92 |
| 503 | Ammonium salicylate/Ammonium chloride | 1.0/2.0 2.0/1.0 | 62 82 | 83.6 85.3 | 14 7 | 1 0 | 10 2 | 97 93 |
| 504 | | | | | | | | |
| 505 | Ammonium salicylate/Ammonium acetate | 1.0/2.0 2.0/1.0 | 58 71 | 65.4 62.4 | 1 1 | 2 1 | 17 9 | 95 91 |
| 506 | | | | | | | | |
| 507 | Ammonium salicylate/Ammonium trifluoroacetate | 1.0/2.0 2.0/1.0 | 77 84 | 88.2 86.6 | 11 7 | 1 0 | 3 2 | 95 95 |
| 508 | | | | | | | | |

Examples 509-523

Synthesis of 2-((1R)-1-aminoethyl)-N-(5-chloro-4-(trifluoromethyl)pyridin-2-yl)-1,3-thiazole-5-carboxamide

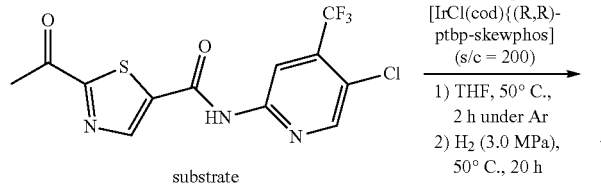
substrate

Additive (x eq.)
Ammonium salicylate (3.0 eq.)
[IrCl(cod){(R,R)-ptbp-skewphos}]
(s/c = 200)

1) THF, 50° C., 2 h under Ar
2) H₂ (3.0 MPa), 50° C., 20 h

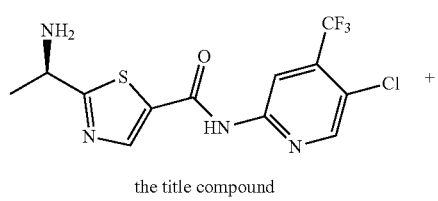
the title compound

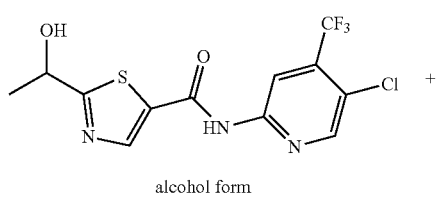
alcohol form

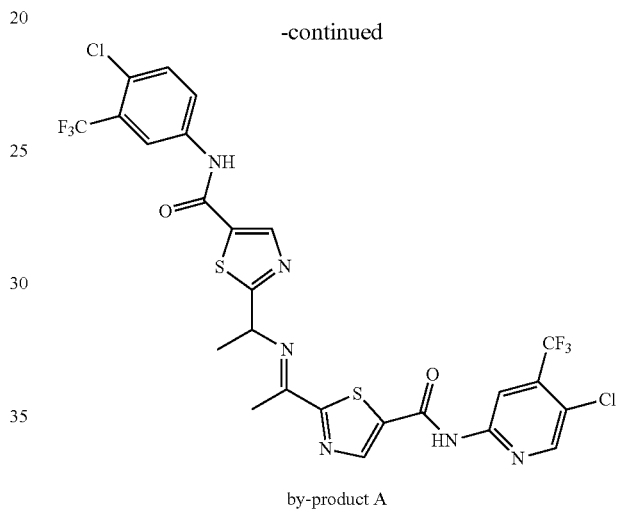
by-product A

2-Acetyl-N-(5-chloro-4-(trifluoromethyl)pyridin-2-yl)-1,3-thiazole-5-carboxamide (0.400 g), ammonium salicylate (0.532 g), [IrCl(cod){(R,R)-ptbp-Skewphos}] (0.0057 g) and additive (amount shown in Table 35) were each weighed, and they were put into an autoclave (SUS316, 120 mL). The atmosphere in the autoclave was decompressed, and the pressure was recovered under argon atmosphere. The procedures were performed five times in total. Under argon atmosphere, super-dehydrated THF (8.0 mL) was added thereto using a syringe, and the mixture was stirred at 50° C. for 2 hr. After the completion of stirring, the atmosphere in the autoclave was purged with hydrogen. Hydrogen was fed into the autoclave until 3.0 MPa, and the mixture was stirred under hydrogen pressure at 50° C. for 2 hr. After the completion of the reaction, the autoclave was cooled, and the hydrogen gas was released. The yield of each product and the enantiomic excess of the title compound were calculated from HPLC. The results are shown in Table 35. The HPLC conditions were the same as in Examples 421-428.

TABLE 35

| Ex. | Additive | eq. | HPLC assay (%) | | | | | |
|---|---|---|---|---|---|---|---|---|
| | | | title compound yield | % ee | alcohol form yield | substrate yield | by-product A yield | total yield |
| 509 | (+)-ammonium ditautrate | 0.2 | 84 | 26.3 | 3 | 0 | 1 | 89 |
| 510 | L-(+)-tautric acid | 0.2 | 85 | 19.3 | 4 | 0 | 3 | 95 |
| 511 | citric acid | 0.2 | 83 | 35.3 | 8 | 0 | 1 | 95 |
| 512 | 18-crown-6 | 0.01 | 80 | 25.1 | 3 | 0 | 3 | 89 |
| 513 | Terpyridine | 0.01 | 86 | 75.5 | 3 | 0 | 2 | 93 |
| 514 | Terpyridine | 0.01 | 77 | 79.7 | 3 | 1 | 4 | 89 |
| 515 | Terpyridine | 0.02 | 87 | 82.4 | 4 | 1 | 1 | 94 |
| 516 | 2,2'-Bipyridine | 0.02 | 74 | 15.9 | 2 | 1 | 6 | 89 |
| 517 | N,N,N',N'-TETRAMETHYL-1,8-NAPHTHALENEDIAMINE | 0.02 | 84 | 27.7 | 4 | 0 | 2 | 92 |
| 518 | TMEDA | 0.02 | 79 | 17.3 | 2 | 1 | 5 | 92 |
| 519 | N,N,N',N'',N''-Pentamethyldiethylenetriamine | 0.02 | 81 | 21.6 | 3 | 0 | 3 | 90 |
| 520 | N-Methyl-N,N-bis(2-pyridylmethyl)amine | 0.02 | 83 | 62.1 | 3 | 0 | 2 | 90 |
| 521 | N-tert-Butyl-N,N-bis(2-pyridylmethyl)amine | 0.02 | 87 | 32.3 | 3 | 0 | 1 | 92 |
| 522 | 2,6-Bis(N,N-dimetnylaminomethyl)pyridine | 0.02 | 81 | 22.5 | 3 | 0 | 3 | 90 |
| 523 | N2,N2,N6,N6-Tetraethylpyridine-2,6-dicarboxamide | 0.02 | 85 | 27.0 | 3 | 0 | 1 | 90 |

Examples 524-542

Synthesis of 2-((1R)-1-aminoethyl)-N-(5-chloro-4-(trifluoromethyl)pyridin-2-yl)-1,3-thiazole-5-carboxamide

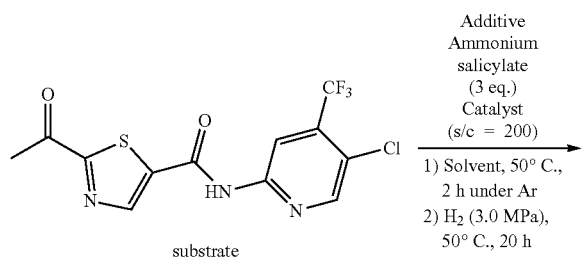
substrate

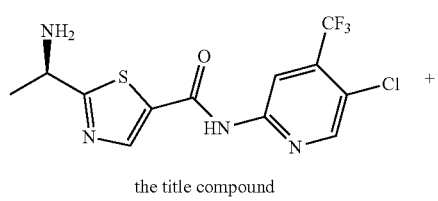
the title compound

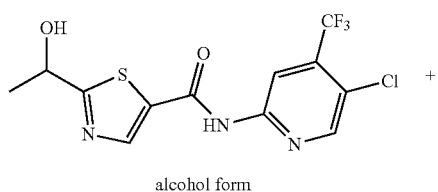
alcohol form

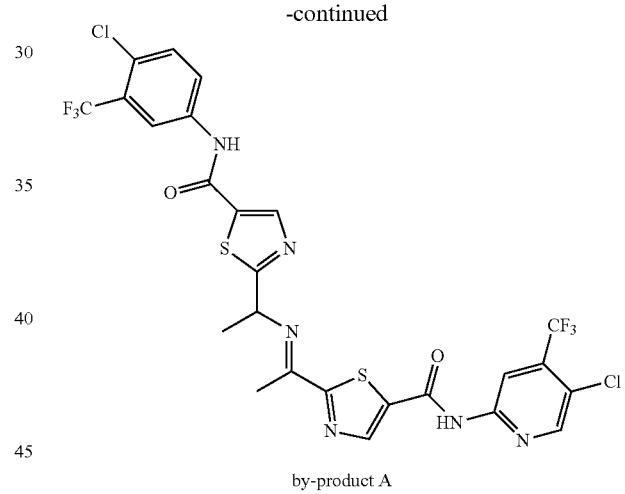
by-product A

The following standard reaction was carried out, except that additive (A), solvent (S) or catalyst (C) in the standard reaction was changed as shown in "change column" in Table 36.

2-Acetyl-N-(5-chloro-4-(trifluoromethyl)pyridin-2-yl)-1,3-thiazole-5-carboxamide (0.400 g), ammonium salicylate (0.532 g), [IrCl(cod){(R,R)-ptbp-Skewphos}](catalyst, 0.0057 g) and an additive (0.2 equivalent relative to the substrate) were each weighed, and they were put into a test tube for Endeavor (registered trademark). The test tube was set in the apparatus. The atmosphere in the apparatus was decompressed, and the pressure was recovered under argon atmosphere. The procedures were performed five times in total. Under argon atmosphere, super-dehydrated THF (solvent, 8.0 mL) was added thereto using a syringe, and the mixture was stirred at 50° C. for 2 hr. After the completion of stirring, the atmosphere in the apparatus was purged with hydrogen. Hydrogen was fed into the apparatus until 3.0 MPa, and the mixture was stirred under hydrogen pressure at 50° C. for 2 hr. The reaction solution was cooled to room temperature, and the hydrogen gas was released. The yield of each product and the enantiomic excess of the title compound were calculated under the same HPLC conditions as in Examples 421-428. The results are shown in Table 36.

TABLE 36

| Ex. | change<br>A: Additive;<br>S: Solvent;<br>C: catalyst | HPLC assay (%) | | | | |
|---|---|---|---|---|---|---|
| | | title compound yield | % ee | alcohol form yield | substrate yield | by-product A yield | total yield |
| 524 | A: InCl$_3$ | 76 | 12.5 | 4 | 2 | 9 | 100 |
| 525 | A: FeCl$_3$ | 70 | 20.9 | 3 | 3 | 8 | 92 |
| 526 | A: ZnCl$_2$ | 88 | 25.0 | 5 | 0 | 2 | 97 |
| 527 | A: LiCl | 86 | 85.6 | 5 | 0 | 1 | 93 |
| 528 | A: Salicylic acid/Cs$_2$CO$_3$ | 85 | 82.1 | 3 | 1 | 2 | 93 |
| 529 | A: Benzophenone | 82 | 87.1 | 5 | 0 | 6 | 99 |
| 530 | A: Benzaldehyde | 44 | 73.3 | 2 | 4 | 16 | 82 |
| 531 | A: Et$_3$N-salicylic acid | 83 | 83.7 | 4 | 0 | 3 | 93 |
| 532 | A: Et$_2$NH-salicylic acid | 85 | 84.9 | 4 | 0 | 2 | 93 |
| 533 | A: Pyridine-disalicylic acid | <89 | 87.5 | 6 | 0 | 1 | 97 |
| 534 | S: THF/Pyridine = 9/1 | <79 | 67.9 | 2 | 1 | 9 | 100 |
| 535 | S: THF/Pyridine = 3/1 | <64 | 47.6 | 1 | 3 | 16 | 100 |
| 536 | S: CPME | 7 | 74.4 | 5 | 46 | 21 | 100 |
| 537 | S: DME | 73 | 79.4 | 6 | 2 | 8 | 97 |
| 538 | S: 1,4-Dioxane | 88 | 94.2 | 2 | 0 | 1 | 92 |
| 539 | S: t-Amyl alcohol | 58 | 81.3 | 3 | 2 | 14 | 91 |
| 540 | S: THF/Dioxane = 9/1 | 83 | 86.8 | 3 | 0 | 3 | 92 |
| 541 | C: [IrOMe(cod)]$_2$ s/c = 400) | 64 | 75.1 | 2 | 2 | 12 | 92 |
| 542 | C: Ir(acac)(cod) (s/c = 400) | 59 | 72.5 | 1 | 2 | 13 | 88 |

Examples 543-565

Synthesis of 2-((1R)-1-aminoethyl)-N-(5-chloro-4-(trifluoromethyl)pyridin-2-yl)-1,3-thiazole-5-carboxamide

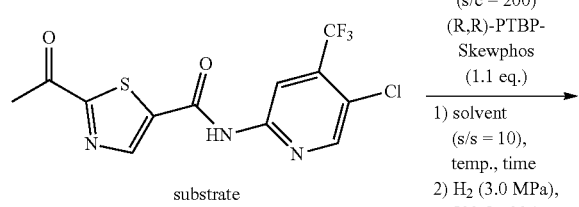

substrate

Ammonium salicylate
(2 or 3 eq.)
[IrCl(cod)]$_2$
(s/c = 200)
(R,R)-PTBP-Skewphos
(1.1 eq.)

1) solvent (s/s = 10), temp., time
2) H$_2$ (3.0 MPa), 50° C., 20 h

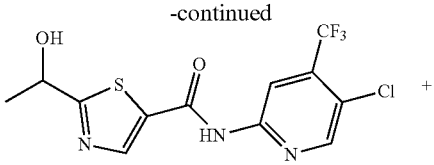

alcohol form

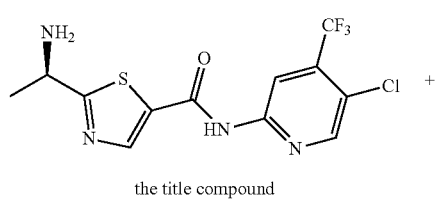

the title compound

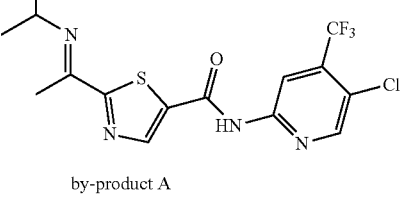

by-product A

2-Acetyl-N-(5-chloro-4-(trifluoromethyl)pyridin-2-yl)-1,3-thiazole-5-carboxamide (0.400 g), ammonium salicylate, [IrCl(cod)]$_2$ (0.0019 g) and (R,R)-PTBP-Skewphos (0.0042 g) were each weighed, and they were put into a test tube for Endeavor (registered trademark). The test tube was set in the apparatus. The atmosphere in the apparatus was decompressed, and the pressure was recovered under argon atmosphere. The procedures were performed five times in total. Under argon atmosphere, super-dehydrated solvent (4.0 mL) was added thereto using a syringe, and the mixture was stirred at a given temperature for a given time. After the completion of stirring, the atmosphere in the apparatus was purged with hydrogen. Hydrogen was fed into the apparatus until 3.0 MPa, and the mixture was stirred under hydrogen pressure at 50° C. for 2 hr. The reaction solution was cooled to room temperature, and the hydrogen gas was released. The yield of each product and the enantiomeric excess of the title compound were calculated from HPLC. The results are shown in Table 37. The HPLC conditions were the same as in Examples 421-428.

Examples 566-576

Synthesis of 2-((1R)-1-aminoethyl)-N-(5-chloro-4-(trifluoromethyl)pyridin-2-yl)-1,3-thiazole-5-carboxamide

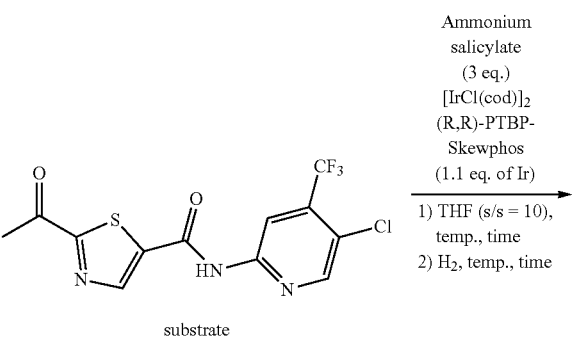

TABLE 37

| | | Ammonium Salicylate (eq.) | premix | | title compound | | alcohol form | substrate | by-product A | total |
|---|---|---|---|---|---|---|---|---|---|---|
| Ex. | solvent | | temp. | time (min) | yield | % ee | yield | yield | yield | yield |
| 543 | THF | 3.0 | 25 | 30 | 36 | 65.4 | 3 | 7 | 20 | 86 |
| 544 | THF | 3.0 | 40 | 30 | 69 | 70.3 | 4 | 1 | 10 | 94 |
| 545 | THF | 3.0 | 40 | 60 | 84 | 83.7 | 6 | 0 | 0 | 90 |
| 546 | THF | 3.0 | 40 | 90 | 85 | 84.7 | 6 | 0 | 0 | 91 |
| 547 | THF | 3.0 | 40 | 120 | 85 | 84.6 | 6 | 0 | 0 | 91 |
| 548 | THF | 3.0 | 40 | 180 | 80 | 85.6 | 7 | 0 | 0 | 87 |
| 549 | THF | 3.0 | 50 | 30 | 81 | 79.7 | 5 | 0 | 1 | 88 |
| 550 | THF | 3.0 | 50 | 45 | 76 | 86.6 | 7 | 0 | 0 | 83 |
| 551 | THF | 3.0 | 50 | 60 | 82 | 84.2 | 6 | 0 | 0 | 88 |
| 552 | THF | 3.0 | 50 | 75 | 82 | 85.5 | 6 | 0 | 0 | 88 |
| 553 | THF | 3.0 | 50 | 90 | 79 | 85.4 | 6 | 0 | 0 | 85 |
| 554 | THF | 3.0 | 50 | 120 | 74 | 80.7 | 6 | 1 | 1 | 83 |
| 555 | THF | 3.0 | 60 | 30 | 77 | 77.9 | 5 | 0 | 3 | 88 |
| 556 | THF | 3.0 | 60 | 60 | 76 | 80.8 | 5 | 0 | 1 | 83 |
| 557 | dioxane | 2.0 | 25 | 30 | 33 | 87.1 | 3 | 11 | 25 | 97 |
| 558 | dioxane | 2.0 | 40 | 30 | 26 | 87.2 | 3 | 16 | 28 | 101 |
| 559 | dioxane | 2.0 | 50 | 30 | 47 | 83.9 | 4 | 7 | 22 | 102 |
| 560 | dioxane | 2.0 | 50 | 60 | 77 | 88.1 | 5 | 1 | 7 | 97 |
| 561 | dioxane | 2.0 | 50 | 90 | 90 | 90.6 | 5 | 0 | 1 | 97 |
| 562 | dioxane | 2.0 | 50 | 120 | 91 | 90.7 | 6 | 0 | 1 | 99 |
| 563 | dioxane | 2.0 | 50 | 180 | 87 | 91.3 | 6 | 0 | 1 | 95 |
| 564 | dioxane | 2.0 | 60 | 30 | 90 | 92.0 | 7 | 0 | 0 | 97 |
| 565 | dioxane | 2.0 | 60 | 60 | 85 | 91.1 | 6 | 0 | 2 | 95 |

-continued

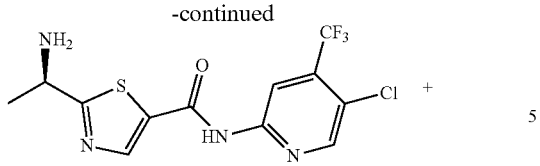
the title compound

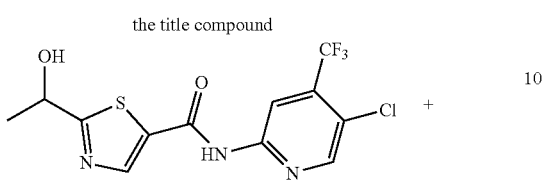
alcohol form

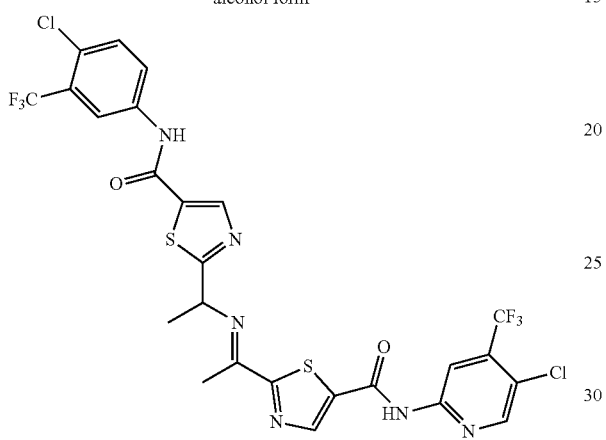
by-product A

[IrCl(cod)]$_2$, (R,R)-PTBP-Skewphos, 2-acetyl-N-(5-chloro-4-(trifluoromethyl)pyridin-2-yl)-1,3-thiazole-5-carboxamide (20.00 g) and ammonium salicylate (26.62 g) were put into an autoclave (1 L). The atmosphere in the apparatus was decompressed, and the pressure was recovered under argon atmosphere. The procedures were performed seven times in total. Under argon atmosphere, super-dehydrated THF (200 mL) was fed to the autoclave, and the mixture was stirred at a given temperature for a given time. After the completion of stirring, the atmosphere in the apparatus was purged ten times with hydrogen. The atmosphere was pressurized with hydrogen gas, and the mixture was stirred under a given hydrogen pressure at a given temperature for 24 hr. The reaction solution was cooled to room temperature, and the hydrogen gas was released. The yield of each product and the enantiomic excess of the title compound were calculated from HPLC. The results are shown in Table 38. The HPLC conditions were the same as in Examples 421-428.

TABLE 38

| | | | | | | | HPLC analysis | | | | | |
|---|---|---|---|---|---|---|---|---|---|---|---|---|
| | | | | | | | | title compound | | | | |
| | | premix | | Hydrogenation | | | | Yield of | alcohol | | by- | |
| Ex. | s/c | temp | time (min.) | temp. | H$_2$ press. | time (h) | yield | % ee | optically active form | form yield | substrate yield | product A yield | total yield |
| 566 | 400 | 40 | 90 | 40 | 5 | 24 | 77 | 82.1 | 70 | 7 | 0 | 1 | 86 |
| 567 | 400 | 40 | 90 | 40 | 5 | 24 | 80 | 86.5 | 75 | 7 | 0 | 2 | 91 |
| 568 | 300 | 40 | 90 | 40 | 5 | 24 | 82 | 88.7 | 77 | 8 | 0 | 1 | 92 |

TABLE 38-continued

| | | premix | | Hydrogenation | | | | | title compound | alcohol | | by- | |
|---|---|---|---|---|---|---|---|---|---|---|---|---|---|
| Ex. | s/c | temp | time (min.) | temp. | H₂ press. | time (h) | yield | % ee | Yield of optically active form | form yield | substrate yield | product A yield | total yield |
| 569 | 400 | 40 | 110 | 40 | 4 | 24 | 74 | 84.8 | 68 | 6 | 0 | 4 | 88 |
| 570 | 400 | 40 | 90 | 40 | 6 | 24 | 81 | 87.5 | 76 | 7 | 0 | 1 | 90 |
| 571 | 400 | 35 | 90 | 40 | 5 | 24 | 79 | 82.8 | 72 | 5 | 0 | 5 | 94 |
| 572 | 400 | 45 | 90 | 40 | 5 | 24 | 76 | 85.0 | 70 | 6 | 0 | 3 | 88 |
| 573 | 400 | 40 | 90 | 35 | 5 | 24 | 72 | 90.2 | 68 | 7 | 1 | 5 | 90 |
| 574 | 400 | 40 | 90 | 45 | 5 | 24 | 81 | 83.1 | 74 | 5 | 0 | 2 | 89 |
| 575 | 400 | 35 | 90 | 40 | 5 | 40 | 86 | 83.0 | 79 | 6 | 0 | 1 | 94 |
| 576 | 400 | 35 | 90 | 35 | 5 | 65 | 85 | 84.7 | 79 | 7 | 0 | 1 | 94 |

Examples 577-587

Synthesis of 2-((1R)-1-aminoethyl)-N-(5-chloro-4-(trifluoromethyl)pyridin-2-yl)-1,3-thiazole-5-carboxamide

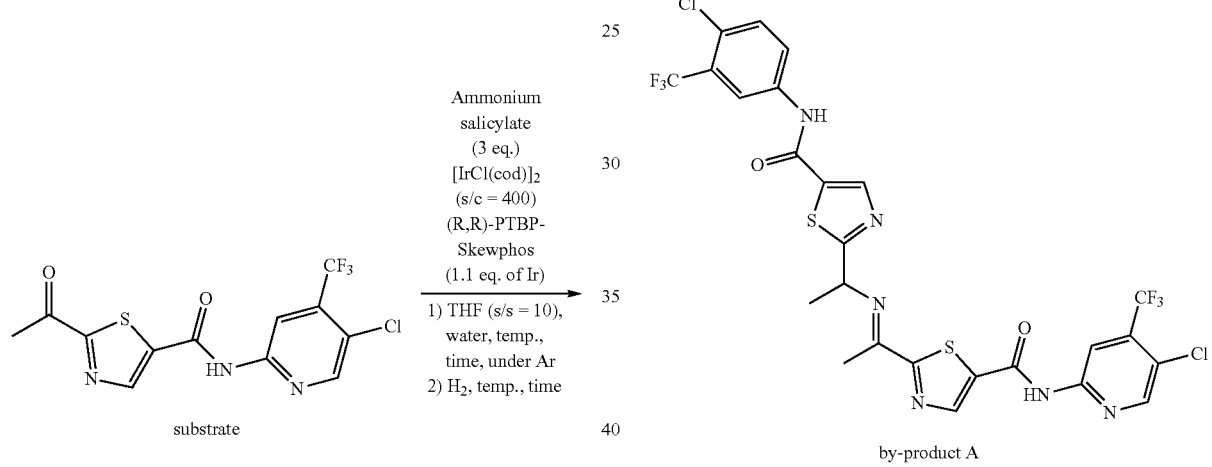

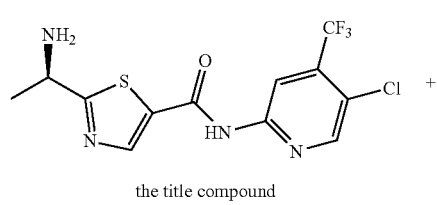

the title compound

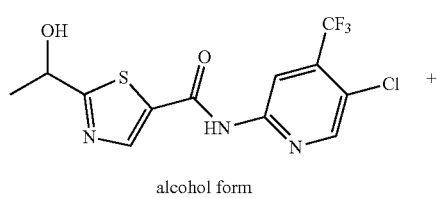

alcohol form

[IrCl(cod)]₂ (0.0480 g), (R,R)-PTBP-Skewphos (0.1046 g), 2-acetyl-N-(5-chloro-4-(trifluoromethyl)pyridin-2-yl)-1,3-thiazole-5-carboxamide (20.00 g) and ammonium salicylate (26.62 g) were put into an autoclave (1 L). The atmosphere in the apparatus was decompressed, and the pressure was recovered under argon atmosphere. The procedures were performed seven times in total. Under argon atmosphere, super-dehydrated THF (200 mL) and ultrapure water (given ppm) were fed to the autoclave, and the mixture was stirred at a given temperature for a given time. After the completion of stirring, the atmosphere in the apparatus was purged ten times with hydrogen. The atmosphere was pressurized with hydrogen gas, and the mixture was stirred under a given hydrogen pressure at a given temperature for 24 hr. The reaction solution was cooled to room temperature, and the hydrogen gas was released. The yield of each product and the enantiomeric excess of the title compound were calculated from HPLC. The results are shown in Table 39. The HPLC conditions were the same as in Examples 421-428.

TABLE 39

| | | premix | | Hydrogenation | | | HPLC analysis | | | | | |
| | | | | | | | | title compound | | yield of | | by- | |
| Ex. | water (ppm) | temp | time (min.) | temp. | H₂ press. | time (h) | yield | % ee | optically active form | alcohol form yield | substrate yield | product A yield | total yield |
|---|---|---|---|---|---|---|---|---|---|---|---|---|---|
| 577 | 100 | 40 | 90 | 40 | 5 | 24 | 80 | 86.4 | 75 | 7 | 0 | 2 | 92 |
| 578 | 1000 | 40 | 90 | 40 | 5 | 24 | 83 | 86.1 | 77 | 7 | 0 | 2 | 94 |
| 579 | 2000 | 40 | 90 | 40 | 5 | 24 | 84 | 86.2 | 78 | 7 | 0 | 3 | 97 |
| 580 | 3000 | 40 | 90 | 40 | 5 | 24 | 83 | 83.2 | 76 | 7 | 1 | 4 | 99 |
| 581 | 4000 | 40 | 90 | 40 | 5 | 24 | 78 | 82.0 | 71 | 6 | 1 | 7 | 99 |
| 582 | 8000 | 40 | 90 | 40 | 5 | 24 | 54 | 73.3 | 47 | 6 | 6 | 18 | 102 |
| 583 | 2000 | rt | 10 | 40 | 5 | 24 | 12 | nd | nd | 2 | 24 | 29 | 96 |
| 584 | 2000 | 40 | 90 | 40 | 5 | 40 | 89 | 83.7 | 82 | 8 | 0 | 1 | 98 |
| 585 | 2000 | 40 | 90 | 40 | 5 | 30 | 86 | 85.9 | 80 | 7 | 0 | 1 | 96 |
| 586 | 2000 | 40 | 90 | 40 | 5 | 40 | 89 | 84.2 | 82 | 7 | 0 | 1 | 97 |
| 587 | 2000 | rt | 10 | 40 | 5 | 24 | 82 | 86.4 | 76 | 7 | 0 | 2 | 93 |

Example 588

Synthesis of 2-((1R)-1-aminoethyl)-N-(5-chloro-4-(trifluoromethyl)pyridin-2-yl)-1,3-thiazole-5-carboxamide

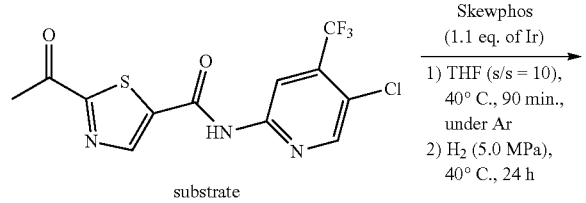

substrate

Ammonium salicylate (3 eq.)
[IrCl(cod)]₂ (s/c = 400)
(R,R)-PTBP-Skewphos (1.1 eq. of Ir)

1) THF (s/s = 10), 40° C., 90 min., under Ar
2) H₂ (5.0 MPa), 40° C., 24 h

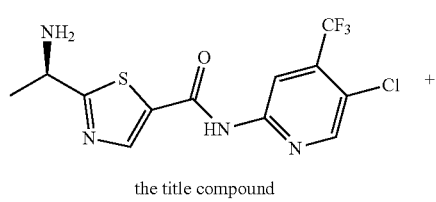

the title compound

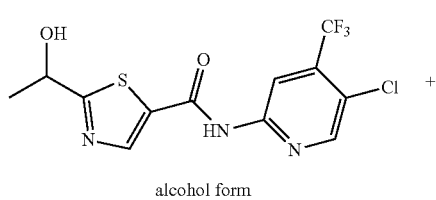

alcohol form

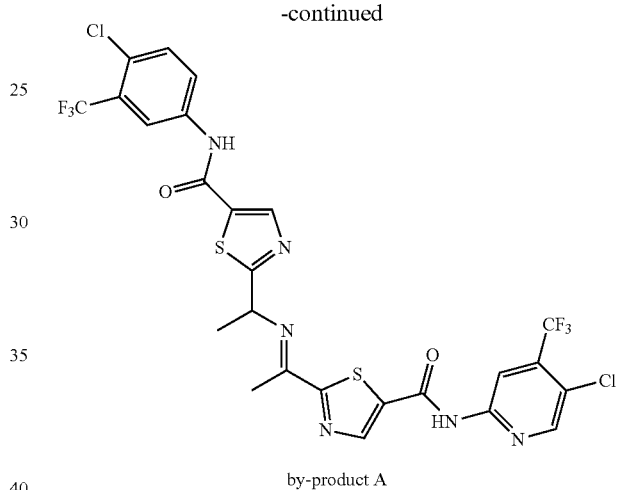

by-product A

[IrCl(cod)]₂ (0.0480 g), (R,R)-PTBP-Skewphos (0.1046 g), 2-acetyl-N-(5-chloro-4-(trifluoromethyl)pyridin-2-yl)-1,3-thiazole-5-carboxamide (20.00 g) and ammonium salicylate (26.62 g) were put into an autoclave (1 L). The atmosphere in the apparatus was decompressed, and the pressure was recovered under argon atmosphere. The procedures were performed seven times in total. Under argon atmosphere, deoxygenated THF (200 mL) was fed to the autoclave, and the mixture was stirred at 40° C. for 90 min. After the completion of stirring, the atmosphere in the apparatus was purged ten times with hydrogen. The atmosphere was pressurized with hydrogen gas, and the mixture was stirred at 5.0 MPa at 40° C. for 24 hr. The reaction solution was cooled to room temperature, and the hydrogen gas was released. The yield of each product and the enantiomeric excess of the title compound were calculated from HPLC. the title compound: yield 81%, 87.1% ee; alcohol form: yield 7%; by-product A: yield 2%.

Conditions for High-Performance Liquid Chromatography Analysis (Area Normalization)

column: YMC-Pack ODS-A (manufactured by YMC. CO., LTD.), 4.6*150 mm
UV detection wavelength: 254 nm
mobile phase A: acetonitrile for high-performance liquid chromatography/0.010 mol/L aqueous potassium dihydrogenphosphate solution=6/4
mobile phase B: acetonitrile for high-performance liquid chromatography/0.010 mol/L aqueous potassium dihydrogenphosphate solution=8/2
flow rate: 1.0 mL/min
gradient program:

TABLE 40

| | Mobile phase A | Mobile phase B |
|---|---|---|
| 0.00 min | 100% | 0% |
| 8.00 min | 100% | 0% |
| 10.00 min | 0% | 100% |
| 25.00 min | 0% | 100% |
| 25.01 min | 100% | 0% |
| 35.00 min | 100% | 0% | retention time: 2.2 min. (the title compound (containing R-form and S-form)), 3.6 min. (alcohol form), 7.0 min. (substrate), 19.8 min. (by-product B)

Conditions for High-Performance Liquid Chromatography Analysis (Optical Purity)
column: IA (manufactured by Daicel Chemical Industries), 4.6*250 mm
UV detection wavelength: 254 nm
mobile phase: acetonitrile for high-performance liquid chromatography/methanol/water=80/15/5
flow rate: 1.0 mL/min
column temperature: 40° C.
retention time: 4.6 min. (substrate), 5.8 min. (alcohol form), 11.6 min. (alcohol form), 16.2 min. (the title compound (R-form)), 24.2 min. (enantiomer (S-form) of the title compound).

Example 589

Synthesis of 2-((1R)-1-aminoethyl)-N-(5-chloro-4-(trifluoromethyl)pyridin-2-yl)-1,3-thiazole-5-carboxamide

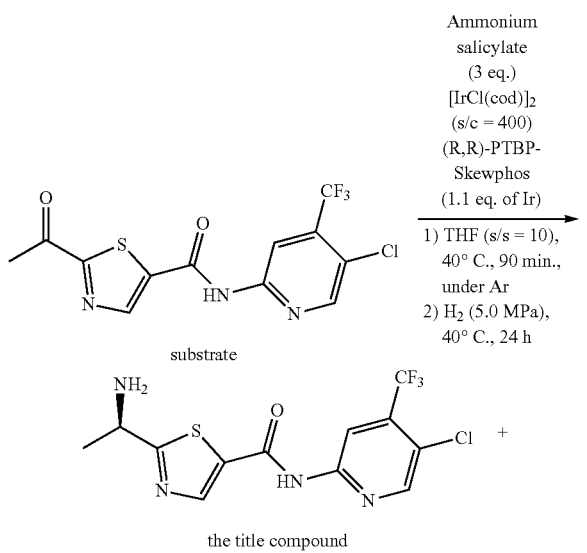

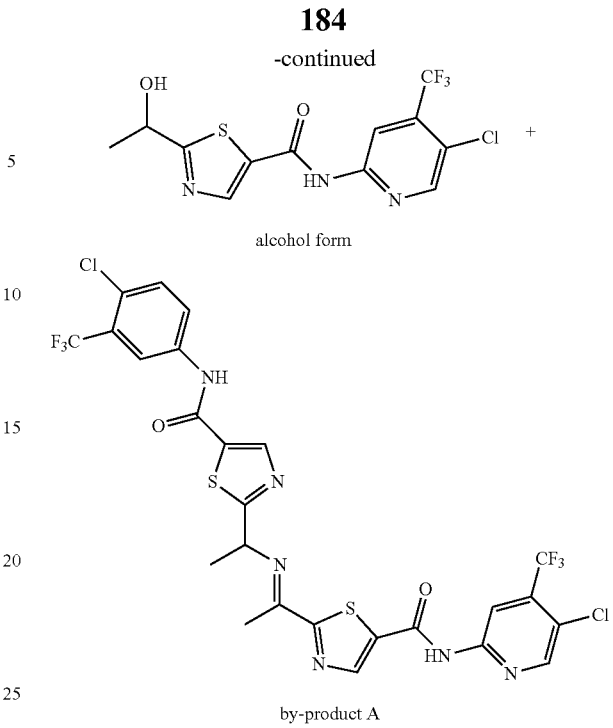

[IrCl(cod)]₂ (0.0480 g), (R,R)-PTBP-Skewphos (0.1046 g), 2-acetyl-N-(5-chloro-4-(trifluoromethyl)pyridin-2-yl)-1,3-thiazole-5-carboxamide (20.00 g) and ammonium salicylate (26.62 g) were put into an autoclave (1 L). The atmosphere in the apparatus was decompressed, and the pressure was recovered under argon atmosphere. The procedures were performed seven times in total. Under argon atmosphere, air-saturated THF (200 mL) was fed to the autoclave, and the mixture was stirred at 40° C. for 90 min. After the completion of stirring, the atmosphere in the apparatus was purged ten times with hydrogen. The atmosphere was pressurized with hydrogen gas, and the mixture was stirred at 5.0 MPa at 40° C. for 24 hr. The reaction solution was cooled to room temperature, and the hydrogen gas was released. The yield of each product and the enantiomic excess of the title compound were calculated from HPLC. the title compound: yield 72%, 82.2% ee; alcohol form: yield 5%; by-product A: yield 7%.

The HPLC conditions were the same as in Example 588.

Example 590

Synthesis of 2-((1R)-1-aminoethyl)-N-(5-chloro-4-(trifluoromethyl)pyridin-2-yl)-1,3-thiazole-5-carboxamide

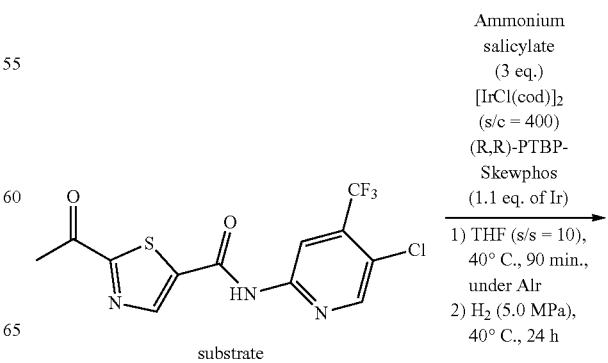

185
-continued

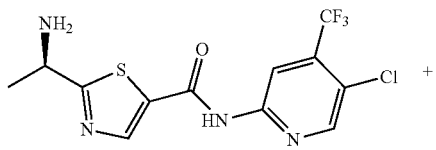

the title compound

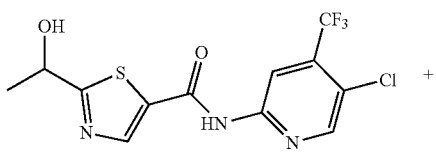

alcohol form

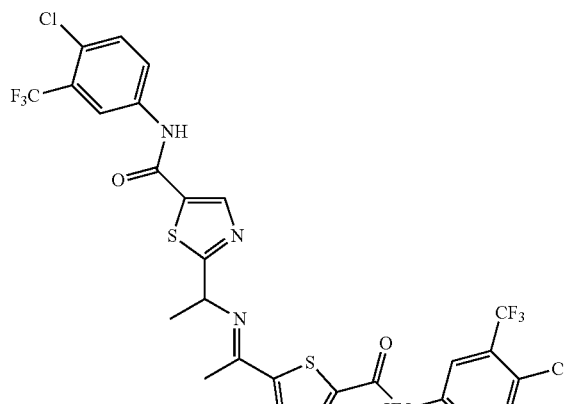

by-product A

[IrCl(cod)]$_2$ (0.0480 g), (R,R)-PTBP-Skewphos (0.1046 g), 2-acetyl-N-(5-chloro-4-(trifluoromethyl)pyridin-2-yl)-1,3-thiazole-5-carboxamide (20.00 g) and ammonium salicylate (26.62 g) were put into an autoclave (1 L). The atmosphere in the apparatus was decompressed, and the pressure was recovered under dry air. The procedures were performed seven times in total. Under dry air, super-dehydrated THF (200 mL) was fed to the autoclave, and the mixture was stirred at 40° C. for 90 min. After the completion of stirring, the atmosphere in the apparatus was purged ten times with hydrogen. The atmosphere was pressurized with hydrogen gas, and the mixture was stirred at 5.0 MPa at 40° C. for 24 hr. The reaction solution was cooled to room temperature, and the hydrogen gas was released. The yield of each product and the enantiomic excess of the title compound were calculated from HPLC. the title compound: yield 6%; alcohol form: yield 1%; by-product A: yield 23%. The HPLC conditions were the same as in Example 588.

186

Example 591

Synthesis of 2-((1R)-1-aminoethyl)-N-(5-chloro-4-(trifluoromethyl)pyridin-2-yl)-1,3-thiazole-5-carboxamide

[IrCl(cod)]$_2$ (0.0480 g), (R,R)-PTBP-Skewphos (0.1046 g), 2-acetyl-N-(5-chloro-4-(trifluoromethyl)pyridin-2-yl)-1,3-thiazole-5-carboxamide (20.00 g) and ammonium salicylate (26.62 g) were put into an autoclave (1 L). The atmosphere in the apparatus was purged ten times with nitrogen. Under nitrogen atmosphere, super-dehydrated THF (200 mL) was fed to the autoclave, and the mixture was stirred at 40° C. for 90 min. After the completion of stirring, the atmosphere in the apparatus was purged ten times with hydrogen. The atmosphere was pressurized with hydrogen gas, and the mixture was stirred at 5.0 MPa at 40° C. for 24 hr. The reaction solution was cooled to room temperature, and the hydrogen gas was released. The yield of each product and the enantiomic excess of the title compound were calculated from HPLC. the title compound: yield 78%, 85.3% ee; alcohol form: yield 6%; by-product A: yield 3%. The HPLC conditions were the same as in Example 588.

Example 592

Synthesis of 2-((1R)-1-aminoethyl)-N-(5-chloro-4-(trifluoromethyl)pyridin-2-yl)-1,3-thiazole-5-carboxamide

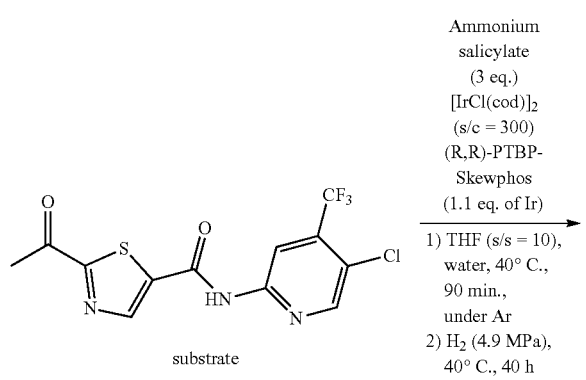

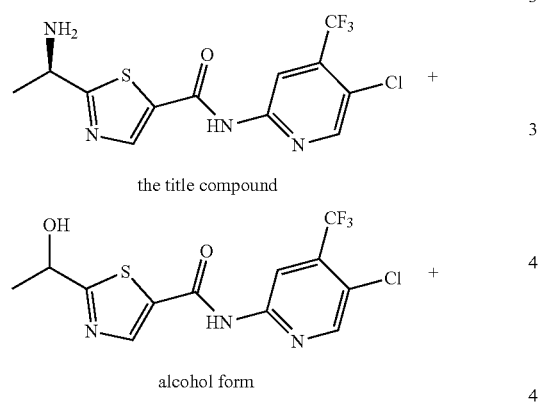

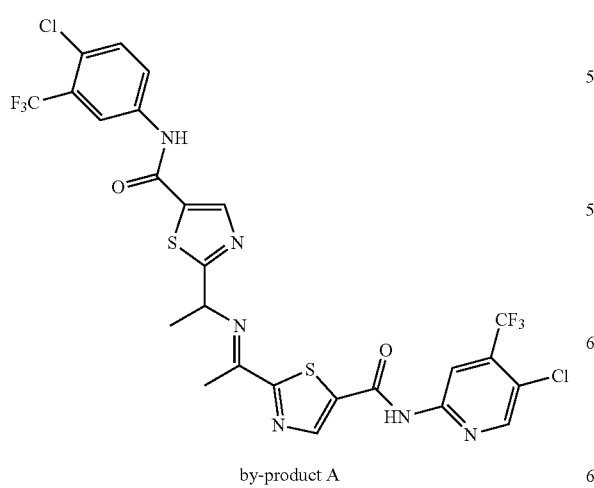

[IrCl(cod)]$_2$ (0.1985 g), (R,R)-PTBP-Skewphos (0.4322 g), 2-acetyl-N-(5-chloro-4-(trifluoromethyl)pyridin-2-yl)-1,3-thiazole-5-carboxamide (62.00 g) and ammonium salicylate (82.52 g) were put into an autoclave (1 L). The atmosphere in the apparatus was decompressed, and the pressure was recovered under argon atmosphere. The procedures were performed seven times in total. Under argon atmosphere, super-dehydrated THF (620 mL) and ultrapure water (1.10 mL) were fed to the autoclave, and the mixture was stirred at 40° C. for 90 min. After the completion of stirring, the atmosphere in the apparatus was purged ten times with hydrogen. The atmosphere was pressurized with hydrogen gas, and the mixture was stirred at 4.9 MPa at 40° C. for 40 hr. After 40 hr, the hydrogen pressure decreased to 3.0 MPa. The reaction solution was cooled to room temperature, and the hydrogen gas was released. The yield of each product and the enantiomic excess of the title compound were calculated from HPLC. the title compound: yield 87%, 82.2% ee; alcohol form: yield 7%; by-product A: yield 1%. The HPLC conditions were the same as in Example 588.

Example 593

Synthesis of 2-((1R)-1-aminoethyl)-N-(5-chloro-4-(trifluoromethyl)pyridin-2-yl)-1,3-thiazole-5-carboxamide

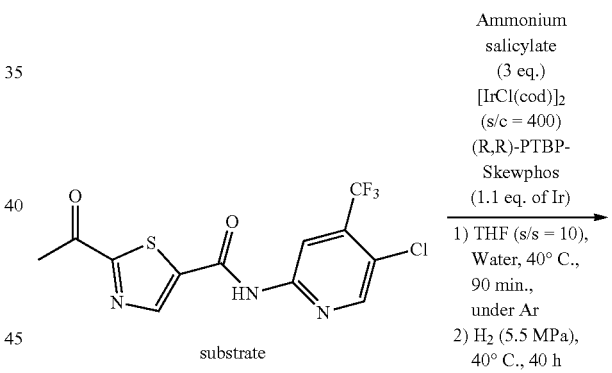

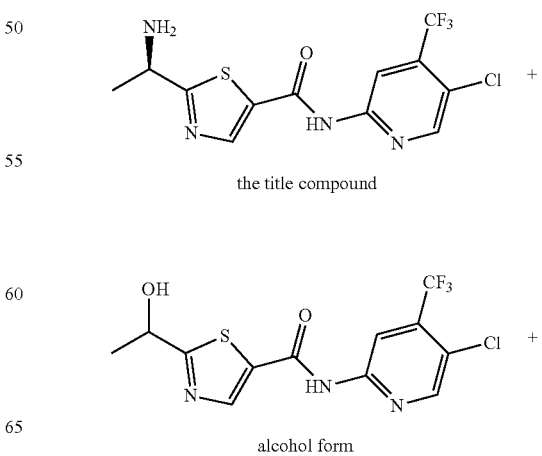

-continued

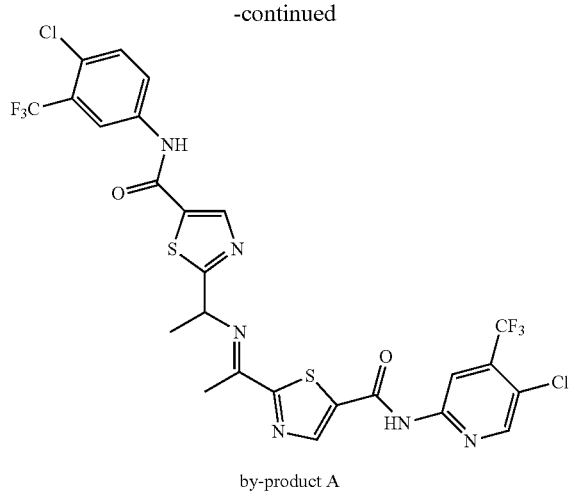

by-product A

[IrCl(cod)]$_2$ (0.1489 g), (R,R)-PTBP-Skewphos (0.3242 g), 2-acetyl-N-(5-chloro-4-(trifluoromethyl)pyridin-2-yl)-1,3-thiazole-5-carboxamide (62.00 g) and ammonium salicylate (82.52 g) were put into an autoclave (1 L). The atmosphere in the apparatus was decompressed, and the pressure was recovered under argon atmosphere. The procedures were performed seven times in total. Under argon atmosphere, super-dehydrated THF (620 mL) and ultrapure water (1.10 mL) were fed to the autoclave, and the mixture was stirred at 40° C. for 90 min. After the completion of stirring, the atmosphere in the apparatus was purged ten times with hydrogen. The atmosphere was pressurized with hydrogen gas, and the mixture was stirred at a constant pressure of 5.5 MPa at 40° C. for 40 hr. The reaction solution was cooled to room temperature, and the hydrogen gas was released. The yield of each product and the enantiomic excess of the title compound were calculated from HPLC. the title compound: yield 86%, 85.2% ee; alcohol form: yield 7%; by-product A: yield 1%.

The HPLC conditions were the same as in Example 588.

Example 594

Synthesis of 2-((1R)-1-aminoethyl)-N-(5-chloro-4-(trifluoromethyl)pyridin-2-yl)-1,3-thiazole-5-carboxamide

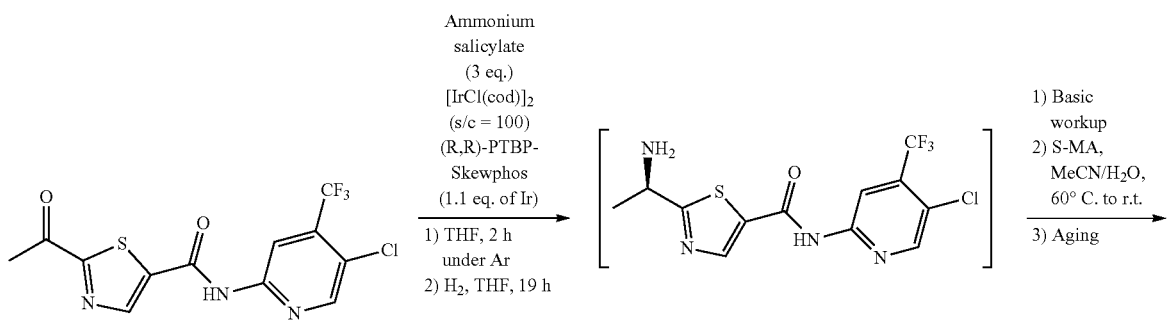

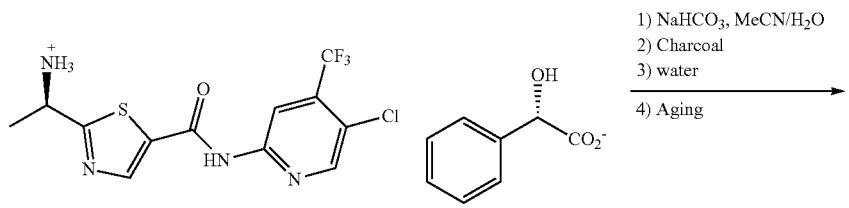

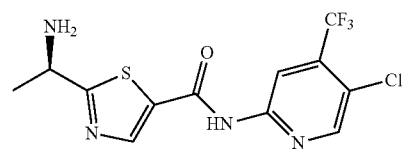

2-Acetyl-N-(5-chloro-4-(trifluoromethyl)pyridin-2-yl)-1,3-thiazole-5-carboxamide (200.00 g), ammonium salicylate (266.18 g), [IrCl(cod)]$_2$ (1.92 g) and (R,R)-PTBP-skewphos (4.18 g) were put into an autoclave (10 L). The atmosphere in the autoclave was decompressed, and the pressure was recovered under argon atmosphere. The procedures were performed seven times in total. Under argon atmosphere, super-dehydrated THF (4.00 L) was added thereto, and the mixture was stirred at 45-52° C. for 2 hr. After the completion of stirring, the atmosphere in the autoclave was purged ten times with hydrogen. Hydrogen was fed into the autoclave until 1.02 MPa, and the mixture was stirred under hydrogen pressure at 52-55° C. for 19 hr. After the completion of the reaction, the autoclave was cooled to 31° C., and the hydrogen gas was released. The yield and enantiomeric excess of the title compound were calculated from HPLC. The production of the title compound (yield 86%, 84.4% ee) was confirmed. The reaction mixture was concentrated under reduced pressure to 1.0 L, toluene (8.0 L) was added thereto, and the reaction mixture was concentrated under reduced pressure to 1.6 L. To the residue were added ethyl acetate (4.0 L) and aqueous ammonia solution (the solution (1.6 L) prepared by diluting 25% aqueous ammonia solution (260 g) with water), and the mixture was stirred at room temperature for 10 min. The aqueous layer was removed, and to the organic layer was added aqueous ammonia solution (the solution (1.6 L) prepared by diluting 25% aqueous ammonia solution (40 g) with water), and the mixture was stirred at room temperature for 10 min. The aqueous layer was removed, and the organic layer was concentrated under reduced pressure to 1.0 L. Acetonitrile (1.0 L) was added thereto, and the mixture was concentrated under reduced pressure to 1.0 L. The procedures were performed twice in total. The residue was put into a reaction container (10 L), and acetonitrile (4.8 L) and water (0.2 L) were added thereto. The mixture was heated to 60° C., (S)-mandelic acid (87.01 g) was added thereto at 60° C., and the mixture was cooled to room temperature over 3 hr. The resulting crystals were collected by filtration using a glass filter, washed with acetonitrile (1.6 L), and dried under reduced pressure at 50° C. to constant weight to give 2-((1R)-1-aminoethyl)-N-(5-chloro-4-(trifluoromethyl)pyridin-2-yl)-1,3-thiazole-5-carboxamide (S)-mandelate (193.93 g, yield 67.4%). The obtained crystal (190 g) and sodium hydrogencarbonate (63.45 g) were put into a reaction container (3 L). Water (1.44 L) and acetonitrile (1.44 L) were added thereto, and the mixture was stirred at 11-22° C. for 2 hr. Activated carbon (5.70 g) was added thereto, and the mixture was stirred at room temperature for 10 min. The reaction mixture was filtered through a membrane filter (45 μm), and the filter was washed with a mixed solvent (190 mL) of acetonitrile/water=1/1. The filtrate and washing were put into a reaction container (10 L), and water (3.23 L) was added dropwise at 13-18° C. The resulting crystals were aged at room temperature for 3 hr. The crystals were collected by filtration using Hirsch funnel, and washed with water (1.9 L). The obtained crystals were dried under reduced pressure at 50° C. to constant weight to give 2-((1R)-1-aminoethyl)-N-(5-chloro-4-(trifluoromethyl)pyridin-2-yl)-1,3-thiazole-5-carboxamide (128.24 g, yield 97%). HPLC 96.8 area %, 98.3% ee.

The HPLC conditions were the same as in Example 588.

INDUSTRIAL APPLICABILITY

According to the present invention, compound (III) or a salt thereof, which is a key intermediate, can be produced with good optical purity in good yield, by subjecting compound (I) or a salt thereof to an asymmetric reduction reaction, followed by deprotection. Particularly, after the deprotection, by crystallization of the diastereomer salt with optically active di-p-toluoyl-tartaric acid or optically active mandelic acid, the salt of compound (III) can be produced with better optical purity. Therefore, the objective compound (V) or a salt thereof can be produced on an industrial scale.

This application is based on patent application No. 2017-filed on May 30, 2017 in Japan, the contents of which are encompassed in full herein.

The invention claimed is:

1. A method of producing an optically active form of a compound represented by the following formula (III):

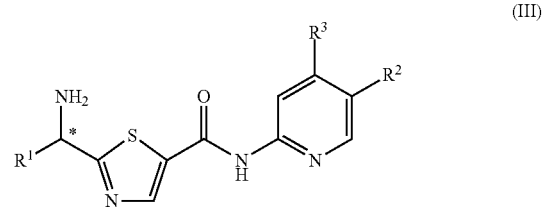

(III)

wherein R$^1$ is a C$_{1-6}$ alkyl group;
R$^2$ is a hydrogen atom or a halogen atom;
R$^3$ is a hydrogen atom or an optionally halogenated C$_{1-6}$ alkyl group; and
the carbon atom marked with * is an asymmetric carbon atom, or a salt thereof,
wherein the method comprises subjecting a compound represented by the following formula (A-c):

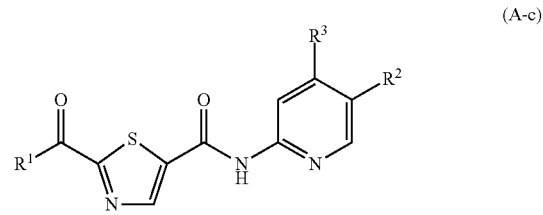

(A-c)

wherein each symbol is as defined above, or a salt thereof, to an asymmetric reductive amination reaction in the presence of an amine source, a reducing agent, and an organic metal complex.

2. The method of claim 1, wherein the reducing agent is a hydrogen donor.

3. The method of claim 2, wherein the hydrogen donor comprises hydrogen gas, a metal hydride, isopropyl alcohol, formic acid, benzthiazoline, or Hantzsch ester.

4. The method of claim 2, wherein the hydrogen donor is hydrogen gas.

5. The method of claim 1, wherein the amine source is an ammonium salt.

6. The method of claim 5, wherein an acid used for forming the ammonium salt is selected from an optionally substituted salicylic acid, optionally substituted nicotinic acid, carbonic acid, formic acid, acetic acid, trifluoroacetic acid and benzoic acid.

7. The method of claim 5, wherein the ammonium salt is ammonium salicylate.

8. The method of claim 1, wherein the organic metal complex is selected from rhodium complexes, ruthenium complexes, iridium complexes, palladium complexes, nickel complexes, copper complexes, osmium complexes, platinum complexes, iron complexes, gold complexes, silver complexes, zinc complexes, titanium complexes, cobalt complexes, zirconium complexes, and samarium complexes.

9. The method of claim 8, wherein the organic metal complex is an iridium complex.

10. The method of claim 1, wherein the organic metal complex comprises a ligand.

11. The method of claim 10, wherein the ligand is selected from 2,4-bis(diphenylphosphino)pentane (SKEWPHOS), SKEWPHOS derivative having 1 to 5 substituents on the benzene ring(s) bonded to the phosphorus atom of SKEWPHOS, 4,12-bis(diphenylphosphino)-[2,2]-paracyclophane (PhanePHOS), substituted-1,1'-bisphosphoranoferrocene (Ferrocelane), and 1-[2-(disubstituted-phosphino)ferrocenyl]ethyl-disubstituted-phosphine (Josiphos).

12. The method of claim 11, wherein the ligand is SKEWPHOS.

13. The method of claim 1, wherein the asymmetric reductive amination reaction is carried out in a solvent.

14. The method of claim 1, wherein the asymmetric reductive amination reaction is carried out in the presence of a base, an acid, or a salt.

15. The method of claim 1, wherein $R^1$ is methyl, $R^2$ is Cl, and $R^3$ is —$CF_3$.

* * * * *